US009278961B2

(12) United States Patent
Gunzner et al.

(10) Patent No.: US 9,278,961 B2
(45) Date of Patent: Mar. 8, 2016

(54) PYRIDYL INHIBITORS OF HEDGEHOG SIGNALLING

(75) Inventors: Janet L. Gunzner, Berkeley, CA (US); Daniel Sutherlin, South San Francisco, CA (US); Mark S. Stanley, Pacifica, CA (US); Liang Bao, San Mateo, CA (US); Georgette M. Castanedo, Redwood City, CA (US); Rebecca L. Lalonde, Berkeley, CA (US); Shumei Wang, Foster City, CA (US); Mark E. Reynolds, Millbrae, CA (US); Scott J. Savage, Burlingame, CA (US); Kimberly Malesky, San Francisco, CA (US); Michael S. Dina, Daly City, CA (US); Michael F. T. Koehler, Palo Alto, CA (US)

(73) Assignees: GENENTECH, INC., South San Francisco, CA (US); CURIS, INC., Lexington, MA (US)

( * ) Notice: Subject to any disclaimer, the term of this patent is extended or adjusted under 35 U.S.C. 154(b) by 1200 days.

(21) Appl. No.: 12/960,609

(22) Filed: Dec. 6, 2010

(65) Prior Publication Data

US 2011/0092461 A1 Apr. 21, 2011

Related U.S. Application Data

(62) Division of application No. 11/217,663, filed on Sep. 2, 2005, now Pat. No. 7,888,364.

(60) Provisional application No. 60/607,367, filed on Sep. 2, 2004.

(51) Int. Cl.

| | |
|---|---|
| ***C07D 213/38*** | (2006.01) |
| ***C07D 417/12*** | (2006.01) |
| ***C07D 401/14*** | (2006.01) |
| ***A61K 31/44*** | (2006.01) |
| ***C07D 213/40*** | (2006.01) |
| ***C07D 213/56*** | (2006.01) |
| ***C07D 213/70*** | (2006.01) |
| ***C07D 213/75*** | (2006.01) |
| ***C07D 213/81*** | (2006.01) |
| ***C07D 213/82*** | (2006.01) |
| ***C07D 401/12*** | (2006.01) |
| ***C07D 405/12*** | (2006.01) |
| ***C07D 409/12*** | (2006.01) |
| ***C07D 413/12*** | (2006.01) |
| ***C07D 417/04*** | (2006.01) |
| ***C07F 9/58*** | (2006.01) |

(52) U.S. Cl.

CPC ............ *C07D 417/12* (2013.01); *C07D 213/38* (2013.01); *C07D 213/40* (2013.01); *C07D 213/56* (2013.01); *C07D 213/70* (2013.01); *C07D 213/75* (2013.01); *C07D 213/81* (2013.01); *C07D 213/82* (2013.01); *C07D 401/12* (2013.01); *C07D 401/14* (2013.01); *C07D 405/12* (2013.01); *C07D 409/12* (2013.01); *C07D 413/12* (2013.01); *C07D 417/04* (2013.01); *C07F 9/588* (2013.01)

(58) Field of Classification Search

None

See application file for complete search history.

(56) References Cited

U.S. PATENT DOCUMENTS

| | | | | |
|---|---|---|---|---|
| 4,670,441 | A | 6/1987 | Kuehne et al. | |
| 4,851,414 | A | 7/1989 | Shiozaki et al. | |
| 5,783,522 | A | 7/1998 | Schaefer et al. | |
| 5,990,133 | A | 11/1999 | Gaster et al. | |
| 7,132,546 | B2 | 11/2006 | Kato et al. | |
| 2002/0193405 | A1 * | 12/2002 | Askew et al. | 514/318 |
| 2002/0198236 | A1 | 12/2002 | Baxter et al. | |
| 2015/0111879 | A1 | 4/2015 | Gunzner et al. | |

FOREIGN PATENT DOCUMENTS

| | | | |
|---|---|---|---|
| EP | 1 344 525 | | 9/2003 |
| WO | WO 96/21645 | | 7/1996 |
| WO | WO 97/03967 | A | 2/1997 |
| WO | WO 02/32856 | A2 | 4/2002 |
| WO | WO 02/051397 | A1 | 7/2002 |
| WO | WO 03/011219 | A2 | 2/2003 |
| WO | WO 03/026415 | A2 | 4/2003 |
| WO | WO 03/032970 | A1 | 4/2003 |
| WO | WO 03/033482 | A1 | 4/2003 |
| WO | WO 03/037274 | A2 | 5/2003 |

(Continued)

OTHER PUBLICATIONS

Pippard et al, British Medical Journal, 1979, 1, 227-229.*

G. Leclerc et al., "Cardionic Agents. 2. Synthesis and Structure Activity Relationships I a New Class of 6-,7-, and 8-Pyridyl-2(1H)quinolone Derivatives," Journal of Medicinal Chemistry, vol. 29, 1986, pp. 2433-2438, XP002362824.

S.M. Bromidge et al., "Biarylcarbamoylindolines are Novel and Selective 5HT2x Receptor Inverse Agonists," Journal of Medicinal Chemistry, vol. 43, 2000, pp. 1123-1134, XP002362825.

(Continued)

*Primary Examiner* — Zinna Northington Davis

(74) *Attorney, Agent, or Firm* — Millen White Zelano and Branigan, PC

(57) ABSTRACT

The invention provides novel inhibitors of hedgehog signaling that are useful as a therapeutic agents for treating malignancies where the compounds have the general formula I:

I

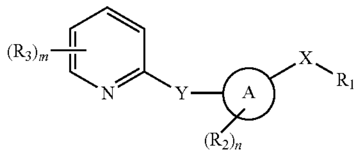

wherein A, X, Y $R_1$, $R_2$, $R_3$, $R_4$, m and n are as described herein.

93 Claims, No Drawings

(56) References Cited

FOREIGN PATENT DOCUMENTS

| | | | | |
|---|---|---|---|---|
| WO | WO 03/051876 | A1 | | 6/2003 |
| WO | WO 03/059258 | A2 | | 7/2003 |
| WO | WO 03/068747 | A1 | | 8/2003 |
| WO | WO 03/068773 | A1 | * | 8/2003 |
| WO | WO 2004/058176 | A2 | | 7/2004 |
| WO | WO 2004/058762 | A1 | | 7/2004 |
| WO | WO 2005/033288 | A2 | | 4/2005 |
| WO | WO 2005/040152 | A | | 5/2005 |
| WO | WO 2005/085227 | A1 | | 9/2005 |
| WO | WO 2006/028958 | | | 3/2006 |

OTHER PUBLICATIONS

I.M. Heilbron et al., "Arylpyridines. Part IV. 3- and 4-Pyridyldiphenyls," Journal of the Chemical Society, vol. 1940, 1940, pp. 1279-1284, XP001027791.

International Search Report dated Jan. 16, 2006 of International Application No. PCT/US2005/031284 filed Sep. 2, 2005.

Abramovitch, Rudolf A., et al., Journal of the Chemistry Society, Chemical Communications 3: 149-150 (1978).

Petrow, V.A. et al., Journal of the Chemical Society 84: 316-317 (1943).

Dilthey, W. et al., Journal Fuer Praktische Chemie (Leipzig) 111: 153-166 (1925).

Marsters, J., "Small Molecule Antagonists of the Hedgehog Pathway", Presentation Slides, Apr. 12-16, 2008, AACR National Meeting, 38 pages.

Yauch, Robert L., et al., "Smoothened Mutation Confers Resistence to a Hedgehog Pathway Inhibitor in Medulloblastoma," Sciencexpress / www.sciencexpress.org / (Sep. 3, 2009).

Kenkare-Mitra, Sara "Personalized Medicine—A perspective From Clinical Dx to Companion Dx," Development Sciences Genentech, Roche (Jan. 2009).

West, Anthony R., "Solid State Chemistry and its Applications," Wiley, New York, 1988, pp. 358-365.

International Search Report dated Oct. 22, 2009 of International Application No. PCT/US2009/040165 filed Apr. 10, 2009.

Robarge, K.D., et al., "GDC-0449—A Potent Inhibitor of the Hedgehog Pathway," Bioorganic & Medicinal Chemistry Letters 19 (2009) 5576-5581.

Marsters, J., "Small Molecule Antagonists of the Hedgehog Pathway," Presentation of AACR National Meeting, Apr. 12-16, 2008, 38 pages.

* cited by examiner

PYRIDYL INHIBITORS OF HEDGEHOG SIGNALLING

This application is a divisional of application Ser. No. 11/217,663, filed Sep. 2, 2005, now U.S. Pat. No. 7,888,364, which claims priority to provisional patent application 60/607,367 filed on 2 Sep. 2004.

FIELD OF THE INVENTION

The present invention relates to organic compounds useful for therapy and/or prophylaxis in a mammal, in particular to pyridyl compounds that inhibit the hedgehog signaling pathway and are useful in the treatment of hyperproliferative diseases and angiogenesis mediated diseases.

BACKGROUND OF THE INVENTION

Hedgehog (Hh) protein was first identified in *Drosophila melanogaster* as a segment-polarity gene involved in embryo patterning (Nusslein-Volhard et al., Roux. Arch. Dev. Biol. 193: 267-282 (1984)). Three orthologs of *Drosophila* hedgehog (Sonic, Desert and Indian) were later identified to occur in all vertebrates including fish, birds and mammals. Desert hedgehog (DHh) is expressed principally in the testes, both in mouse embryonic development and in the adult rodent and human; Indian hedgehog (IHh) is involved in bone development during embryogenesis and in bone formation in the adult; and, Sonic hedgehog (SHh) is expressed at high levels in the notochord and floor plate of developing vertebrate embryos. In vitro explant assays as well as ectopic expression of SHh in transgenic animals have shown that SHh plays a key role in neuronal tube patterning (Echelard et al., supra.; Ericson et al., Cell 81: 747-56 (1995); Marti et al., Nature 375: 322-5 (1995); Krauss et al., Cell 75, 1432-44 (1993); Riddle et al., Cell 75: 1401-16 (1993); Roelink et al, Cell 81:445-55 (1995); Hynes et al., Neuron 19: 15-26 (1997)). Hh also plays a role in the development of limbs (Krauss et al., Cell 75: 1431-44 (1993); Laufer et al., Cell 79, 993-1003 (1994)), somites (Fan and Tessier-Lavigne, Cell 79, 1175-86 (1994); Johnson et al., Cell 79: 1165-73 (1994)), lungs (Bellusci et al., Develop. 124: 53-63 (1997) and skin (Oro et al., Science 276: 817-21 (1997)). Likewise, IHh and DHh are involved in bone, gut and germinal cell development (Apelqvist et al., Curr. Biol. 7: 801-4 (1997); Bellusci et al., Dev. Suppl. 124: 53-63 (1997); Bitgood et al., Curr. Biol. 6: 298-304 (1996); Roberts et al., Development 121: 3163-74 (1995)).

Human SHh is synthesized as a 45 kDa precursor protein that upon autocatalytic cleavage yields a 20 kDa N-terminal fragment that is responsible for normal hedgehog signaling activity; and a 25 kDa C-terminal fragment that is responsible for autoprocessing activity in which the N-terminal fragment is conjugated to a cholesterol moiety (Lee, J. J., et al. (1994) Science 266, 1528-1536; Bumcrot, D. A., et al. (1995), Mol. Cell Biol. 15, 2294-2303; Porter, J. A., et al. (1995) Nature 374, 363-366). The N-terminal fragment consists of amino acid residues 24-197 of the full-length precursor sequence which remains membrane-associated through the cholesterol at its C-terminus (Porter, J. A., et al. (1996) Science 274, 255-258; Porter, J. A., et al. (1995) Cell 86, 21-34). Cholesterol conjugation is responsible for the tissue localization of the hedgehog signal.

At the cell surface, the Hh signal is thought to be relayed by the 12 transmembrane domain protein Patched (Ptc) (Hooper and Scott, Cell 59: 751-65 (1989); Nakano et al., Nature 341: 508-13 (1989)) and the G-protein-coupled-like receptor Smoothened (Smo) (Alcedo et al., Cell 86: 221-232 (1996); van den Heuvel and Ingham, Nature 382: 547-551 (1996)). Both genetic and biochemical evidence support a receptor model where Ptc and Smo are part of a multicomponent receptor complex (Chen and Struhl, Cell 87: 553-63 (1996); Marigo et al., Nature 384: 176-9 (1996); Stone et al., Nature 384: 129-34 (1996)). Upon binding of Hh to Ptc, the normal inhibitory effect of Ptc on Smo is relieved, allowing Smo to transduce the Hh signal across the plasma membrane. However, the exact mechanism by which Ptc controls Smo activity still has yet to be clarified.

The signaling cascade initiated by Smo results in activation of Gli transcription factors that translocate into the nucleus where they control transcription of target genes. Gli has been shown to influence transcription of Hh pathway inhibitors such as Ptc and Hip1 in a negative feedback loop indicating that tight control the Hh pathway activity is required for proper cellular differentiation and organ formation. Uncontrolled activation of Hh signaling pathway are associated with malignancies in particular those of the brain, skin and muscle as well as angiogenesis. An explanation for this is that Hh pathway has been shown to regulate cell proliferation in adults by activation of genes involved in cell cycle progression such as cyclin D which is involved in G1-S transition. Also, SHh blocks cell-cycle arrest mediated by p21, an inhibitor of cyclin dependent kinases. Hh signaling is further implicated in cancer by inducing components in the EGFR pathway (EGF, Her2) involved in proliferation as well as components in the PDGF (PDGFα) and VEGF pathways involved in angiogenesis. Loss of function mutations in the Ptc gene have been identified in patients with the basal cell nevus syndrome (BCNS), a hereditary disease characterized by multiple basal cell carcinomas (BCCs). Dysfunctional Ptc gene mutations have also been associated with a large percentage of sporadic basal cell carcinoma tumors (Chidambaram et al., Cancer Research 56: 4599-601 (1996); Gailani et al., Nature Genet. 14: 78-81 (1996); Hahn et al., Cell 85: 841-51 (1996); Johnson et al., Science 272: 1668-71 (1996); Unden et al., Cancer Res. 56: 4562-5; Wicking et al., Am. J. Hum. Genet. 60: 21-6 (1997)). Loss of Ptc function is thought to cause an uncontrolled Smo signaling in basal cell carcinoma. Similarly, activating Smo mutations have been identified in sporadic BCC tumors (Xie et al., Nature 391: 90-2 (1998)), emphasizing the role of Smo as the signaling subunit in the receptor complex for SHh.

Various inhibitors of hedgehog signaling have been investigated such as Cyclopamine, a natural alkaloid that has been shown to arrest cell cycle at G0-G1 and to induce apoptosis in SCLC. Cyclopamine is believed to inhibit Smo by binding to its heptahelical bundle. Forskolin has been shown to inhibit the Hh pathway downstream from Smo by activating protein kinase A (PKA) which maintains Gli transcription factors inactive. Despite advances with these and other compounds, there remains a need for potent inhibitors of the hedgehog signaling pathway.

SUMMARY OF THE INVENTION

In one aspect of the present invention there is provided novel hedgehog inhibitors having the general formula (I)

I

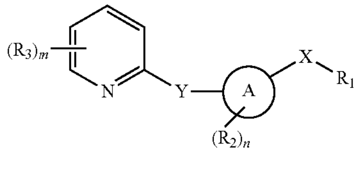

wherein

A is a carbocycle or heterocycle;

X is alkylene, $NR_4C(O)$, $NR_4C(S)$, $N(C(O)R_1)C(O)$, $NR_4SO$, $NR_4SO_2$, $NR_4C(O)NH$, $NR_4C(S)NH$, $C(O)NR_4$, $C(S)NR_4$, $NR_4PO$ or $NR_4PO(OH)$;

Y is absent, $CHR_4$, O, S, SO, $SO_2$ or $NR_4$;

$R_1$ is selected from the group consisting of alkyl, a carbocycle or a heterocycle each of which is optionally substituted with hydroxyl, halogen, amino, carbonyl, nitro, cyano, acyl, alkyl, haloalkyl, alkylsulfonyl, alkylsulfinyl, alkoxy, alkylcarbamoyl, alkanoylamine, alkylsulfamoyl, alkylsulfonamide, a carbocycle or a heterocycle; wherein said amino, alkyl, acyl, alkylsulfonyl, alkylsulfinyl, alkoxy, alkylcarbamoyl, alkanoylamine, alkylsulfamoyl, alkylsulfonamide, carbocycle and heterocycle substituent is optionally substituted with amino, halogen, hydroxyl, carbonyl, or a carbocycle or heterocycle that is optionally substituted with hydroxyl, amino, halogen, haloalkyl, alkyl, alkoxy or acyl;

$R_2$ is halogen, hydroxyl, alkyl, acyl or alkoxy each optionally substituted with hydroxyl, halogen, amino, nitro, alkyl, acyl, alkylsulfonyl or alkoxy;

$R_3$ is halogen, hydroxyl, carboxyl, alkyl, acyl, alkoxy, alkoxycarbonyl, carbamoyl, alkylsulfide, alkylsulfinyl, alkylsulfonyl, a carbocycle or a heterocycle wherein each alkyl, acyl, alkoxy, alkoxycarbonyl, carbamoyl, alkylsulfide, alkylsulfinyl, alkylsulfonyl, carbocycle and heterocycle is optionally substituted with hydroxyl, halogen, amino, nitro, alkyl, acyl, alkylsulfonyl or alkoxy;

$R_4$ is H or alkyl;

m is 0-3;

n is 0-3;

and salts and solvates thereof.

In another aspect of the invention, there are provided compositions comprising compounds of formula I and a carrier, diluent or excipient.

In another aspect of the invention, there is provided a method for treating cancer comprising administering an effective amount of a compound of formula I to a mammal in need thereof.

In another aspect of the invention, there is provided a method for inhibiting hedgehog signaling in a cell comprising contacting said cell with a compound of formula I.

In another aspect of the invention, there is provided a method for treating a disease or condition associated with the hedgehog signaling in a mammal, comprising administering to said mammal an effective amount of a compound of formula I.

In another aspect of the invention, there are provided processes for preparing compounds of the invention.

DETAILED DESCRIPTION OF THE PREFERRED EMBODIMENTS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion is preferably a saturated hydrocarbon chain, however also includes unsaturated hydrocarbon carbon chains such as "alkenylamino" and "alkynylamino. "Alkylphosphinate" means a —P(O)R-alkyl group wherein R is H, alkyl, carbocycle-alkyl or heterocycle-alkyl. Examples of preferred alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one (preferably), two, three or four substituents which may be the same or different. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding-ethyl, -propyl, -butyl, -pentyl, -hexyl groups, etc. Preferred substituted alkyls are substituted methyls e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" or "amidino" means the group —C(NH)—NRR wherein each R is independently H, OH, alkyl, alkoxy, a carbocycle, a heterocycle, a carbocycle-substituted alkyl or a heterocycle-substituted alkyl; or both R groups together form a heterocycle. A preferred amidine is the group —C(NH)—$NH_2$.

"Amino" denotes primary (i.e. —$NH_2$), secondary (i.e. —NRH) and tertiary (i.e. —NRR) amines wherein R is independently alkyl, a carbocycle (e.g. aryl), a heterocycle (e.g. heteroaryl), carbocycle-substituted alkyl (e.g. benzyl) or a heterocycle-substituted alkyl or alternatively two R groups together with the nitrogen atom from which they depend form a heterocycle. Particular secondary and tertiary amines are alkylamine, dialkylamine, arylamine, diarylamine, aralkylamine and diaralkylamine. Particular secondary and tertiary amines are methylamine, ethylamine, propylamine, isopropylamine, phenylamine, benzylamine dimethylamine, diethylamine, dipropylamine and diisopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Preferred amino protecting groups are Boc, Fmoc and Cbz. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Aryl groups include phenyl, naphthyl, biphenyl, phenanthrenyl, naphthacenyl, and the like (see e.g. *Lang's Handbook of Chemistry* (Dean, J. A., ed) $13^{th}$ ed. Table 7-2 [1985]). In a particular embodiment aryl may be phenyl. Substituted phenyl or substituted aryl denotes a phenyl group or aryl group substituted with one, two, three, four or five, such as 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or more methyne (CH) and/or methylene ($CH_2$) groups in these substituents may in turn be substituted with a similar group as those denoted above. Examples of the term "substituted phenyl" includes but is not limited to a mono- or di(halo) phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl) phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Substituted phenyl groups include 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any (for example 1, 2 or 3) of the substituents specified herein in the same manner as substituted alkyl groups.

"Carbamoyl" means an aminocarbonyl containing substituent represented by the formula —$C(O)N(R)_2$ in which R is H, hydroxyl, alkoxy, alkyl, a carbocycle, a heterocycle, carbocycle-substituted alkyl or alkoxy, or heterocycle-substituted alkyl or alkoxy wherein the alkyl, alkoxy, carbocycle and heterocycle are as herein defined. Carbamoyl groups include alkylaminoecarbonyl (e.g. ethylaminocarbonyl, Et-NH—CO—), arylaminocarbonyl (e.g. phenylaminocarbonyl), aralkylaminocarbonyl (e.g. benzoylaminocarbonyl) a heterocycleaminocarbonyl (e.g. piperizinylaminocarbonyl), and in particular a heteroarylaminocarbonyl (e.g. pyridylaminocarbonyl).

"Carbocyclyl", "carbocyclic", "carbocycle" and "carbocyclo" alone and when used as a moiety in a complex group such as a carbocycloalkyl group, refers to a mono-, bi-, or tricyclic aliphatic ring having 3 to 14 carbon atoms and preferably 3 to 7 carbon atoms which may be saturated or unsaturated, aromatic or non-aromatic. Preferred saturated carbocyclic groups include cyclopropyl, cyclobutyl, cyclopentyl and cyclohexyl groups and more preferred are cyclopropyl and cyclohexyl and most preferred is cyclohexyl. Preferred unsaturated carbocycles are aromatic e.g. aryl groups as previously defined, the most preferred being phenyl. The terms "substituted carbocyclyl", "substituted carbocycle" and "substituted carbocyclo" unless otherwise specified mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAlH_4$. (Such harsh removal conditions are also to be avoided when removing amino-protecting groups and hydroxy-protecting groups, discussed below.) Preferred carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" means the group —NH—C(NH)—NHR wherein R is H, alkyl, a carbocycle, a heterocycle, a carbocycle-substituted alkyl, or a heterocycle-substituted alkyl. A particular guanidine group is —NH—C(NH)—$NH_2$ "Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen) and preferably 1 to 4 heteroatoms. "Heterocyclosulfonyl" means a —$SO_2$-heterocycle group; "heterocyclosulfinyl" means a —SO-heterocycle group. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Preferred non-aromatic heterocycles include morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Preferred 5-membered heterocycles containing a sulfur or oxygen atom and one to three nitrogen atoms include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. Preferred 5-membered ring heterocycles containing 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl. Preferred benzo-fused 5-membered heterocycles are benzoxazol-2-yl, benzthiazol-2-yl and benzimidazol-2-yl. Preferred 6-membered heterocycles contain one to three nitrogen atoms and optionally a sulfur or oxygen atom, for example pyridyl, such as pyrid-2-yl, pyrid-3-yl, and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a preferred group. Substituents for optionally substituted heterocycles, and further examples of the 5- and 6-membered ring systems discussed above can be found in W. Druckheimer et al., U.S. Pat. No. 4,278,793.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and preferably at least one heteroatom is nitrogen (*Lang's Handbook of Chemistry*, supra). Included in the definition are any bicyclic groups where any of the above heteroaryl rings are fused to a benzene ring. Heteroaryls in which nitrogen or oxygen is the heteroatom are preferred. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particularly preferred group of "heteroaryl" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, TEA, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

"Phosphinate" means —P(O)R—OR wherein each R is independently H, alkyl, carbocycle, heterocycle, carbocycloalkyl or heterocycloalkyl. Particular phosphinate groups are alkylphosphinate (i.e. —P(O)R—O-alkyl), for example —P(O)Me-OEt.

"Sulfamoyl" means $—SO_2—N(R)_2$ wherein each R is independently H, alkyl, carbocycle, heterocycle, carbocycloalkyl or heterocycloalkyl. Particular sulfamoyl groups are alkylsulfamoyl, for example methylsulfamoyl ($—SO_2—$NHMe); arylsulfamoyl, for example phenylsulfamoyl; aralkylsulfamoyl, for example benzylsulfamoyl.

"Sulfinyl" means a —SO—R group wherein R is alkyl, carbocycle, heterocycle, carbocycloalkyl or heterocycloalkyl. Particular sulfinyl groups are alkylsulfinyl (i.e. —SO-alkyl), for example methylsulfinyl; arylsulfinyl (i.e. —SO-aryl) for example phenylsulfinyl; aralkylsulfinyl, for example benzylsulfinyl.

"Sulfonamide" means $—NR—SO_2—R$ wherein each R is independently H, alkyl, carbocycle, heterocycle, carbocycloalkyl or heterocycloalkyl), a carbocycle or a heterocycle. Particular sulfonamide groups are alkylsulfonamide (e.g. $—NH—SO_2$-alkyl), for example methylsulfonamide; arylsulfonamdie (i.e. $—NH—SO_2$-aryl) for example phenylsulfonamide; aralkylsulfonamide, for example benzylsulfonamide.

"Sulfonyl" means a $—SO_2—R$ group wherein R is alkyl, carbocycle, heterocycle, carbocycloalkyl or heterocycloalkyl. Particular sulfonyl groups are alkylsulfonyl (i.e. $—SO_2$-alkyl), for example methylsulfonyl; arylsulfonyl, for example phenylsulfonyl; aralkylsulfonyl, for example benzylsulfonyl.

The phrase "and salts and solvates thereof" as used herein means that compounds of the inventions may exist in one or a mixture of salts and solvate forms. For example a compound of the invention may be substantially pure in one particular salt or solvate form or else may be mixtures of two or more salt or solvate forms.

The present invention provides novel compounds having the general formula I:

I

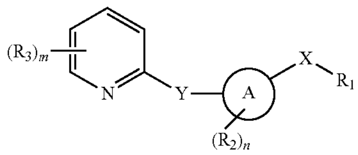

wherein A, X, Y, $R_1$, $R_2$, and $R_3$ are as defined herein.

A is a carbocycle or heterocycle ring substituted with 0 to 3 (e.g. n is 0-3) $R_2$ groups selected from the group consisting of halogen, hydroxyl, alkyl, acyl or alkoxy each optionally substituted with hydroxyl, halogen, amino, nitro, alkyl, acyl, alkylsulfonyl or alkoxy. In a particular embodiment, A is optionally substituted aryl or heteroaryl. In particular embodiment A is optionally substituted benzene, thiophene, thiazole, imidazole, pyrrole, N-alkyl pyrrole, pyridine, pyrazole or N-alkyl pyrazole. In a particular embodiment A is a ring selected from the group consisting of $A^1$, $A^2$, $A^3$, $A^4$ $A^5$, $A^6$ and $A^7$:

$A^1$

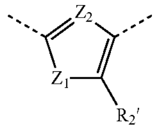

$A^2$

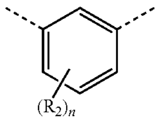

$A^3$

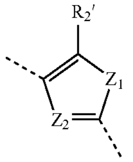

$A^4$

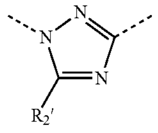

$A^5$

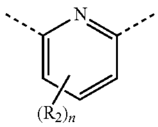

-continued

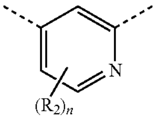

$A^6$

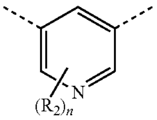

$A^7$ wherein $Z_1$ is O, S or $NR_5$ wherein $R_5$ is H or alkyl; $Z_2$ is CH, $CR_2$ or N; $R_2$ is halogen, hydroxyl, alkyl, acyl or alkoxy each optionally substituted with hydroxyl, halogen, amino, nitro, alkyl, acyl, alkylsulfonyl or alkoxy; $R_{2'}$ is H, halogen, hydroxyl, alkyl, acyl or alkoxy each optionally substituted with hydroxyl, halogen, amino, nitro, alkyl, acyl, alkylsulfonyl or alkoxy; and n is 0-3. In a particular embodiment A is the ring of formula $A^1$. In a particular embodiment, A is the ring of formula $A^1$ wherein $Z_1$ is S and $Z_2$ is CH or N. In another embodiment, A is the ring of formula $A^1$ wherein $Z_1$ is S and $Z_2$ is CH, i.e. thiophene. In another embodiment, A is the ring of formula $A^1$ wherein $Z_1$ is S and $Z_2$ is N, i.e. thiazole. In another embodiment, A is the ring of formula $A^1$ wherein $R_{2'}$ is H. In embodiment, A is the ring of formula $A^1$ wherein $R_{2'}$ is methyl. In another embodiment, A is the ring $A^1$ wherein $R_{2'}$ is methyl. In a particular embodiment A is ring $A^2$. In another embodiment, A is the ring of formula $A^1$ wherein $R_2$ may be absent, i.e. n is 0. In another embodiment, n is 1 and $R_2$ is Cl. In another particular embodiment A is the ring of formula $A^3$. In an embodiment, A is a ring of formula $A^3$ wherein $Z_1$ is S and $Z_2$ is N, i.e. a thiazole. In another embodiment, A is a ring of formula $A^3$ wherein $Z_1$ is S, $Z_2$ is N and $R_{2'}$ is Cl. In another embodiment, A is a ring of formula $A^3$ wherein $Z_1$ is S, $Z_2$ is CH (i.e. thiophene) and $R_{2'}$ is Cl.

In a particular embodiment A is the ring $A^{1a}$, $A^{1b}$, $A^{2a}$, $A^{3a}$, $A^{3b}$, $A^{4a}$, $A^{5a}$, $A^{6a}$, $A^{7a}$:

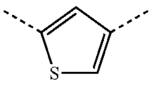

$A^{1a}$

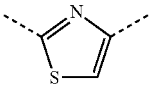

$A^{1b}$

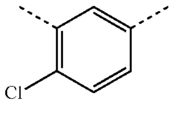

$A^{2a}$

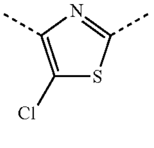

$A^{3a}$

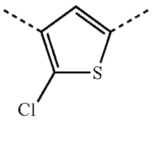

$A^{3b}$

-continued

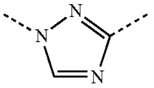

$A^{4a}$

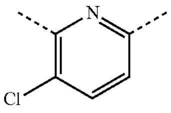

$A^{5a}$

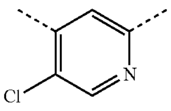

$A^{6a}$

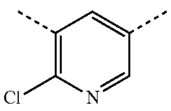

$A^{7a}$

In a particular embodiment A is the ring of formula $A^{1a}$. In another embodiment A is the ring of formula $A^{1b}$. In another embodiment A is the ring of formula $A^{2a}$. In another embodiment A is the ring of formula $A^{3a}$. In another embodiment A is the ring of formula $A^{3b}$. In another embodiment A is the ring of formula $A^{4a}$.

X is alkylene, $NR_4C(O)$, $NR_4C(S)$, $N(C(O)R_1)C(O)$, $NR_4SO$, $NR_4SO_2$, $NR_4C(O)NH$, $NR_4C(S)NH$, $C(O)NR_4$, $C(S)NR_4$, $NR_4PO$ or $NR_4PO(OH)$ wherein $R_4$ is H or alkyl. In a particular embodiment X is $NR_4C(O)$ which forms an amide linkage between ring A and $R_1$. In another embodiment, X is $N_4C(S)$, which forms a thioamide linkage between ring A and $R_1$. In another embodiment, X is $NR_4C(O)NH$ which forms a urea linkage between ring A and $R_1$. In another embodiment X is $NR_4C(S)NH$ which with $NR_2$ forms a thiourea linkage between ring A and $R_1$. In another embodiment X is $N(C(O)R_1)C(O)$ i.e. a nitrogen with two —$C(O)R_1$ groups pending therefrom.

Y is absent, $CHR_4$, O, S, SO, $SO_2$ or $NR_4$ wherein $R_4$ is as defined herein. In a particular embodiment Y is $CHR_4$. In a particular embodiment Y is $NR_4$. In a particular embodiment Y is O. In a particular embodiment Y is S. In a particular embodiment Y is SO. In a particular embodiment Y is $SO_2$. In another embodiment Y is absent i.e. ring A is directly attached to the pyridyl ring at the 2-position.

$R_1$ is selected from the group consisting of alkyl, a carbocycle or a heterocycle each of which is optionally substituted with hydroxyl, halogen, amino, carboxyl, amidino, guanidino, carbonyl (i.e. =O), nitro, cyano, acyl, alkyl, haloalkyl, sulfonyl, sulfinyl, alkoxy, alkylthio, carbamoyl, acylamino, sulfamoyl, sulfonamide, a carbocycle or a heterocycle; wherein said amino, amidino, alkyl, acyl, sulfonyl, sulfinyl, alkoxy, alkylthio, carbamoyl, acylamino, sulfamoyl, sulfonamide, carbocycle and heterocycle substituent is optionally substituted with, halogen, haloakyl, hydroxyl, carboxyl, carbonyl, or an amino, alkyl, alkoxy, acyl, sulfonyl, sulfinyl, phosphinate, carbocycle or heterocycle that is optionally substituted with hydroxyl, carboxyl, carbonyl, amino, halogen, haloalkyl, alkyl, alkoxy, alkylthio, sulfonyl, sulfinyl, acyl, a carbocycle or a heterocycle.

In another embodiment $R_1$ is selected from the group consisting of alkyl, a carbocycle or a heterocycle each of which is optionally substituted with hydroxyl, halogen, amino, carbonyl, nitro, cyano, acyl, alkyl, haloalkyl, alkylsulfonyl, alkylsulfinyl, alkoxy, alkylcarbamoyl (i.e. —CONR-alkyl wherein R is H or alkyl), alkanoylamine (i.e. —NRCO-alkyl wherein R is H or alkyl), alkylsulfamoyl (i.e. —$SO_2$NR-alkyl wherein R is H or alkyl), alkylsulfonamide (i.e. —NR—$SO_2$-alkyl wherein R is H or alkyl), a carbocycle or a heterocycle; wherein said amino, alkyl, acyl, alkylsulfonyl, alkylsulfinyl, alkoxy, alkylcarbamoyl, alkanoylamine, alkylsulfamoyl, alkylsulfonamide, carbocycle and heterocycle substituent is optionally substituted with amino, halogen, hydroxyl, carbonyl, or a carbocycle or heterocycle that is optionally substituted with hydroxyl, amino, halogen, haloalkyl, alkyl, alkoxy or acyl.

In a particular embodiment $R_1$ is an optionally substituted aryl or heteroaryl. In a particular embodiment $R_1$ is an optionally substituted phenyl group. In another particular embodiment $R_1$ is an optionally substituted pyridine group. In a particular embodiment $R_1$ is of formula IIa, IIb, IIc, IId, IIe, IIf, IIg, IIh, IIi, IIj, IIk, IIl, IIm, IIn or IIo:

IIa

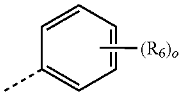

IIb

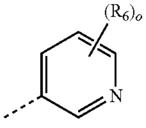

IIc

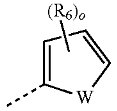

IId

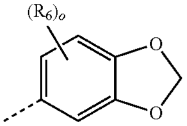

IIe

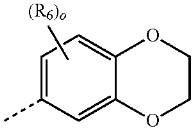

IIf

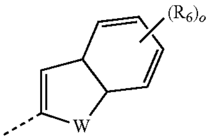

IIg

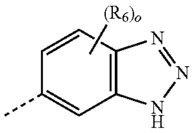

IIh

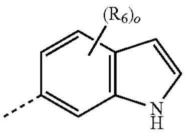

-continued

IIi

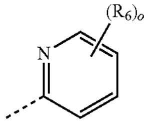

IIj

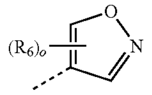

IIk

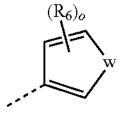

IIl

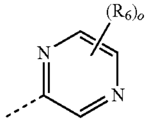

IIm

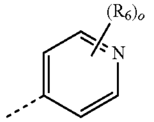

IIn

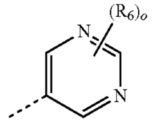

IIo

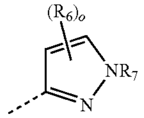

wherein W is O, S or $NR_7$ wherein $R_7$ is H, alkyl, acyl, a carbocycle or a heterocycle wherein said alkyl, acyl, carbocycle and heterocycle are each optionally substituted with 1-3 amino, halogen, hydroxyl and haloalkyl; o is 0-3. In a particular embodiment W is S.

$R_6$ in each instance is independently hydroxyl, halogen, amino, carboxyl, amidino, guanidino, carbonyl, nitro, cyano, acyl, alkyl, haloalkyl, sulfonyl, sulfinyl, alkoxy, alkylthio, carbamoyl, acylamino, sulfamoyl, sulfonamide, a carbocycle or a heterocycle; wherein said amino, amidino, alkyl, acyl, sulfonyl, sulfinyl, alkoxy, alkylthio, carbamoyl, acylamino, sulfamoyl, sulfonamide, carbocycle and heterocycle substituent is optionally substituted with, halogen, haloakyl, hydroxyl, carboxyl, carbonyl, or an amino, alkyl, alkoxy, acyl, sulfonyl, sulfinyl, phosphinate, carbocycle or heterocycle that is optionally substituted with hydroxyl, carboxyl, carbonyl, amino, halogen, haloalkyl, alkyl, alkoxy, alkylthio, sulfonyl, sulfinyl, acyl, a carbocycle or a heterocycle.

In a particular embodiment $R_6$ in each instance is independently hydroxyl, halogen, amino, carbonyl, nitro, cyano, acyl, alkyl, sulfonyl, alkylsulfonyl, alkylsulfinyl, alkoxy, alkylcarbamoyl, alkanoylamine, alkylsulfamoyl, alkylsulfonamide, a carbocycle or a heterocycle; wherein said amino, alkyl, carbonyl, acyl, sulfonyl, alkylsulfonyl, alkylsulfinyl, alkoxy, alkylcarbamoyl, alkanoylamine, alkylsulfamoyl, alkylsulfonamide, carbocycle and heterocycle substituent is optionally substituted with amino, halogen, hydroxyl, carbonyl, or a carbocycle or heterocycle that is optionally substituted with hydroxyl, amino, halogen, haloalkyl, alkyl, alkoxy or acyl.

In a particular embodiment $R_6$ is independently in each instance optionally substituted alkyl (e.g. methyl, trifluoromethyl, dimethylaminomethyl, piperidinylmethyl, morpholinomethyl, thiomorpholinomethyl); halogen (e.g. chloro); alkoxy (e.g. methoxy); carbonyl (e.g. morpholinocarbonyl, acetyl); a heterocycle (e.g. morpholino, N-methyl-piperazin-4-yl, N-acetyl-piperazin-4-yl, 1H-1,2,4-triazole); alkylamino (e.g. i-butylamino, benzylamino, hydroxyethylamino, methoxyethylamino, dimethylaminoethylamino, morpholinoethylamino, morpholinopropylamino, pyrrolidin-2-one-substituted propylamino, imidazole-ethylamino, imidazole-propylamino); arylamino (e.g. phenylamino); alkylcarbamoyl (e.g. dimethylcarbamoyl, i-butylaminocarbonyl); alkylsulfamoyl (e.g. propylaminosulfonyl, i-butylaminosulfonyl, dimethylaminosulfonyl, dimethylaminoethyl hydroxyethylaminosulfonyl, methoxyethylaminosulfonyl, methoxypropylaminosulfonyl, methylsulfonylethylaminosulfonyl, imidazole-substituted propylaminosulfonyl, hydroxypropylaminosulfonyl, 2-hydroxypropylaminosulfonyl); or sulfonyl (e.g. methylsulfonyl, ethylsulfonyl, aminosulfonyl, dimethylaminopropylsulfonyl, N-methyl-piperazin-4-yl-sulfonyl, morpholino-4-yl-sulfonyl, trifluoromethylsulfonyl).

In a particular embodiment $R_7$ is H. In another particular embodiment $R_7$ is optionally substituted acyl. In another particular embodiment $R_7$ is optionally substituted alkyl (e.g. methyl). In another particular embodiment $R_7$ is optionally substituted acyl (e.g. acetyl, benzoyl). In another particular embodiment $R_7$ is an optionally substituted aryl group (e.g. phenyl, benzyl).

In a particular embodiment $R_1$ is the group of formula IIa. In such embodiment $R_6$ may be alkoxy and o is 1, 2 or 3. Particular IIa groups are $IIa^1$-$IIa^{28}$:

$IIa^1$

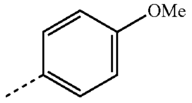

$IIa^2$

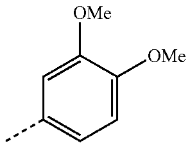

$IIa^3$

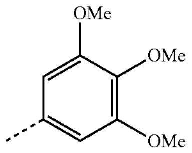

$IIa^4$

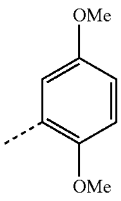

-continued $IIa^5$

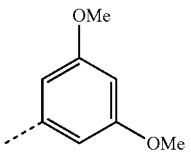

$IIa^6$

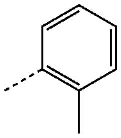

$IIa^7$

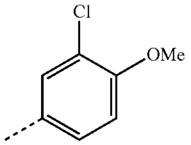

$IIa^8$

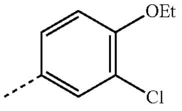

$IIa^9$

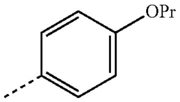

$IIa^{10}$

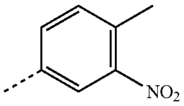

$IIa^{11}$

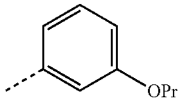

$IIa^{12}$

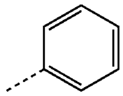

$IIa^{13}$

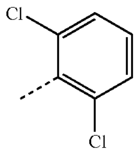

$IIa^{14}$

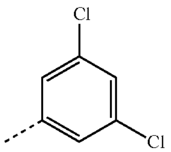

$IIa^{15}$

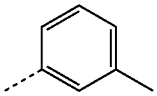

-continued $IIa^{16}$

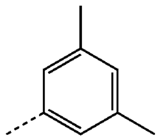

$IIa^{17}$

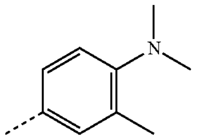

$IIa^{18}$

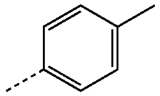

$IIa^{19}$

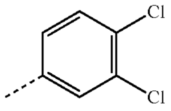

$IIa^{20}$

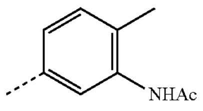

$IIa^{21}$

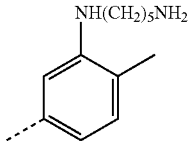

$IIa^{22}$

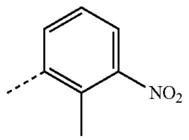

$IIa^{23}$

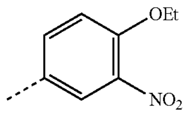

$IIa^{24}$

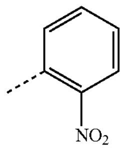

$IIa^{25}$

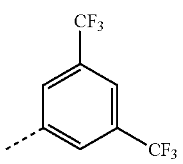

$IIa^{26}$

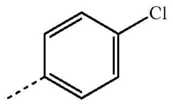

-continued $IIa^{27}$

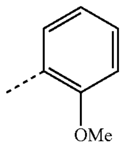

$IIa^{28}$

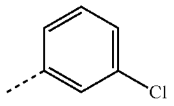

In another particular embodiment $R_1$ is the group of formula IIb. In such embodiment $R_6$ may be alkyl or haloalkyl (e.g. $CF_3$). Particular IIb groups are $IIb^1$-$IIb^3$:

$IIb^1$

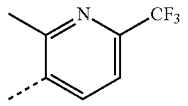

$IIb^2$

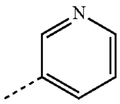

$IIb^3$

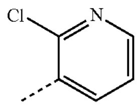

In a particular embodiment $R_1$ is the group of formula IIc. In such embodiment W may be S and o is 0. In another particular embodiment $R_1$ is the group of formula IId. In such embodiment o may be 0. In another particular embodiment $R_1$ is the group of formula IIe. In such embodiment o may be 0. In another particular embodiment $R_1$ is the group of formula IIf. In such embodiment o may be 0.

In another particular embodiment $R_1$ is the group of formula IIn. In such embodiment o may be 0 or 2 and $R_6$ may be alkyl or aryl. In a particular embodiment, group IIn has the formula $IIn^1$:

$IIn^1$

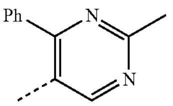

In another particular embodiment $R_1$ is the group of formula IIo. In such embodiment o may be 0 or 2 and $R_6$ may be alkyl or aryl. In a particular embodiment, group IIo has the formula $IIo^1$:

$IIo^1$

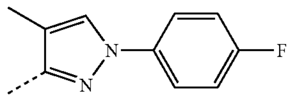

$R_2$ is halogen, hydroxyl, alkyl, acyl or alkoxy each optionally substituted with hydroxyl, halogen, amino, nitro, alkyl, acyl, alkylsulfonyl or alkoxy. n is 0-3, for example 0 or 1. In a particular embodiment $R_2$ is hydroxyl. In a particular embodiment $R_2$ is alkyl or alkyl substituted with halogen, methyl or trifluoromethyl. In a particular embodiment $R_2$ is acyl, for example alkanoyl e.g. acetyl. In a particular embodiment $R_2$ is halogen, for example Cl or F. In another particular embodiment $R_2$ is alkoxy, for example methoxy or ethoxy.

$R_3$ is halogen, hydroxyl, carboxyl, alkyl, acyl, alkoxy, alkoxycarbonyl, carbamoyl, alkylsulfide, sulfinyl, sulfonyl, a carbocycle or a heterocycle wherein each alkyl, acyl, alkoxy, alkoxycarbonyl, carbamoyl, alkylsulfide, sulfinyl, sulfonyl, carbocycle and heterocycle is optionally substituted with hydroxyl, halogen, amino, nitro, alkyl, acyl, sulfonyl or alkoxy. In a particular embodiment $R_3$ is halogen, hydroxyl, carboxyl, alkyl, acyl, alkoxy, alkoxycarbonyl, carbamoyl, alkylsulfide, alkylsulfinyl, alkylsulfonyl, a carbocycle or a heterocycle wherein each alkyl, acyl, alkoxy, alkoxycarbonyl, carbamoyl, alkylsulfide, alkylsulfinyl, alkylsulfonyl, carbocycle and heterocycle is optionally substituted with hydroxyl, halogen, amino, nitro, alkyl, acyl, alkylsulfonyl or alkoxy; while m is 0 to 3. In a particular embodiment, $R_3$ is halogen (e.g. F), carboxyl, or optionally substituted alkyl (e.g. methyl, hydroxymethyl, dimethylaminomethyl), alkoxycarbonyl (e.g. methoxycarbonyl) or carbamoyl (e.g. dimethylaminocarbonyl). In a particular embodiment m is 0, i.e. $R_3$ is absent. In another particular embodiment m is 1-3.

In a particular embodiment, compounds of the invention are represented by the general formula Ib:

Ib

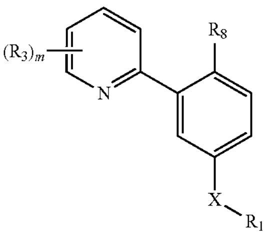

wherein X, $R_1$, $R_3$ and m are as defined herein and $R_8$ is halogen. In an embodiment, compounds of the invention have the general formula Ib and X is $NR_4CO$. In further embodiment, compounds are of formula Ib and $R_3$ is H or methyl.

In another particular embodiment, compounds of the invention are represented by the general formula Ib':

Ib'

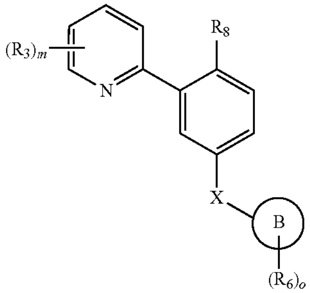

wherein X, $R_3$, $R_6$, m and o are as defined herein; $R_8$ is a halogen; and ring B is a carbocycle or heterocycle. In a particular embodiment $R_8$ is Cl. In a particular embodiment ring B is phenyl or pyridyl. In a particular embodiment X is $NR_4C(O)$ and $R_4$ is as defined herein.

In another particular embodiment, compounds of the invention have the general formula Ic:

Ic

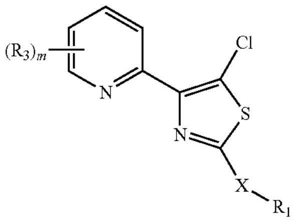

wherein X, $R_1$, $R_3$ and m are as defined herein. In an embodiment, compounds of the invention have the general formula Ib and X is $NR_4CO$. In a further embodiment, compounds are of formula Ic and $R_3$ is H or methyl and m is 0 or 1.

In another particular embodiment, compounds of the invention have the general formula Id:

Id

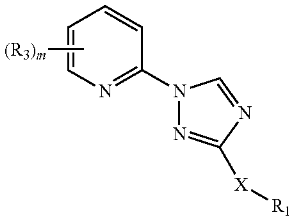

wherein X, $R_1$, $R_3$ and m are as defined herein. In an embodiment, compounds of the invention have the general formula Ib and X is $NR_4CO$. In a further embodiment, compounds are of formula Id and $R_3$ is H, Cl or trifluoromethyl and m is 0 or 1.

Particular compounds of the invention include, but are not limited to the following:

1

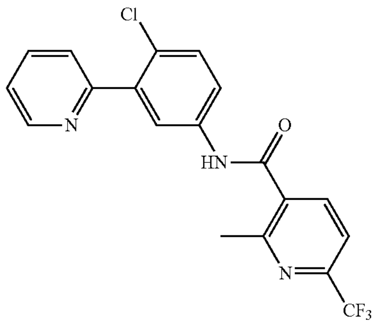

-continued
2
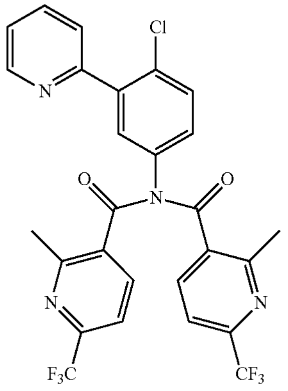
3
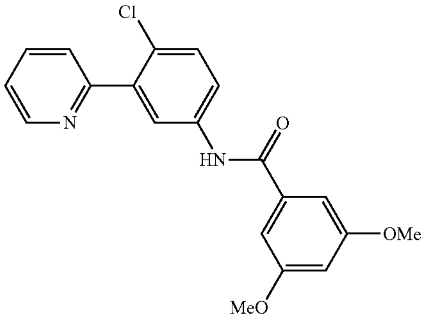
4
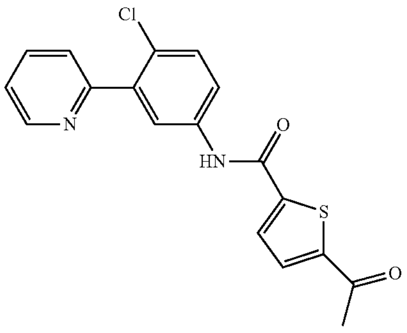
5
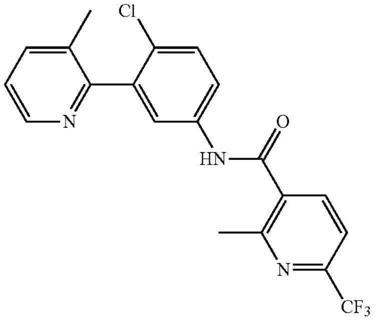
-continued
6
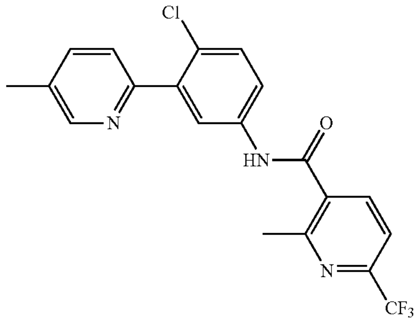
7
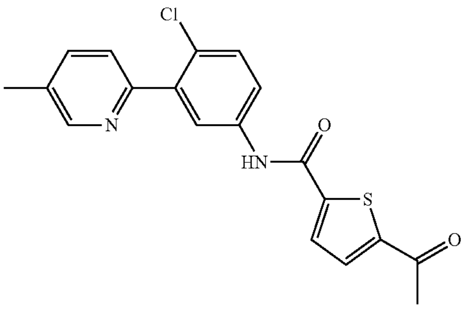
8
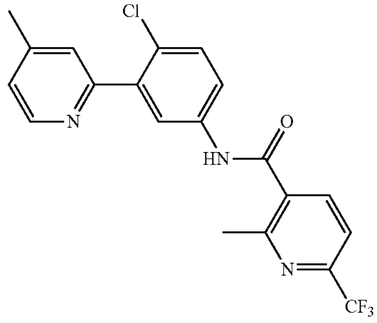
9
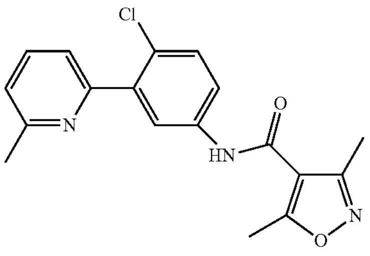
10
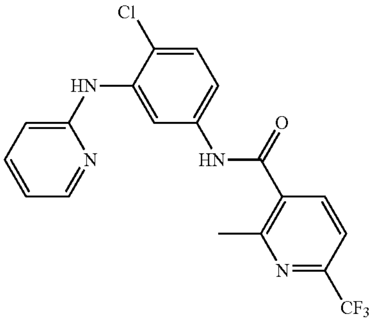

-continued
11
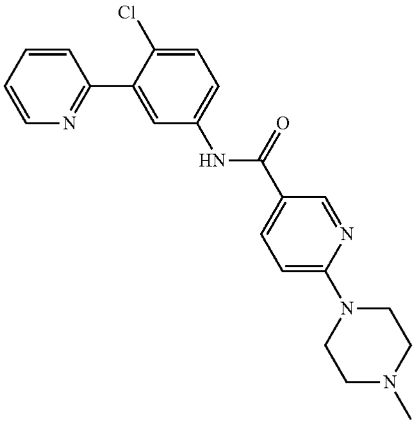
12
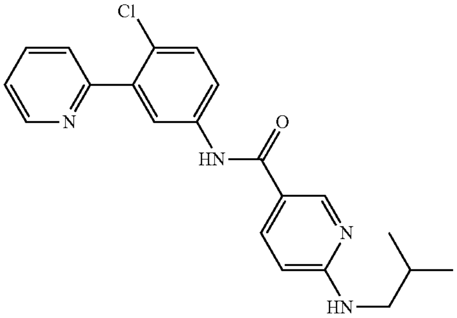
13
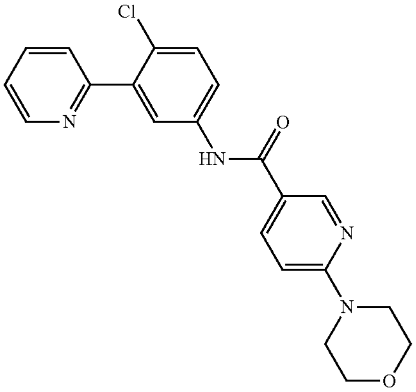
14
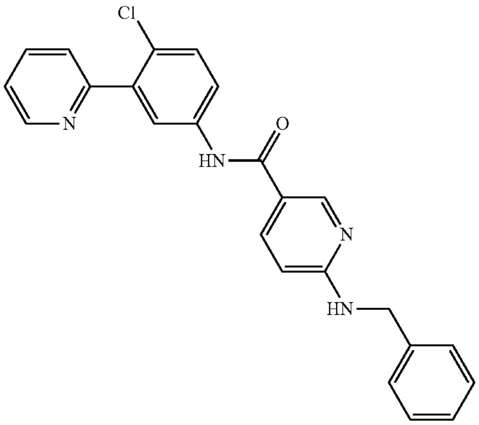
-continued
15
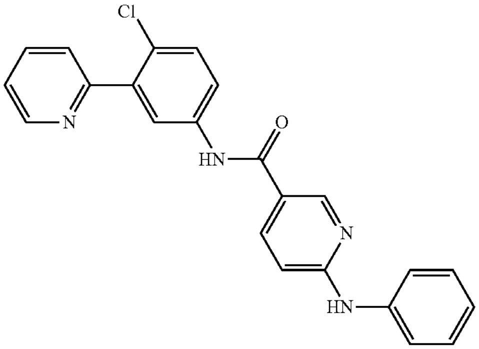
16
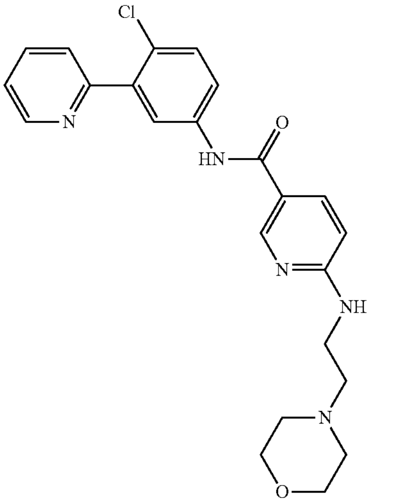
17
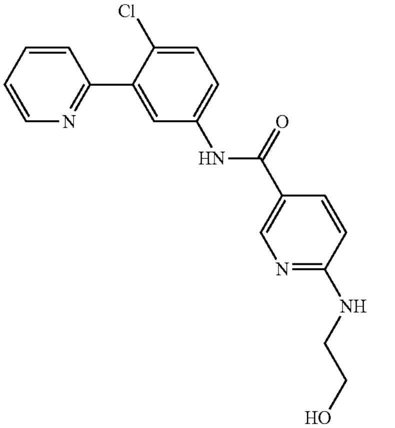
18
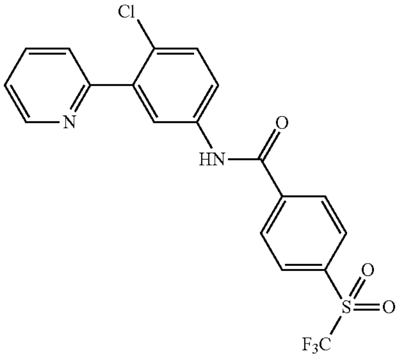

-continued
19
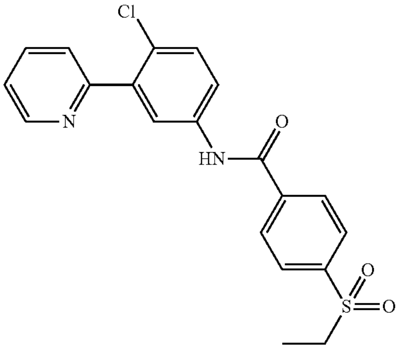
20
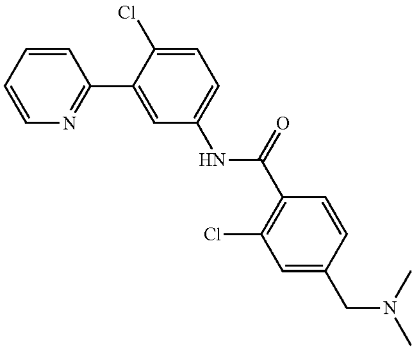
21
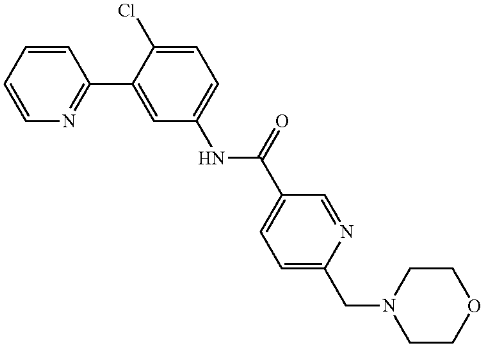
22
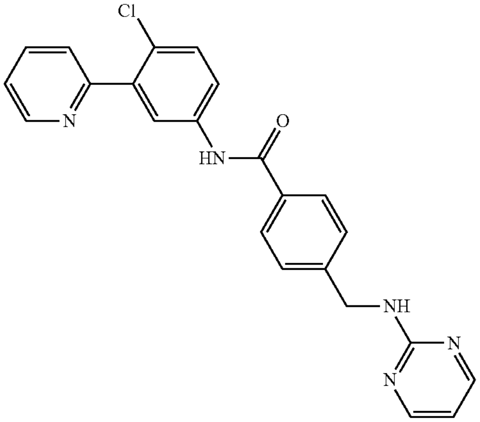
-continued
23
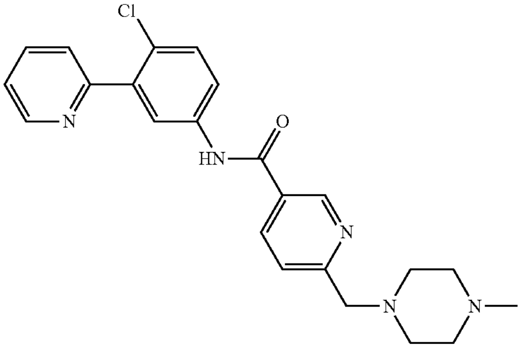
24
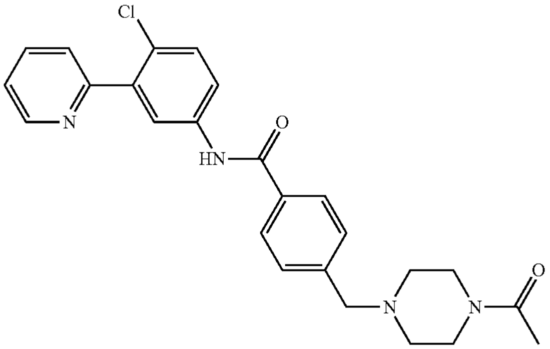
25
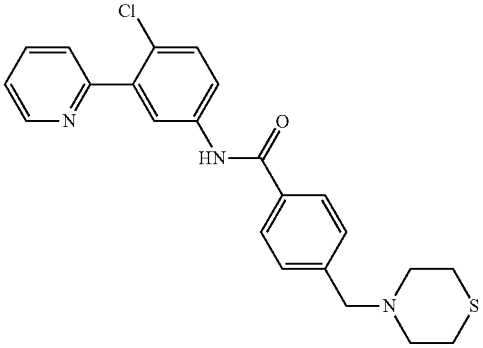
26
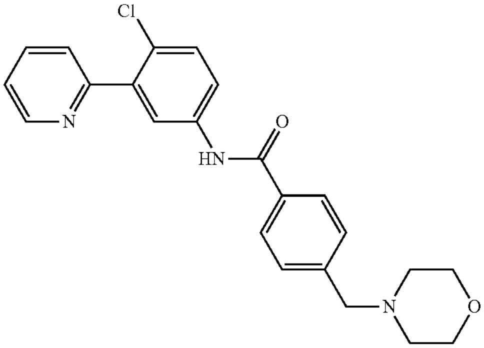

-continued
27
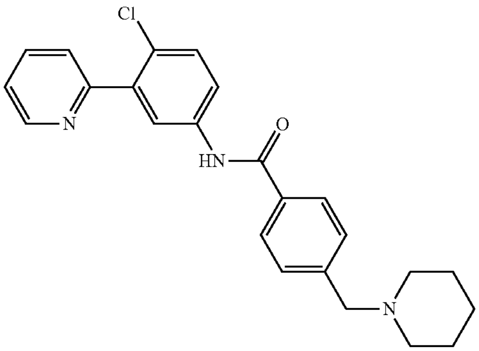
28
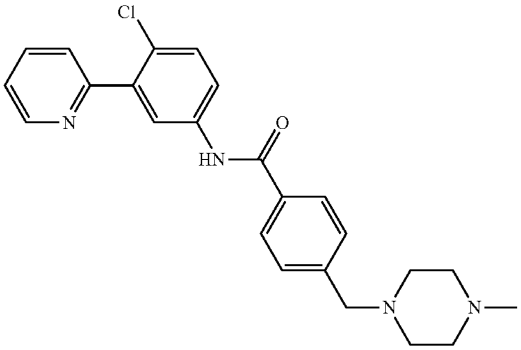
29
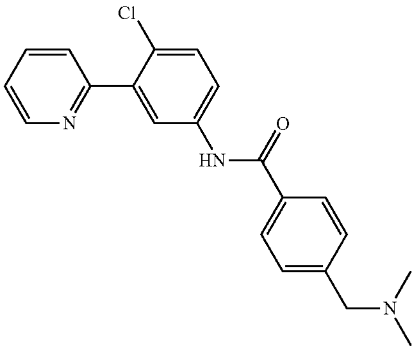
30
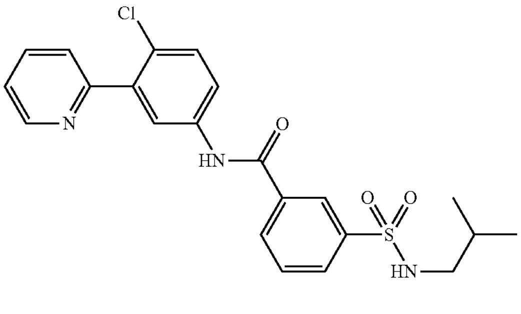
-continued
31
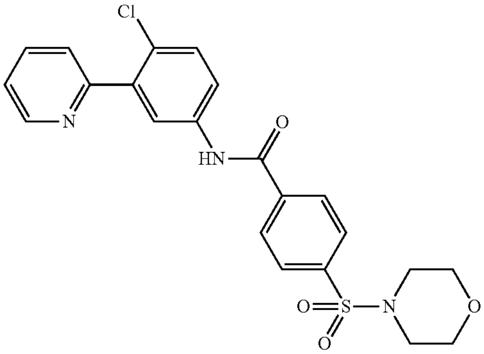
32
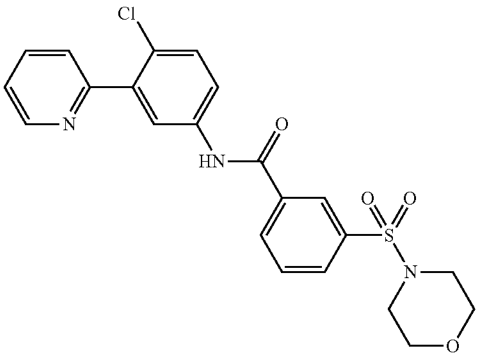
33
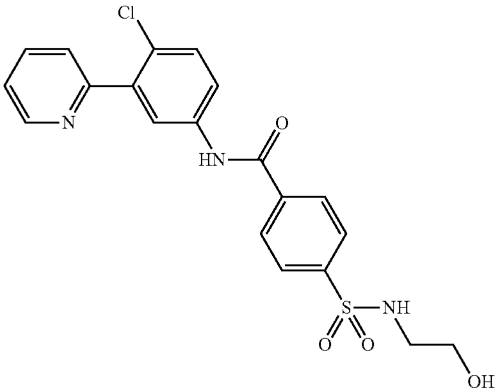
34
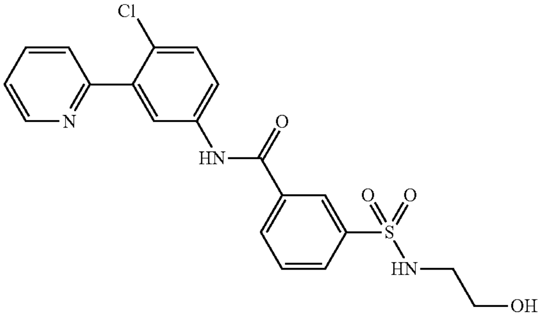

-continued
35
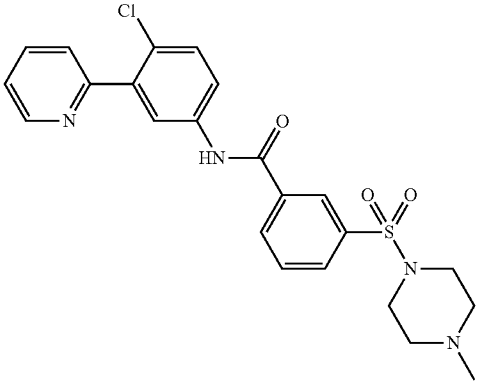
36
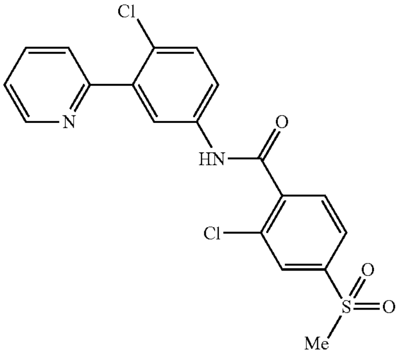
37
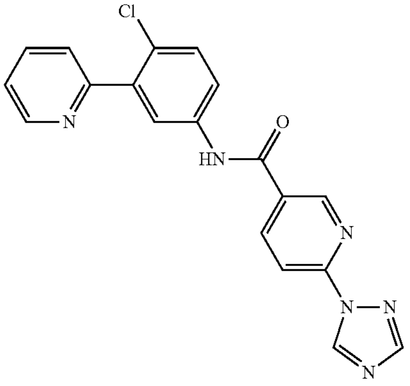
38
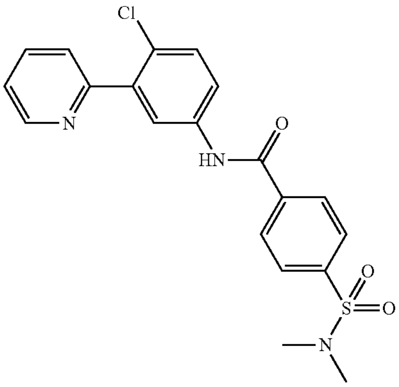
-continued
39
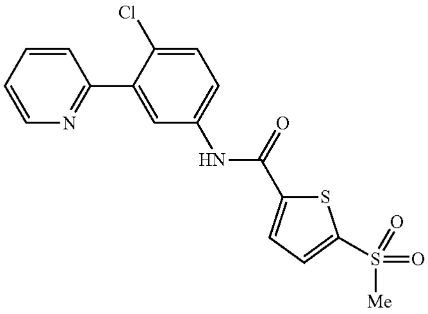
40
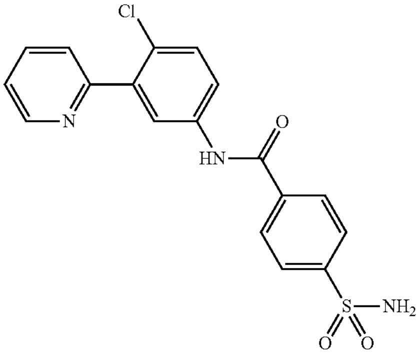
41
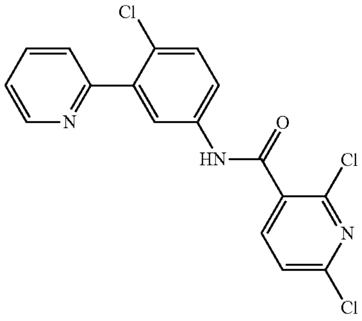
42
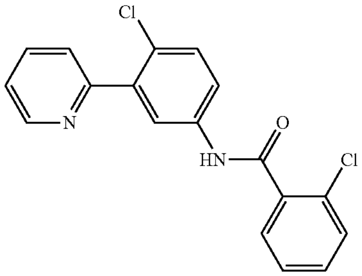
43
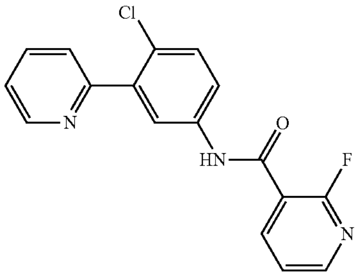

-continued
44
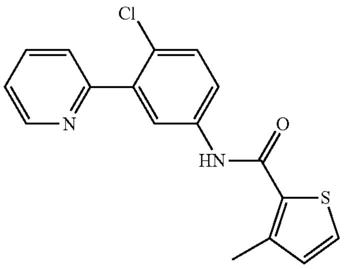
45
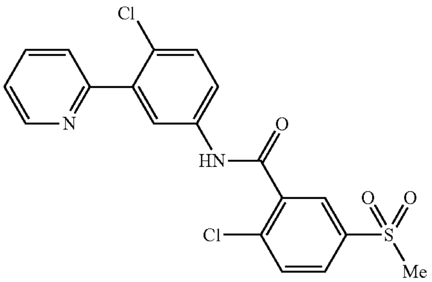
46
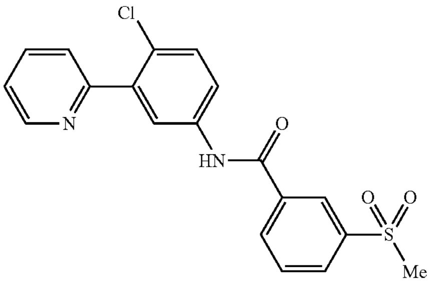
47
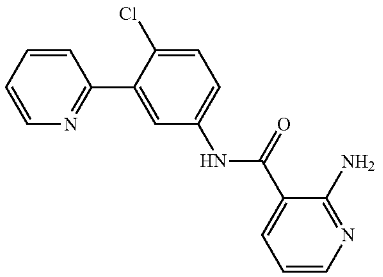
48
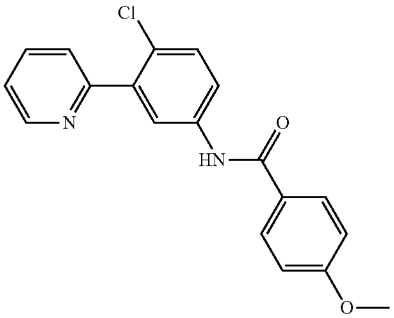
-continued
49
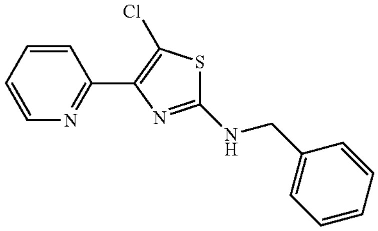
50
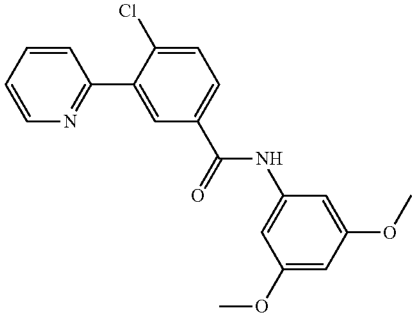
51
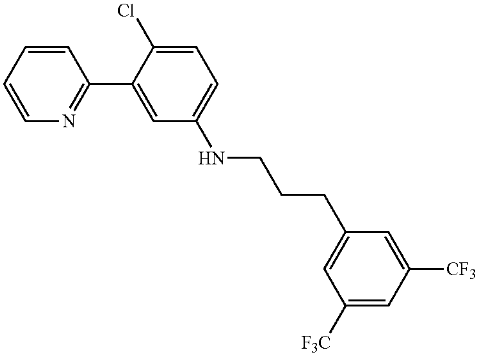
52
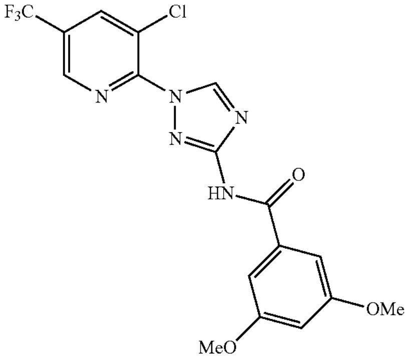
53
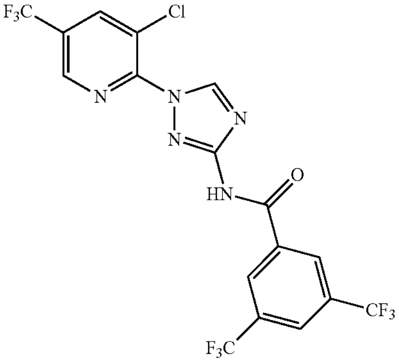

-continued
54
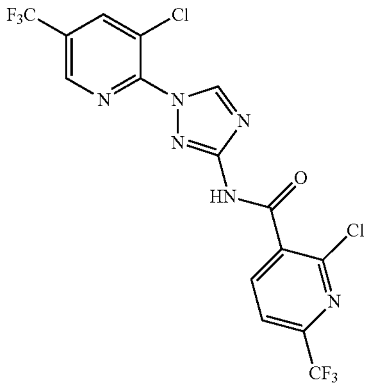
55
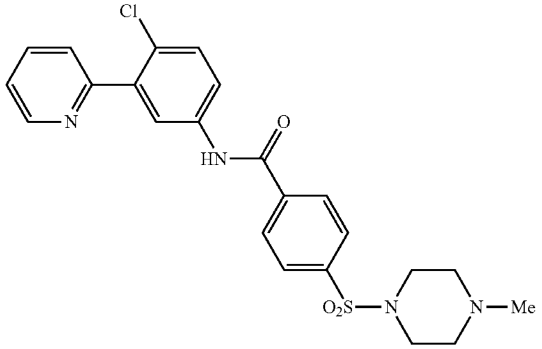
56
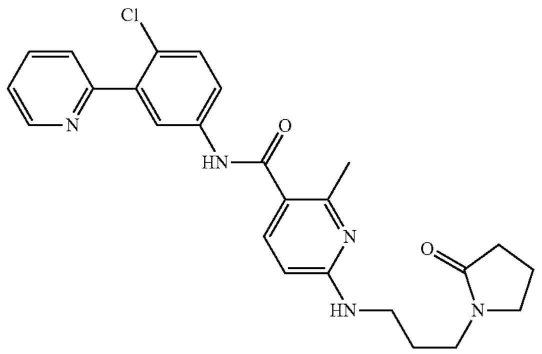
57
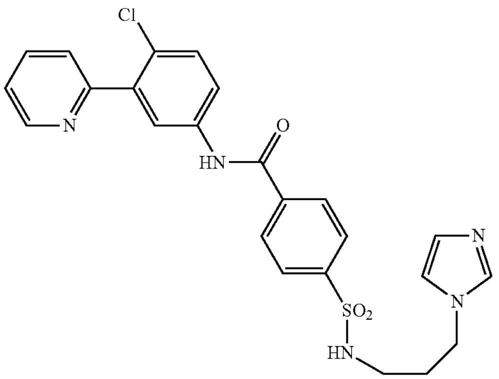
-continued
58
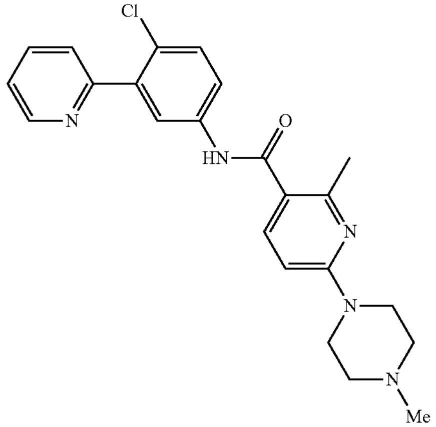
59
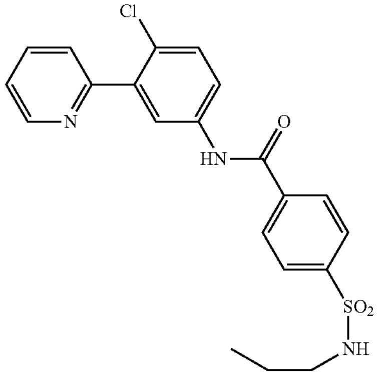
60
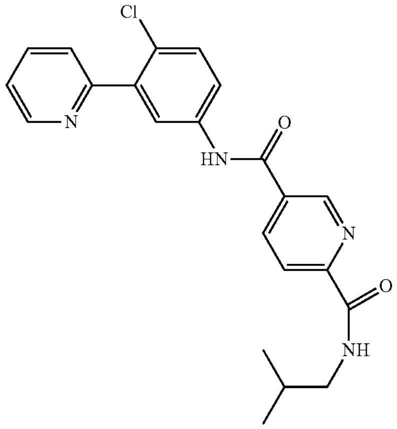
61
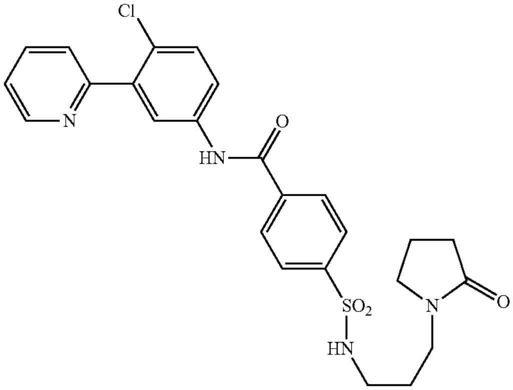

-continued
62
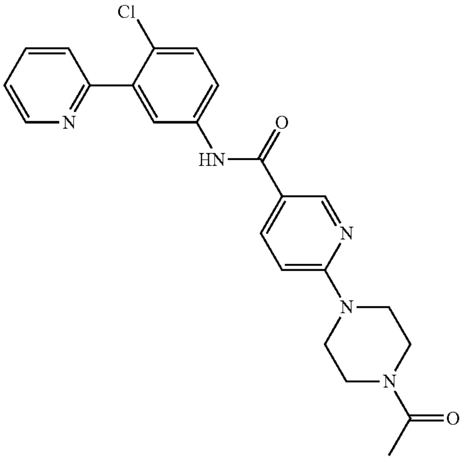
63
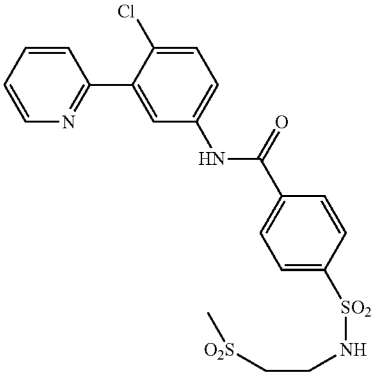
64
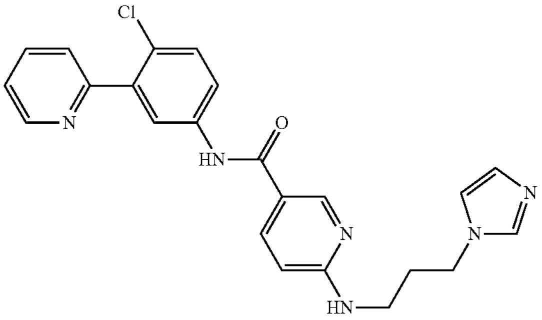
65
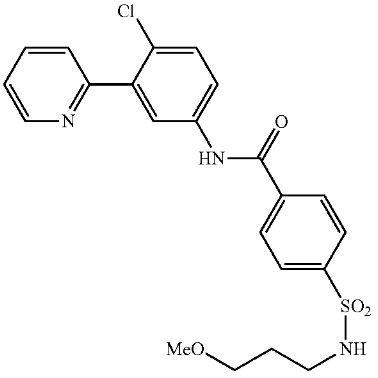
-continued
66
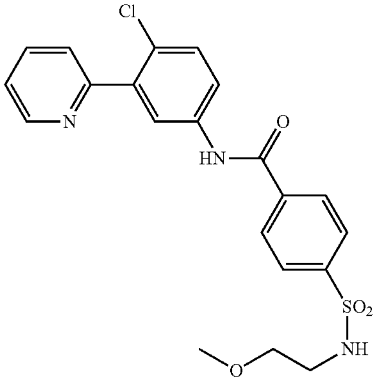
67
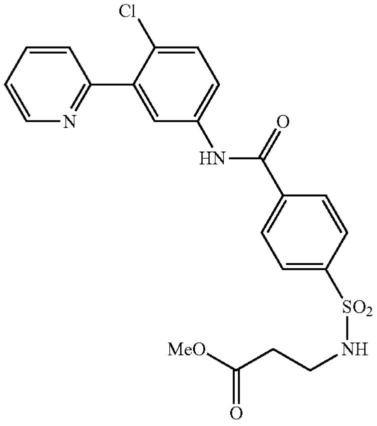
68
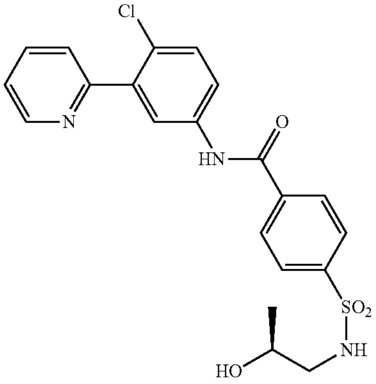
69
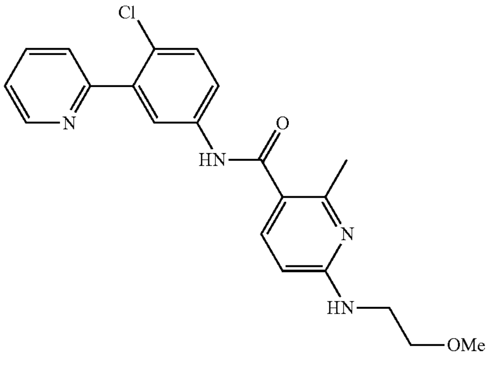

-continued
70
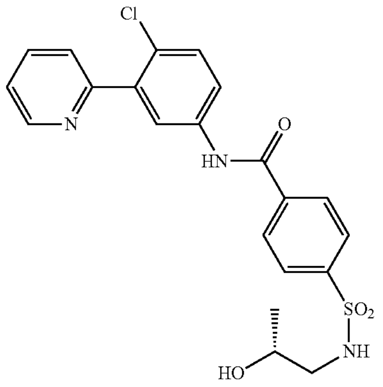
71
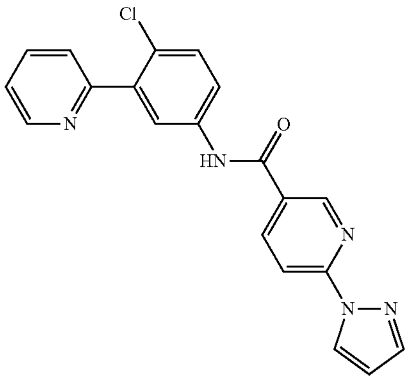
72
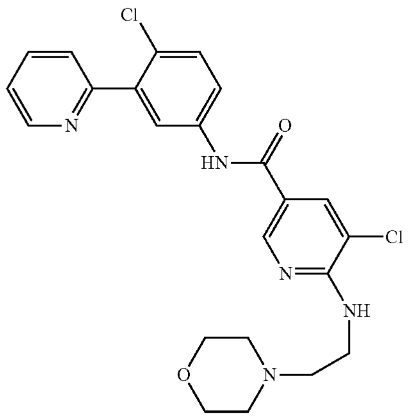
73
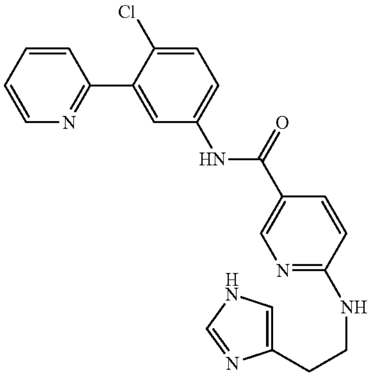
-continued
74
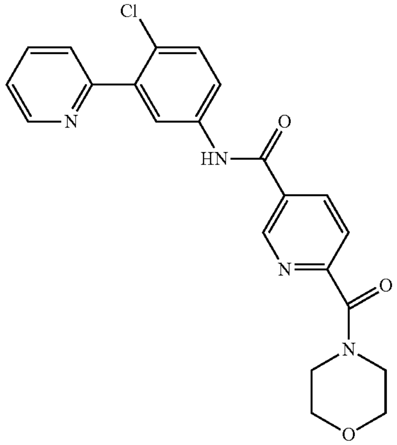
75
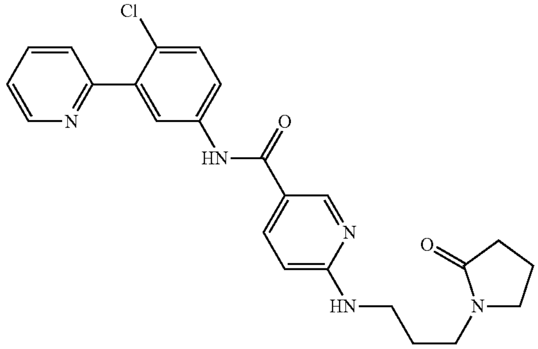
76
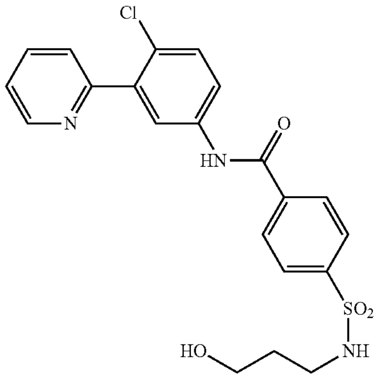
77
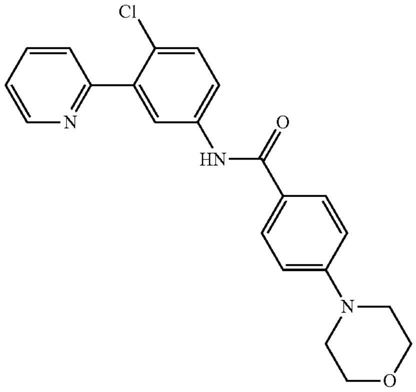

-continued
78
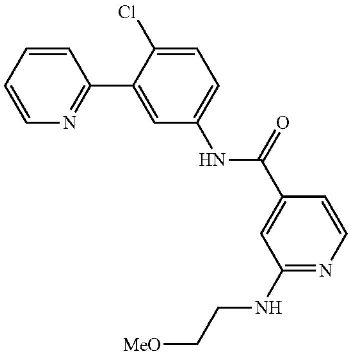
79
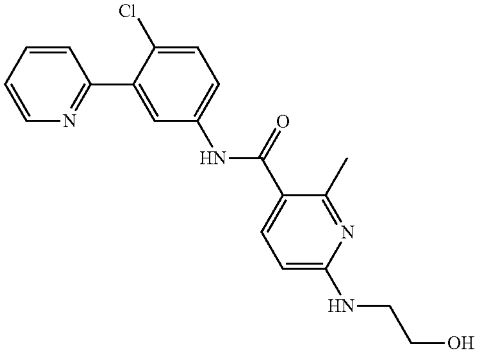
80
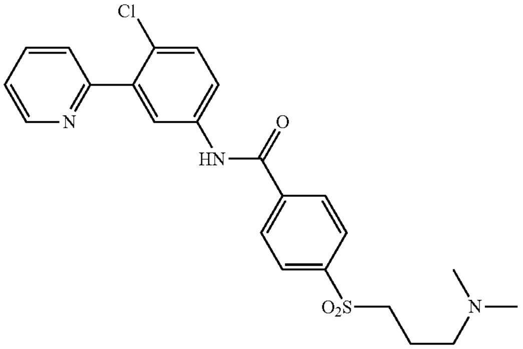
81
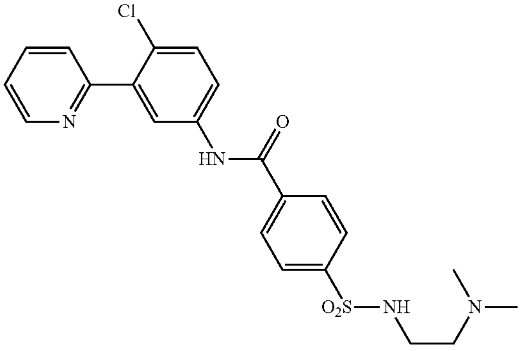
-continued
82
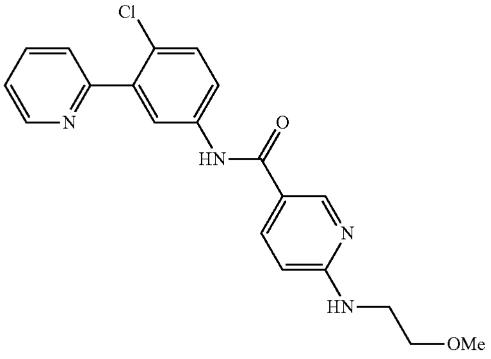
83
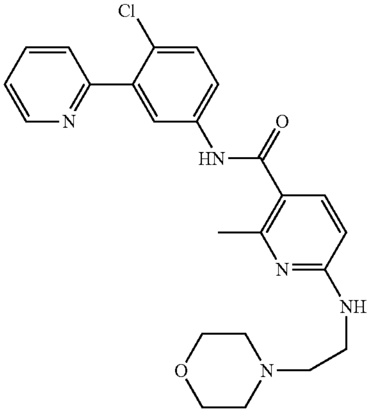
84
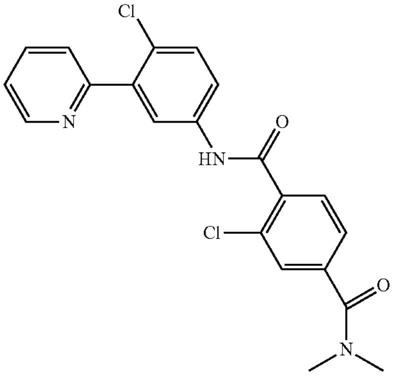
85
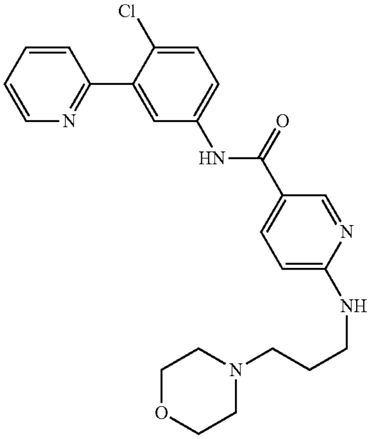

-continued
86
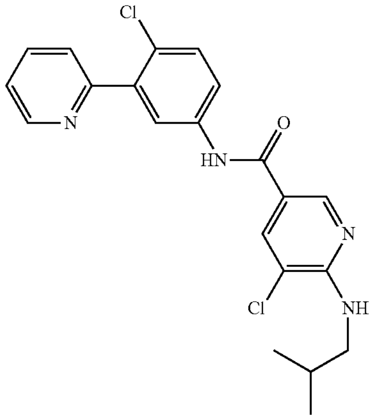
87
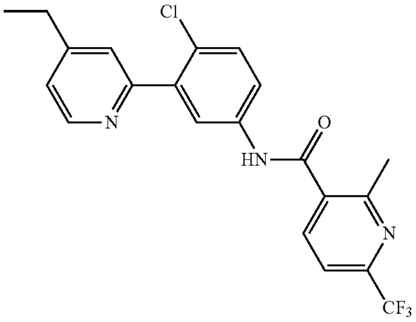
88
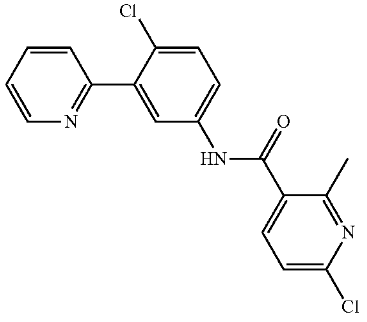
89
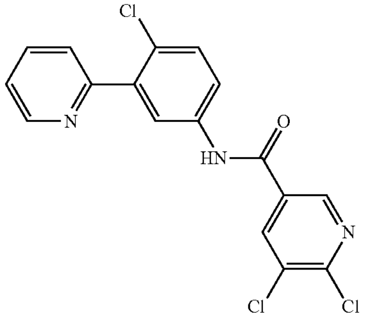
-continued
90
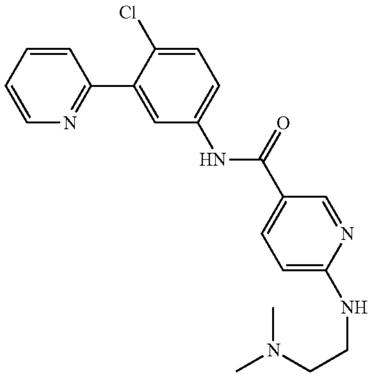
91
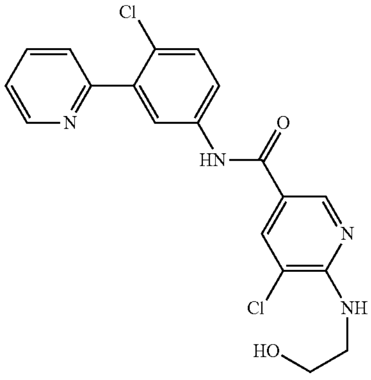
92
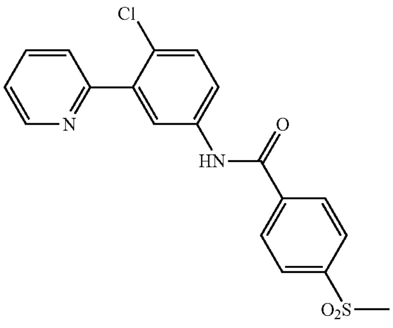
93
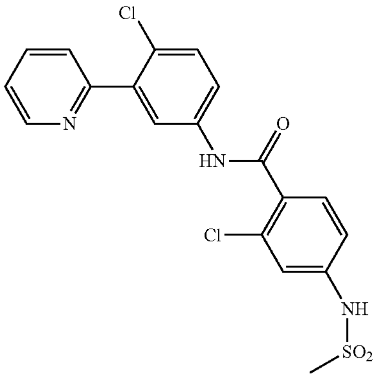

-continued
94
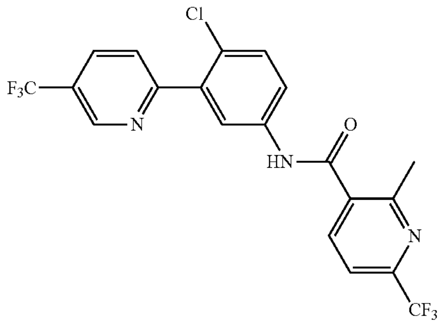
95
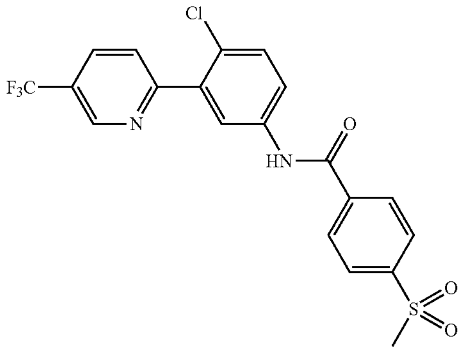
96
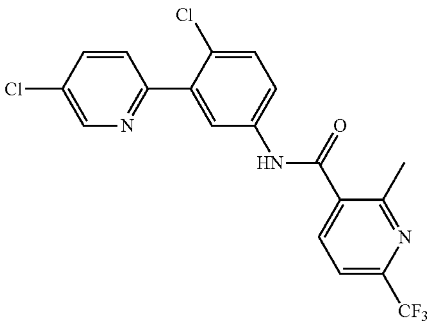
97
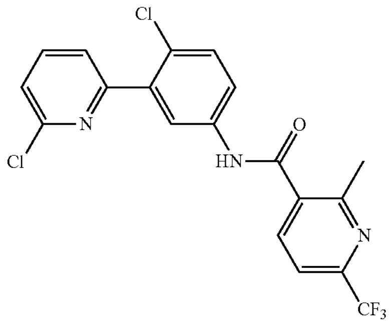
-continued
98
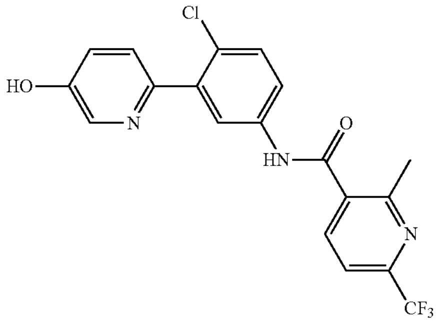
99
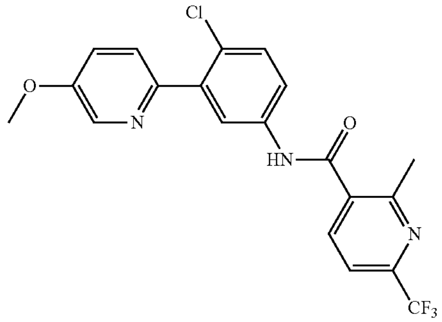
100
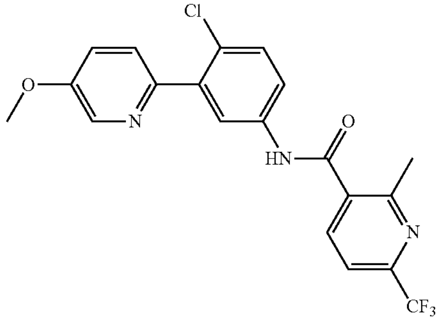
101
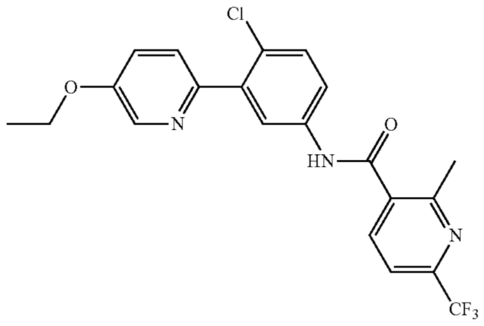
102
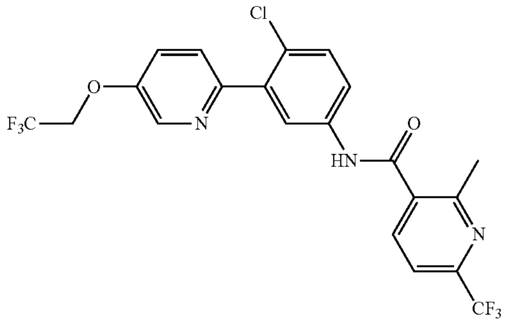

-continued
103
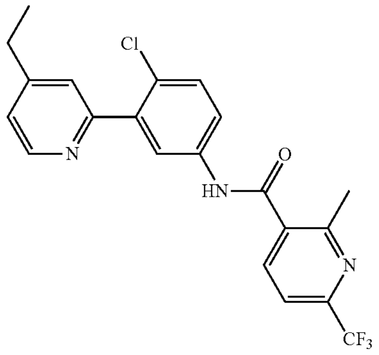
104
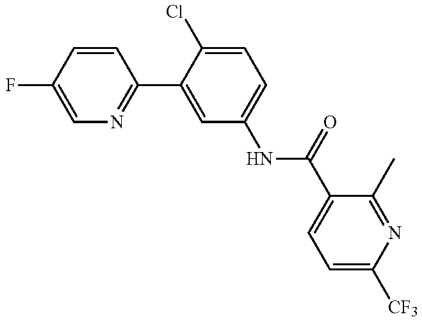
105
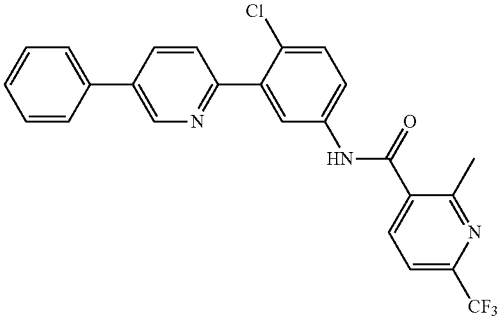
106
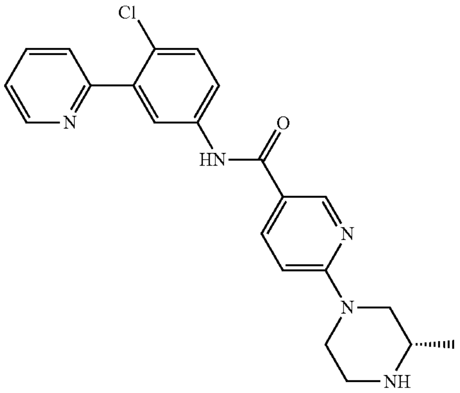
-continued
107
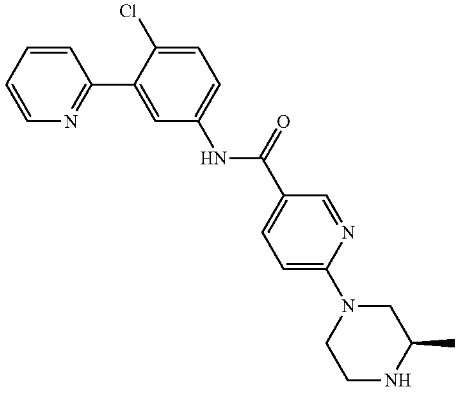
108
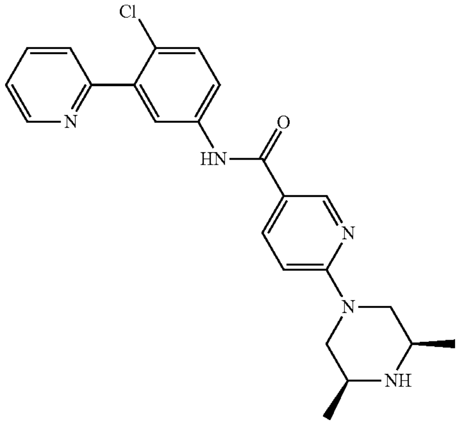
109
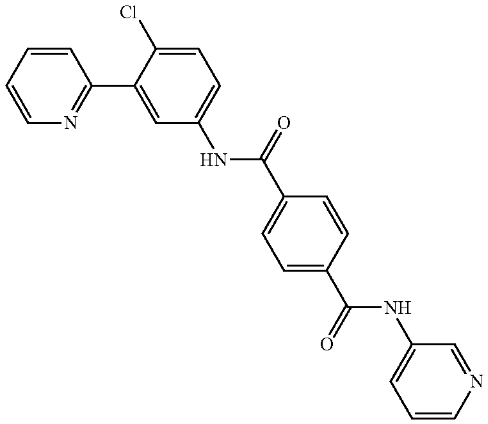

-continued
110
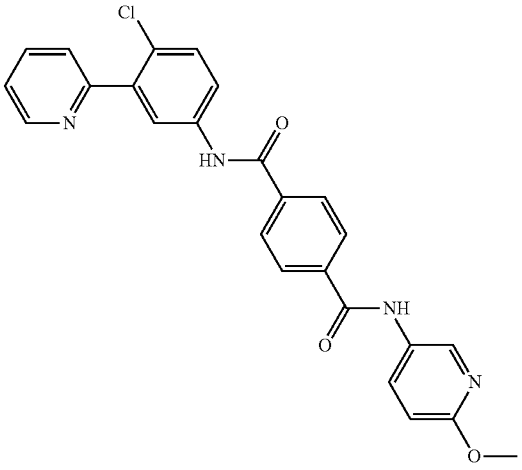
111
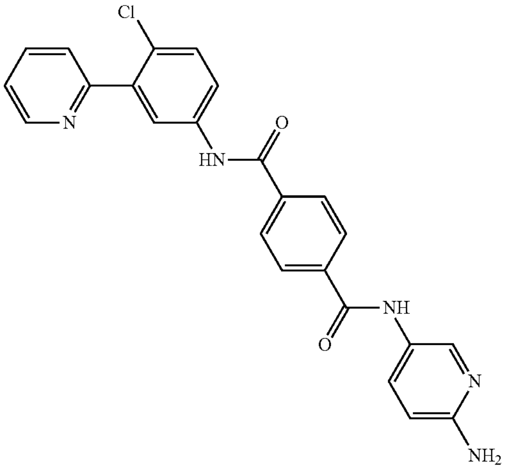
112
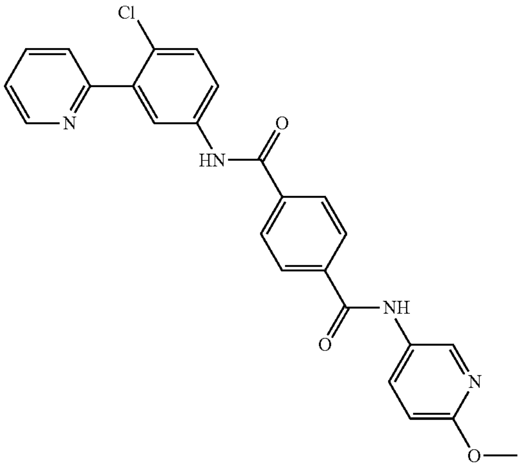
-continued
113
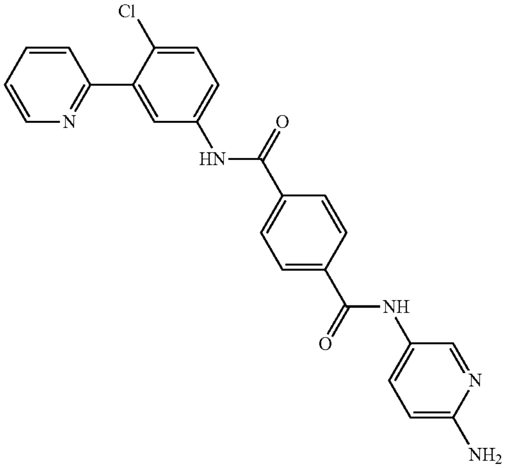
114
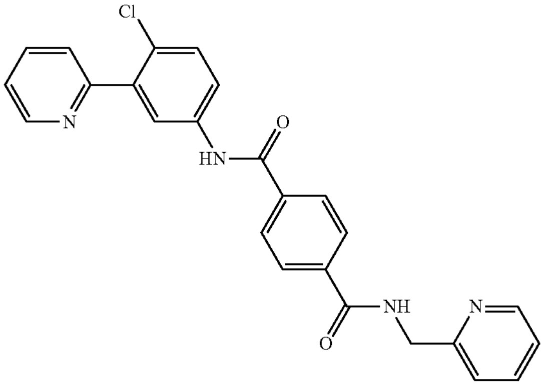
115
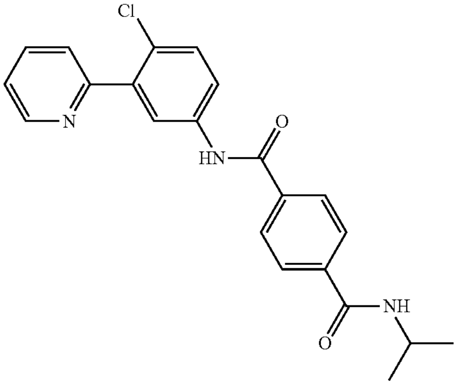
116
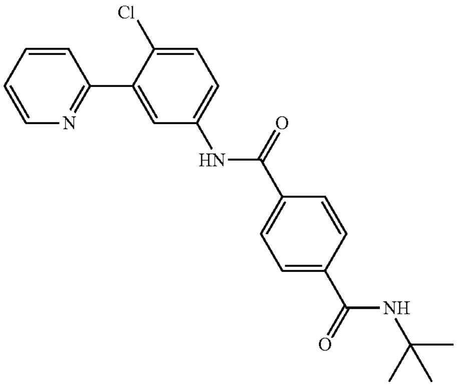

-continued
117
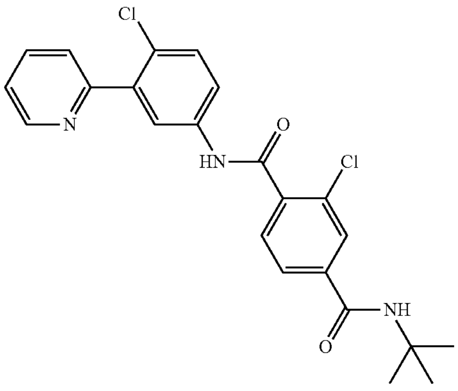
118
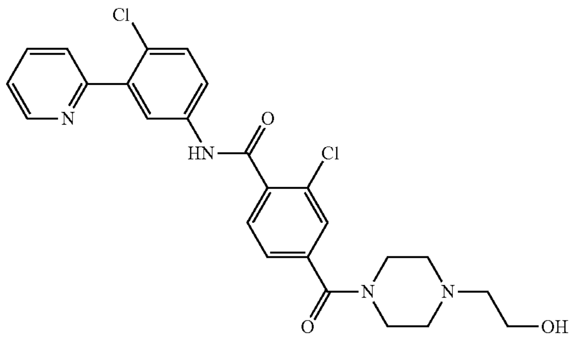
119
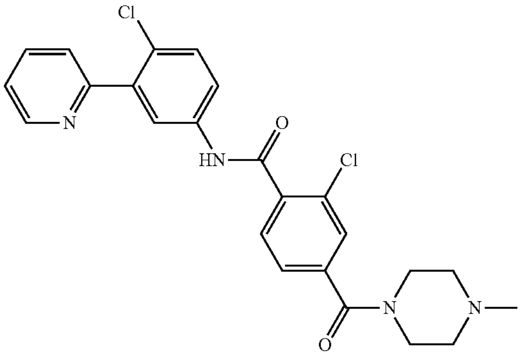
120
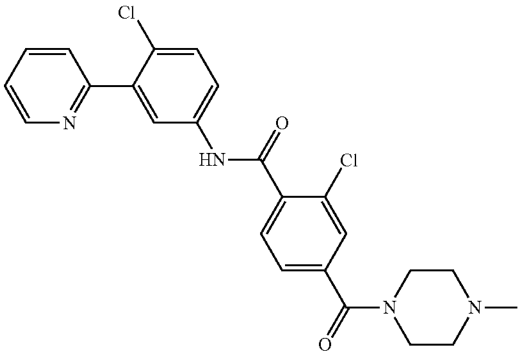
-continued
121
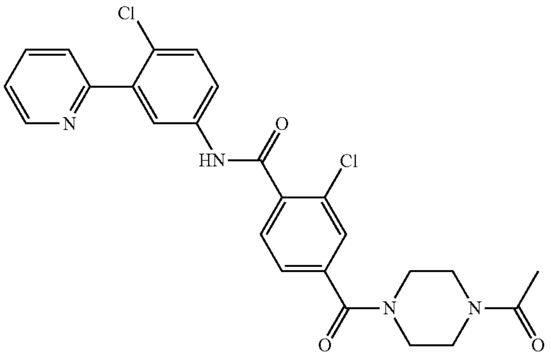
122
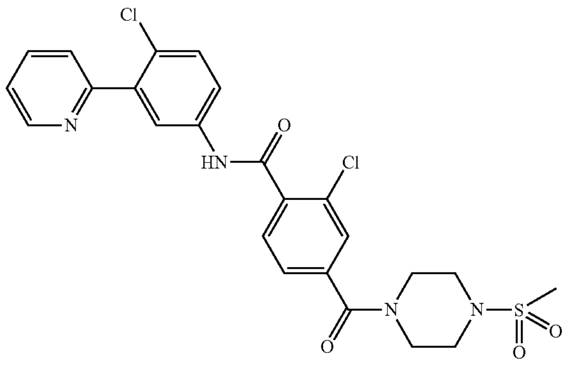
123
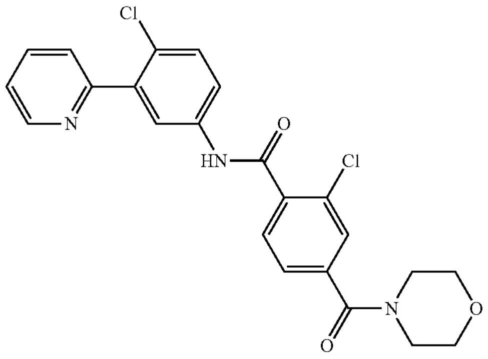
124
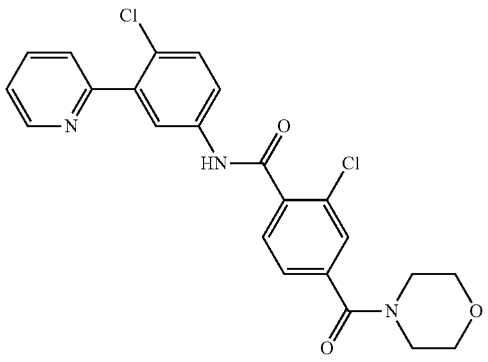

-continued
125
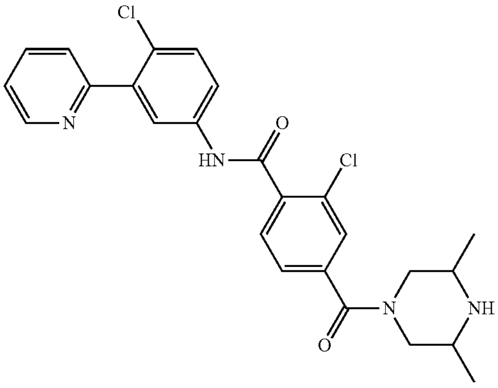
126
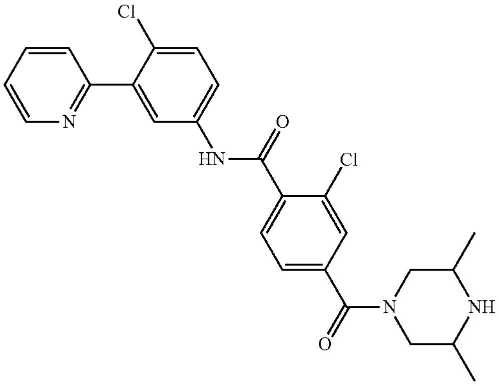
127
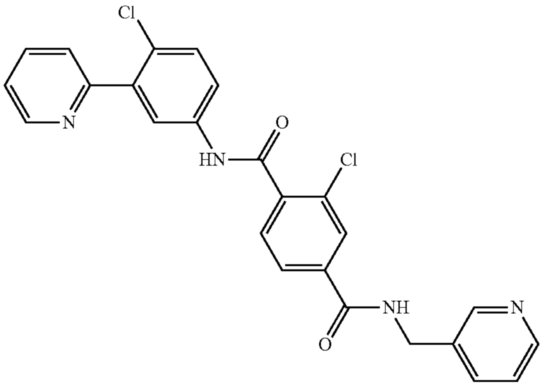
128
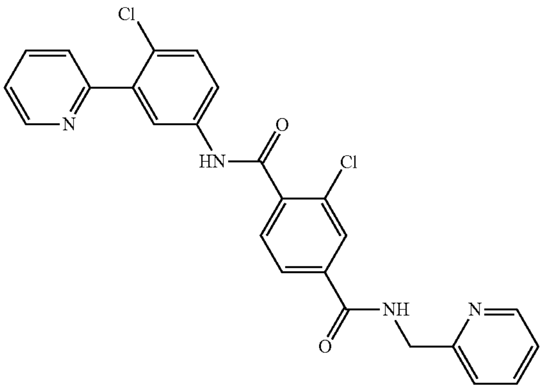
-continued
129
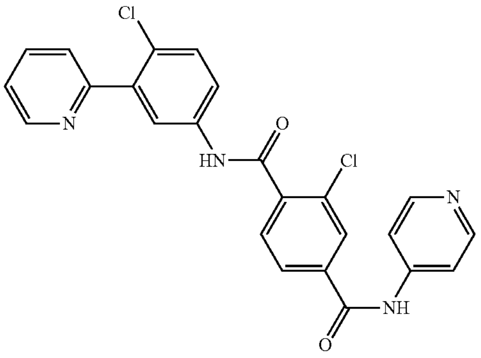
130
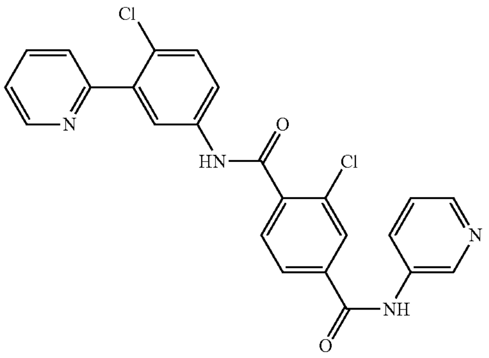
131
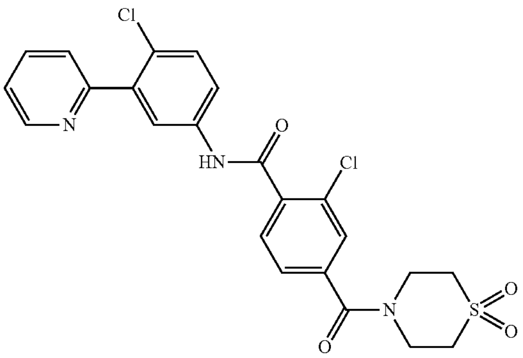
132
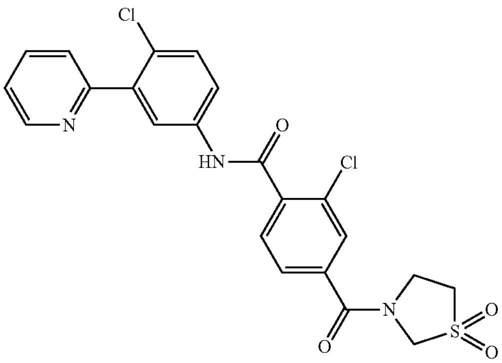

-continued
133
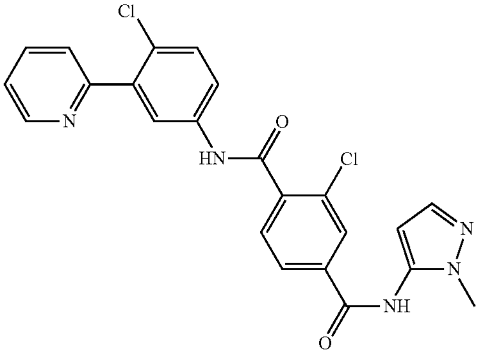
134
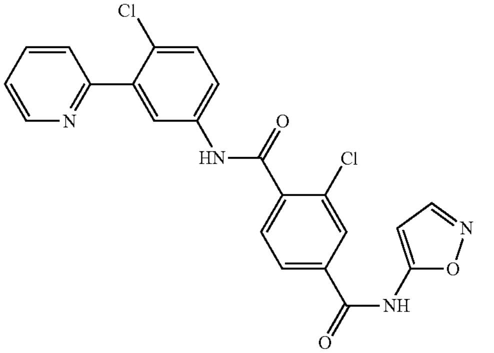
135
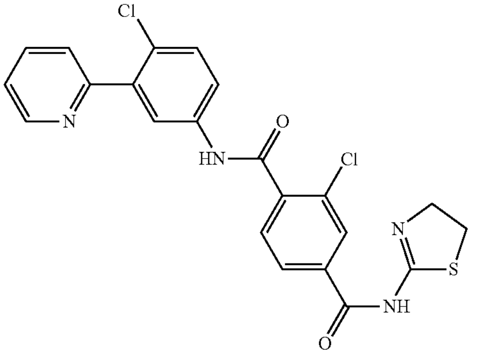
136
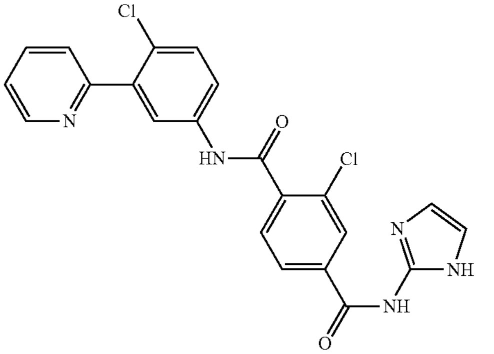
-continued
137
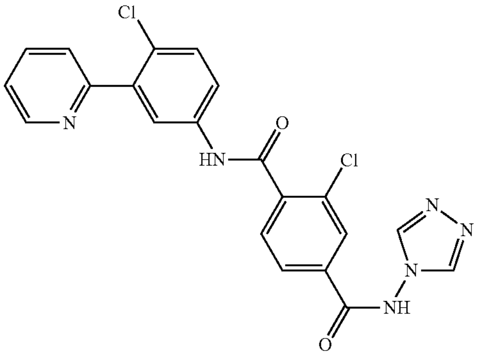
138
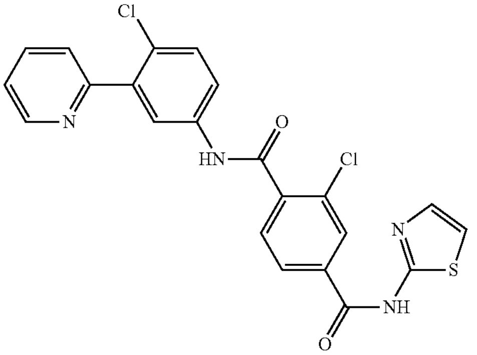
139
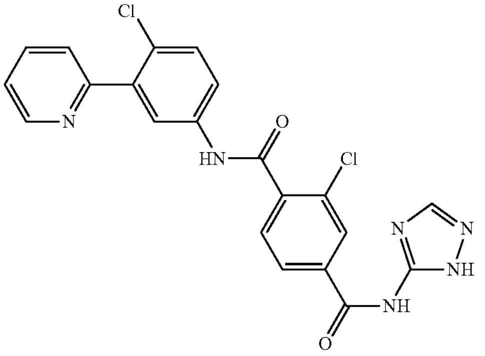
140
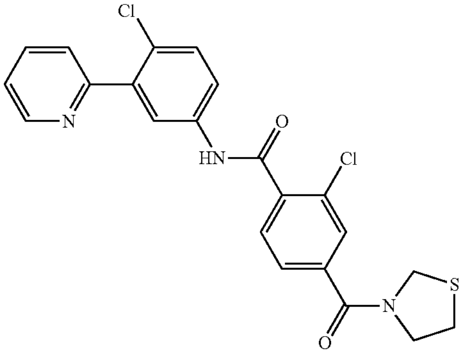

-continued
141
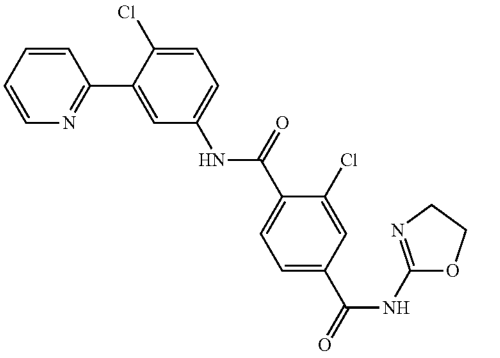
142
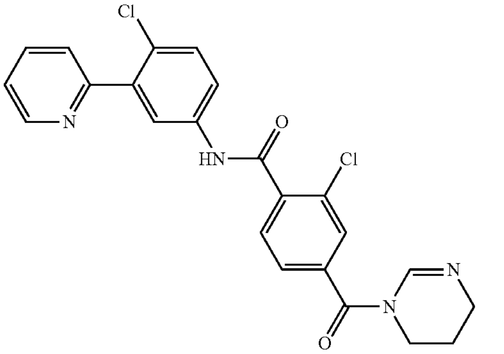
143
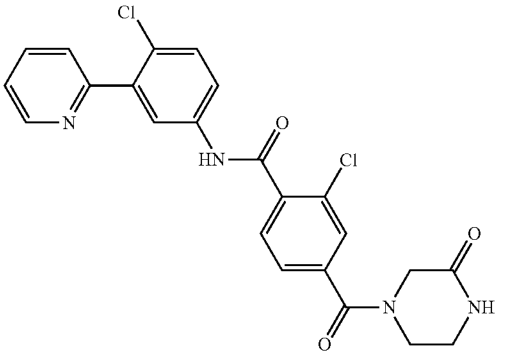
144
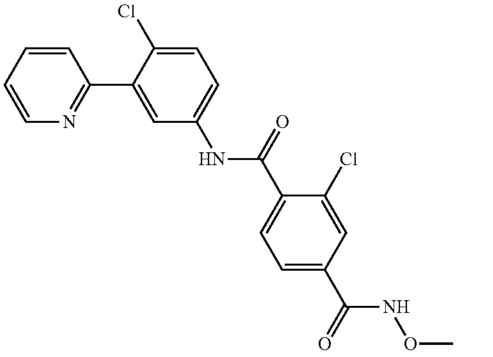
-continued
145
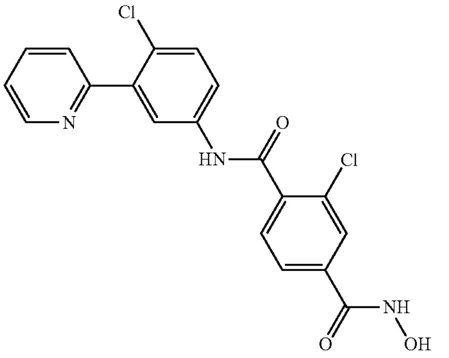
146
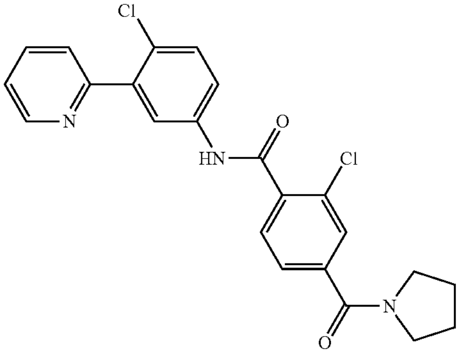
147
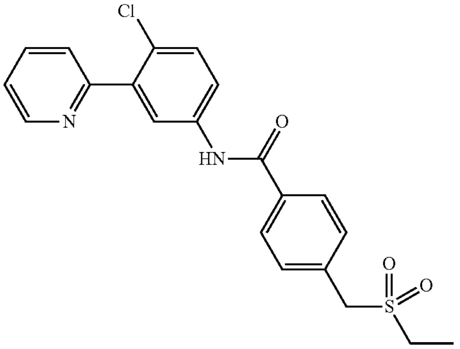
148
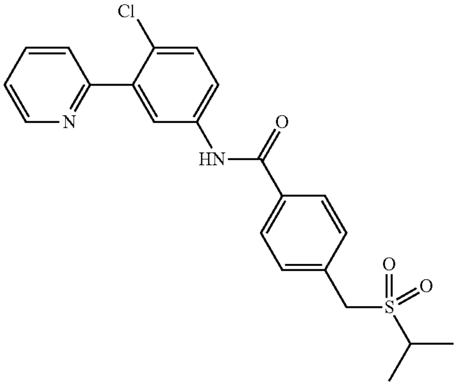

-continued
149
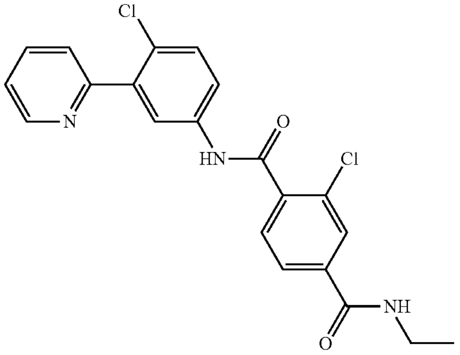
150
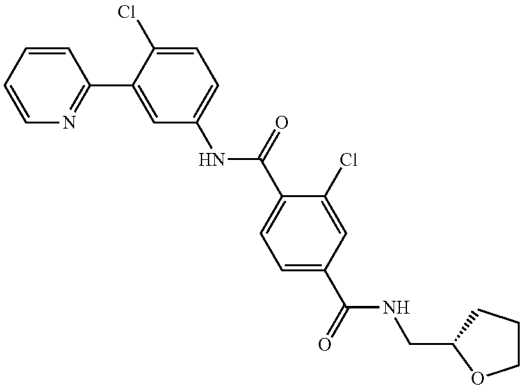
151
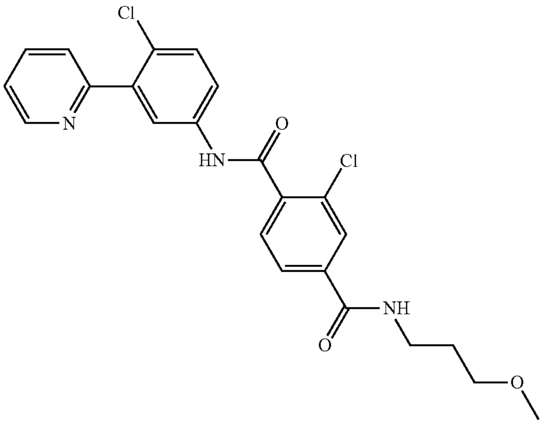
152
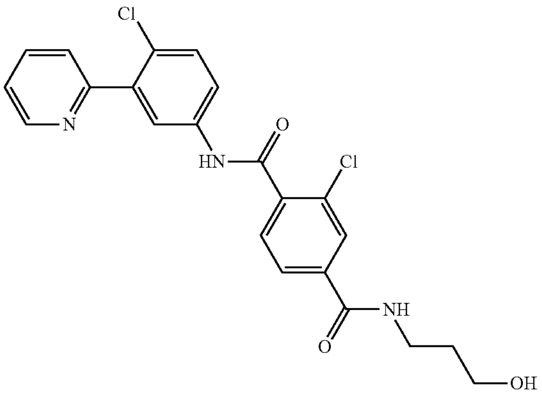
-continued
153
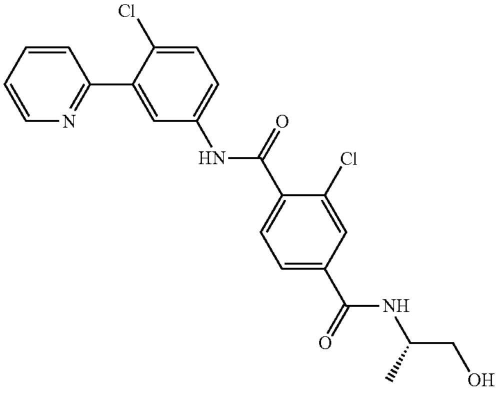
154
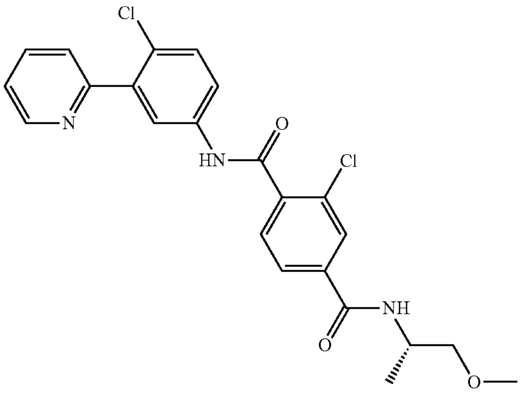
155
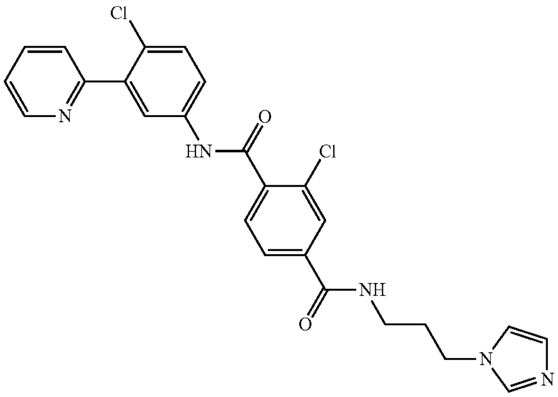

-continued
156
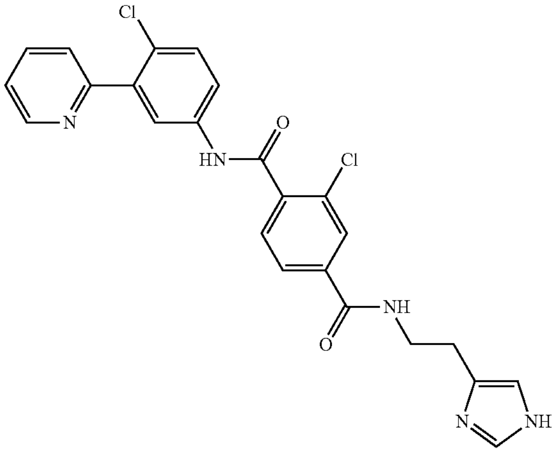
157
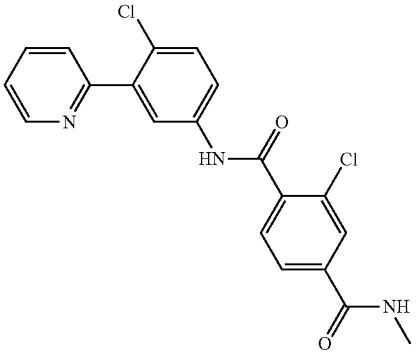
158
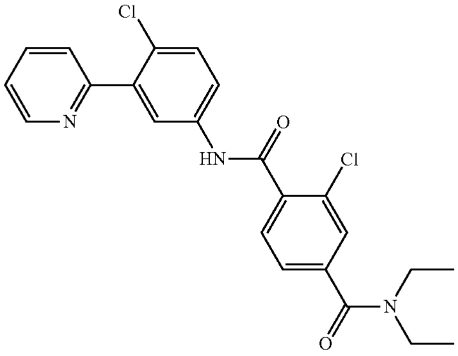
159
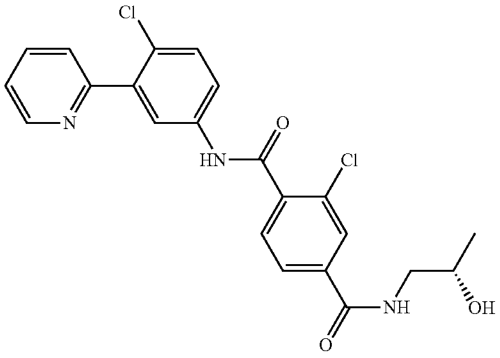
-continued
160
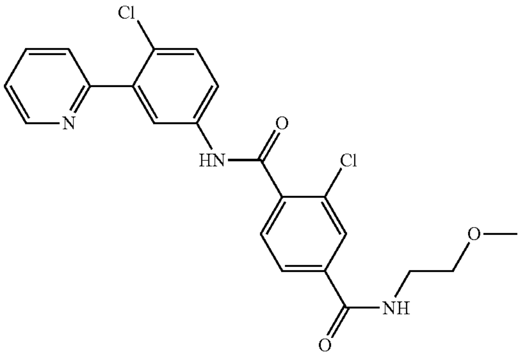
161
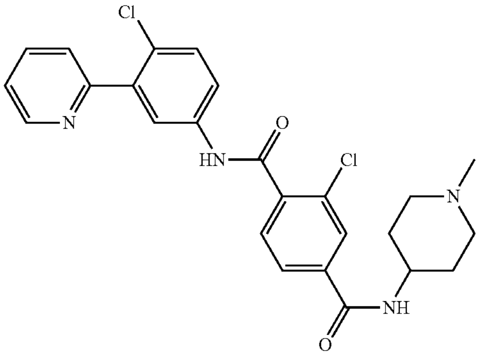
162
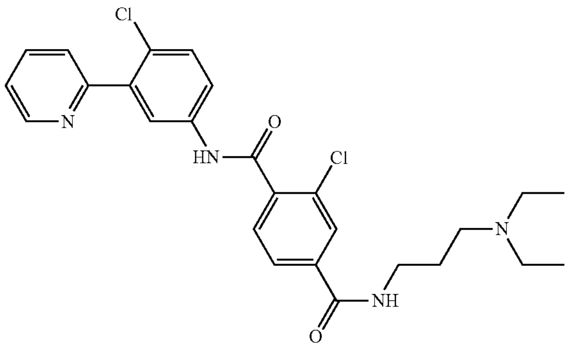
163
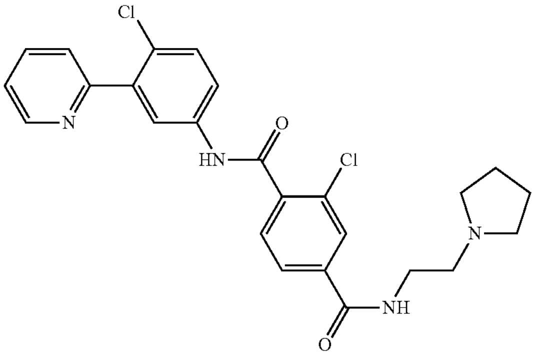

-continued
164
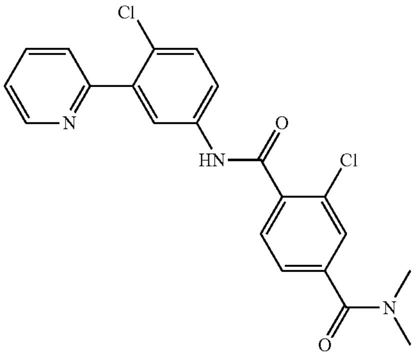
165
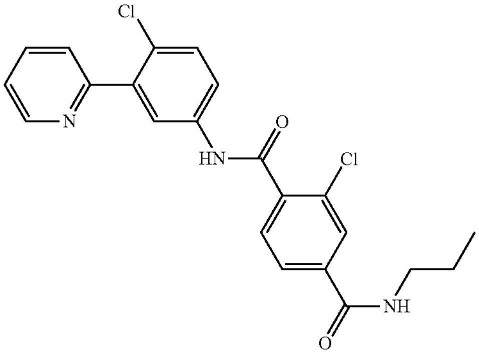
166
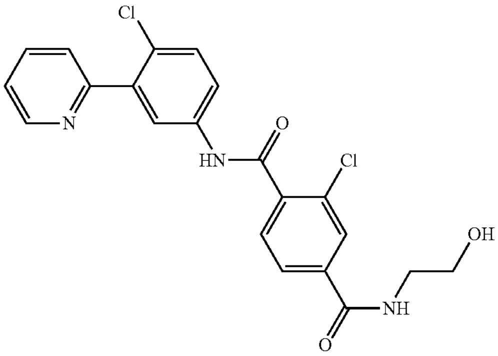
167
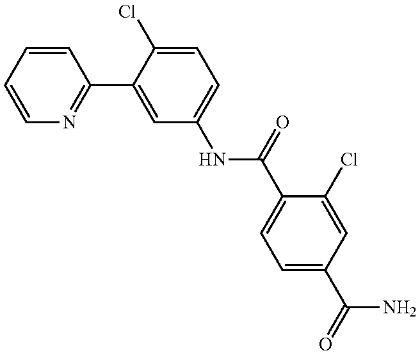
-continued
168
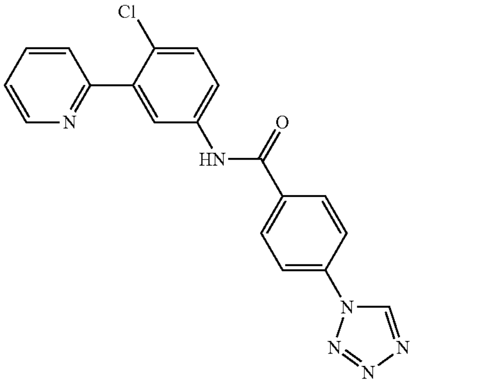
169
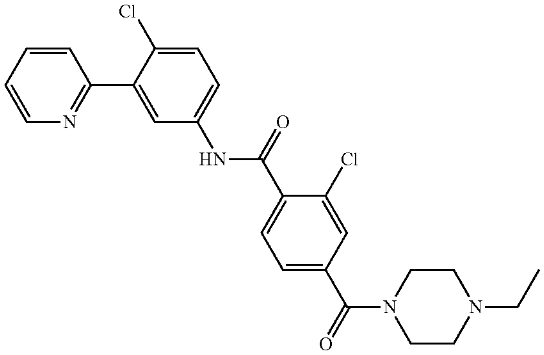
170
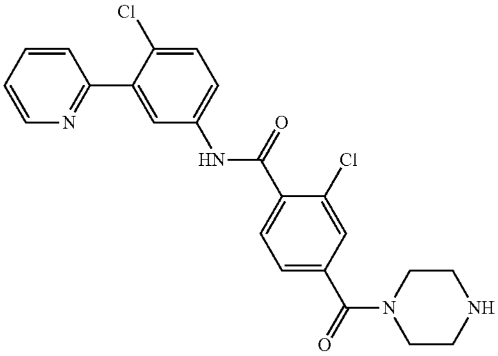
171
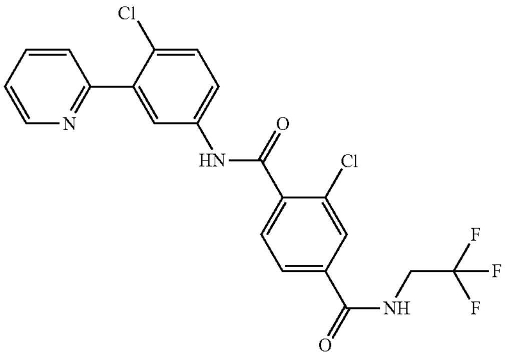

-continued
172
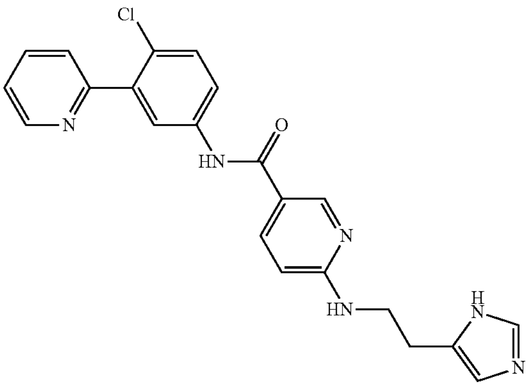
173
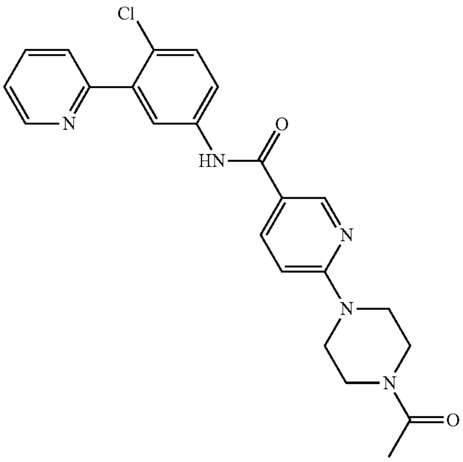
174
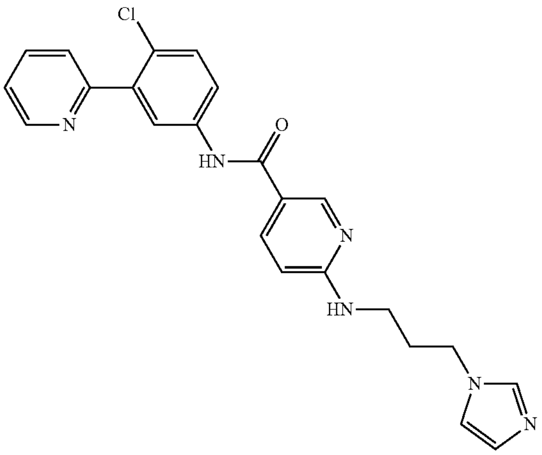
-continued
175
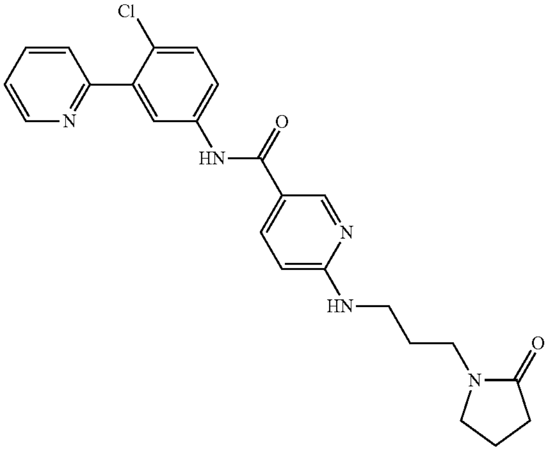
176
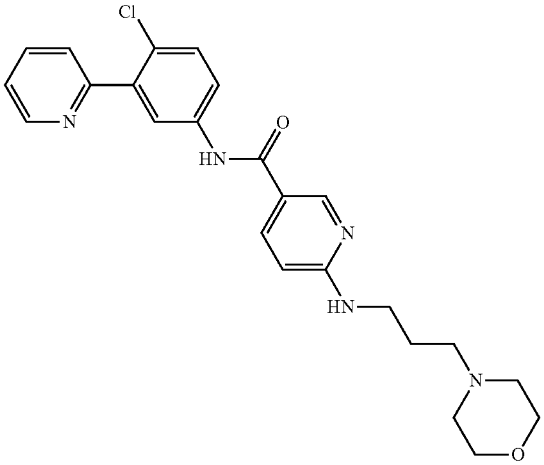
177
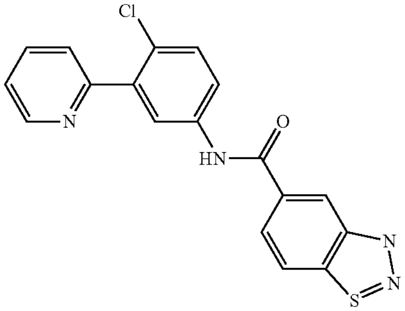

-continued
178
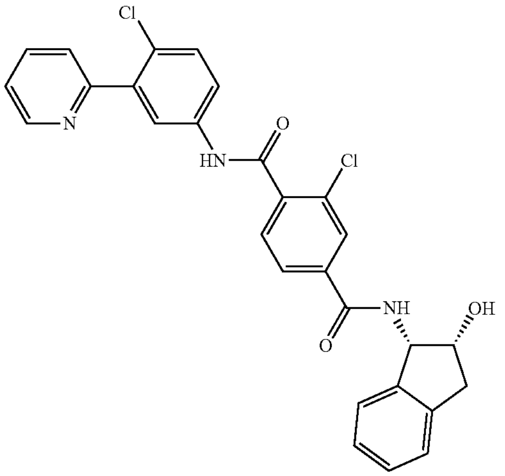
179
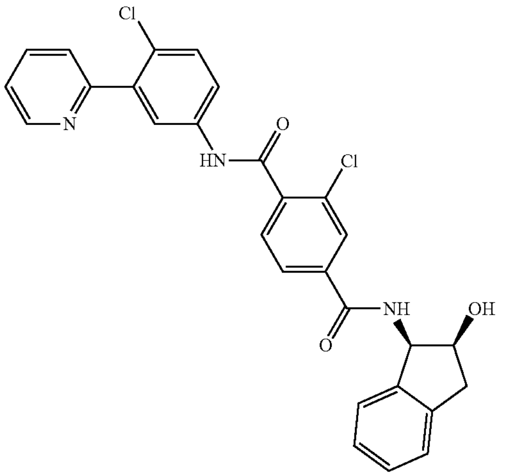
180
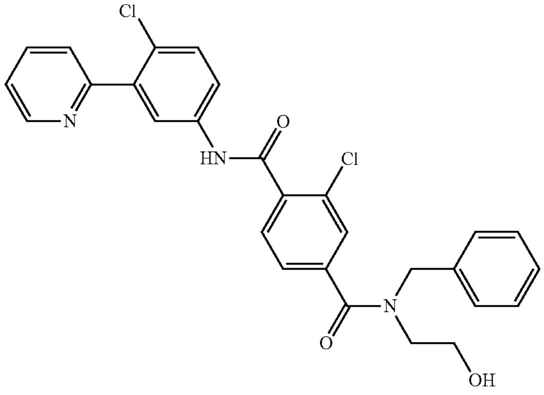
-continued
181
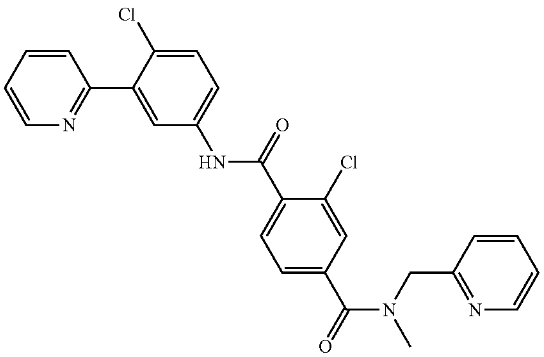
182
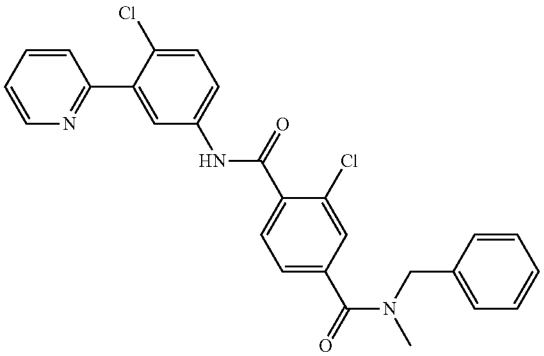
183
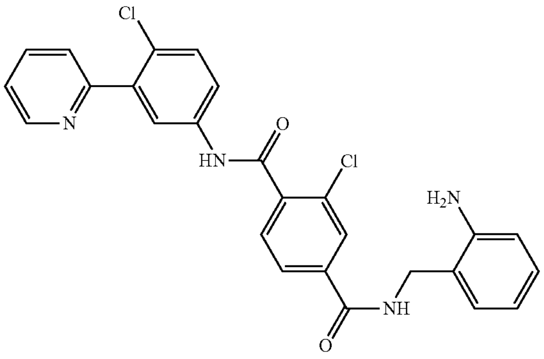
184
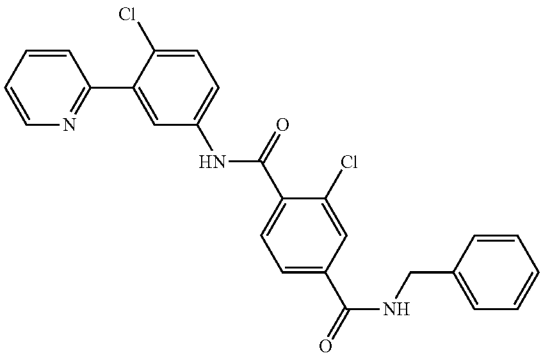

-continued
185
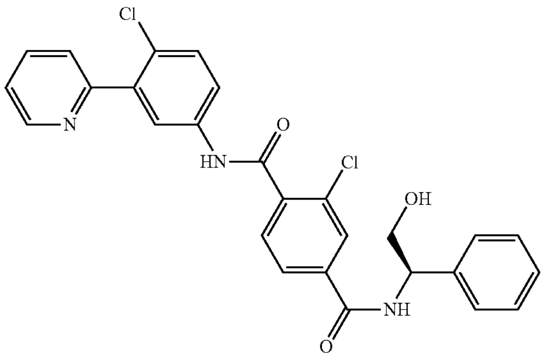
186
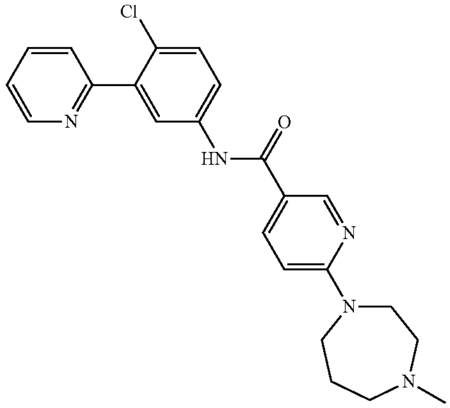
187
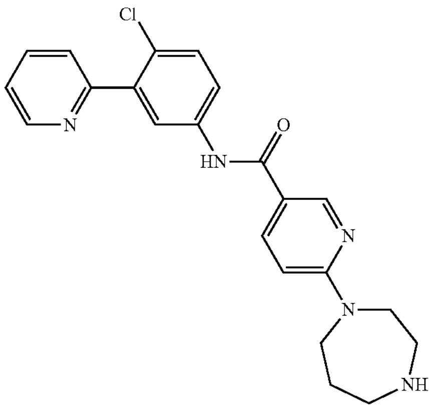
188
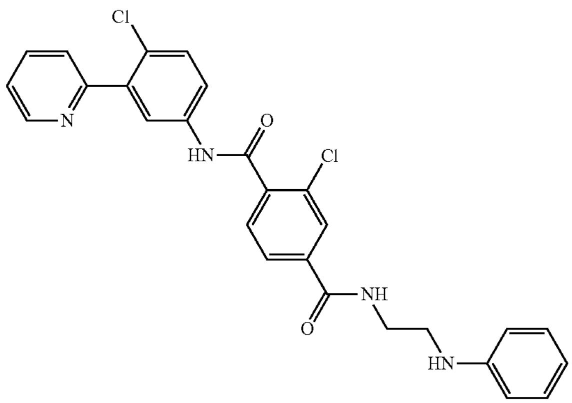
-continued
189
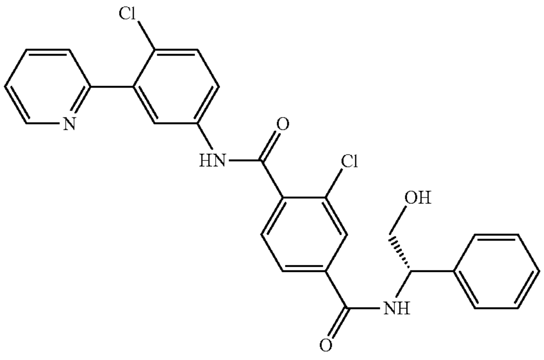
190
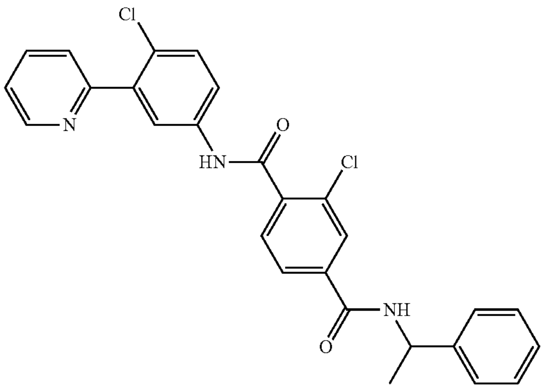
191
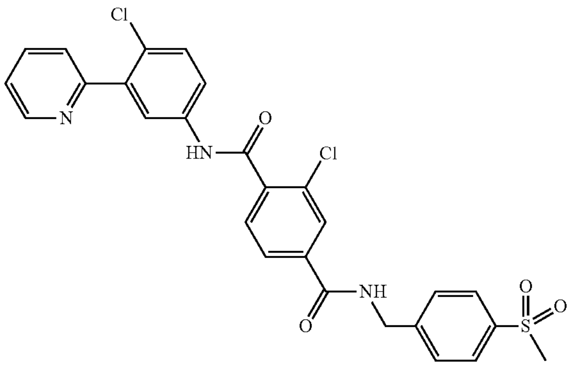
192
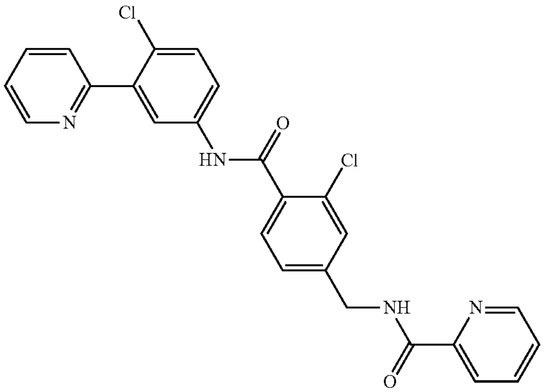

-continued
193
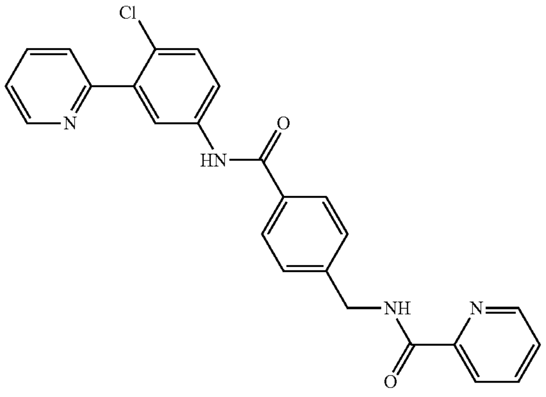
194
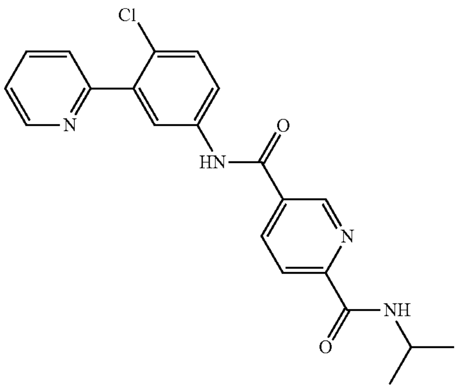
195
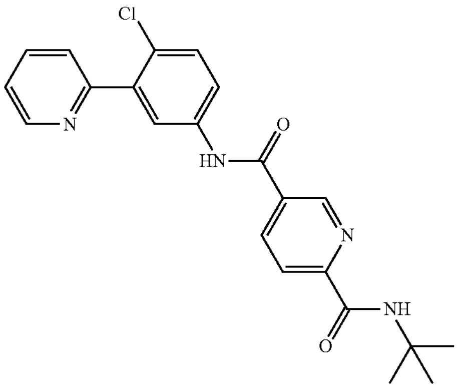
196
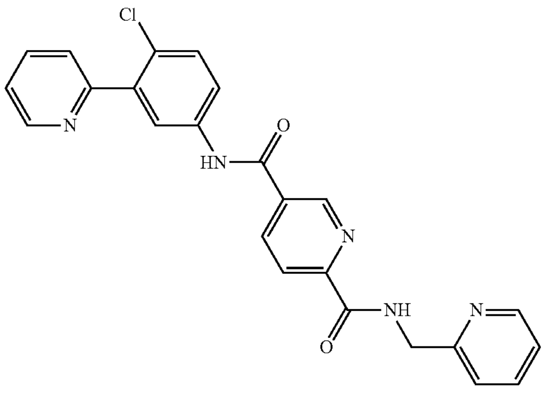
-continued
197
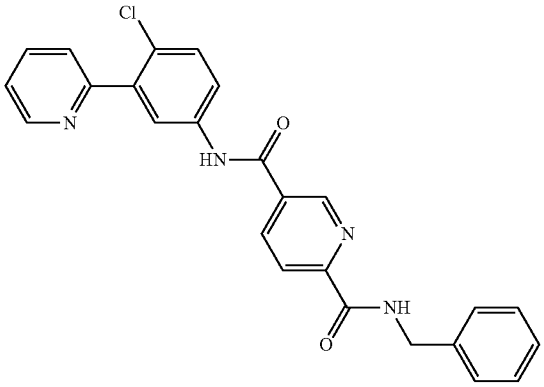
198
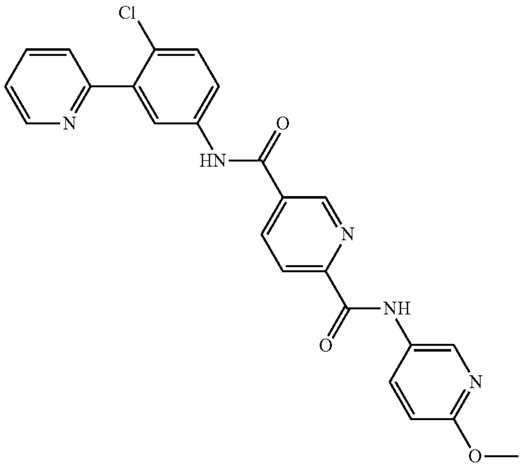
199
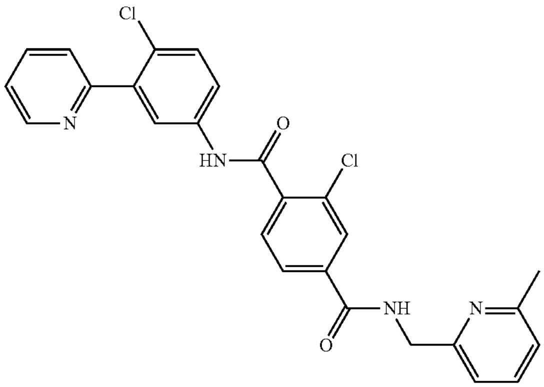

-continued
200
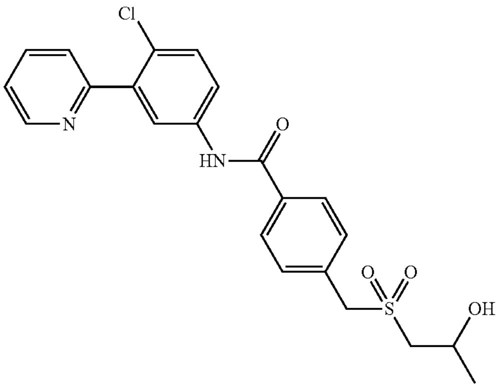
201
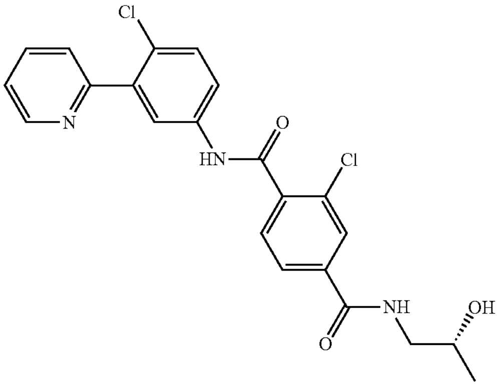
202
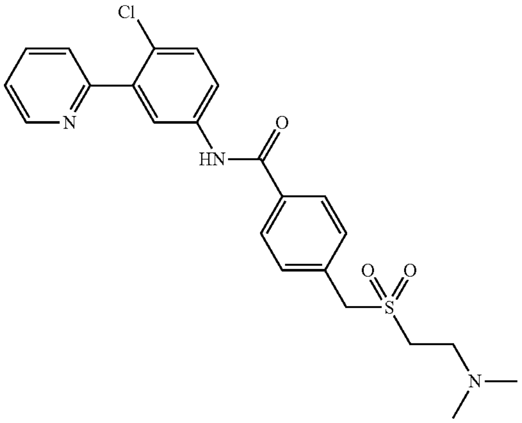
-continued
203
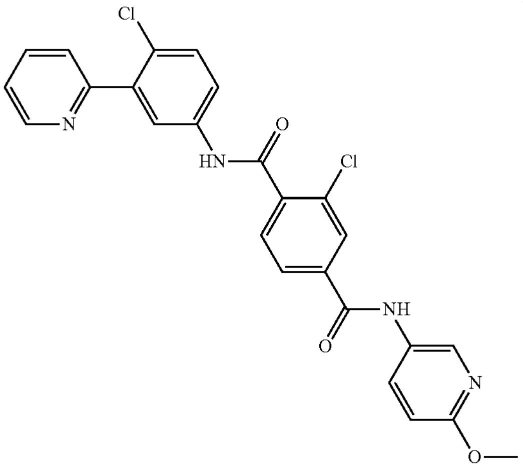
204
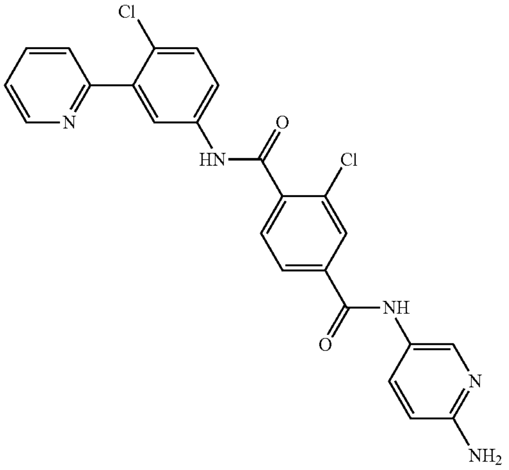
205
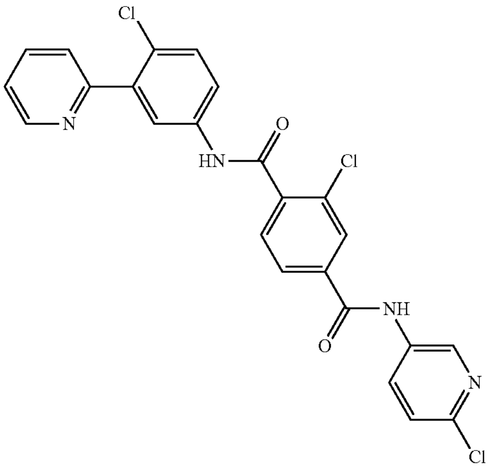

-continued
206
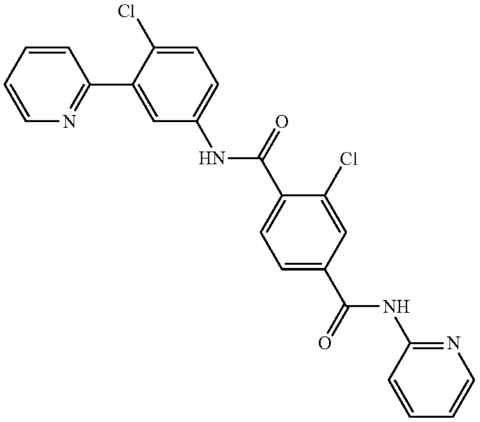
207
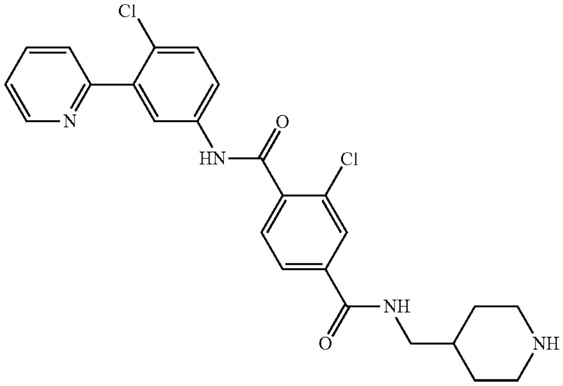
208
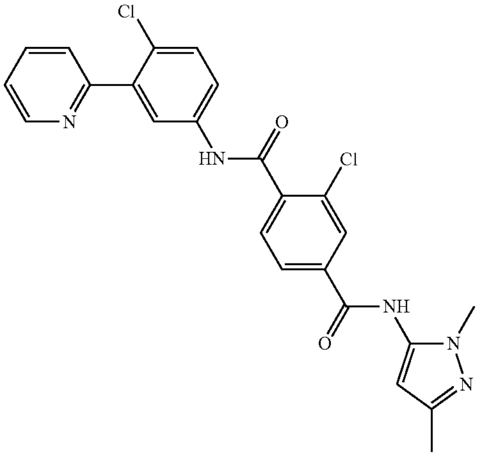
-continued
209
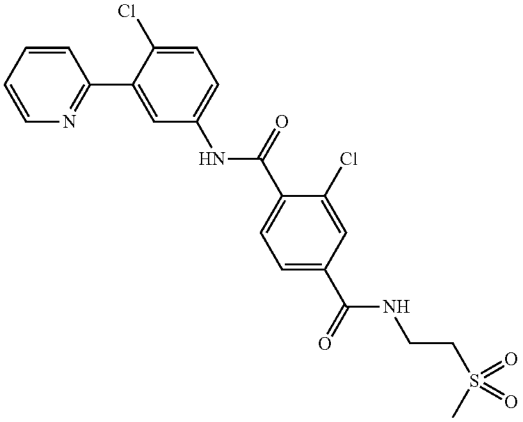
210
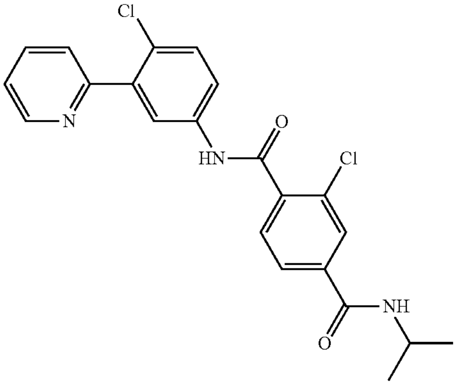
211
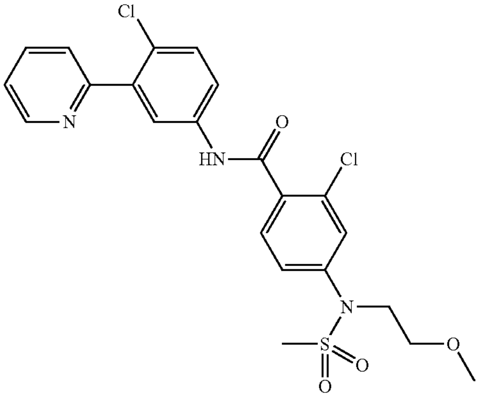
212
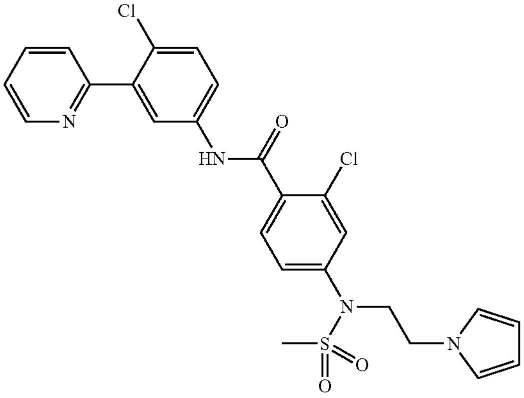

-continued
213
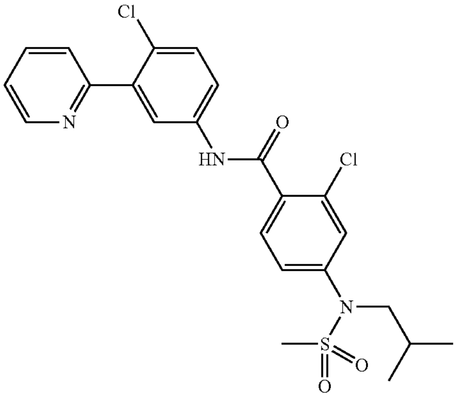
214
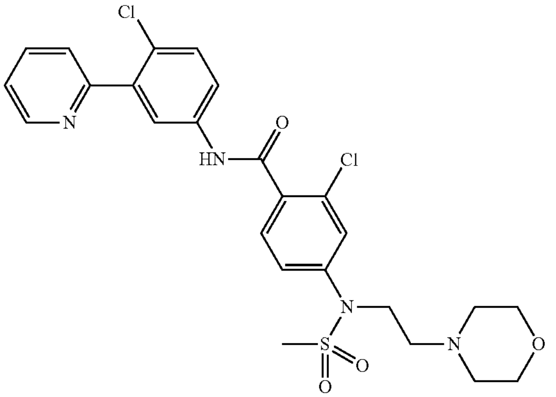
215
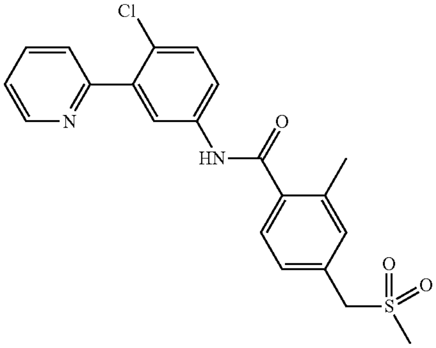
216
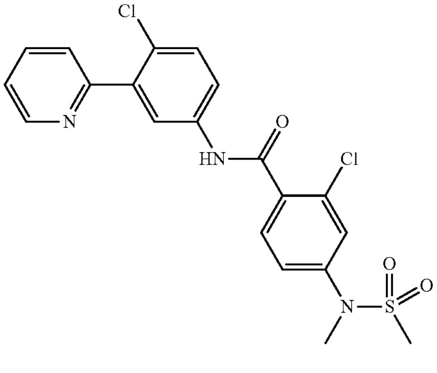
-continued
217
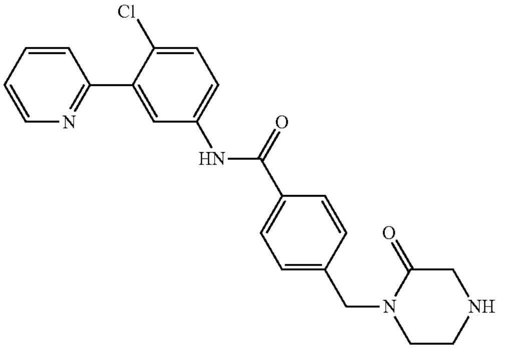
218
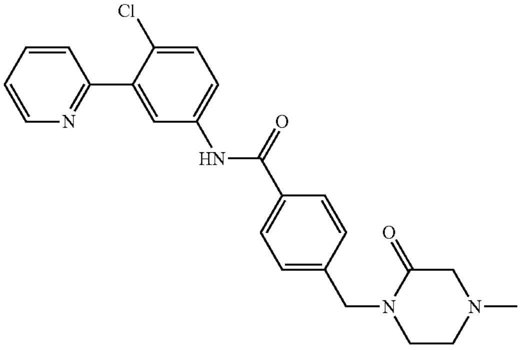
219
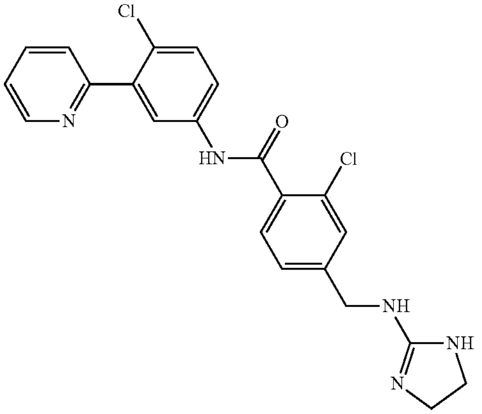
220
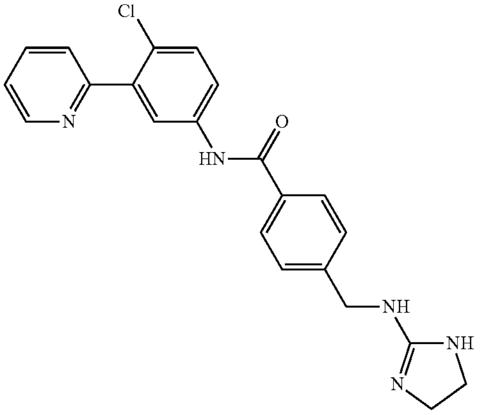

-continued
221
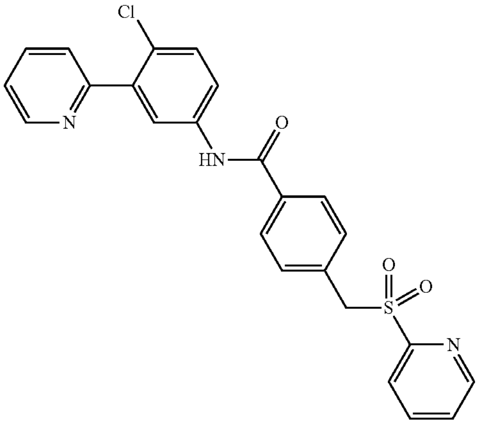
220
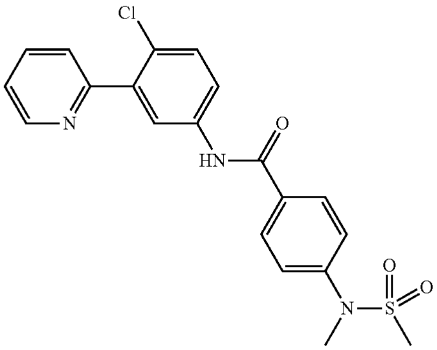
223
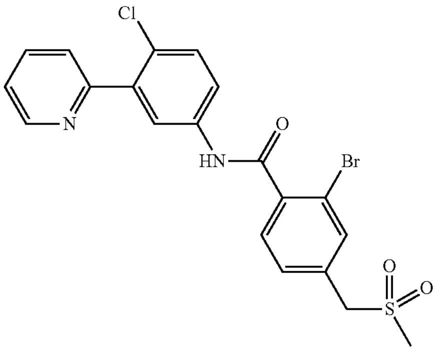
222
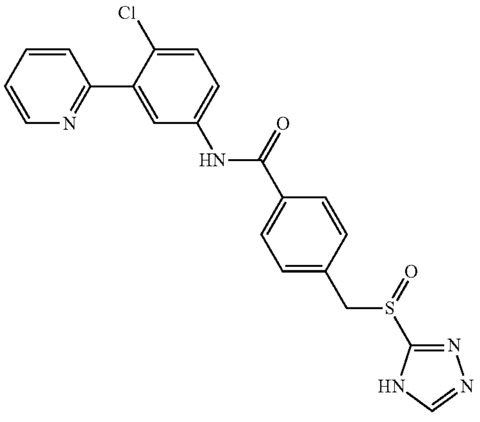
-continued
225
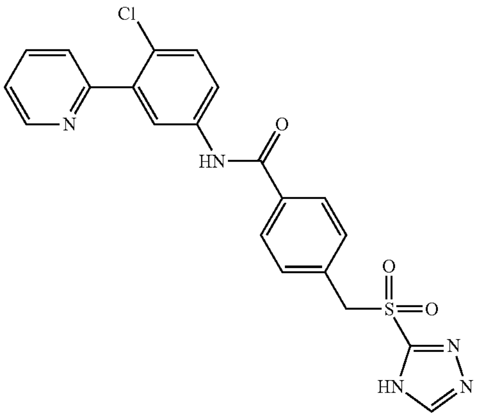
224
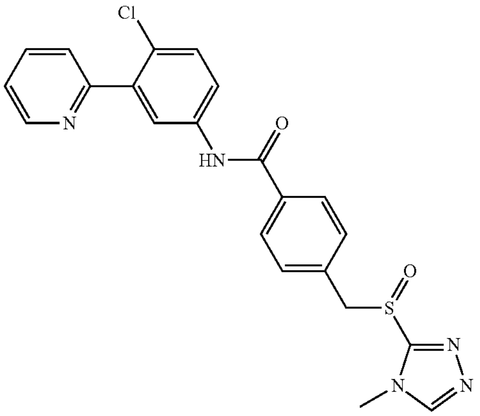
227
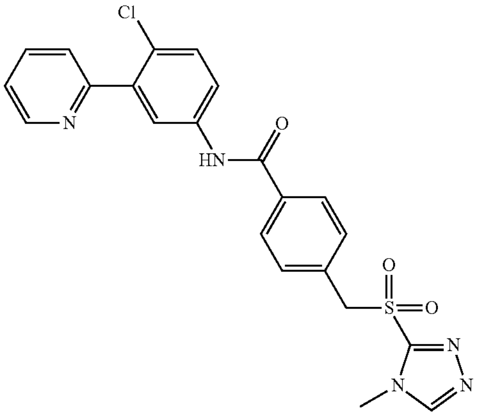
226
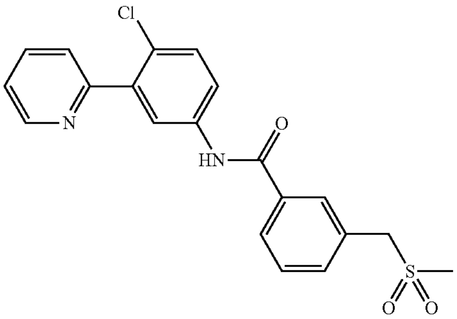

-continued
229
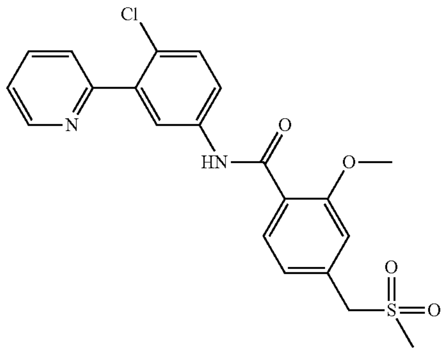
228
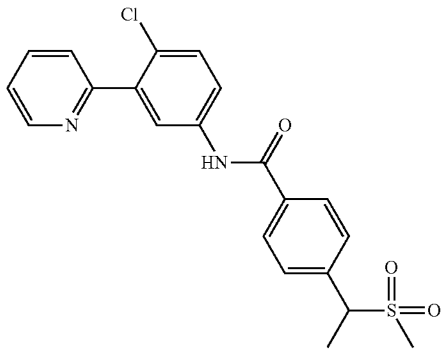
231
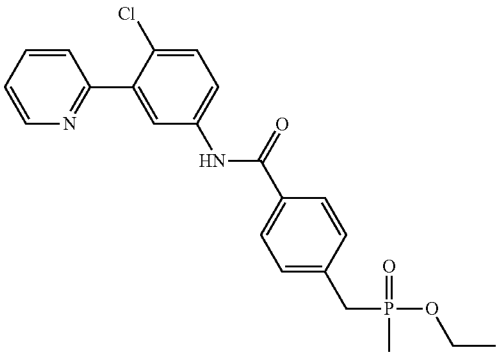
230
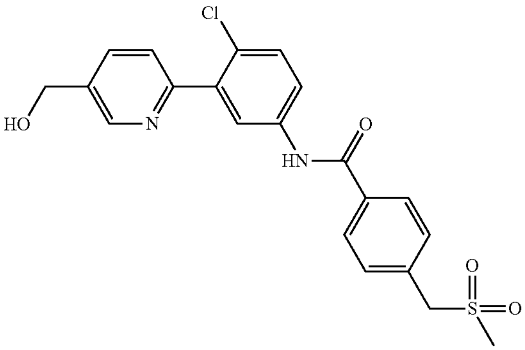
-continued
233
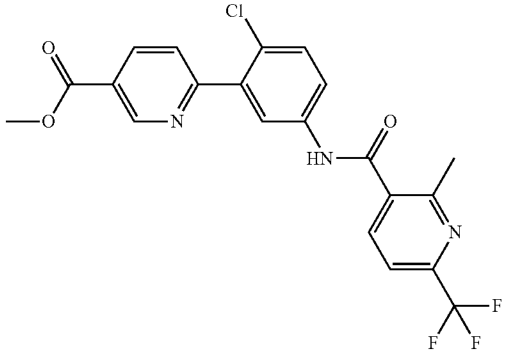
232
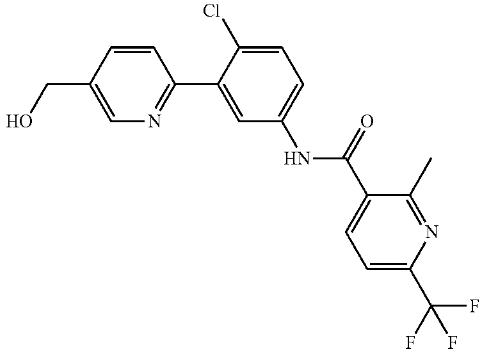
235
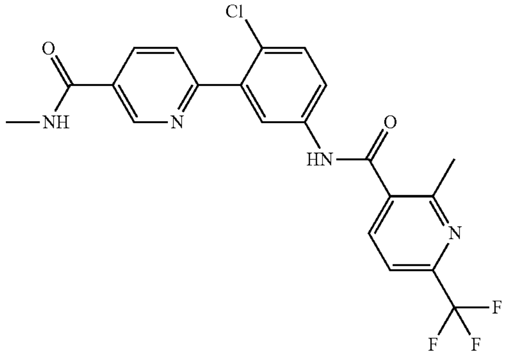
234
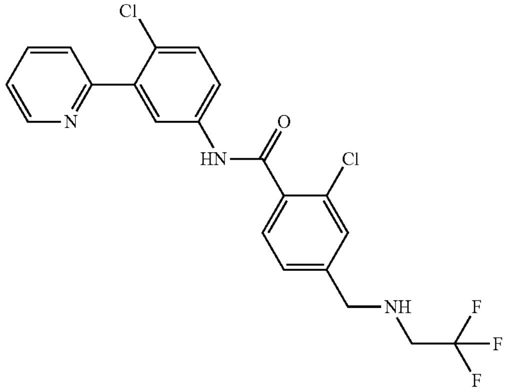

237
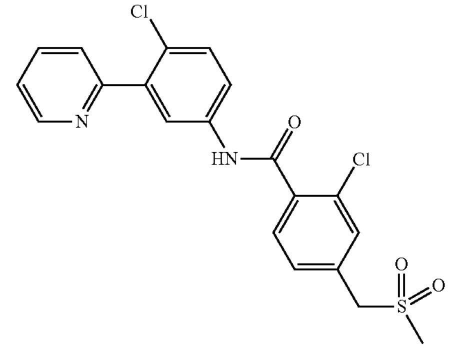
236
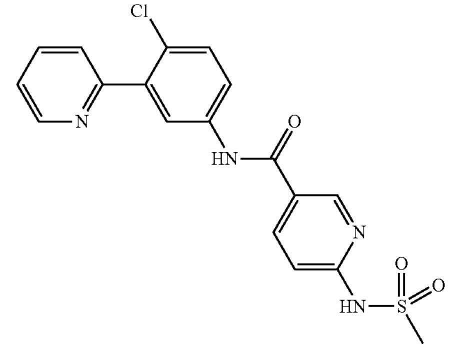
239
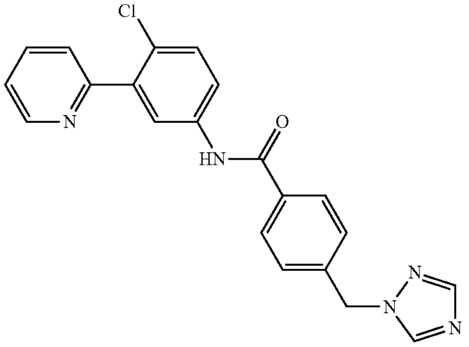
238
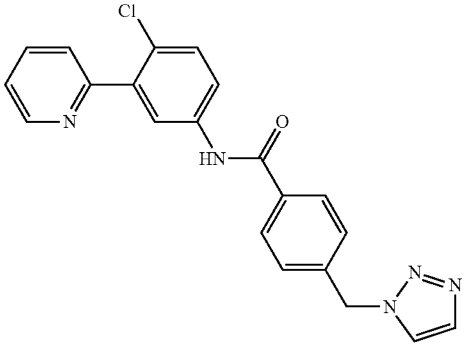
241
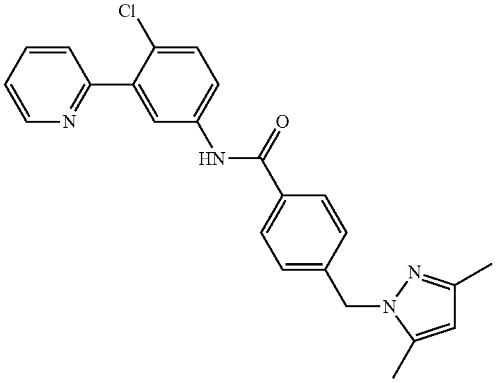
240
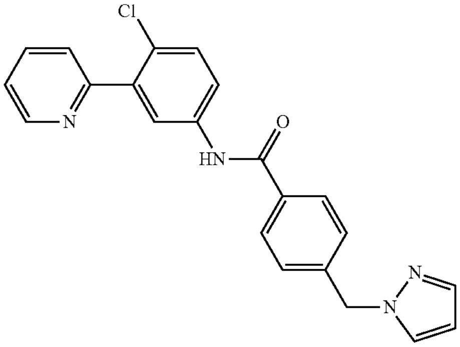
243
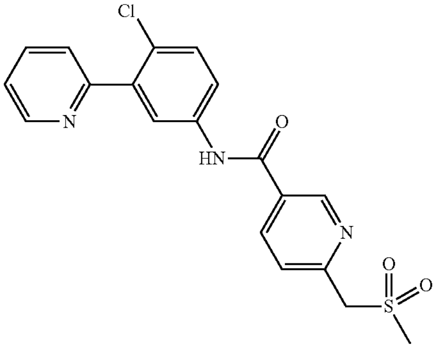
242
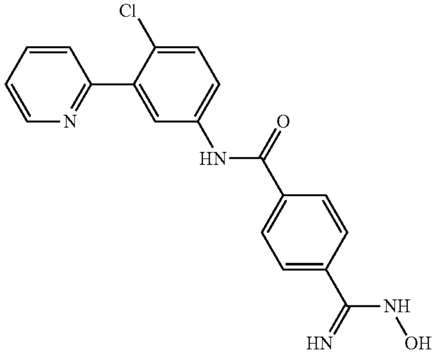

-continued
245
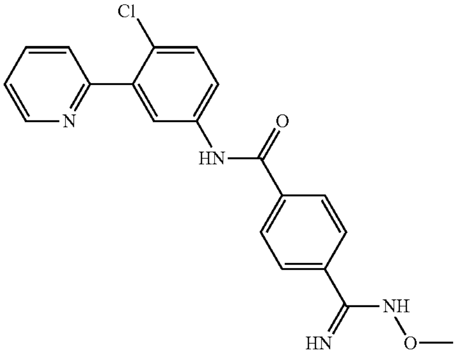
244
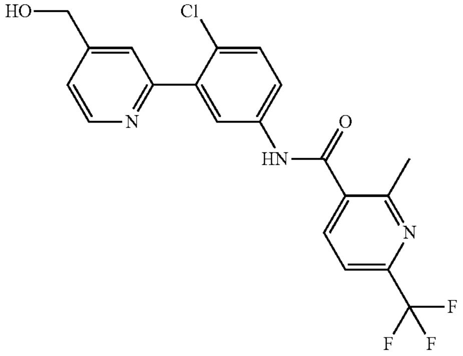
247
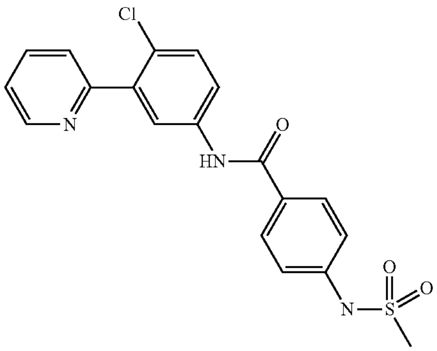
246
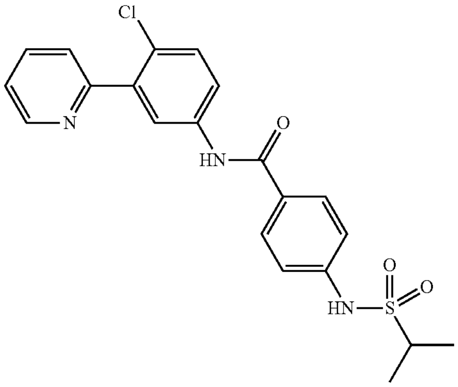
-continued
249
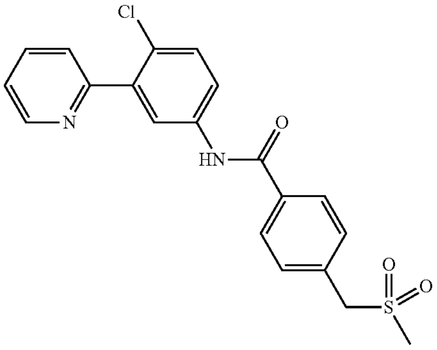
250
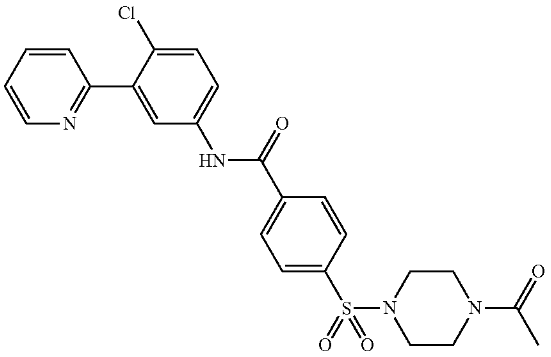
251
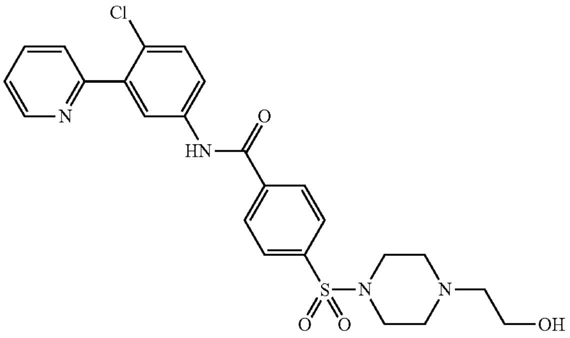
252
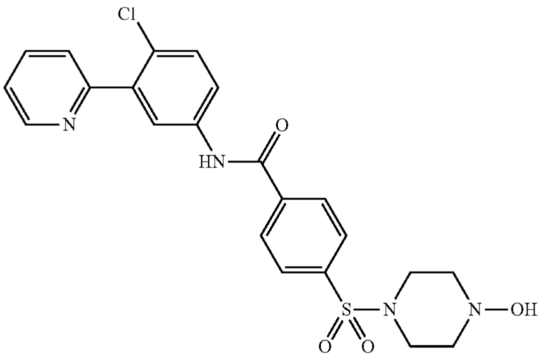

-continued
253
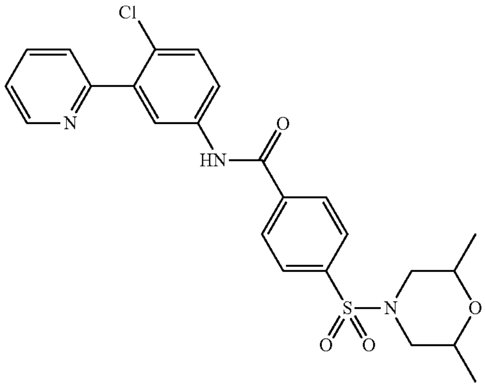
254
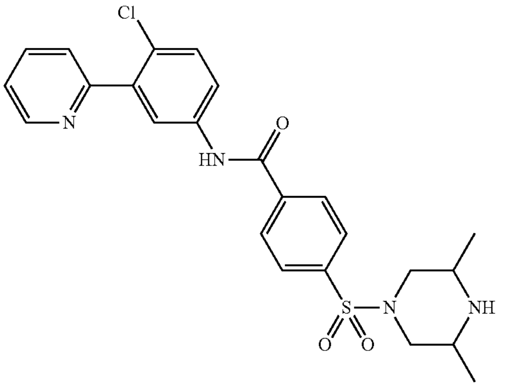
255
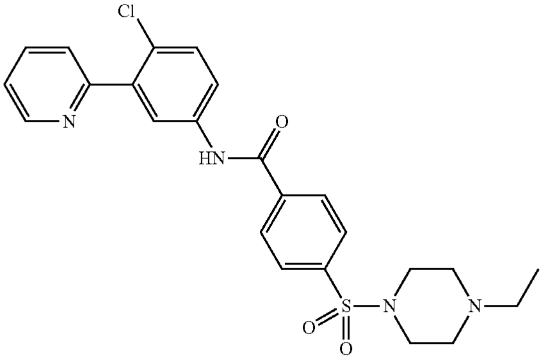
256
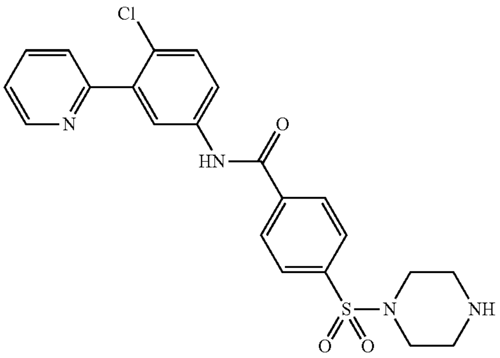
-continued
257
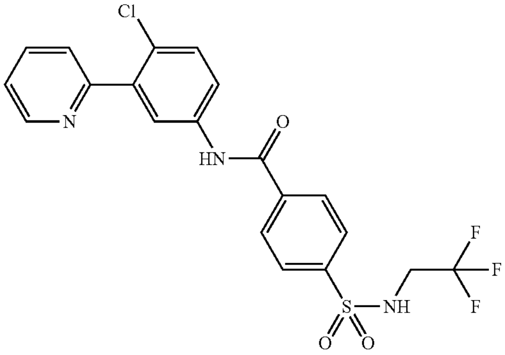
258
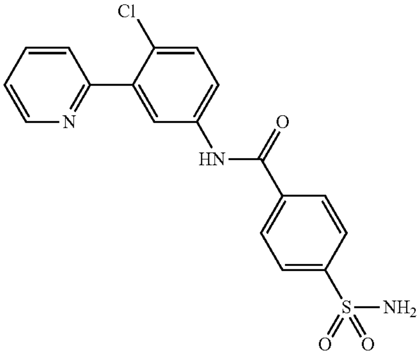
259
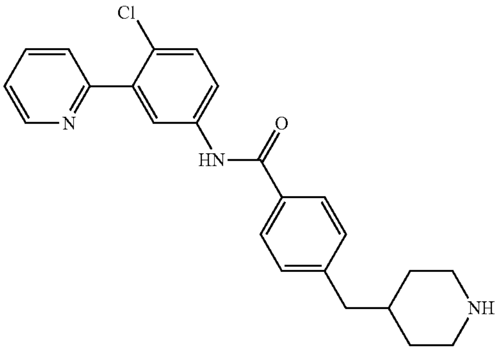
260
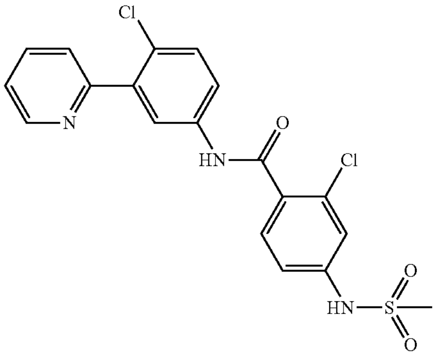

-continued
261
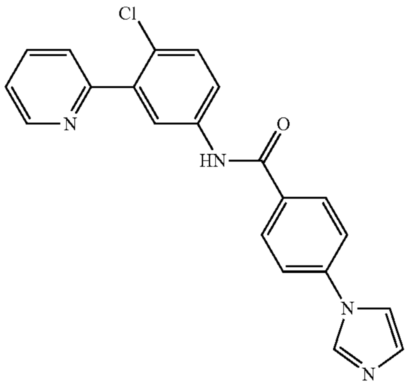
262
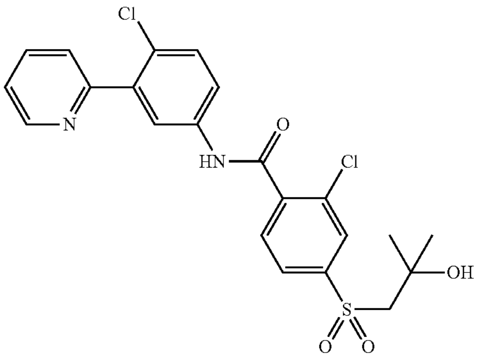
263
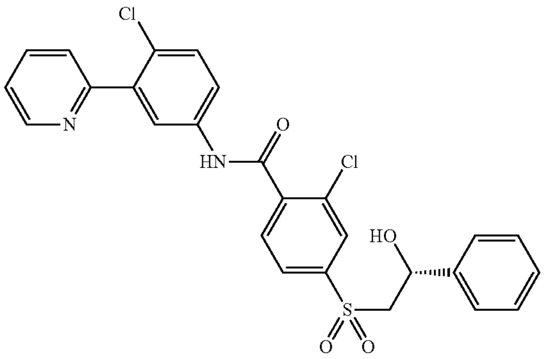
264
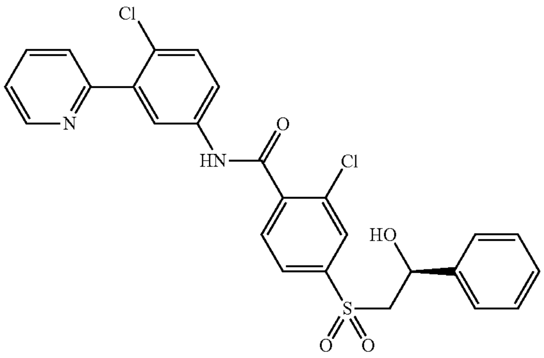
-continued
265
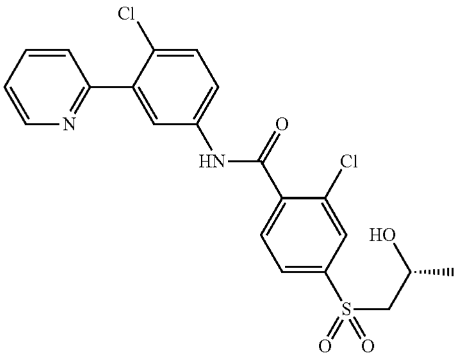
266
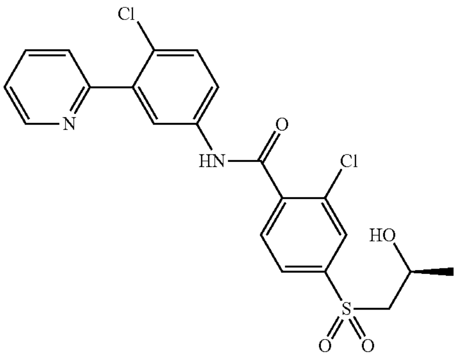
267
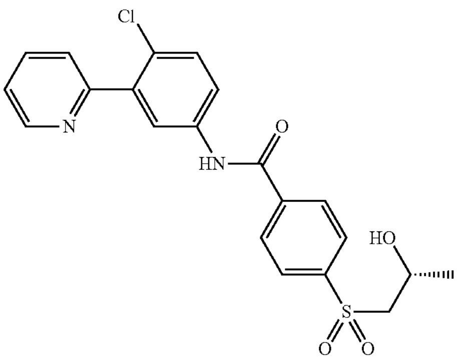
268
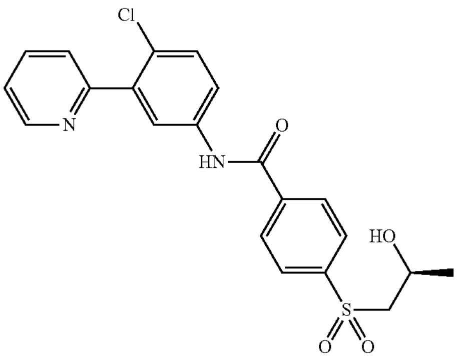

-continued
269
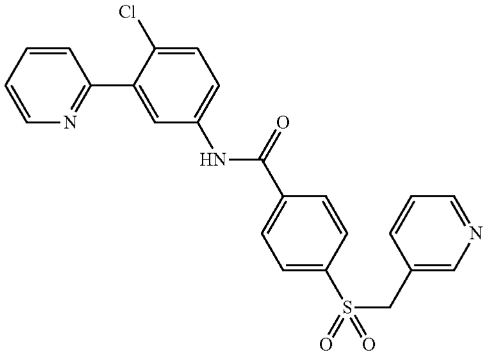
270
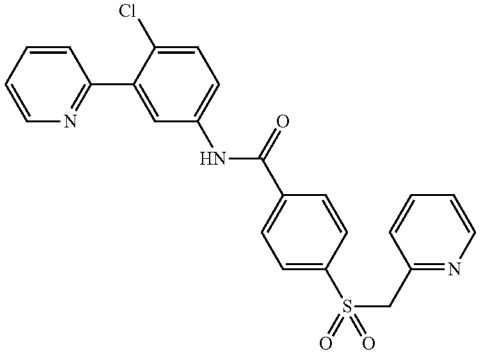
271
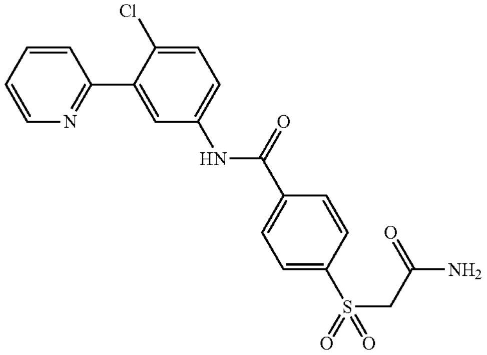
272
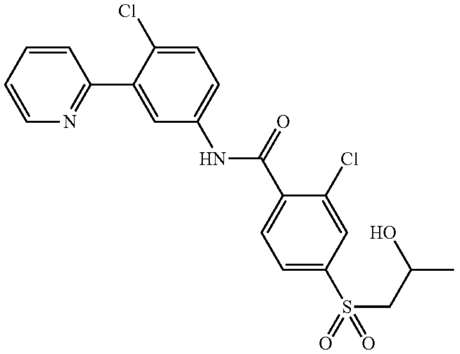
-continued
273
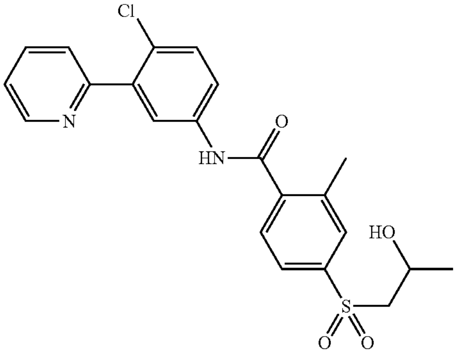
274
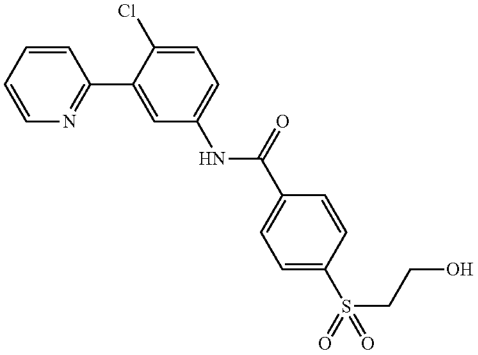
275
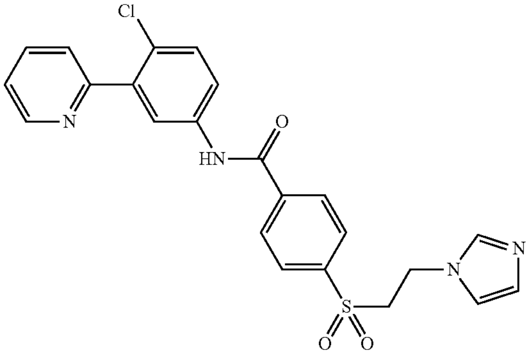
276
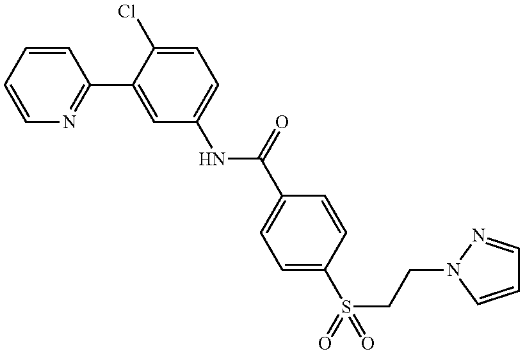

-continued
277
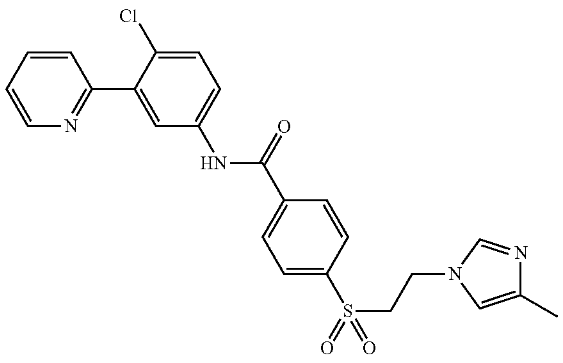
278
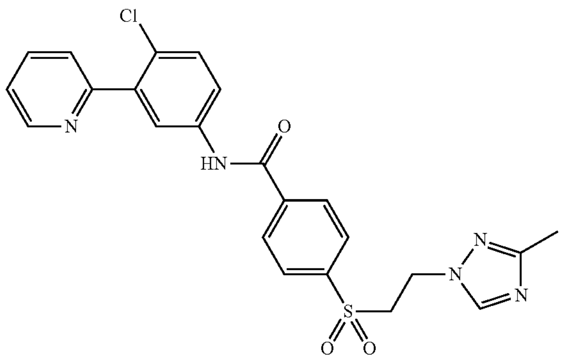
279
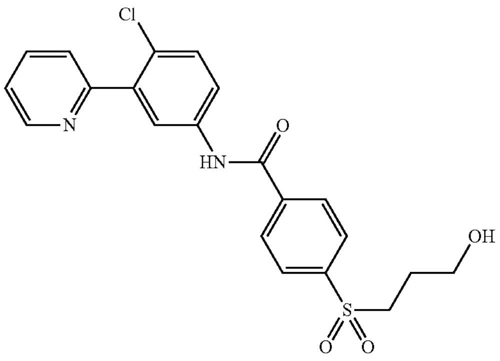
280
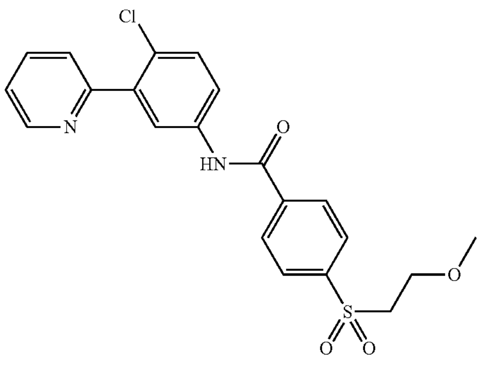
-continued
281
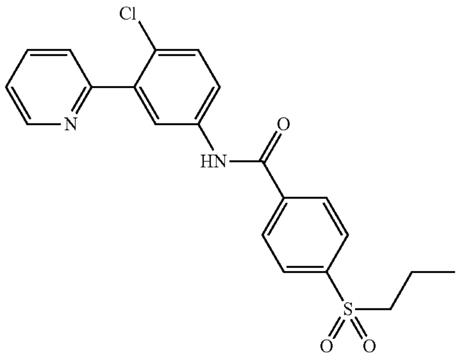
282
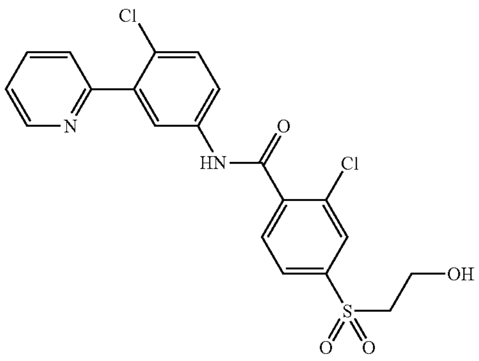
283
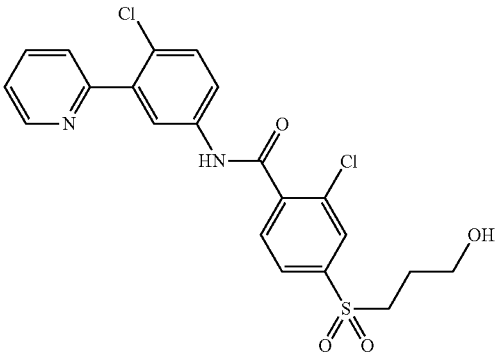
284
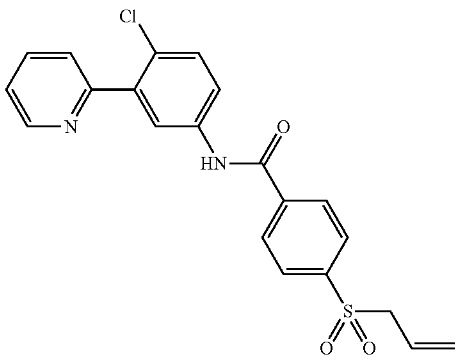

-continued
285
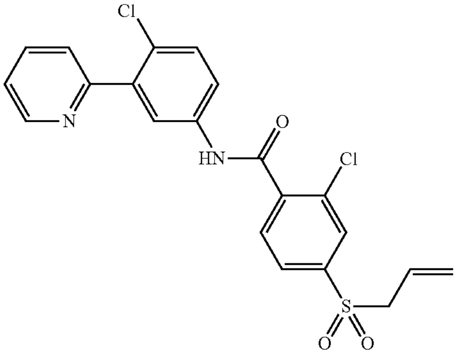
286
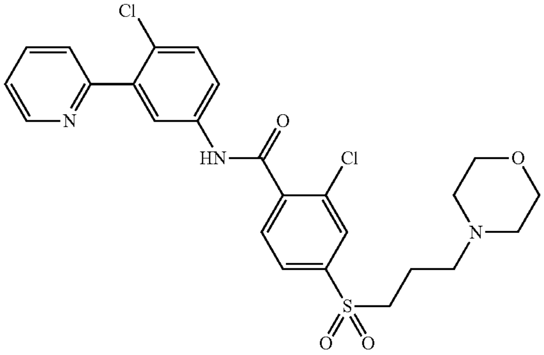
287
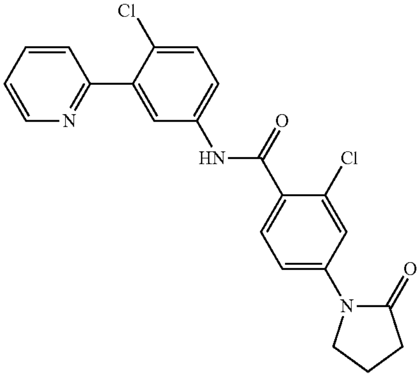
288
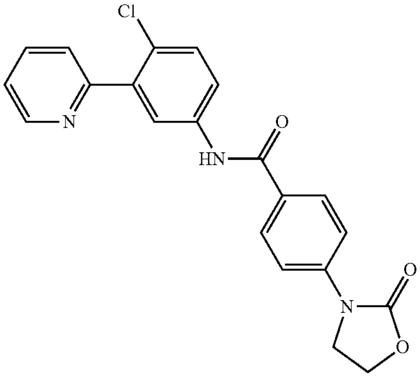
-continued
289
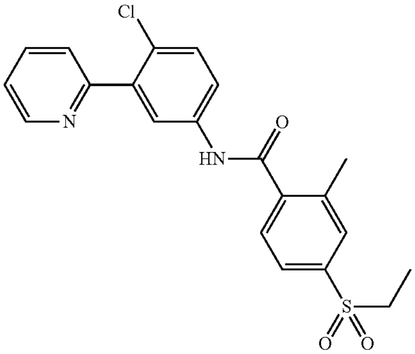
290
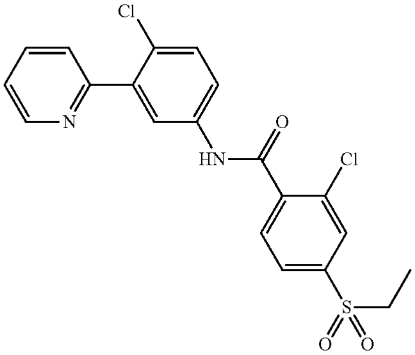
291
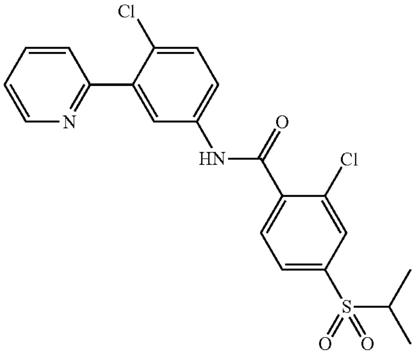
292
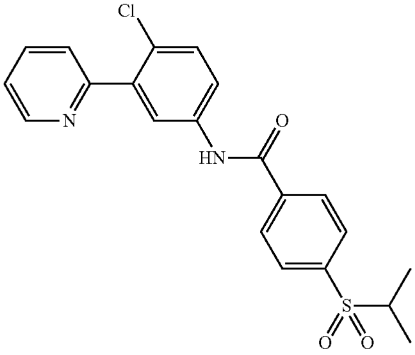

-continued
293
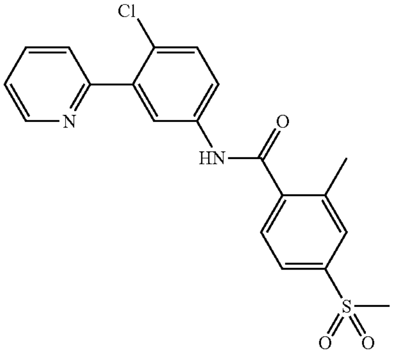
294
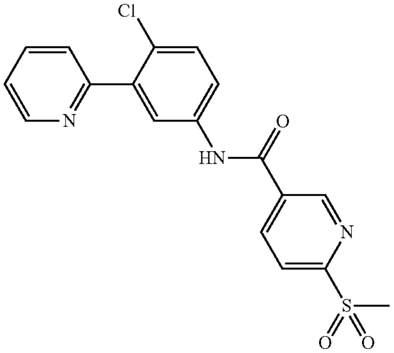
295
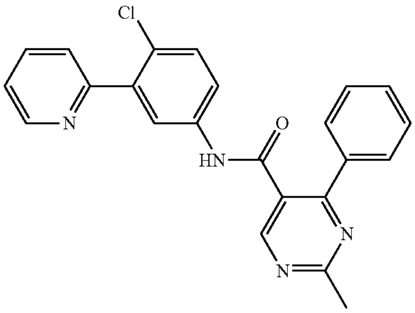
296
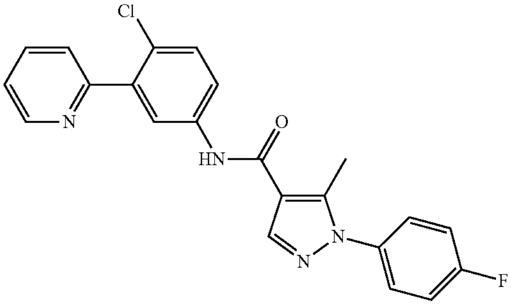
-continued
297
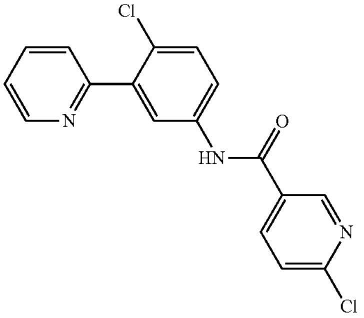
298
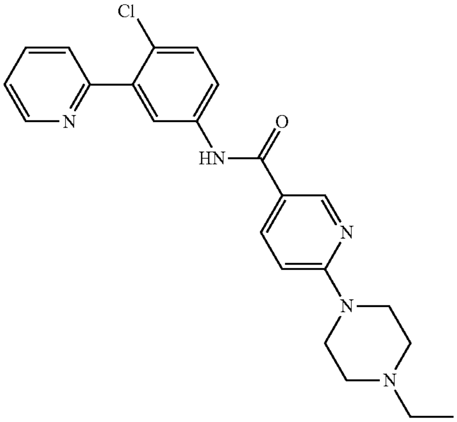
299
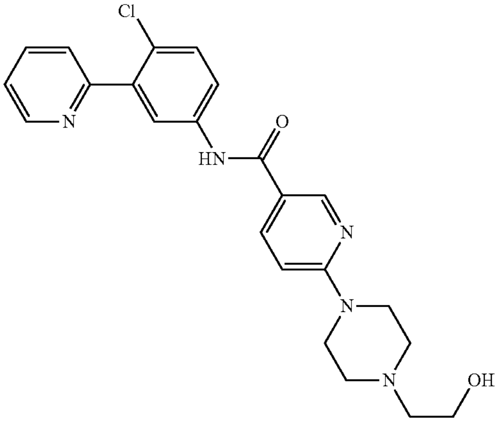
300
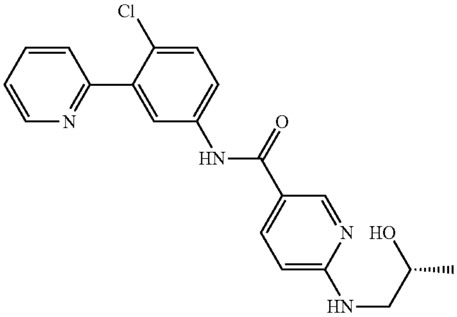

-continued
301
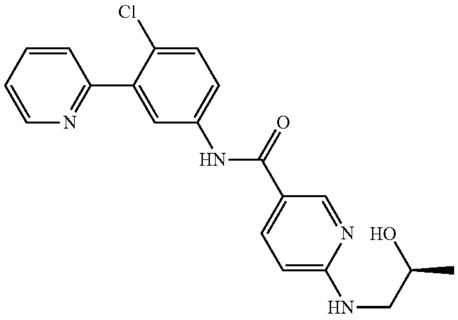
302
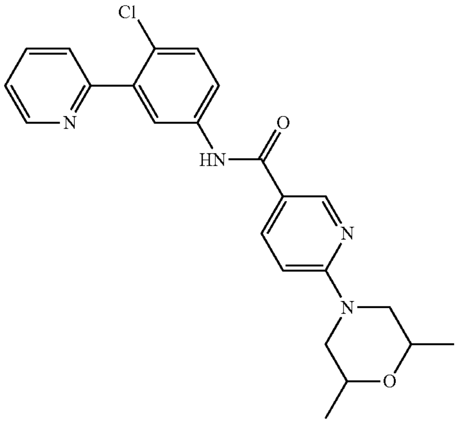
303
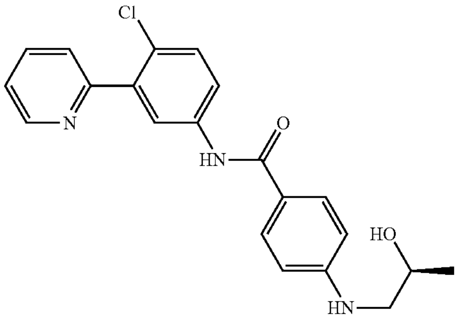
304
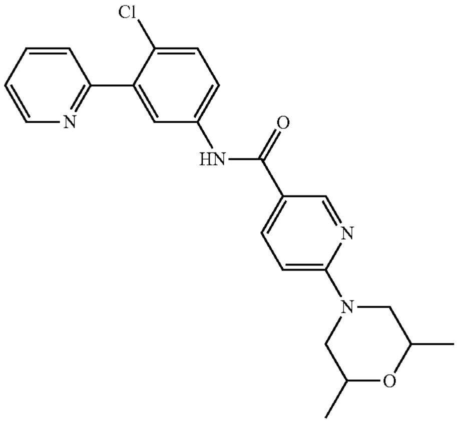
-continued
305
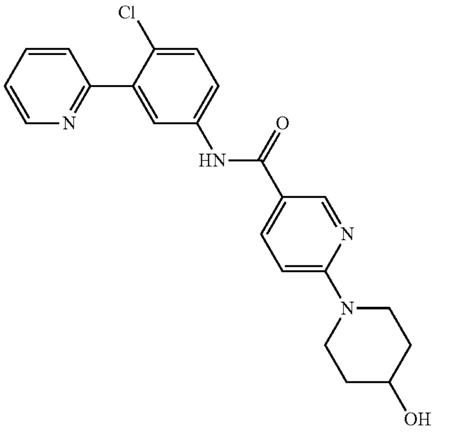
306
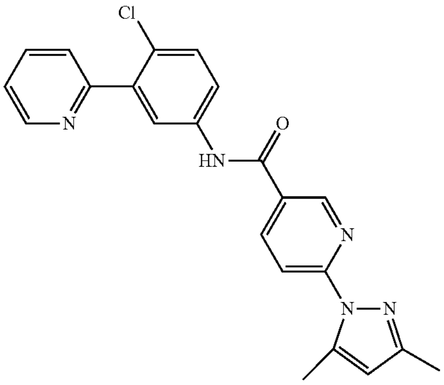
307
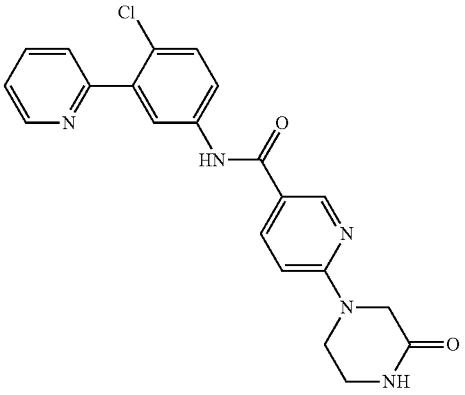
308
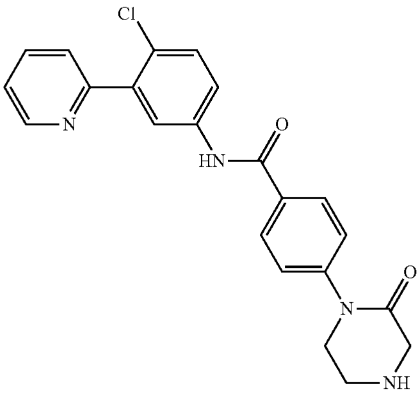

-continued
309
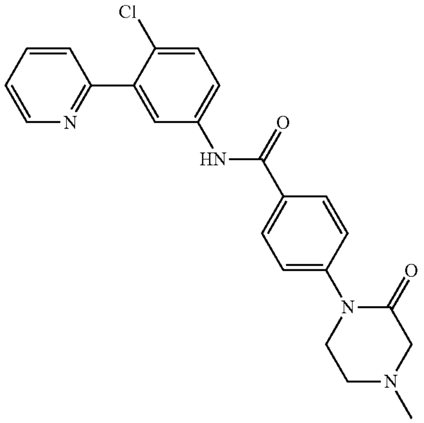
310
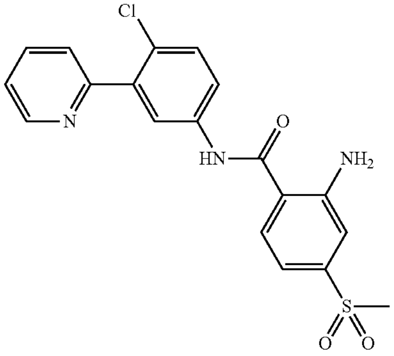
311
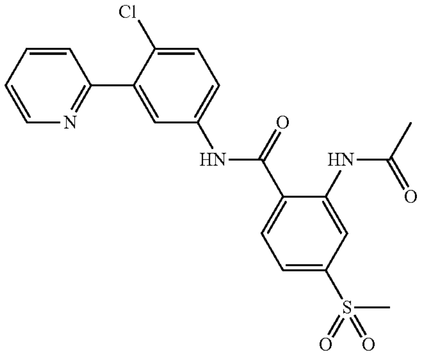
312
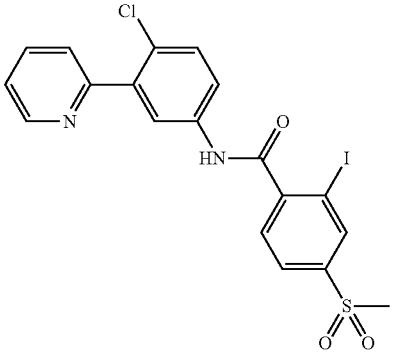
-continued
313
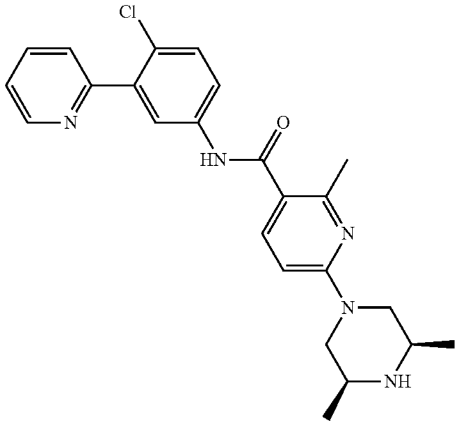
314
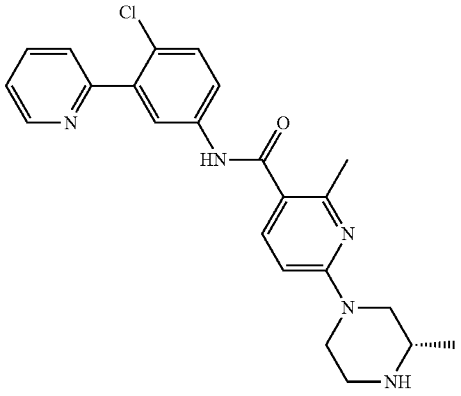
315
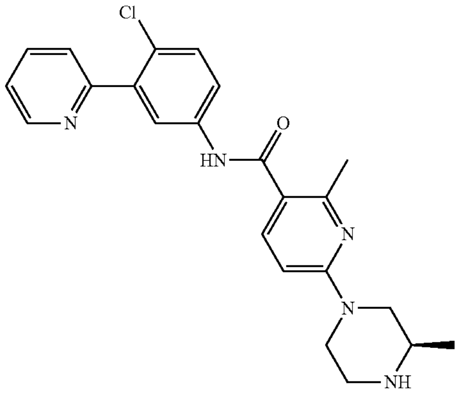
316
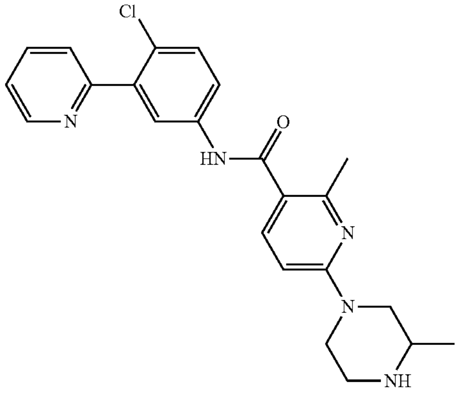

-continued
317
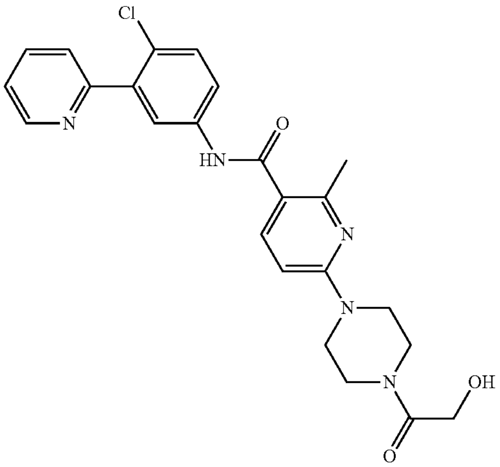
318
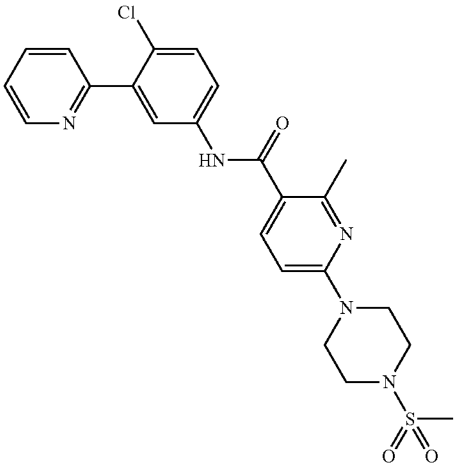
319
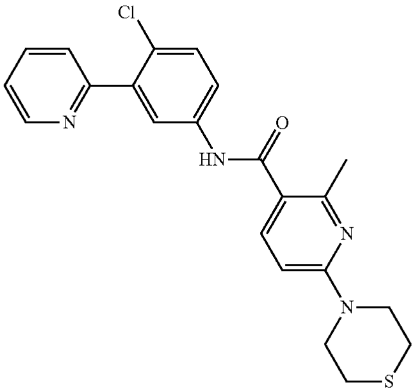
-continued
320
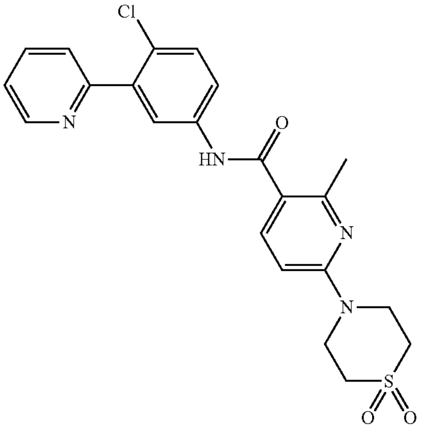
321
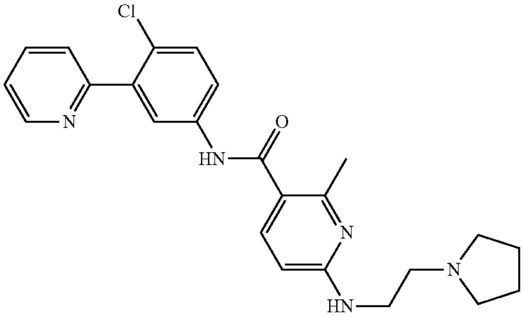
322
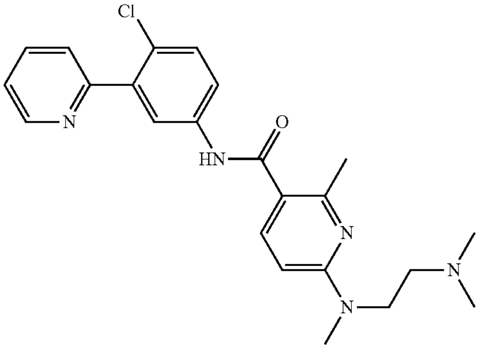
323
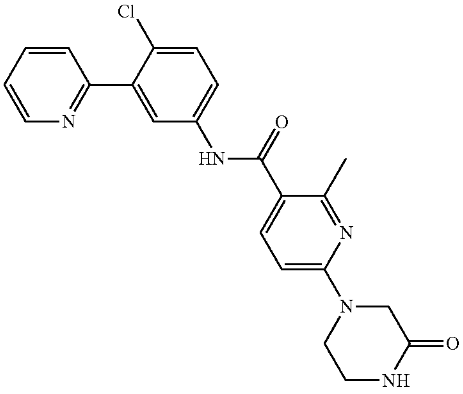

-continued
324
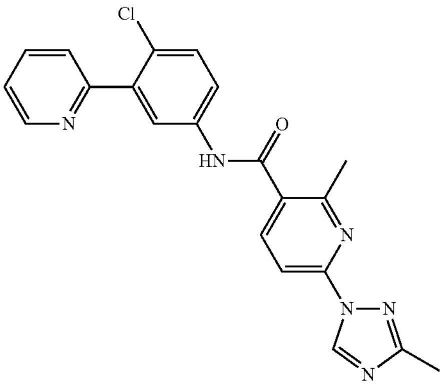
325
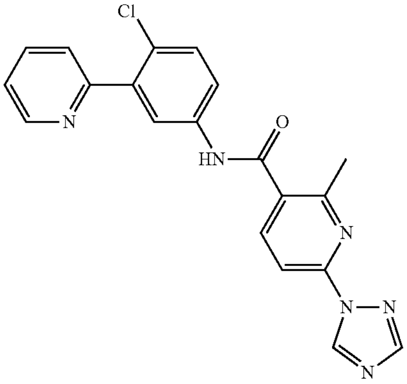
326
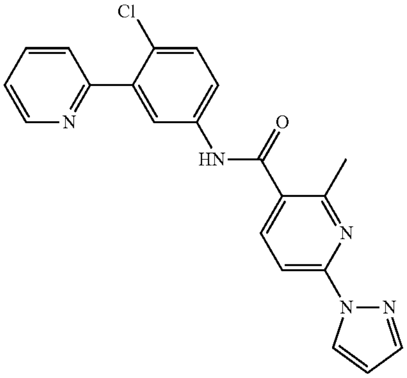
327
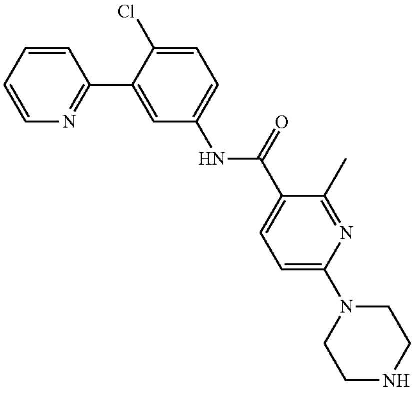
-continued
328
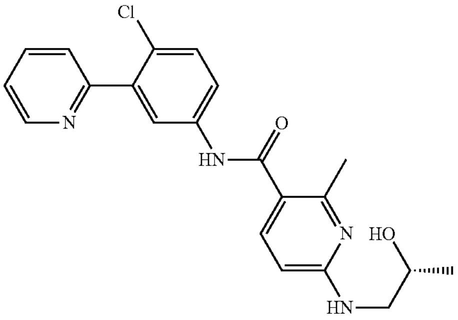
329
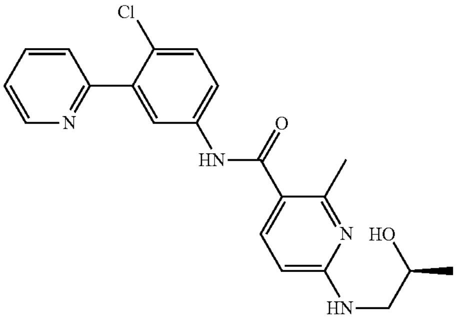
330
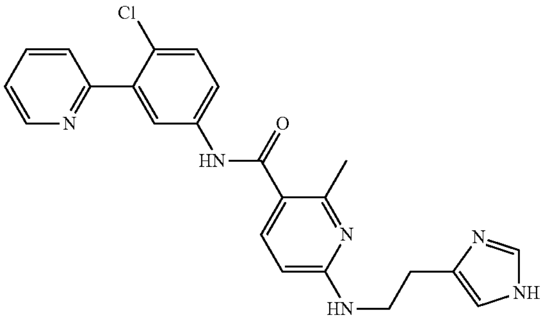
331
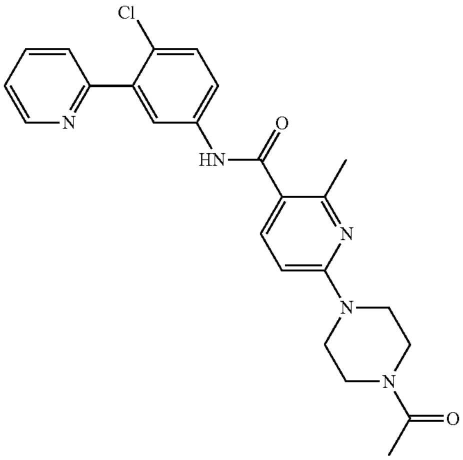

332
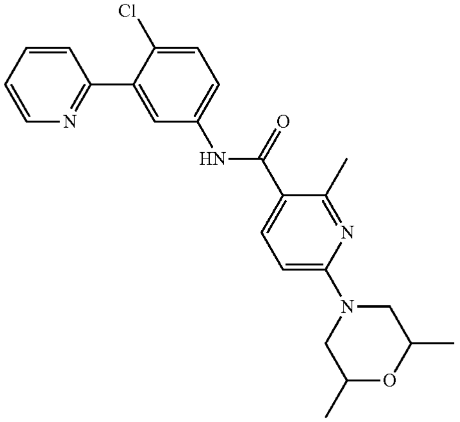
333
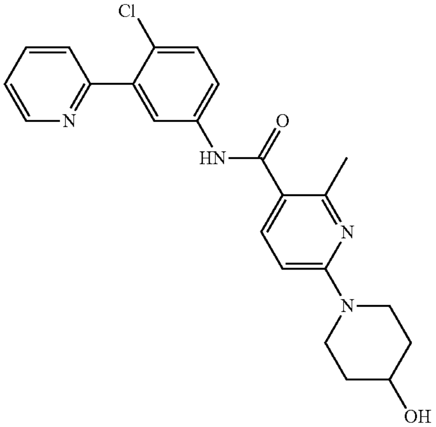
334
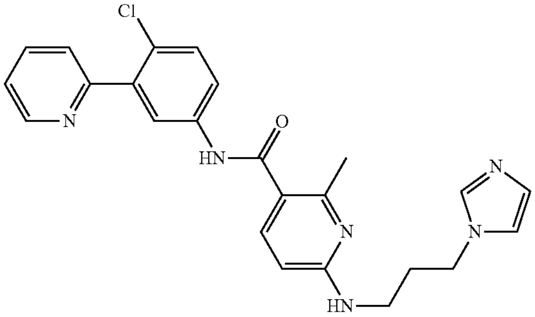
335
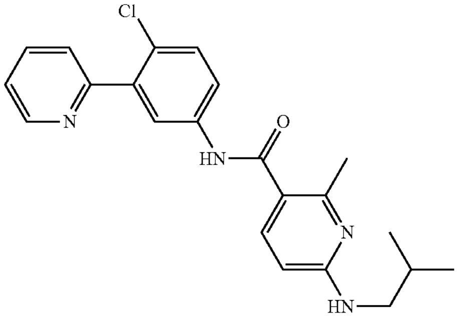
336
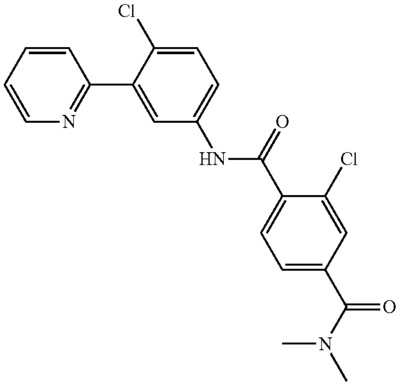
337
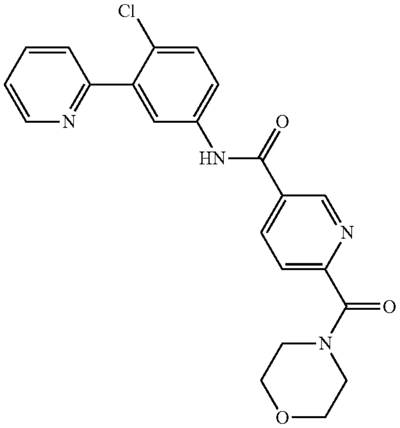
338
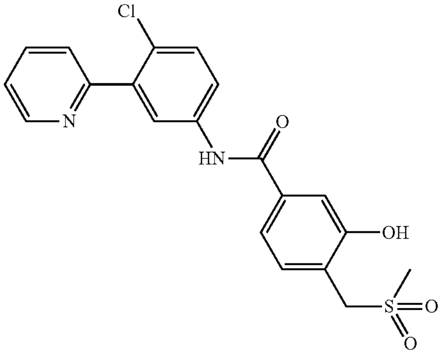
339
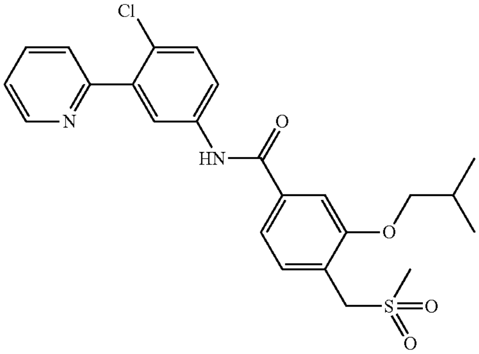

340
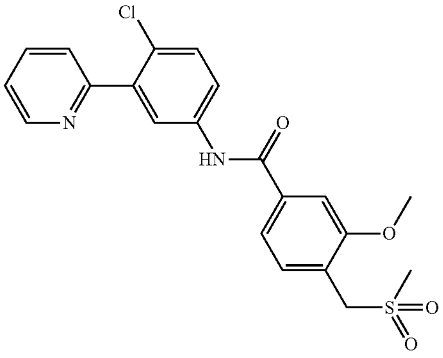
341
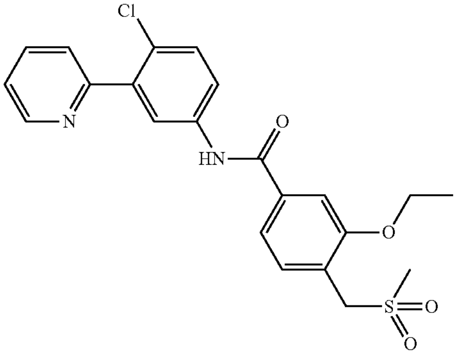
342
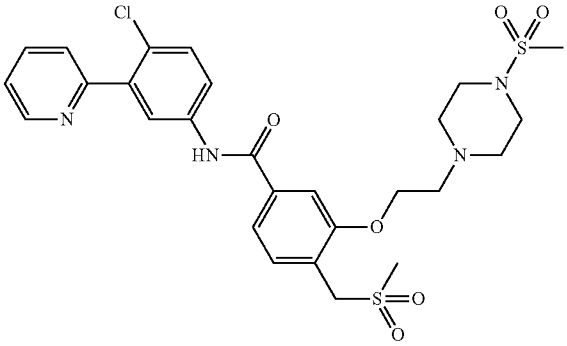
343
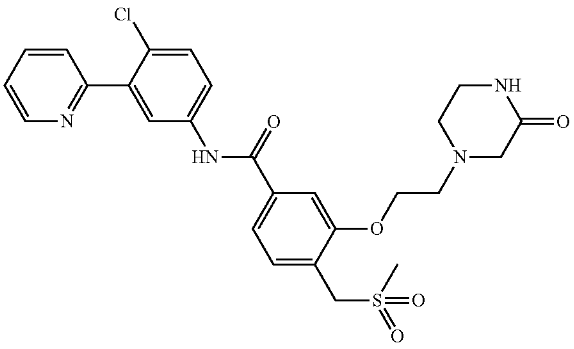
344
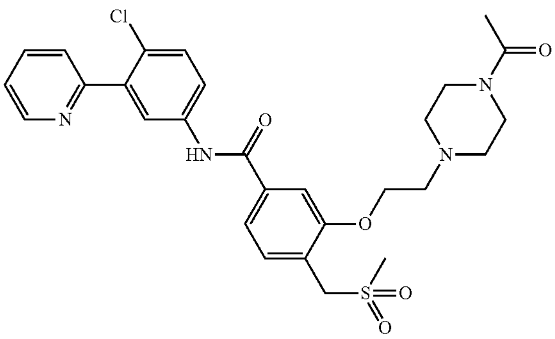
345
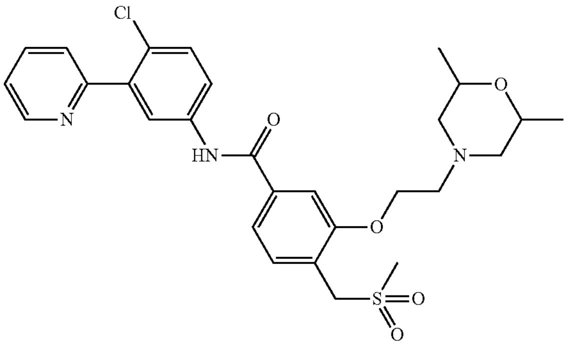
346
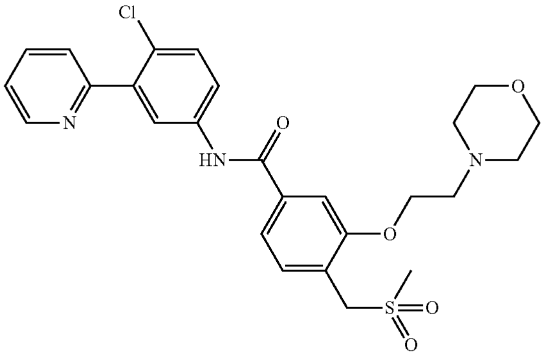
347
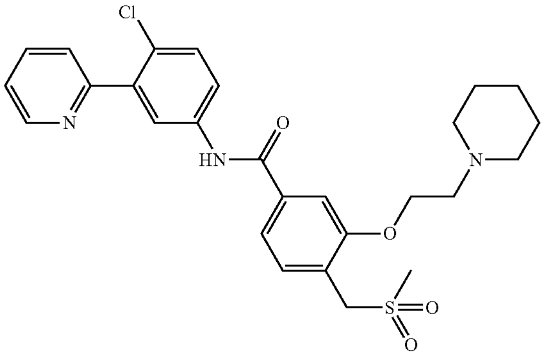

-continued
348
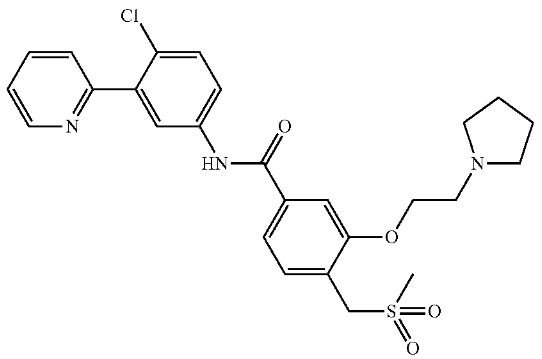
349
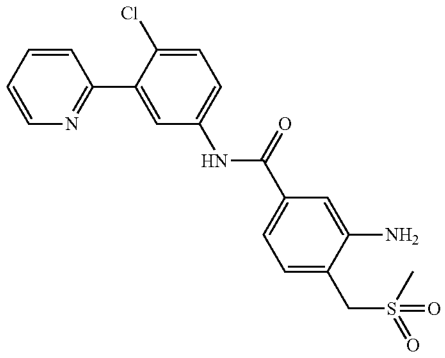
350
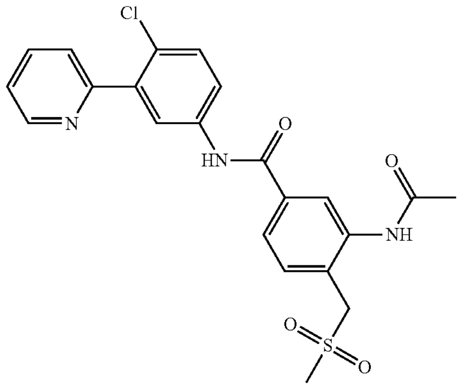
351
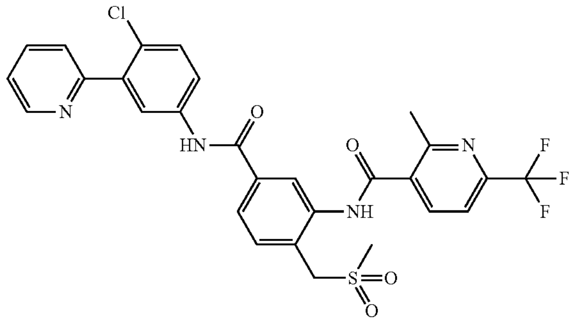
-continued
352
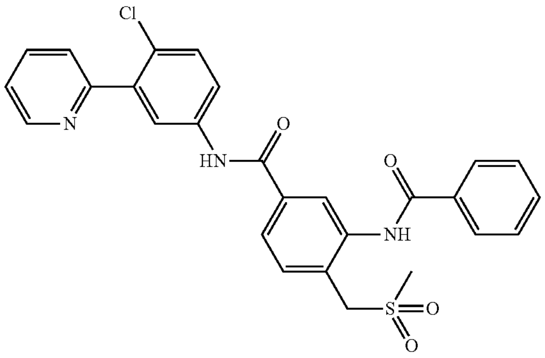
353
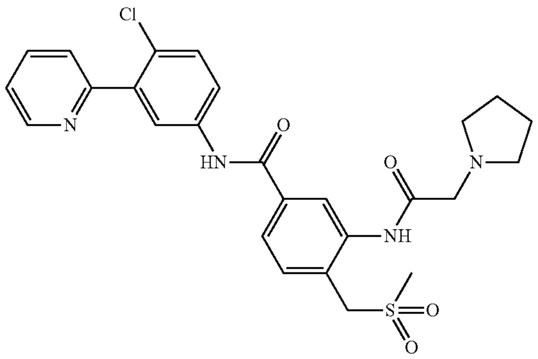
354
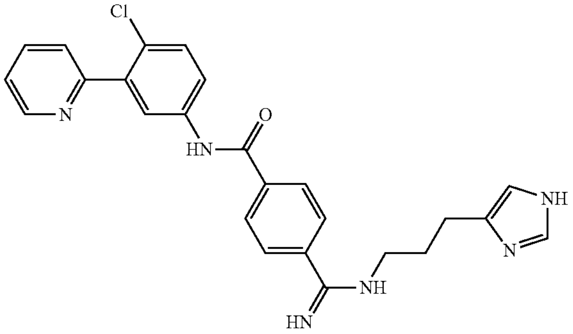
355
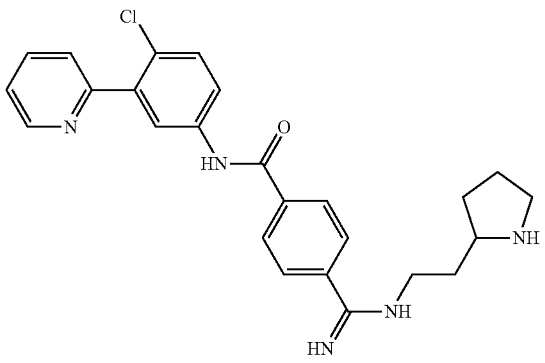

-continued
356
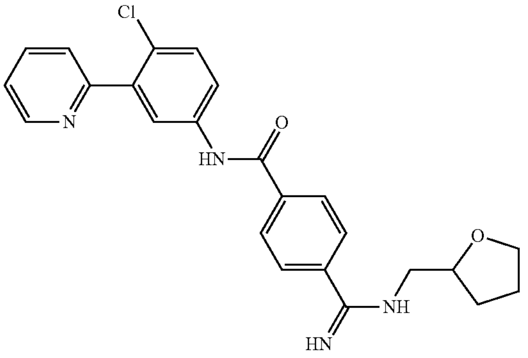
357
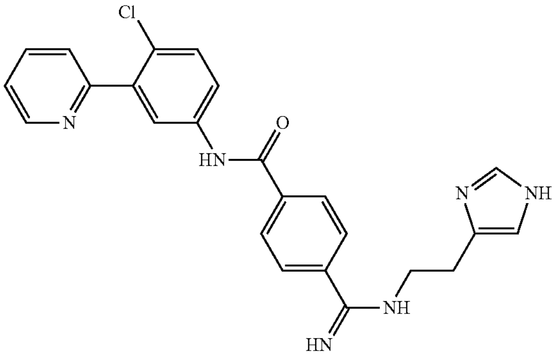
358
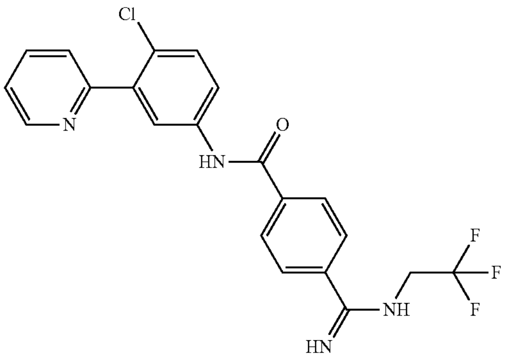
359
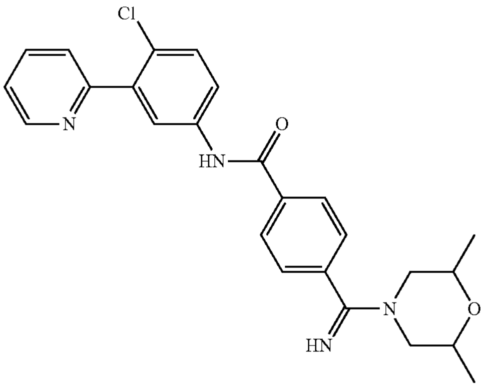
-continued
360
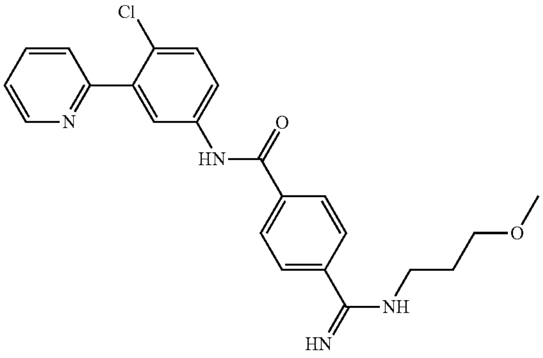
361
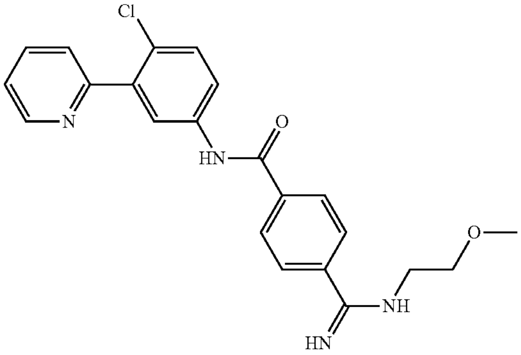
362
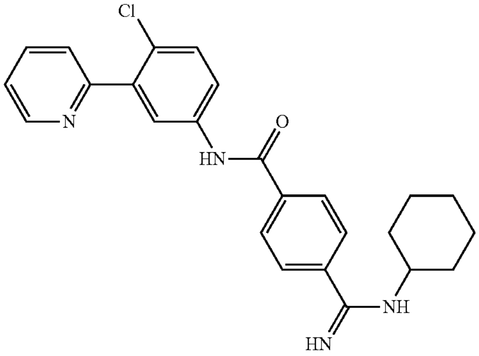
363
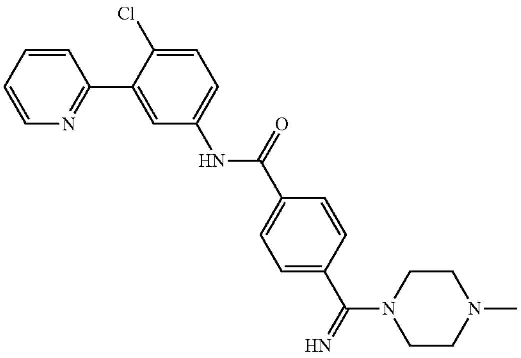

-continued

364

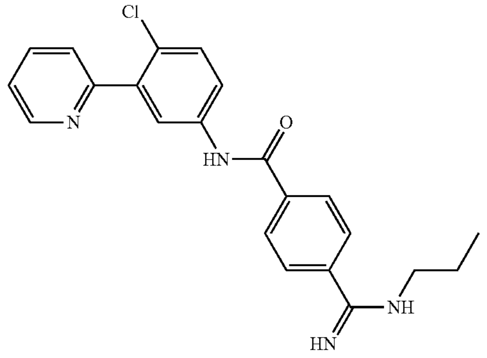

365

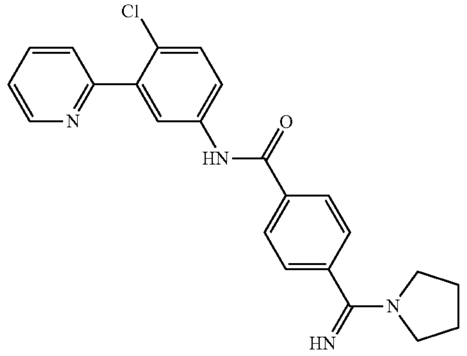

366

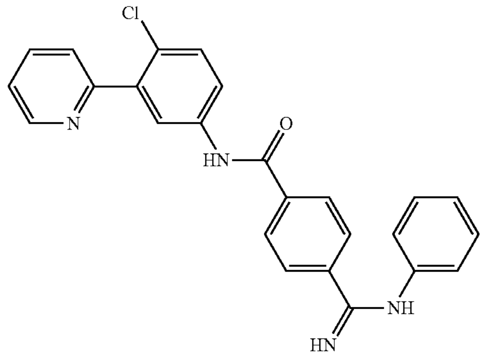

367

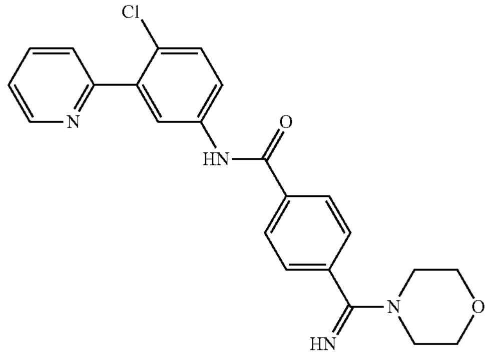

-continued

368

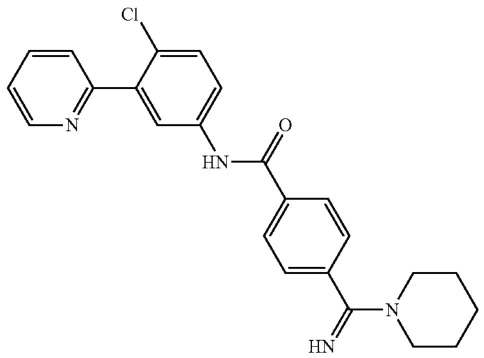

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

The invention also encompasses prodrugs of the compounds described above. Suitable prodrugs include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. Prodrug compounds may be prepared by reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50° C. The reactions are usually also carried out in the presence of an inorganic base such as potassium carbonate or sodium bicarbonate, or an organic base such as an amine, including pyridine, TEA, etc. One manner of preparing prodrugs is described in U.S. Ser. No. 08/843,369 filed Apr. 15, 1997 (corresponding to PCT publication WO9846576) the contents of which are incorporated herein by reference in their entirety.

Synthesis

Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection procedures may be required as is standard in organic synthesis. Compounds of the invention in which Y is absent may prepared by a Negishi coupling procedure according to the following general scheme 1:

scheme 1

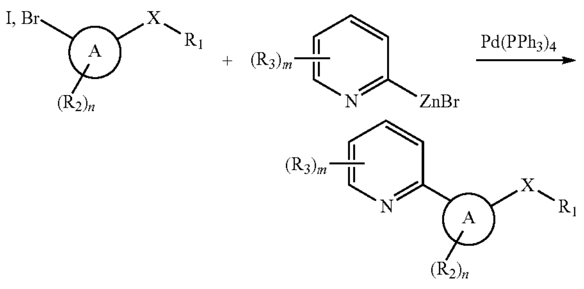

Ia in which the pyridyl zinc bromide (or alternatively pyridylzinc chloride) is reacted with an iodo or bromo substituted ring A to give the final compound Ia. Alternatively, compounds Ia of the invention may be prepared using a Suzuki coupling reaction of a borylated ring A to provide direct linkage between the appropriate pyridyl and ring A according to scheme 2.

scheme 2

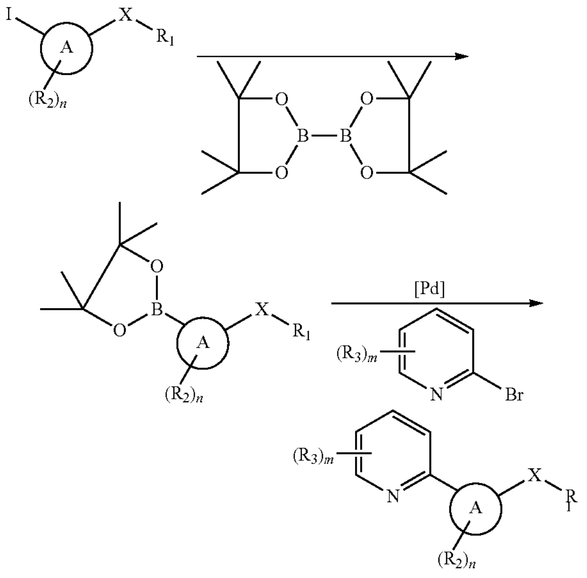

Ia

A halogen-substituted ring A is reacted with a boron ester such as pinacol diborane in the presence of palladium catalyst such as $PdCl_2$(dppf) and the resulting boronate ester is heated with a 2-halogen-substituted pyridine and a palladium catalyst to give a final compound Ia of the invention.

Compounds of the invention in which Y is $NR_4$ may prepared by palladium catalyzed amination of halogen-substituted ring A with the desired 2-aminopyridine according to scheme 3.

scheme 3

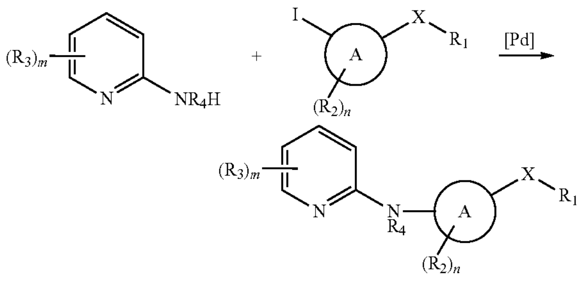

Ib

Compounds of the invention in which X is $NR_4CO$ may be prepared by the general scheme 4 in which amine-substituted ring A is reacted with the desired acid chloride $C_1$—C(O)—$R_1$.

scheme 4

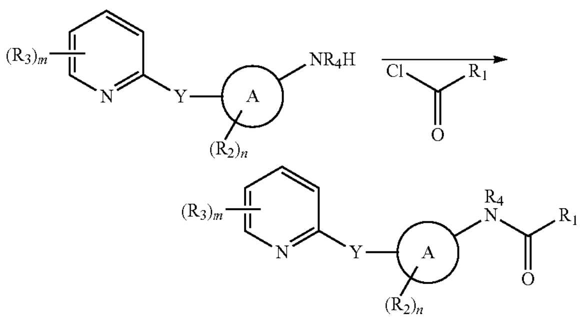

Alternatively, such compounds may be prepared from by EDC catalyzed coupling of a carboxy-substituted ring A with an amine-substituted $R_1$ group, i.e. $R_1$—$NR_4H$. The same scheme may be used to prepare thioamide compounds of the invention, i.e. X is $NR_4C(S)$, by employing an appropriate thio acid chloride Cl—C(S)—$R_1$, in the acylation step.

Compounds of the invention in which X is $C(O)NR_4$ may be similarly prepared by reacting an amine-substituted ring A with a carboxy-substituted $R_1$ group and EDC catalyst according to scheme 5.

scheme 5

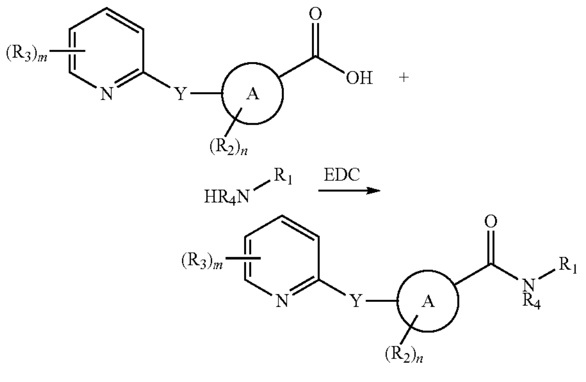

A similar scheme may be used to prepare thioamide compounds of the invention, i.e. X is $C(S)NR_4$, by employing an appropriate thioic acid-substituted ring A (e.g. —C(S)OH) or by converting the amide with Lawesson's reagent.

Compounds of the invention in which X is $NR_4C(O)NH$ may be prepared according to the general scheme 6 by reacting amine-substituted ring A with the appropriate isocyanate $R_1$—NCO.

Scheme 6

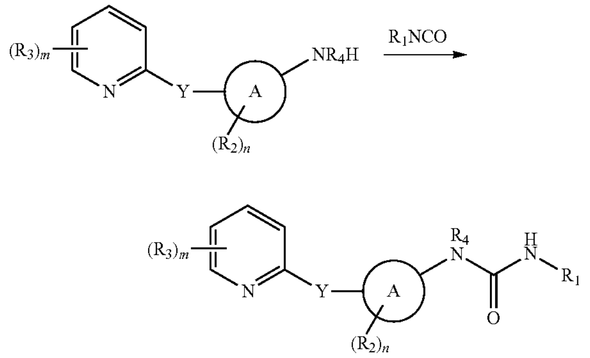

The same scheme may be used to prepare thiourea compounds of the invention, i.e. X is $NR_4C(S)NH$, by employing an appropriate isothiocyanate $R_1$—NCS in place of the isocyanate $R_1$—NCO.

Compounds of the invention in which X is $NR_4SO_2$ may be prepared according to the general scheme 7 by reacting an amine-substituted ring A with the appropriate sulfonyl chloride $R_1$—$S(O_2)Cl$ in the presence of a non-nucleophilic base such as TEA or diisopropylethylamine to form the desired sulfonamide.

Scheme 7

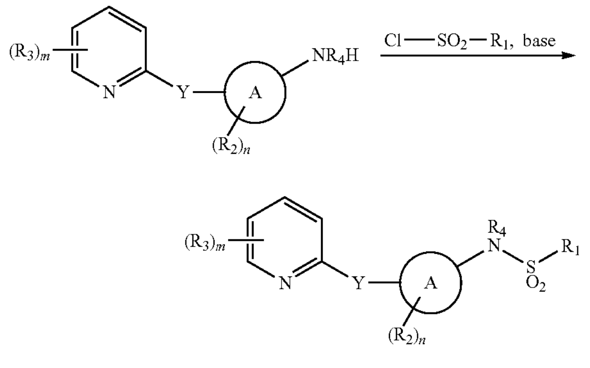

Compounds of the invention in which X is $NR_4SO$ are similarly prepared using the appropriate sulfinyl chloride $R_1$—SO—Cl instead of the sulfonyl chloride $R_1$—$S(O_2)Cl$.

Compounds of the invention having the structure of formula Ib' in which X is NHCO (i.e. formula Ib") may be prepared according to the general scheme 8 in which $R_3$, $R_6$, m and o are as defined herein and Q is Cl, Br or I; Q' is halogen, OH, OR wherein R is an activating group; L is Br, I or OTf (e.g. O—SO2-$CF_3$):

Scheme 8

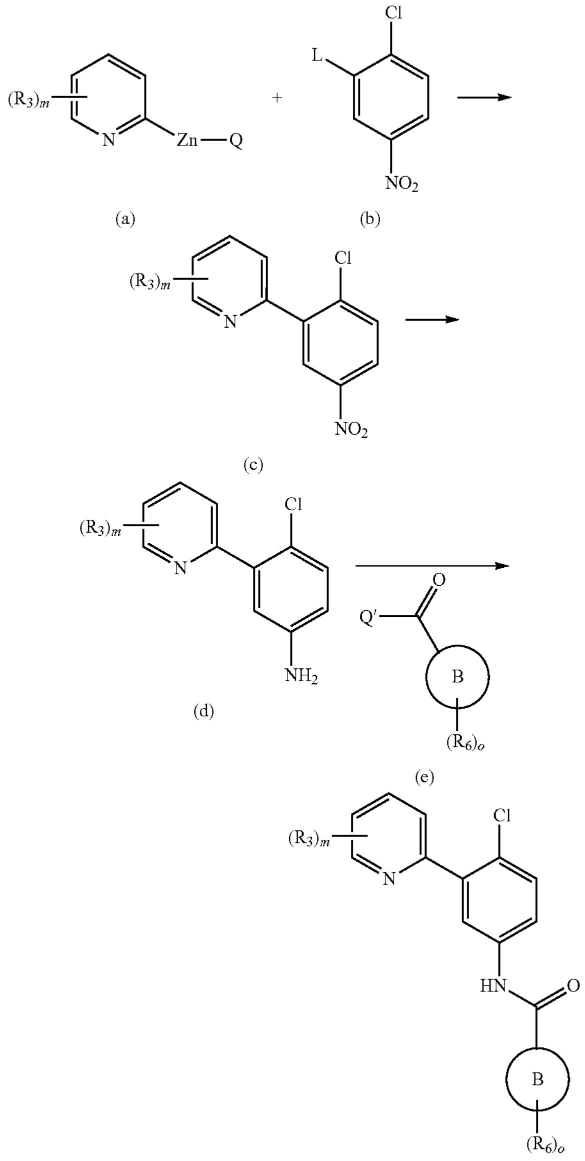
(a) (b)
(c)
(d) (e)

Ib"

The zinc halide pyridine reagent (a) is reacted with 2-chloro-5-nitro-benzene reagent (b) in a Negishi coupling reaction in the presence of a suitable catalyst such as palladium tetrakis(triphenylphosphine) complex ($Pd(PPh_3)_4$). In a particular embodiment, the palladium tetrakis(triphenylphosphine) catalyst is stablized with triphenylphosphine ($PPh_3$). In a particular embodiment Q is Br. In a particular embodiment L is I. In a particular embodiment, the coupling reaction is performed from about 50° C. to about 60° C.

The nitrobenzene reagent (b) may be obtained from activating the corresponding amine (i.e. 2-chloro-5-nitroaniline) in an aqueous sulfuric acid solution with sodium nitrite and displacing with an L group (e.g. with KI, KBr). In a particular embodiment, L is I. In a particular embodiment the reaction is performed at less than about 15° C.

The resulting intermediate (c) is reduced, for example with Fe, Zn or $SnCl_2$ in presence of acid to give the amine intermediate (d). In a particular embodiment, intermediate (c) is reduced with Fe, for example, in the presence of AcOH in EtOH. In a particular embodiment, intermediate (c) is reduced with Zn, for example in the presence of AcOH in EtOH. In a partiuclar embodiment, intermediate (c) is reduced with $SnCl_2$, for example in the presence of HCl in EtOH. In a particular embodiment the reduction reaction is performed at about 60° C.

Finally, intermediate (d) is reacted with an activated acid (e) to yield final compound Ib". In a particular embodiment, the activated acid (e) is an acid halide (e.g. Q' is chloride) or activated ester (e.g. Q' is O-EDC). In a particular embodiment the final reaction is performed at about 0° C.

The compounds of the invention inhibit the hedgehog signaling and are useful for the treatment of cancers associated with aberrant hedgehog signaling, for example when Patched fails to, or inadequately, represses Smoothened (Ptc loss-of-function phenotype) and/or when Smoothened is active regardless of Patched repression (Smo gain-of-function phenotype). Examples of such cancer types include basal cell carcinoma, neuroectodermal tumors such as medullablastoma, meningioma, hemangioma, glioblastoma, pancreatic adenocarcinoma, squamous lung carcinoma, small-cell lung carcinoma, non-small cell lung carcinoma, chondrosarcoma, breast carcinoma, rhabdomyosarcoma, oesophageal cancer, stomach cancer, biliary tract cancer, renal carcinoma, thyroid carcinoma. Compounds of the invention may be administered prior to, concomitantly with, or following administration of other anticancer treatments such as radiation therapy or chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphteria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, ST1571 (CPG 57148B) or UCN-01 (7-hydroxystaurosporine); (x) miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present invention are coadministered with a cytostatic compound selected from the group consisting of cisplatin, doxorubicin, taxol, taxotere and mitomycin C.

Another class of active compounds which can be used in the present invention are those which are able to sensitize for or induce apoptosis by binding to death receptors ("death receptor agonists"). Such agonists of death receptors include death receptor ligands such as tumor necrosis factor a (TNF-α), tumor necrosis factor β (TNF-β, lymphotoxin-α), LT-β (lymphotoxin-β), TRAIL (Apo2L, $DR_4$ ligand), CD95 (Fas, APO-1) ligand, TRAMP ($DR_3$, Apo-3) ligand, $DR_6$ ligand as well as fragments and derivatives of any of said ligands. In a particular embodiment, the death receptor ligand is TNF-α. In another particular embodiment the death receptor ligand is Apo2L/TRAIL. Furthermore, death receptors agonists comprise agonistic antibodies to death receptors such as anti-CD95 antibody, anti-TRAIL-$R_1$ ($DR_4$) antibody, anti-TRAIL-$R_2$ ($DR_5$) antibody, anti-TRAIL-$R_3$ antibody, anti-TRAIL-$R_4$ antibody, anti-$DR_6$ antibody, anti-TNF-$R_1$ antibody and anti-TRAMP ($DR_3$) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration including the location of the tumor in relation to other organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention. Furthermore, the present invention encompasses types of non-ionizing radiation like e.g. ultraviolet (UW) radiation, high energy visible light, microwave radiation (hyperthermia therapy), infrared (IR) radiation and lasers. In a particular embodiment of the present invention UV radiation is applied.

Compounds of the invention inhibit angiogenesis and are therefore useful in the treatment of diseases or conditions mediated by angiogenesis such as tumors, in particular solid tumors such as colon, lung, pancreatic, ovarian, breast and glioma. Furthermore, compounds of the invention are useful for treating macular degeneration e.g. wet age-related macular degeneration. Compounds of the invention are also useful for treating inflammatory/immune diseases such as Crohn's, inflammatory bowel disease, Sjogren's syndrome, asthma, organ transplant rejection, systemic lupus erythmatoses, rheumatoid arthritis, psoriatic arthritis, psoriasis and multiple sclerosis. Compounds of the invention are also useful as a depilatory.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of the invention used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but may range from about 3 to about 8. A particular formulation is an acetate buffer at pH 5. The compounds for use herein may be in a sterile formulation. The compound may be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to decrease hedgehog pathway signaling or else is the minimum amount necessary to cause reduction in size, volume or mass of a tumor that is responsive to hedgehog signaling, or a reduction in the increase in size, volume or mass of such a tumor relative to the increase in the absence of administering the compound of the invention. Alternatively "effective amount" of the compound means the amount necessary to reduce the number of malignant cells or the rate in increase of the number of malignant cells. Alternatively, "effective amount" is the amount of the compound of the invention required to increase survival of patients afflicted with an anti-hedgehog pathway sensitive tumor. Such amount may be below the amount that is toxic to normal cells, or the mammal as a whole. With respect to non-malignant indications, "effective amount" means the amount of compound of the invention required to decrease severity of the particular indication or symptoms thereof.

Generally, the initial pharmaceutically effective amount of the compound of the invention administered parenterally per dose will be in the range of about 0.01 to about 100 mg/kg, for example about 0.1 to about 20 mg/kg of patient body weight per day, for example about 0.3 to about 15 mg/kg/day. Oral unit dosage forms, such as tablets and capsules, may contain from about 25 to about 1000 mg of the compound of the invention.

The compound of the invention may be administered by any suitable means, including oral, topical, transdermal, parenteral, subcutaneous, rectal, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants. Topical formulations include ointments, creams, lotions, powders, solutions, pessaries, sprays, aerosols and capsules. Ointments and creams may be formulated with an aqueous or oily base with the addition of suitable thickening and/or gelling agents and/or solvents. Such bases may include water and/or an oil such a liquid paraffin or a vegetable oil such as arachis oil or castor oil or a solvent such as a polyethylene glycol. Thickening agents which may be used include soft paraffin, aluminum stearate, cetostearyl alcohol, polyethylene glycols, microcrystalline wax and beeswax. Lotions may be formulated with an aqueous or oily base and may contain one or more emulsifying agents, stabilizing agents, dispersing agents, suspending agents or thickening agents. Powders for external application may be formed with the aid of any suitable powder base e.g. talc, lactose or starch. Drops may be formulated with an aqueous or non-aqueous base also comprising one or more dispersing agents, solubilizing agents or suspending agents.

EXAMPLES

The invention will be more fully understood by reference to the following examples. They should not, however, be construed as limiting the scope of the invention. Abbreviations used herein are as follows:

BuOH: butanol;
DIPEA: diisopropylethylamine;
DMA: N,N-dimethylacetamide;
DMAP: 4-dimethylaminopyridine;
DME: 1,2-dimethoxyethane;
DMF: dimethylformamide;
EDC: 1-ethyl-3-(3-dimethylaminopropyl)carbodiimide;
HATU: O-(7-Azobenzotriazol-1-yl)-1,1,3,3-tetramethyluronium hexafluorophosphate;
HPLC: high pressure liquid chromatography
MPLC: medium pressure liquid chromatography
NBS: N-Bromosuccinimide;
TEA: Triethylamine;
TASF: tris(dimethylamino)sulfonium difluorotrimethylsilicate;
THF: tetrahydrofuran;
EtOH: Ethanol;
MeOH: Methanol;
□L: microliter All reagents were obtained commercially unless otherwise noted. Reactions were performed using oven-dried glassware under an atmosphere of nitrogen. Air and moisture sensitive liquids and solutions were transferred via syringe or stainless steel cannula. Organic solutions were concentrated under reduced pressure (ca. 15 mm Hg) by rotary evaporation. Unless otherwise noted all solvents used were obtained commercially. Chromatographic purification of products was accomplished by use of an Isco CombiFlash Companion and media. Reaction times are given for illustration only. The course of reactions was followed by thin-layer chromatography (TLC) and liquid chromatography-mass spectrometry (LC-MS). Thin-layer chromatography (TLC) was performed on EM Science silica gel 60 $F_{254}$ plates (250 μm). Visualization of the developed chromatogram was accomplished by fluorescence quenching. LC-MS were acquired with a Shimadzu 10AD LC on a Phenomenex column (50×4.6 mm, 5 μm) operating at 3 mL/min. A Shimadzu SPD-10A detector monitoring at 214 and 254 nm was used. Single quadrupole mass spectrometry was performed on an Applied Biosystems mass spectrometer. Nuclear magnetic resonance (NMR) spectra were acquired on a Varian Inova spectrometer operating at 400 MHz for $^{1}H$ and are referenced internally to tetramethylsilane (TMS) in parts per million (ppm). Data for $^{1}H$ NMR are recorded as follows: chemical shift (δ, ppm), multiplicity (s, singlet; bs, broad singlet; d, doublet; t, triplet; q, quartet; quint, quintet; sext, sextet; hept, heptet; m, multiplet; bm, broad multiplet), and integration. The structure and purity of all final products were assessed by at least one of the following techniques: LC-MS, NMR, TLC.

Example 1

General Procedures

Compounds of examples 2-51 were prepared according to the following general procedures.

A: Suzuki Coupling Procedure

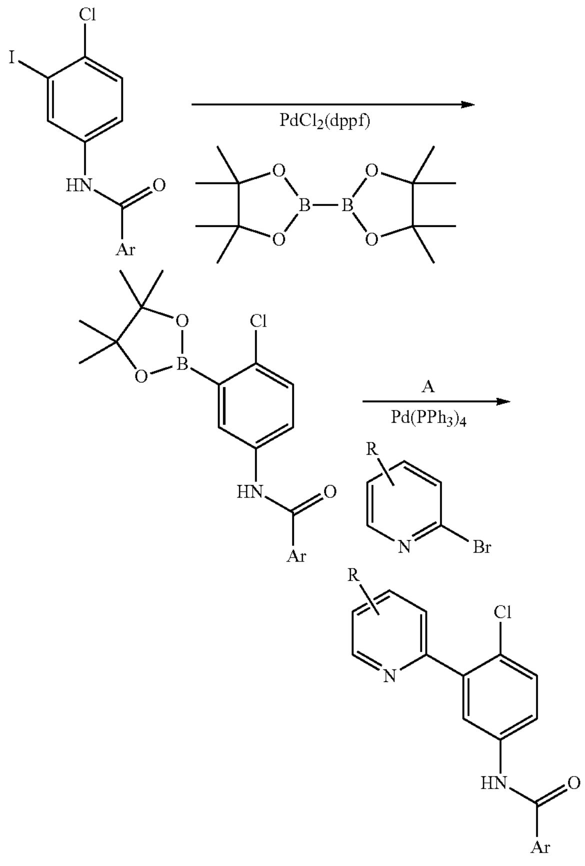

2 M aq. Potassium carbonate (5.0 eq) and 4:1 toluene: ethanol mixture (2.5 mL) were added to a microwave vial charged with the appropriate boronate ester (2.6 eq), aryl halide (0.35 mmol, 1.0 eq), and $Pd(PPh_3)_4$ (0.04 eq). The vial was sealed and heated with stirring in the microwave to 160° C. for ten minutes. The solution was poured onto 2 M aq. Sodium hydroxide (20 mL), extracted with ethyl acetate (2×20 mL), dried ($MgSO_4$), and concentrated. Purification of the crude product by chromatography on silica gel (conditions given below) afforded the desired product.

B: Negishi Coupling Procedure

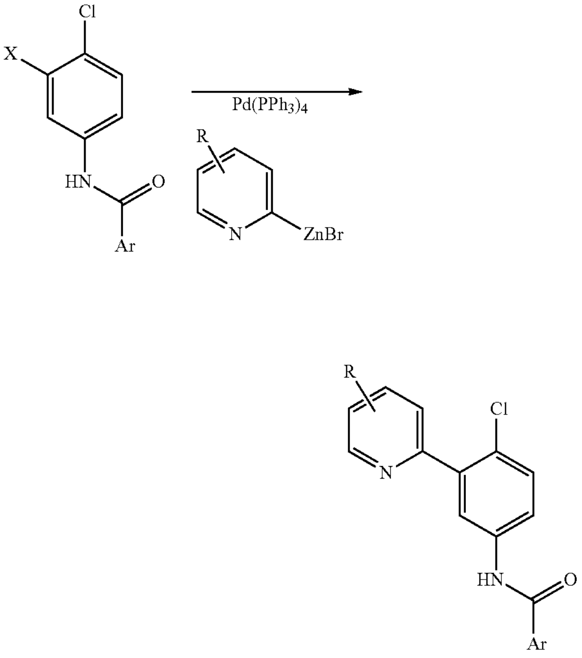

X = I or Br
R = H, 3-Me, 4-Me, 5-Me, 6-Me

Aryl zinc bromide (0.5 M in THF, 2.5 eq) was added to an oven-dried microwave vial charged with the appropriate aryl halide (1.0 eq) and $Pd(PPh_3)_4$ (0.04 eq). The vial was sealed and heated with stirring in the microwave to 140° C. for 10 minutes. The crude reaction mixture was concentrated and purified by chromatography on silica gel (conditions given below) to afford the desired product.

C: Iron Reduction of Aryl Nitro Group

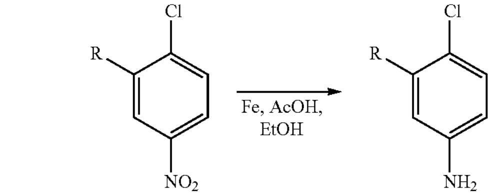

R = I or pyridin-2-yl

The appropriate nitro aryl (1 mmol, 1 eq) in AcOH/EtOH (1:1, 0.42 M) was added slowly to a solution of Iron powder (6.0 eq) in AcOH/EtOH (1:2, 2 M) at 60° C. The solution was stirred at 70° C. for 30-60 minutes. The reaction mixture was cooled to 23° C., filtered through celite, washed with ethyl acetate, and concentrated. The oily residue was dissolved in ethyl acetate (30 mL), washed with saturated aq. $NaHCO_3$ (2×15 mL) and water (2×10 mL), dried ($MgSO_4$), and concentrated. The oily residue was used with out further purification.

D: Amide Bond Formation

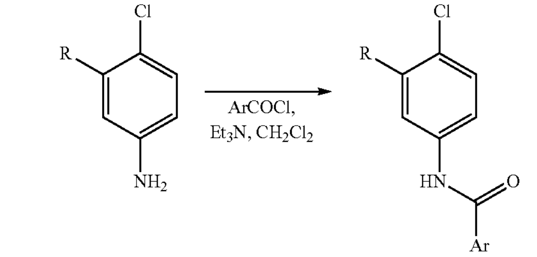

R = I or pyridin-2-yl

Acid chloride (1.05-1.1 eq) was added to a solution of aniline (1.0 eq) and TEA (1.1-1.5 eq) in methylene chloride at the indicated temperature. The solution was stirred for 0.5-3 hours, poured onto saturated aq. $NaHCO_3$, extracted twice with methylene chloride, dried ($MgSO_4$), and concentrated. Purification of the crude product by chromatography on silica gel (conditions given below) afforded the desired product.

E: EDC Amide Bond Formation

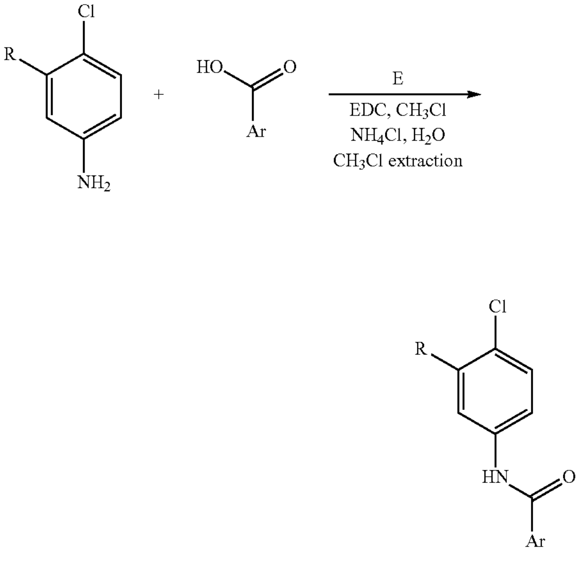

R = I or pyridin-2-yl

Carboxylic acid (1.1 eq) was added to a solution of aniline (1.0 eq) and EDC (1.4 eq) in methylene chloride (0.7 M in aniline). The solution was stirred at 23° C. for 2 hours, poured onto a 1:1 mixture of saturated aq. $NH_4Cl$ and water, extracted twice with methylene chloride, dried ($MgSO_4$), and concentrated. Purification of the crude product by chromatography on silica gel (conditions given below) afforded the desired product.

F: Addition of Amines to 2-Chloropyridine

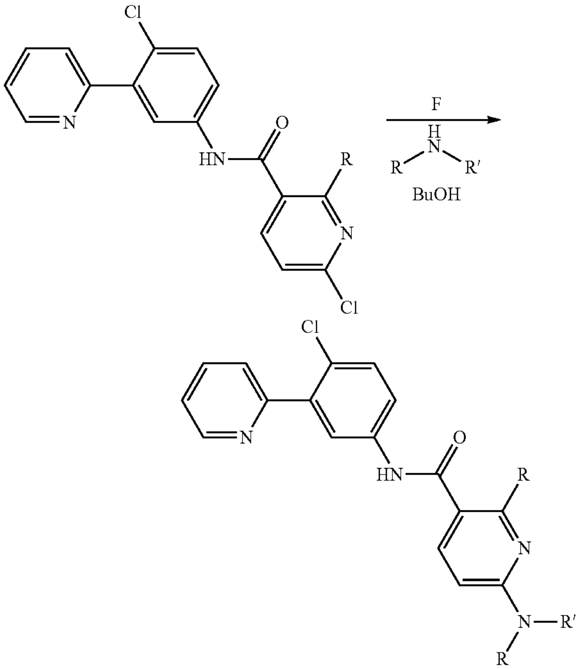

[R = H, $CH_3$]
NHRR' = ethanolamine, analine, benzylamine, 2-methylpropylamine, N-methylpiperazine, morpholine, 2-morpholinoethylamine Primary or secondary amine (5 eq) in either BuOH or a mixture of BuOH/ethylene gylcol was heated to 170 to 220° C. for 20 min in a sealed tube. The BuOH was removed under reduced pressure. In cases where ethylene glycol was used, the reaction was diluted with water, and the product was extracted into ethyl acetate, dried ($MgSO_4$), and concentrated. The crude residue was purified by reverse phase HPLC to afford the desired product.

G: Amide Bond Coupling with HATU

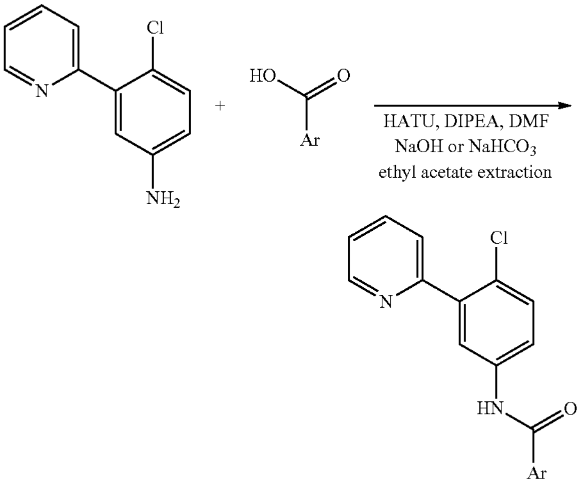

Aniline (1.0 eq) was added to a mixture of carboxylic acid (1.1 eq), HATU (1.1 eq) and DIPEA (2 eq) in DMF (0.1-0.2 M). After stirring overnight, the reaction mixture was diluted with 0.1 N sodium hydroxide or saturated $NaHCO_3$, extracted into ethyl acetate and the combined organic layers were washed with brine. The organic layer was dried ($MgSO_4$), concentrated and the crude mixture was purified by reverse phase HPLC.

H: Preparation of Sulfonamide Benzoic Acids

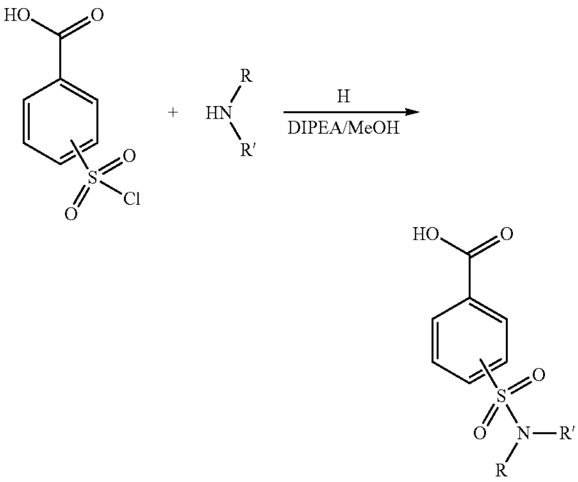

Chlororsulfonylbenzoic acid (1.0 eq) was added to a solution of amine (1.1 eq) in 10-20% DIPEA/methanol (1 M) at 4° C. After 1 h, the reaction mixture was concentrated, and the crude residue was purified by reverse phase HPLC.

I: Stannylation of 2-Pyridyl Triflates

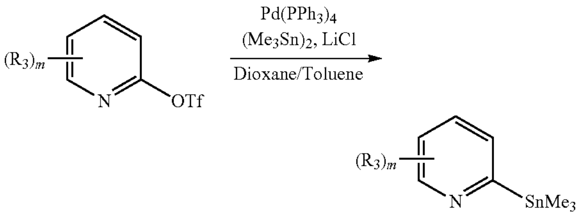

A solution of tetrakis-triphenylphosphinepalladium (0.04 eq.) in toluene (1 mL) was added to degassed solution of aryltriflate (1 eq), bis-trialkyltin (1.05 eq), and lithium chloride (3 eq) in dioxane. Heated to reflux for 2 hours, cooled to 23° C., diluted with ethyl acetate, washed with 10% $NH_4OH_{(aq)}$ and brine, dried ($MgSO_4$) and concentrated. The crude material was used without further purification.

J: Stannylation of Substituted Pyridines

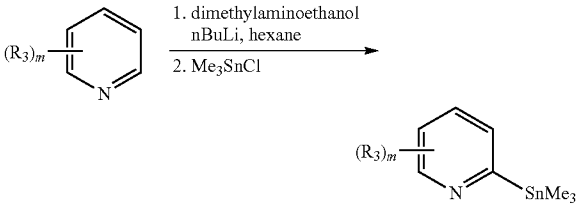

n-Butyl lithium (6 eq, 2.5 M in hexanes) was added dropwise to a solution of dimethylaminoethanol (3 eq) in hexane at 0° C. The solution was stirred at 0° C. for thirty minutes before dropwise addition of the substituted pyridine (1 eq). The solution was stirred at 0° C. for an additional hour, then cooled to −78° C. A solution of trialkyltin in hexane was added dropwise. The solution was stirred at −78° C. for thirty minutes, warmed to 0° C., quenched with water, extracted twice with ether, dried ($MgSO_4$), and concentrated.

K: Stille Coupling

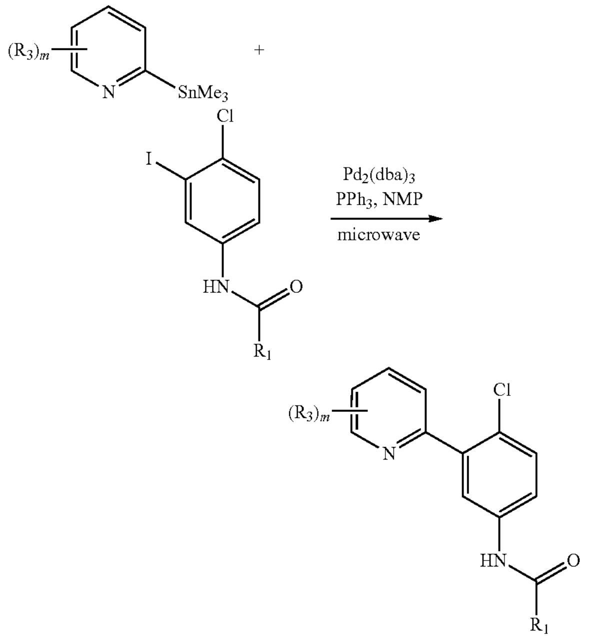

Palladium catalyst (0.02 eq) was added to a degassed solution of aryliodide (1 eq), arylstannane (2 eq), and triphenylphosphine (0.16 eq) in NMP. Heated in the microwave to 130° C. for 15 minutes. The reaction mixture was diluted with ethylacetate, washed with 10% $NH_4OH_{(aq)}$ and brine, dried ($MgSO_4$), concentrated and purified by silica gel chromatography.

L: Synthesis of Alkylethers

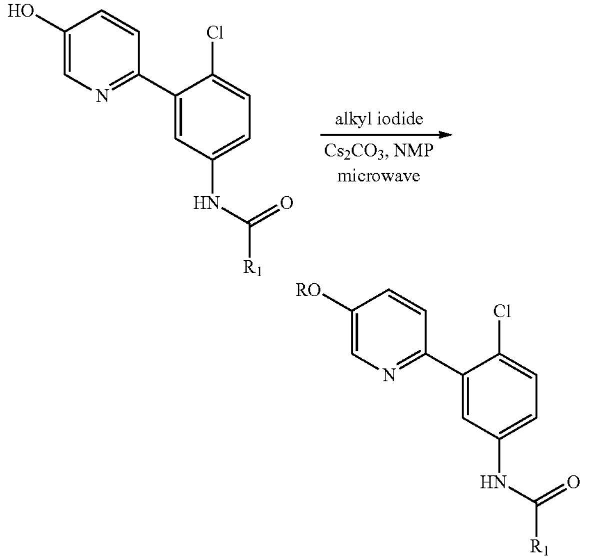

A solution of hydroxypyridine (1 eq), alkyliodide (excess), and cesium carbonate in NMP was heated in the microwave to 100° C. for ten minutes. The reaction mixture was diluted with ethylacetate, washed with 10% $NH_4OH_{(aq)}$ and brine, dried ($MgSO_4$), concentrated and purified by silica gel chromatography.

M: Methyl Ester Saponification

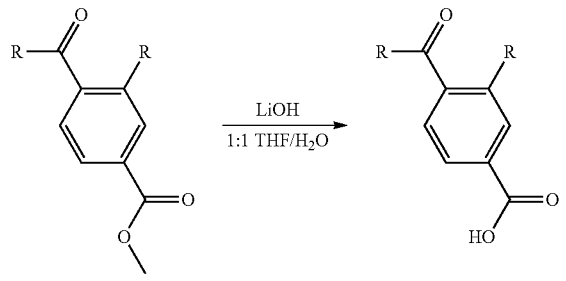

The methyl ester (1eq) was hydrolyzed with LiOH (2eq) in 50/50 THF/water mix. Upon completion of the reaction the THF was evaporated under reduced pressure and the solution is acidified with HCl to pH 2. The resultant solid was filtered and dried to give the pure acid.

N: Bromination in the Presence of a Free Acid Functionality

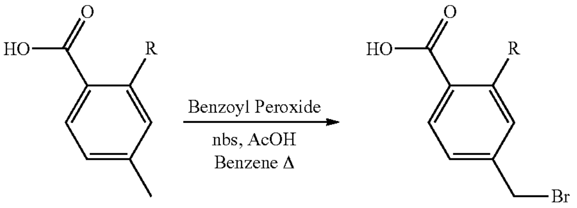

The paramethylbenzoic acid (1eq) was combined with Benzoyl Peroxide (0.1eq) and N-Bromosuccinimde (0.9eq) in a solution of 5% AcOH in Benzene and heated in the microwave at 120° C. for 5-15 minutes. The product was separated from the starting material and di-bromo product via ISCO flash chromatography with an ethyl acetate (with 1% AcOH) and hexanes solvent system.

O: Sodium Methanesulfinate Displacement of Bromine

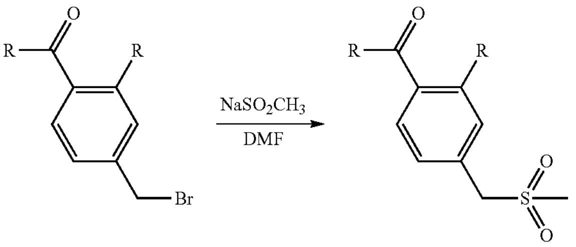

To the bromine starting material (1eq) was added sodium methanesulfinate (2eq) in DMF and heated to 120° C. in the microwave for 5 minutes. Alternatively, the reaction was heated to 60° C. in an oil bath for several hours until completed. Reaction mixture was concentrated under reduced pressure and extracted in ethyl acetate and water. The organic layer was dried over Magnesium Sulfate, filtered and concentrated in vacuo to yield generic methylsulfone.

P: Amine Displacement of Bromine

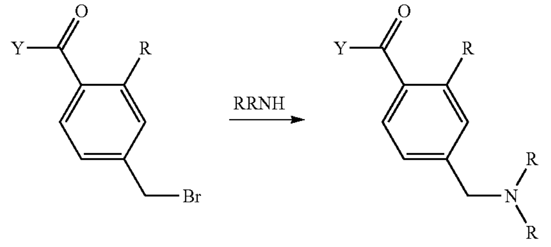

To the bromo starting material (1eq) was added appropriate amine (3eq) in either DMSO or BuOH and stirred at room temperature until complete. For less nucleophilic amines or anilines, the reactions were forced to completion using microwave conditions ranging from 150°-170° C. for 15 minutes. Crude reactions were concentrated to dryness and either extracted with ethyl acetate and saturated bicarbonate if the reaction resulted in an intermediate or purified via HPLC if the reaction resulted in a final product.

Q: Thiol Displacement of Halogen

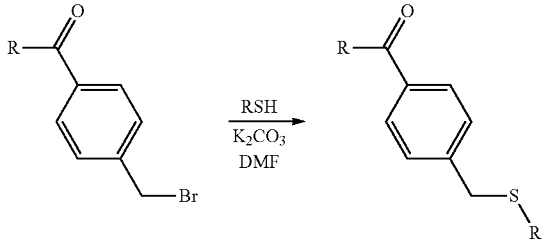

The paramethylbromo benzoate (1eq) was treated with Potassium (or Cesium) Carbonate (1.5eq) and appropriate thiol derivative (1.1eq) in DMF (or $CH_3CN$) and stirred overnight at room temperature. The DMF was evaporated in vacuo and the reaction was extracted with ethyl acetate and water. The organic layer was dried over Magnesium Sulfate, filtered and concentrated to yield the thiol or derivatized thiol compound.

R: Oxone Oxidation

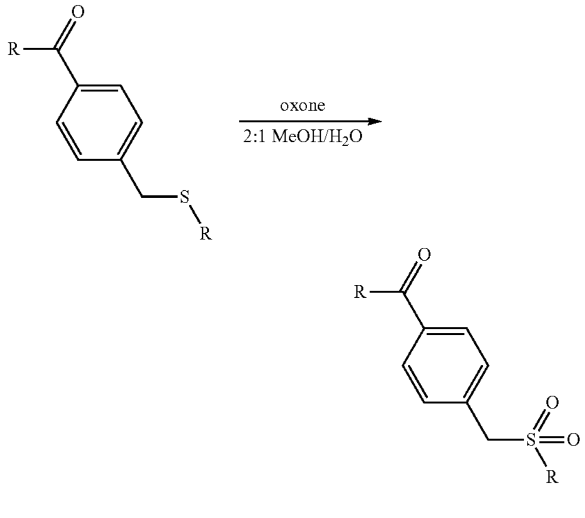

Derivatized thiol (1eq) was dissolved in MeOH while Oxone (2eq) was separately dissolved in half the amount of water. Once all the oxone was dissolved, the solution was added to the thiol in MeOH solution at once and stirred until complete. The MeOH was evaporated in vacuo and the remaining water was extracted twice with Ethyl Acetate. The organic layer was dried over Magnesium Sulfate and concentrated to yield the sulfone.

S: Thiolysis of Epoxides at Alumina Surfaces

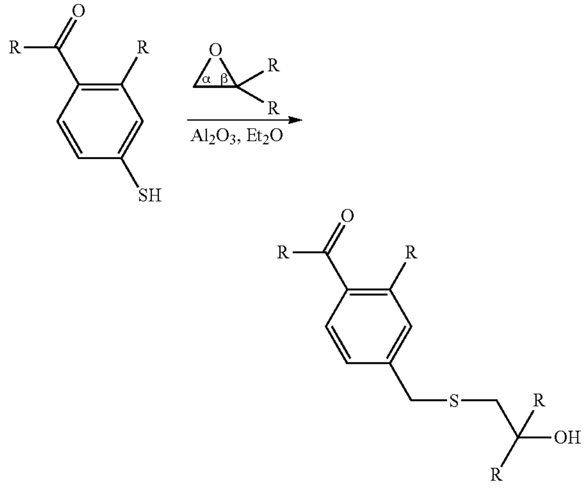

A mixture of epoxides (1.0 eq), thiophenol (1.5 eq) and neutral aluminum oxide (~70 eq) in diethyl ether was stirred for 3 h at room temperature while being monitored by TLC. The reaction mixture was filtered through Celite, washed with ethyl acetate and concentrated. Purified by silica gel chromatography (0-40% ethyl acetate/hexane) to yield β-hydroxysulfide product.

T: Conversion of Nitrile Group to Carboxylic Acid

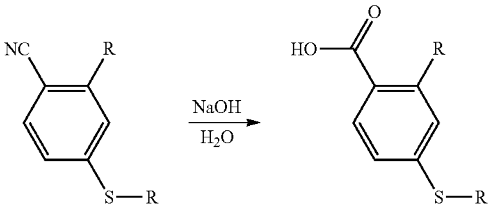

A solution of benzonitrile (1.0 eq) and sodium hydroxide (2.0 eq) in $H_2O$ was heated to 120° C. for 2 h. The reaction mixture was cooled to room temperature and acidified with HCl to pH 2. The resulting solid was filtered to afford the pure acid product.

U. Alkylation of Phenols

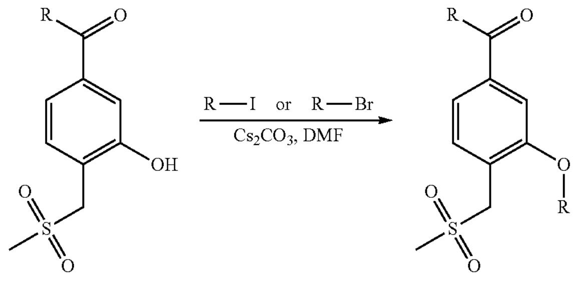

The phenol was dissolved in DMF (1.0 ml). Cesium carbonate (1.0 eq.) and an alkyl bromide or alkyl iodide (1.0 to 2.0 eq.) were added, and the reaction was stirred at room temperature for 18 hrs or 50° C. for 1 to 24 hours. The reaction was quenched in water, and extracted with ethyl acetate twice. The organic extracts were washed with water once, brine once, dried with $MgSO_4$, and evaporated to a crude oil which was purified on reverse phase HPLC.

V. Amide Bond Formation with an Acid Chloride and an Aniline

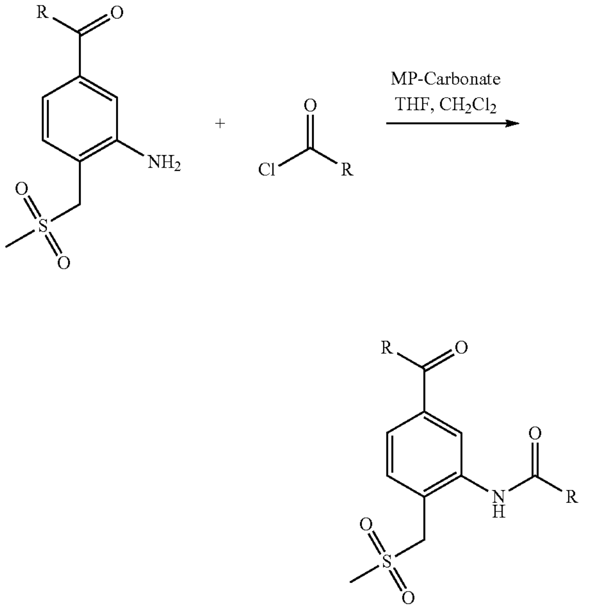

The aniline was dissolved in THF (1.5 ml) and dichloromethane (1.5 ml). MP-Carbonate (1.5 eq.) and an acid chloride (1.1 eq.) were added, and the solution was stirred at room temperature for 18 hours. The reaction was diluted with methanol and dichloromethane, and filtered to remove the MP-Carbonate. The mother liquors were evaporated to a solid and purified by reverse phase HPLC.

W. Amidine Formation from an Imidate

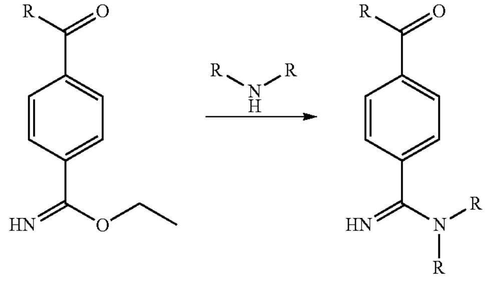

A solution of freshly formed imidate in methanol was treated with a primary or secondary amine (1.5 eq.) at room temperature for 18 hours. The methanol was removed on a rotary evaporator and the residue purified by reverse phase HPLC.

Example 2

6-(2-morpholinoethylamino)-N-(4-chloro-3-(pyridin-2-yl)phenyl)pyridine-3-carboxamide

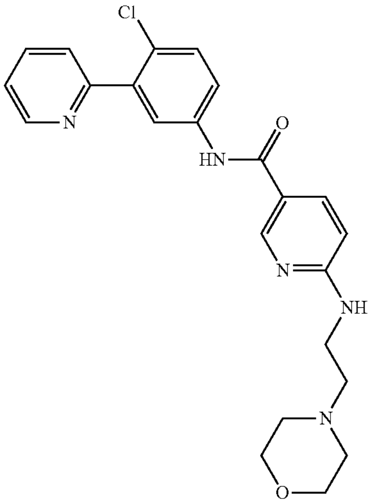 [SMILES: O=C(Nc1ccc(Cl)c(-c2ccccn2)c1)c1ccc(NCCN2CCOCC2)nc1]

Procedure F was performed using N-(4-chloro-3-(pyridin-2-yl)phenyl)-6-chloro-3-carboxamide (50 mg) and 2-morpholinoethylamine in butanol (0.5 mL). The crude reaction was purified by reverse phase HPLC to yield 6-(2-morpholinoethylamino)-N-(4-chloro-3-(pyridin-2-yl)phenyl)pyridine-3-carboxamide as a white solid. MS (Q1) 438.3 $(M)^+$.

Example 3

N,N-(4-Chloro-3-(pyridin-2-yl)phenyl)-bis[6-(trifluoromethyl)-2-methylpyridine-3]-carboxamide

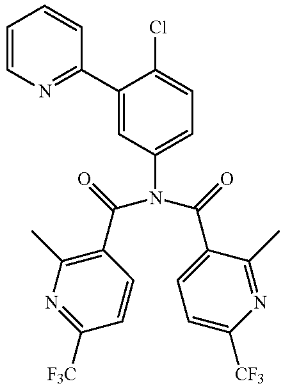 [SMILES: Cc1nc(C(F)(F)F)ccc1C(=O)N(C(=O)c1ccc(C(F)(F)F)nc1C)c1ccc(Cl)c(-c2ccccn2)c1]

Procedure B was performed with 2-pyridylzinc bromide (4 mL, 2.0 mmol, 0.5 M in THF) and 3-bromo-4-chloro-nitrobenzene (236 mg, 1.0 mmol). Purified by chromatography on silica gel (10% ethyl acetate/hexanes) to yield 2-(2-chloro-5-nitrophenyl)pyridine as a light yellow solid.

Procedure C was performed with 2-(2-chloro-5-nitrophenyl)pyridine (122 mg, 0.52 mmol) to yield 4-chloro-3-(pyridin-2-yl)aniline as a light yellow solid, which was used without further purification.

Procedure D was performed using 4-chloro-3-(pyridin-2-yl)aniline (40 mg, 0.2 mmol). The crude residue was purified by silica gel chromatography (15-60% ethyl acetate/hexanes) to yield N,N-(4-Chloro-3-(pyridin-2-yl)phenyl)-bis[6-(trifluoromethyl)-2-methylpyridine-3]-carboxamide as an oily residue: TLC $R_f$=0.42 (35% ethyl acetate/hexanes); $^1$H NMR ($CDCl_3$, 400 MHz) δ 8.72 (m, 1H), 7.84 (d, 2H0, 7.77 (dd, 1H), 7.68 (m, 1H), 7.57 (d, 1H), 7.51 (m, 3H), 7.33 (m, 1H), 7.12 (dd, 1H), 2.78 (s, 6H); MS (Q1) 579 $(M)^+$.

Example 4

N-(4-Chloro-3-(pyridin-3-yl)phenyl)-3,5-dimethoxybenzamide

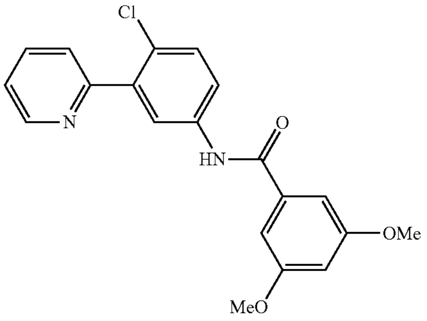 [SMILES: COc1cc(OC)cc(C(=O)Nc2ccc(Cl)c(-c3ccccn3)c2)c1]

4-Chloro-3-(pyridin-2-yl)aniline (40 mg, 0.2 mmol) was used in procedure D with 3,5-dimethoxybenzoyl chloride (43 mg, 0.216 mmol) at 23° C. for 2 hours. The crude residue was purified by crystallization ($CH_2Cl_2$/hexanes) to yield N-(4-chloro-3-(pyridin-3-yl)phenyl)-3,5-dimethoxybenzamide as an off-white solid: TLC $R_f$=0.30 (15% ethyl acetate/hexanes); $^1$H NMR ($CDCl_3$, 400 MHz) δ 8.72 (m, 1H), 7.91 (m, 1H), 7.88 (dd, 1H), 7.78 (m, 2H), 7.74 (dd, 1H), 748 (d, 1H), 7.35 (m, 1H), 6.96 (d, 2H), 6.62 (t, 1H), 3.82 (s, 6H); MS (Q1) 369 $(M)^+$.

Example 5

5-Acetyl-N-(4-chloro-3-(pyridin-2-yl)phenyl)thiophene-2-carboxamide

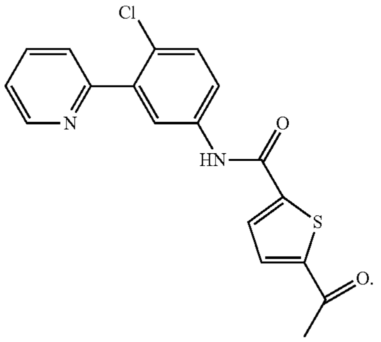 [SMILES: CC(=O)c1ccc(C(=O)Nc2ccc(Cl)c(-c3ccccn3)c2)s1]

4-Chloro-3-iodoaniline (2.5 g, 9.88 mmol) was used in Procedure E with 5-acetylthiophene-2-carboxylic acid (1.85 g, 10.8 mmol) at 23° C. for 2 hours. The crude material was purified by silica gel chromatography (20-100% ethyl acetate/hexanes) to yield 5-Acetyl-N-(4-chloro-3-iodophenyl)thiophene-2-carboxamide as a yellow solid.

5-Acetyl-N-(4-chloro-3-iodophenyl)thiophene-2-carboxamide (202 mg, 0.5 mmol) was used in Procedure B with 2-pyridylzincbromide (2.5 mL, 1.25 mmol, 0.5 M in THF). Purified by silica gel chromatography (10-100% ethyl acetate/hexanes) to yield 5-acetyl-N-(4-chloro-3-(pyridin-2-yl)phenyl)thiophene-2-carboxamide as a yellow solid: TLC $R_f$=0.19 (50% ethyl acetate/hexanes); $^1$H NMR ($CDCl_3$, 400 MHz) δ 8.96 (bs, 1H), 8.67 (d, 1H), 7.79 (dt, 1H), 7.68 (m, 3H), 7.61 (d, 1H), 7.58 (d, 1H), 7.37 (d, 1H), 7.32 (m, 1H), 2.58 (s, 3H); MS (Q1) 357.0 $(M)^+$.

Example 6

N-(4-Chloro-3-(3-methylpyridin-2-yl)phenyl)-6-(trifluoromethyl)-2-methylpyridine-3-carboxamide

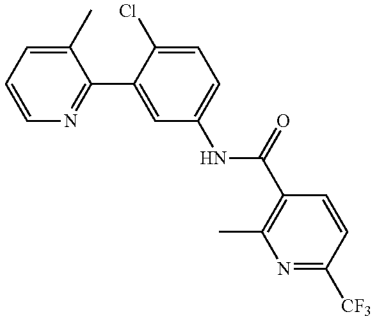 [SMILES: Cc1cccnc1-c1cc(NC(=O)c2ccc(C(F)(F)F)nc2C)ccc1Cl]

N-(4-Chloro-3-iodophenyl)-6-(trifluoromethyl)-2-methylpyridine-3-carboxamide (142 mg, 0.32 mmol) was used in Procedure B with 6-methyl-2-pyridylzinc bromide (1.75 mL, of a 0.5 M in THF). Purified by silica gel chromatography (5-100% Ethyl acetate/Hexanes) to yield N-(4-chloro-3-(3-methylpyridin-2-yl)phenyl)-6-(trifluoromethyl)-2-methylpyridine-3-carboxamide as a white solid: TLC $R_f$=0.23 (30% ethyl acetate/hexanes); $^1$H NMR ($CDCl_3$, 400 MHz) δ 8.81 (bs, 1H), 7.95 (dd, 1H), 7.67 (m, 3H), 7.53 (t, 2H), 7.38 (d, 1H), 7.07 (d, 1H), 2.71 (s, 3H), 2.43 (s, 3H); MS (Q1) 406.1 $(M)^+$.

Example 7

N-(4-Chloro-3-(5-methylpyridin-2-yl)phenyl)-6-(trifluoromethyl)-2-methylpyridine-3-carboxamide

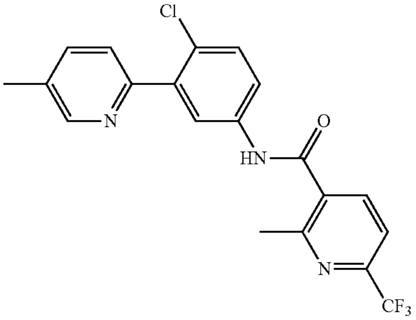 [SMILES: Cc1ccc(-c2cc(NC(=O)c3ccc(C(F)(F)F)nc3C)ccc2Cl)nc1]

N-(4-Chloro-3-iodophenyl)-6-(trifluoromethyl)-2-methylpyridine-3-carboxamide (150 mg, 0.34 mmol) was used in Procedure B with 4-methyl-2-pyridylzinc bromide (1.7 mL of a 0.5 M in THF). Purified by silica gel chromatography (5-75% Ethyl acetate/Hexanes) to yield N-(4-chloro-3-(5-methylpyridin-2-yl)phenyl)-6-(trifluoromethyl)-2-methylpyridine-3-carboxamide as a white solid: TLC $R_f$=0.23 (35% ethyl acetate/hexanes); $^1$H NMR ($CDCl_3$, 400 MHz) δ 10.62 (bs, 1H), 8.12 (dd, 1H), 7.89 (d, 1H), 7.58 (d, 1H), 7.47 (m, 3H), 7.18 (d, 1H), 6.89 (d, 1H), 2.62 (s, 3H), 2.38 (s, 3H); MS (Q1) 406.3 $(M)^+$.

Example 8

5-Acetyl-N-(4-chloro-3-(5-methylpyridin-2-yl)phenyl)thiophene-2-carboxamide

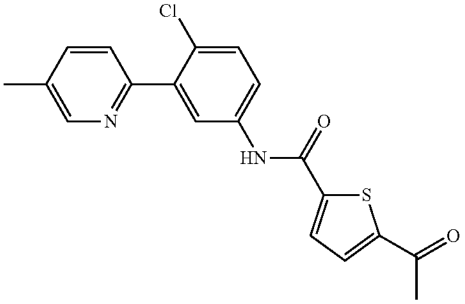 [SMILES: CC(=O)c1ccc(C(=O)Nc2ccc(Cl)c(-c3ccc(C)cn3)c2)s1]

5-Acetyl-N-(4-chloro-3-iodophenyl)thiophene-2-carboxamide (203 mg, 0.5 mmol), was used in Procedure B with 4-methyl-2-pyridylzinc bromide (2.5 mL, 1.25 mmol, 0.5 M in THF). Purified by silica gel chromatography (30-100% ethyl acetate/hexanes) to yield 5-acetyl-N-(4-chloro-3-(5-methylpyridin-2-yl)phenyl)thiophene-2-carboxamide as a yellow solid: TLC $R_f$=0.25 (50% ethyl acetate/hexanes); $^1$H NMR ($CDCl_3$, 400 MHz) δ 9.52 (bs, 1H), 8.51 (d, 1H), 7.60 (m, 4H), 7.39 (s, 1H), 7.29 (d, 1H), 7.14 (d, 1H), 2.55 (s, 3H), 2.42 (s, 3H); MS (Q1) 371 $(M)^+$.

Example 9

N-(4-Chloro-3-(4-methylpyridin-2-yl)phenyl)-6-(trifluoromethyl)-2-methylpyridine-3-carboxamide

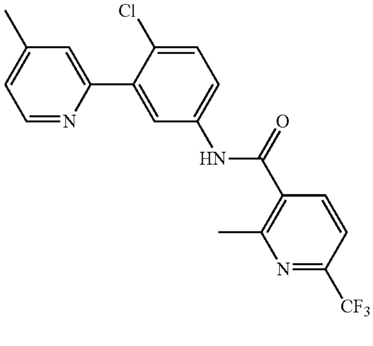 [SMILES: Cc1ccnc(-c2cc(NC(=O)c3ccc(C(F)(F)F)nc3C)ccc2Cl)c1]

Procedure B was performed with N-(4-Chloro-3-iodophenyl)-6-(trifluoromethyl)-2-methylpyridine-3-carboxamide (440 mg, 1.0 mmol) and 4-methyl-2-pyridylzinc bromide (5 mL of a 0.5 M solution in THF). The crude residue was purified silica gel chromatography (5-100% Ethyl acetate/Hexanes) to yield N-(4-chloro-3-(4-methylpyridin-2-yl)phenyl)-6-(trifluoromethyl)-2-methylpyridine-3-carboxamide as a white solid: TLC $R_f$=0.43 (35% ethyl acetate/hexanes); $^1$H NMR ($CDCl_3$, 400 MHz) δ 10.39 (bs, 1H), 8.11 (dd, 1H), 7.87 (s, 1H), 7.61 (d, 1H), 7.59 (d, 1H), 7.49 (m, 3H), 2.66 (s, 3H), 2.21 (s, 3H); MS (Q1) 406.1 $(M)^+$.

Example 10

N-(4-chloro-3-(6-methylpyridin-2-yl)phenyl)-3,5-dimethylisoxazole-4-carboxamide

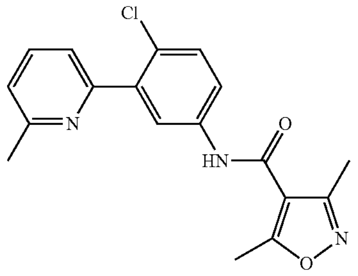 [SMILES: Cc1cccc(-c2cc(NC(=O)c3c(C)noc3C)ccc2Cl)n1]

4-Chloro-3-iodoaniline (1.01 g, 4 mmol) was used in procedure E with 3,5-dimethyl-4-isoxazolecarboxylic acid (0.565 g, 4 mmol), EDC (1.32 g, 6.8 mmol), TEA (0.5 mL), DMAP (50 mg, 0.4 mmol) at 23° C. for overnight. The crude reaction was purified by silica gel chromatography (0-15% ethyl acetate/$CH_2Cl_2$) to yield 3,5-dimethyl-N-(4-chloro-3-iodophenyl)isoxazole-4-carboxamide as a white solid.

Procedure B was performed with 3,5-dimethyl-N-(4-chloro-3-iodophenyl)isoxazole-4-carboxamide (190 mg, 0.5 mmol) and 3-methyl-2-pyridylzinc bromide (2.5 mL of a 0.5 M solution in THF). The crude reaction was purified by silica gel chromatography (5-100% Ethyl acetate/Hexanes) to yield N-(4-chloro-3-(6-methylpyridin-2-yl)phenyl)-3,5-dimethylisoxazole-4-carboxamide as a white solid: TLC $R_f$=0.43 (50% ethyl acetate/hexanes); $^1$H NMR ($CDCl_3$, 400 MHz) δ 8.52 (bs, 1H), 7.68 (m, 2H), 7.48 (m, 3H), 2.70 (s, 3H), 2.49 (s, 3H), 2.21 (s, 3H); MS (Q1) 342.3 $(M)^+$.

Example 11

N-(4-chloro-3-(pyridin-2-ylamino)phenyl)-6-(trifluoromethyl)-2-methylpyridine-3-carboxamide

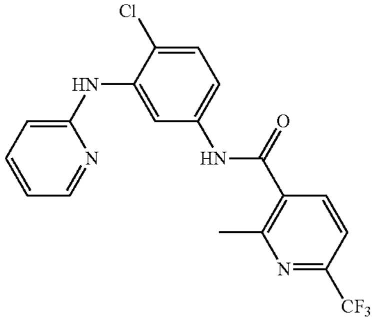 [SMILES: Cc1nc(C(F)(F)F)ccc1C(=O)Nc1ccc(Cl)c(Nc2ccccn2)c1]

N-(4-Chloro-3-iodophenyl)-6-(trifluoromethyl)-2-methylpyridine-3-carboxamide (220 mg, 0.5 mmol), 2-aminopyridine (40 mg, 0.42 mmol), potassium t-butoxide (66 mg, 0.59 mmol), $Pd_2(dba)_3$ (20 mg, 0.21 mmol), dppf (24 mg, 0.042 mmol) in toluene (2.1 mL) were heated to 100° C. for 1.5 days. The solution was cooled to 23° C., diluted with ether, filtered through celite, washed with ethyl acetate, and concentrated. Purified by reverse phase HPLC to yield N-(4-chloro-3-(pyridin-2-ylamino)phenyl)-6-(trifluoromethyl)-2-methylpyridine-3-carboxamide as a white solid: $^1$H NMR ($CDCl_3$, 400 MHz) δ 11.53 (s, 1H), 9.68 (s, 1H), 8.05 (m, 2H), 7.85 (m, 2H), 7.55 (d, 1H), 7.26 (d, 1H), 7.13 (dd, 1H), 6.91 (t, 1H), 6.88 (d, 1H), 2.75 (s, 3H); MS (Q1) 407.0 $(M)^+$.

Example 12

N-(4-chloro-3-(pyridin-2-yl)phenyl)-6-(4-methylpiperazin-1-yl)pyridine-3-carboxamide

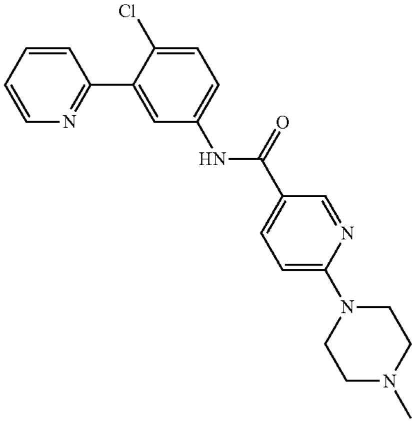 [SMILES: CN1CCN(c2ccc(C(=O)Nc3ccc(Cl)c(-c4ccccn4)c3)cn2)CC1]

Procedure F was performed using N-(4-chloro-3-(pyridin-2-yl)phenyl)-6-chloro-3-carboxamide (50 mg) and N-methylpiperazine in butanol (0.5 mL). The crude reaction was purified by reverse phase HPLC to yield N-(4-chloro-3-(pyridin-2-yl)phenyl)-6-(4-methylpiperazin-1-yl)pyridine-3-carboxamide as a white solid. MS (Q1) 408.4 $(M)^+$.

Example 13

N-(4-chloro-3-(pyridin-2-yl)phenyl)-6-(isobutylamino)pyridine-3-carboxamide

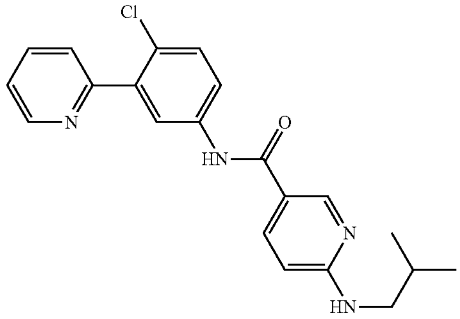 [SMILES: CC(C)CNc1ccc(C(=O)Nc2ccc(Cl)c(-c3ccccn3)c2)cn1]

Procedure F was performed using N-(4-chloro-3-(pyridin-2-yl)phenyl)-6-chloro-3-carboxamide (50 mg) and 2-methylpropylamine in butanol (0.5 mL). The crude reaction was purified by reverse phase HPLC to yield N-(4-chloro-3-(pyridin-2-yl)phenyl)-6-(isobutylamino)pyridine-3-carboxamide as a white solid. MS (Q1) 381.1 $(M)^+$.

Example 14

N-(4-chloro-3-(pyridin-2-yl)phenyl)-6-morpholinopyridine-3-carboxamide

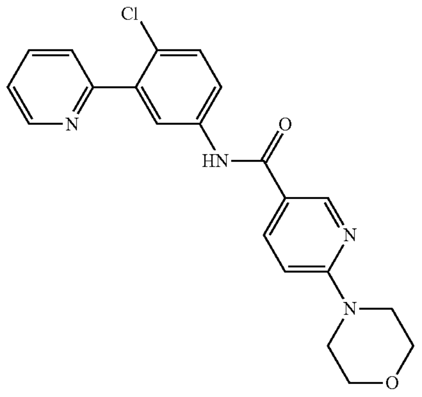 [SMILES: O=C(Nc1ccc(Cl)c(-c2ccccn2)c1)c1ccc(N2CCOCC2)nc1]

Procedure F was performed using N-(4-chloro-3-(pyridin-2-yl)phenyl)-6-chloro-3-carboxamide (50 mg) and morpholine in butanol (0.5 mL). The crude reaction was purified by reverse phase HPLC to yield N-(4-chloro-3-(pyridin-2-yl)phenyl)-6-morpholinopyridine-3-carboxamide as a white solid. MS (Q1) 401.3 $(M)^+$.

Example 15

6-(benzylamino)-N-(4-chloro-3-(pyridin-2-yl)phenyl)pyridine-3-carboxamide

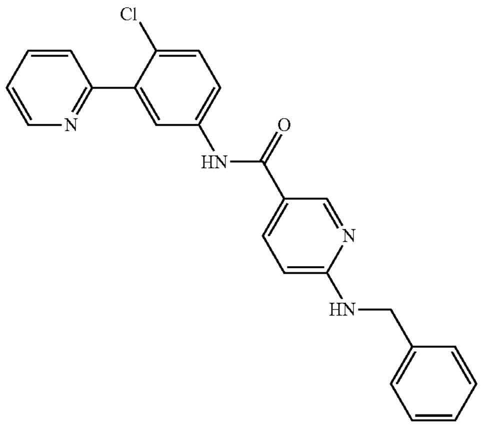 [SMILES: O=C(Nc1ccc(Cl)c(-c2ccccn2)c1)c1ccc(NCc2ccccc2)nc1]

Procedure F was performed using N-(4-chloro-3-(pyridin-2-yl)phenyl)-6-chloro-3-carboxamide (50 mg) and benzylamine in butanol (0.5 mL). The crude reaction was purified by reverse phase HPLC to yield 6-(benzylamino)-N-(4-chloro-3-(pyridin-2-yl)phenyl)pyridine-3-carboxamide as a white solid. MS (Q1) 415.1 $(M)^+$.

Example 16

N-(4-chloro-3-(pyridin-2-yl)phenyl)-6-(phenylamino)pyridine-3-carboxamide

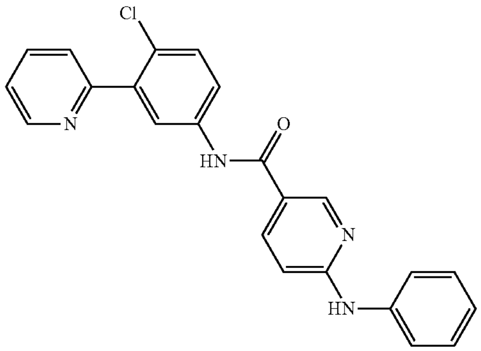 [SMILES: O=C(Nc1ccc(Cl)c(-c2ccccn2)c1)c1ccc(Nc2ccccc2)nc1]

Procedure F was performed using N-(4-chloro-3-(pyridin-2-yl)phenyl)-6-chloro-3-carboxamide (50 mg) and analine in butanol (0.5 mL). The crude reaction was purified by reverse phase HPLC to yield N-(4-chloro-3-(pyridin-2-yl)phenyl)-6-(phenylamino)pyridine-3-carboxamide as a white solid. MS (Q1) 401.0 $(M)^+$.

Example 17

N-(4-Chloro-3-(pyridin-2-yl)phenyl)-6-(trifluoromethyl)-2-methylpyridine-3-carboxamide

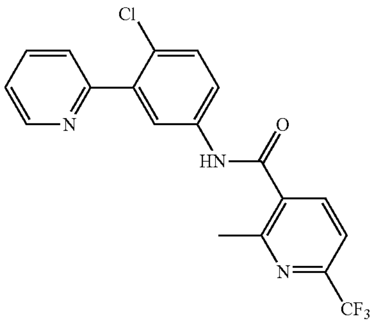 [SMILES: Cc1nc(C(F)(F)F)ccc1C(=O)Nc1ccc(Cl)c(-c2ccccn2)c1]

Procedure C was performed with 1-chloro-2-iodo-4-nitrobenzene (283 mg, 1 mmol) to produce 4-chloro-3-iodoaniline which was used without further purification.

Procedure D was performed with 4-chloro-3-iodoaniline (225 mg, 0.889 mmol) and 6-(trifluoromethyl)-2-methylpyridine-3-carbonyl chloride (237 mg, 0/93 mmol, 1.05 eq) at 0° C. for 30 minutes. The crude residue was purified by silica gel chromatography (2-50% ethyl acetate/hexanes) to yield N-(4-chloro-3-iodophenyl)-6-(trifluoromethyl)-2-methylpyridine-3-carboxamide as a white solid.

Procedure B was performed using N-(4-Chloro-3-iodophenyl)-6-(trifluoromethyl)-2-methylpyridine-3-carboxamide (88 mg, 0.2 mmol) with 2-pyridylzinc bromide (1 mL, 0.5 mmol, 0.5 M in THF). Purified by silica gel chromatography (10-80% ethyl acetate/hexanes) to yield N-(4-chloro-3-(pyridin-2-yl)phenyl)-6-(trifluoromethyl)-2-methylpyridine-3-carboxamide as a yellow solid: TLC $R_f$=0.28 (35% ethyl acetate/hexanes); TLC $R_f$=0.28 (35% ethyl acetate/hexanes); $^1H$ NMR ($CDCl_3$, 400 MHz) 8.88 (bs, 1H), 8.41 (d, 1H), 7.96 (dd, 1H), 7.74 (m, 4H), 7.52 (d, 1H), 7.22 (m, 1H), 2.75 (s, 3H); MS (Q1) 392 $(M)^+$.

An alternative synthetic procedure is as follows. 75 g (435 mmol) of 2-chloro-5-nitroaniline was added to a solution of water (600 mL) and conc. sulfuric acid (60 mL) in a 3 L 3-neck flask equipped for mechanical stirring. The solution was cooled to 0° C. and a solution of sodium nitrite (34.2 g, 496 mmol) in water (130 mL) was added slowly. The mixture was stirred for ½ hr. and then a solution of potassium iodide (130 g, 783 mmol) in water (520 mL) was added dropwise over ½ hr keeping the temperature below 15° C. The solution was stirred for 2 hr, then extracted with EtOAc (3×500 mL). The combined organic extracts were washed with sat. $Na_2S_2O_3$ (2×500 mL), dried ($Na_2SO_4$), and concentrated. The crude iodide was dissolved in hot iPrOH (500 mL) and hexanes (200 mL) were added. The reaction was allowed to cool with stirring and the product was collected by suction filtration after stirring at 0° C. for 2 hr yielding 90 g (318 mmol, 73%) 2-chloro-5-nitro-iodobenzene as a light tan crystalline solid.

The 2-chloro-5-nitro-iodobenzene (5 g, 17.6 mmol) was dissolved in 5 mL DMA in an oven dried flask and a 0.5M solution of 2-pyridylzincbromide (53 mL, 26.5 mmol, 0.5 M in THF) was added. The solution was degassed with $N_2$ for ½ hr., the $PPh_3$ (0.185 g, 0.7 mmol) and $Pd(PPh_3)_4$ (0.825 g, 0.7 mmol) were added, rinsed in with several mLs THF and the solution was degassed for a further 10 min before heating to 60° C. under $N_2$. The reaction was complete by TLC in ~8 h, cooled to RT, and poured into a 1:1 mixture of EtOAc/2.5N NaOH (500 mL). This solution was stirred for 10 min, passed through a course fritted filter containing celite to remove the solid, and then extracted. The organics were washed with brine and concentrated to a brown solid. The combined aqueous layers were backextracted with $Et_2O$ (1×200 mL). This was used to suspend the crude product, which was extracted with 1N HCl (1×200 mL, 3×100 mL). The combined aqueous extracts were cooled to 0° C., diluted with EtOAc (250 mL), and made basic with 10N NaOH (100 mL). This solution was separated, the aqueous layer extracted with EtOAc, and the combined organics were dried over $Na_2SO_4$ and charcoal with stirring. This solution was filtered through celite and concentrated to yield pure 4-chloro-3-(pyridin-2-yl)nitrobenzene (2.47 g, 10.5 mmol, 60% yield) which was used in the next reaction without further purification.

4-chloro-3-(pyridin-2-yl)nitrobenzene (1.47 g, 6.26 mmol) was suspended in EtOH (35 mL), and the $SnCl_2$ (3.87 g; 20.4 mmol) and conc. HCl (5 mL) were added and rinsed in with a further 5 mLs EtOH. The solution was placed in a 40° C. oil bath and heated to 60° C. The solution was stirred at 60° C. for 1½ hr., cooled to RT and diluted with 1 N HCl (100 mL). This solution was poured into an $Et_2O$/1 N HCl solution (100 mL:150 mL) and extracted. The aqueous layer was diluted with EtOAc (250 mL), cooled to 0° C., and made basic with 10 N NaOH (50 mL). This solution was extracted (EtOAc, 2×), and the combined organics were washed with brine and dried over $Na_2SO_4$ and charcoal. Suction filtration through celite gave a clear colorless solution which was concentrated to yield 4-chloro-3-(pyridine-2-yl)aniline (1.21 g, 5.93 mmol, 94% yield) as a cream colored crystalline solid which was used in the next reaction without further purification.

6-(trifluoromethyl)-2-methylpyridine-3-carbonyl chloride (1.68 g, 7.51 mmol) in 3 mL THF was added dropwise to a solution of 4-chloro-3-(pyridine-2-yl)aniline (1.21 g, 5.93 mmol) in THF (15 mL) at 0° C. The solution was stirred for 10 min., poured into EtOAc and washed with saturated aq. $NaHCO_3$ (2×), and brine. The organics were dried ($Na_2SO_4$) and concentrated. The crude product was suspended in $iPrOAc/Et_2O$ (10 mL, 1:1), stirred at 0° C. for ½ hr, and collected by suction filtration to yield N-(4-chloro-3-(pyridin-2-yl)phenyl)-6-(trifluoromethyl)-2-methylpyridine-3-carboxamide (2.04 g, 5.21 mmol, 88% yield) as a white solid: TLC $R_f$=0.28 (35% EtOAc/Hex); $^1H$ NMR ($CDCl_3$, 400 MHz) δ 8.88 (bs, 1H), 8.41 (d, 1H), 7.96 (dd, 1H), 7.74 (m, 4H), 7.52 (d, 1H), 7.22 (m, 1H), 2.75 (s, 3H); MS (Q1) 392 $(M)^+$.

Example 18

6-(2-hydroxyethylamino)-N-(4-chloro-3-(pyridin-2-yl)phenyl)pyridine-3-carboxamide

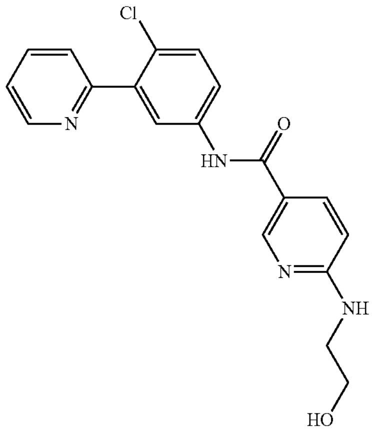 [SMILES: O=C(Nc1ccc(Cl)c(-c2ccccn2)c1)c1ccc(NCCO)nc1]

Procedure F was performed using N-(4-chloro-3-(pyridin-2-yl)phenyl)-6-chloro-3-carboxamide (50 mg) and ethanolamine in butanol (0.5 mL). The crude reaction was purified by reverse phase HPLC to yield 6-(2-hydroxyethylamino)-N-(4-chloro-3-(pyridin-2-yl)phenyl)pyridine-3-carboxamide as a white solid. MS (Q1) 369.0 $(M)^+$.

Example 19

N-(4-chloro-3-(pyridin-2-yl)phenyl)-4-(trifluoromethylsulfonyl)benzamide

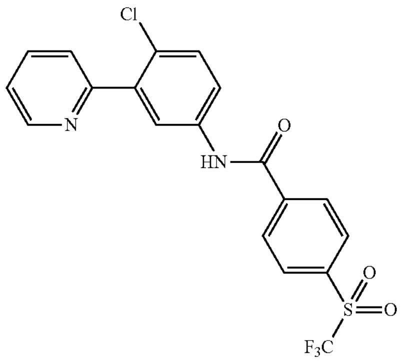 [SMILES: O=C(Nc1ccc(Cl)c(-c2ccccn2)c1)c1ccc(S(=O)(=O)C(F)(F)F)cc1]

4-(trifluoromethylthio)benzoic acid (200 mg, 0.9 mmol) was dissolved in water (2 mL) and acetic acid (4 mL) and treated with potassium permanganate (711 mg, 4.5 mmol) at room temperature. The reaction was allowed to stir for 16 h, diluted with ethyl acetate and washed with water. The organic layer was dried ($MgSO_4$) and concentrated to yield 4-(trifluoromethylsulfone)benzoic acid.

General procedure G was performed using 4-(trifluoromethylsulfone)benzoic acid and 4-chloro-3-(pyridin-2-yl) aniline. The crude reaction mixture was purified by reverse phase HPLC to yield N-(4-chloro-3-(pyridin-2-yl)phenyl)-4-(trifluoromethylsulfonyl)benzamide. MS (Q1) 440.95 $(M)^+$.

Example 20

N-(4-chloro-3-(pyridin-2-yl)phenyl)-4-(ethylsulfonyl)benzamide

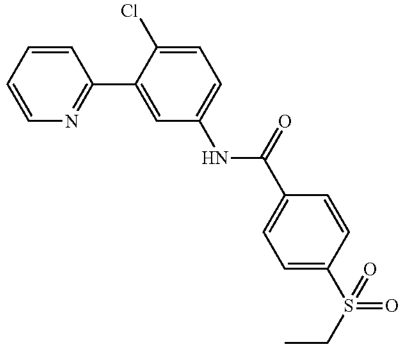 [SMILES: CCS(=O)(=O)c1ccc(C(=O)Nc2ccc(Cl)c(-c3ccccn3)c2)cc1]

General procedure G was performed using 4-(ethylthio) benzoic acid and 4-chloro-3-(pyridin-2-yl)aniline to produce N-(4-chloro-3-(pyridin-2-yl)phenyl)-4-(ethylthio)benzamide.

A solution of N-(4-chloro-3-(pyridin-2-yl)phenyl)-4-(ethylthio)benzamide (40 mg, 0.11 mmol) in MeOH (3 mL), cooled to 0° C. was treated with oxone (133 mg, 0.22 mmol), and the ice bath was removed. After 1 h of stirring, the reaction mixture was concentrated, and the residue was dissolved in ethyl acetate. The organic solution was washed with water, dried ($MgSO_4$) and concentrated. The crude reaction mixture was purified by reverse phase HPLC to yield N-(4-chloro-3-(pyridin-2-yl)phenyl)-4-(ethylsulfonyl)benzamide. MS (Q1) 401.0 $(M)^+$.

Example 21

2-chloro-N-(4-chloro-3-(pyridin-2-yl)phenyl)-4-((dimethylamino)methyl)benzamide

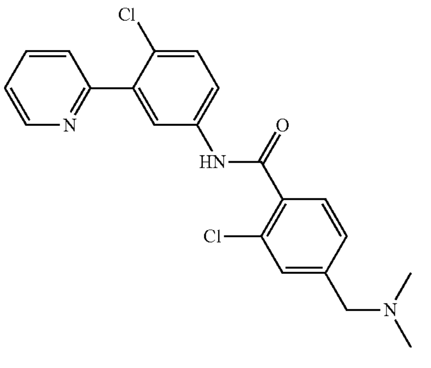 [SMILES: CN(C)Cc1ccc(C(=O)Nc2ccc(Cl)c(-c3ccccn3)c2)c(Cl)c1]

General procedure G was used to couple 4-(BOC-aminomethyl)-2-chloro-benzoic acid and 4-chloro-3-(pyridin-2-yl) aniline to yield 2-chloro-N-(4-chloro-3-(pyridin-2-yl)-phenyl)-4-(BOC-aminomethyl)-benzamide with. The crude reaction mixture was treated to TFA and trace water for 1 h prior to concentrating to dryness to yield 2-chloro-N-(4-chloro-3-(pyridin-2-yl)-phenyl)-4-(aminomethyl)-benzamide.

2-chloro-N-(4-chloro-3-(pyridin-2-yl)phenyl)-4-(aminomethyl)benzamide (80 mg, 0.20 mmol) was dissolved in DMF (5 mL) and treated with AcOH (10 uL), paraformaldehyde (43 mg, 0.47 mmol), and sodium triacetoxyborohydride (125 mg, 0.59 mmol). After stirring for 16 h, the solvent was evaporated and the residue was dissolved in ethyl acetate. The organic layer was washed with 1 N Sodium hydroxide, dried ($MgSO_4$) and concentrated. The crude product was purified by reverse phase HPLC to produce 2-chloro-N-(4-chloro-3-(pyridin-2-yl)phenyl)-4-((dimethylamino)methyl)benzamide. MS (Q1) 400.0 $(M)^+$.

Example 22

N-(4-chloro-3-(pyridin-2-yl)phenyl)-6-(morpholinomethyl)pyridine-3-carboxamide

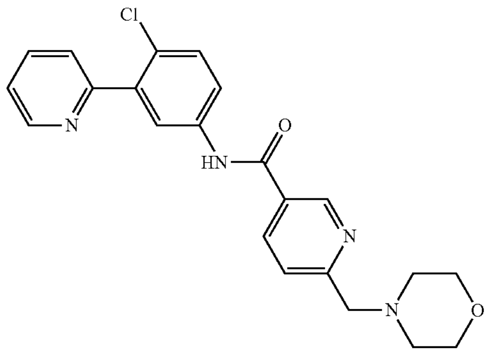 [SMILES: O=C(Nc1ccc(Cl)c(-c2ccccn2)c1)c1ccc(CN2CCOCC2)nc1]

6-methylnicotinic acid (100 mg 0.14 mmol) was dissolved in 10% AcOH/benzene (1 mL) and treated with NBS (117 mg, 0.18 mmol) and benzoylperoxide (18 mg, 0.07 mmol). The reaction mixture was heated in a sealed microwave reactor at 120° C. for 1 min. The reaction mixture was diluted with ethyl acetate, washed with saturated aqueous $NaHCO_3$, dried ($MgSO_4$), concentrated and purified by silica gel chromatography to yield 6-(bromomethyl)pyridine-3-carboxylic acid.

6-(bromomethyl)pyridine-3-carboxylic acid was coupled to 4-chloro-3-(pyridin-2-yl)aniline as described in general procedure E to yield 6-(bromomethyl)-N-(4-chloro-3-(pyridin-2-yl)phenyl)pyridine-3-carboxamide.

6-(bromomethyl)-N-(4-chloro-3-(pyridin-2-yl)phenyl) pyridine-3-carboxamide was dissolved in DMSO (1 mL) treated with morpholine (33 uL) for 1 h. The reaction was concentrated, and the crude residue was purified by reverse phase HPLC to produce N-(4-chloro-3-(pyridin-2-yl)phenyl)-6-(morpholinomethyl)pyridine-3-carboxamide. MS (Q1) 409.3 $(M)^+$.

Example 23

N-(4-chloro-3-(pyridin-2-yl)phenyl)-4-((pyrimidin-2-ylamino)methyl)benzamide

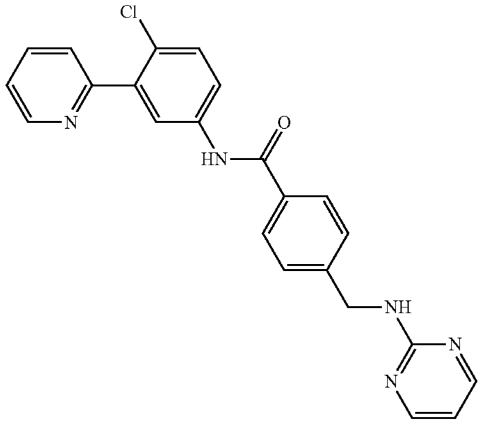 [SMILES: O=C(Nc1ccc(Cl)c(-c2ccccn2)c1)c1ccc(CNc2ncccn2)cc1]

4-(bromomethyl)benzoic acid was coupled to 4-chloro-3-(pyridin-2-yl)aniline as described in general procedure E to yield 4-(bromomethyl)-N-(4-chloro-3-(pyridin-2-yl)phenyl) benzamide.

4-(bromomethyl)-N-(4-chloro-3-(pyridin-2-yl)phenyl) benzamide (85 mg) was dissolved in DMSO (0.5 mL) and treated with 2-aminopyridine (59 mg) at 150° C. in a sealed microwave reactor for 5 min. The reaction mixture was concentrated, and the crude residue was purified by reverse phase HPLC to produce pure N-(4-chloro-3-(pyridin-2-yl)phenyl)-4-((pyrimidin-2-ylamino)methyl)benzamide. MS (Q1) 416.3 $(M)^+$.

Example 24

N-(4-chloro-3-(pyridin-2-yl)phenyl)-6-((4-methylpiperazin-1-yl)methyl)pyridine-3-carboxamide

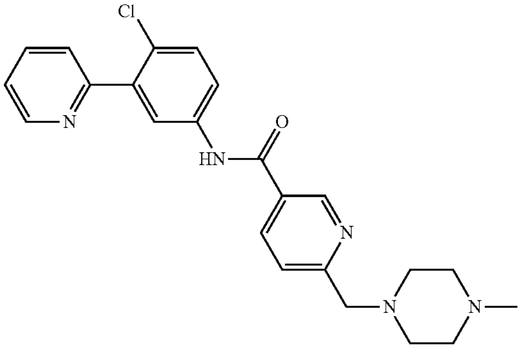 [SMILES: CN1CCN(Cc2ccc(C(=O)Nc3ccc(Cl)c(-c4ccccn4)c3)cn2)CC1]

6-(bromomethyl)-N-(4-chloro-3-(pyridin-2-yl)phenyl) pyridine-3-carboxamide was dissolved in 1 mL of DMSO and stirred for 1 h with N-methylpiperazine. The reaction was concentrated, and the crude residue was purified by reverse phase HPLC to yield N-(4-chloro-3-(pyridin-2-yl)phenyl)-6-((4-methylpiperazin-1-yl)methyl)pyridine-3-carboxamide as a pure product. MS (Q1) 422.3 $(M)^+$.

Example 25

4-((4-acetylpiperazin-1-yl)methyl)-N-(4-chloro-3-(pyridin-2-yl)phenyl)benzamide

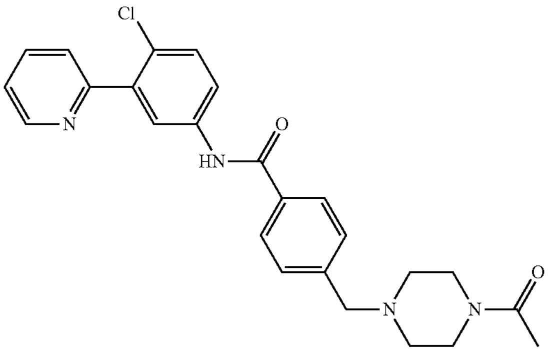 [SMILES: CC(=O)N1CCN(Cc2ccc(C(=O)Nc3ccc(Cl)c(-c4ccccn4)c3)cc2)CC1]

6-(bromomethyl)-N-(4-chloro-3-(pyridin-2-yl)phenyl) pyridine-3-carboxamide (85 mg) was dissolved in DMSO (1 mL) and stirred for 1 h with N-acetylpiperazine. The reaction mixture was concentrated, and the crude residue was purified by revered phase HPLC to yield 4-((4-acetylpiperazin-1-yl) methyl)-N-(4-chloro-3-(pyridin-2-yl)phenyl)benzamide. MS (Q1) 449.1 $(M)^+$.

Example 26

N-(4-chloro-3-(pyridin-2-yl)phenyl)-4-(thiomorpholinomethyl)benzamide

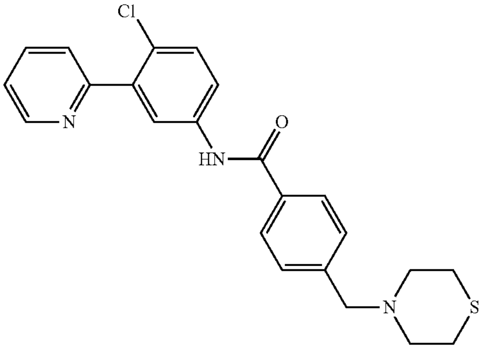 [SMILES: O=C(Nc1ccc(Cl)c(-c2ccccn2)c1)c1ccc(CN2CCSCC2)cc1]

4-(bromomethyl)-N-(4-chloro-3-(pyridin-2-yl)phenyl) benzamide (85 mg) was dissolved in DMSO (1 mL) and stirred for 1 h with thiomorpholine. The reaction mixture was concentrated, and the crude residue was purified by reverse phase HPLC to yield N-(4-chloro-3-(pyridin-2-yl)phenyl)-4-(thiomorpholinomethyl)benzamide. MS (Q1) 424.0 $(M)^+$.

Example 27

N-(4-chloro-3-(pyridin-2-yl)phenyl)-4-(morpholinomethyl)benzamide

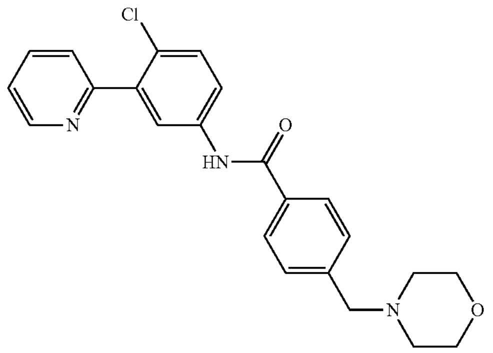

4-(bromomethyl)-N-(4-chloro-3-(pyridin-2-yl)phenyl)benzamide (85 mg) was dissolved in DMSO (1 mL) and stirred for 1 h with morpholine. The reaction mixture was concentrated, and the crude residue was purified by reverse phase HPLC to yield N-(4-chloro-3-(pyridin-2-yl)phenyl)-4-(morpholinomethyl)benzamide. MS (Q1) 408.4 $(M)^+$.

Example 28

N-(4-chloro-3-(pyridin-2-yl)phenyl)-4-((piperidin-1-yl)methyl)benzamide

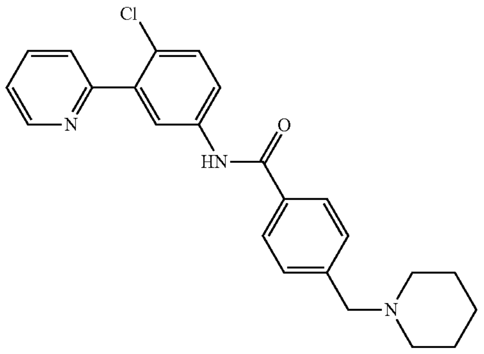 [SMILES: O=C(Nc1ccc(Cl)c(-c2ccccn2)c1)c1ccc(CN2CCCCC2)cc1]

4-(bromomethyl)-N-(4-chloro-3-(pyridin-2-yl)phenyl)benzamide (85 mg) was dissolved in DMSO (1 mL) and stirred for 1 h with piperidine. The reaction mixture was concentrated, and the crude residue was purified by reverse phase HPLC to yield N-(4-chloro-3-(pyridin-2-yl)phenyl)-4-((piperidin-1-yl)methyl)benzamide. MS (Q1) 406.4 $(M)^+$.

Example 29

N-(4-chloro-3-(pyridin-2-yl)phenyl)-4-((4-methylpiperazin-1-yl)methyl)benzamide

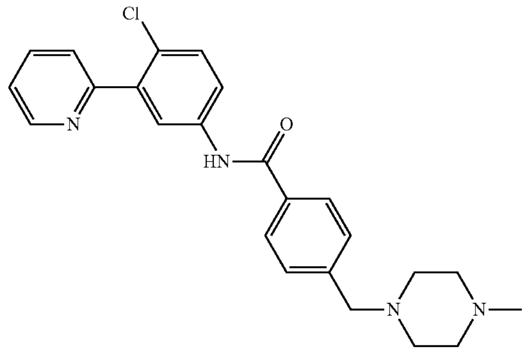

4-(bromomethyl)-N-(4-chloro-3-(pyridin-2-yl)phenyl)benzamide (85 mg) was dissolved in DMSO (1 mL) and stirred for 1 h with methylpiperazine. The reaction mixture was concentrated, and the crude residue was purified by reverse phase HPLC to yield N-(4-chloro-3-(pyridin-2-yl)phenyl)-4-((4-methylpiperazin-1-yl)methyl)benzamide. MS (Q1) 421.3 $(M)^+$.

Example 30

N-(4-chloro-3-(pyridin-2-yl)phenyl)-4-((dimethylamino)methyl)benzamide

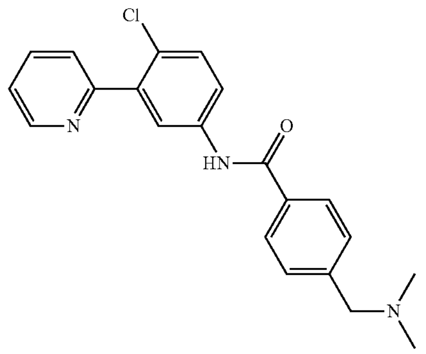 [SMILES: CN(C)Cc1ccc(C(=O)Nc2ccc(Cl)c(-c3ccccn3)c2)cc1]

Procedure G was used to couple BOC-4-(aminomethyl)benzoic acid (48 mg) with 4-chloro-3-(pyridin-2-yl)aniline (35 mg). The crude reaction mixture was treated with TFA (1 mL) containing trace amounts of water for 1 h. The reaction mixture was concentrated to yield 4-(aminomethyl)-N-(4-chloro-3-(pyridin-2-yl)phenyl)benzamide. 4-(aminomethyl)-N-(4-chloro-3-(pyridin-2-yl)phenyl)benzamide (80 mg) was dissolved in DMF (5 mL) and treated with AcOH (10 L), paraformaldehyde (48 mg), and sodium triacetoxyborohydride (125 mg) for 16 h. The reaction mixture was concentrated, and the crude residue was dissolved in ethyl acetate and washed with 1 N sodium hydroxide, dried ($MgSO_4$) and concentrated. The crude product was purified by reverse phase HPLC to yield N-(4-chloro-3-(pyridin-2-yl)phenyl)-4-((dimethylamino)methyl)benzamide. MS (Q1) 365.0 (M)+.

Example 31

N-(4-chloro-3-(pyridin-2-yl)phenyl)-3-[(2-methylpropyl)aminosulfonyl]-benzamide

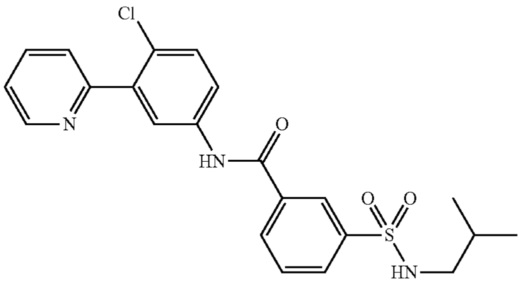 [SMILES: CC(C)CNS(=O)(=O)c1cccc(C(=O)Nc2ccc(Cl)c(-c3ccccn3)c2)c1]

Procedure H was performed to couple 3-(chlorosulfonyl) benzoic acid with sec-butyl amine to produce 3-(sec-butylsulfamoyl)benzoic acid which was purified by reverse phase HPLC.

Procedure G was used to couple 3-(sec-butylsulfamoyl) benzoic acid with 4-chloro-3-(pyridin-2-yl)aniline (28 mg) to yield N-(4-chloro-3-(pyridin-2-yl)phenyl)-3-[(2-methylpropyl)aminosulfonyl]-benzamide. MS (Q1) 444.0 (M)+.

Example 32

N-(4-chloro-3-(pyridin-2-yl)phenyl)-4-(4-morpholinylsulfonyl)-benzamide

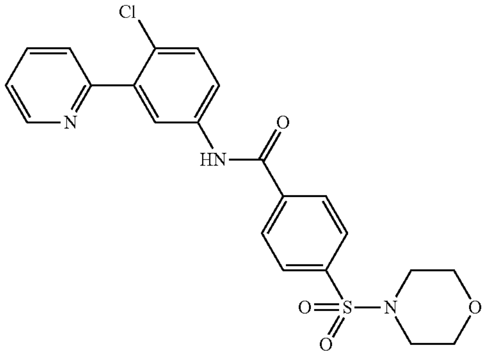 [SMILES: O=C(Nc1ccc(Cl)c(-c2ccccn2)c1)c1ccc(S(=O)(=O)N2CCOCC2)cc1]

Procedure H was performed to couple 4-(chlorosulfonyl) benzoic acid with morpholine to produce 4-(morpholinosulfamoyl)benzoic acid which was purified by reverse phase HPLC.

Procedure G was used to couple 4-(morpholinosulfamoyl) benzoic acid with 4-chloro-3-(pyridin-2-yl)aniline (34 mg) to yield N-(4-chloro-3-(pyridin-2-yl)phenyl)-4-(4-morpholinylsulfonyl)-benzamide. MS (Q1) 458.1 (M)+.

Example 33

N-(4-chloro-3-(pyridin-2-yl)phenyl)-3-(4-morpholinylsulfonyl)-benzamide

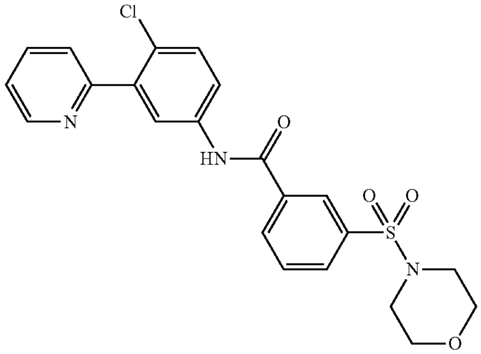 [SMILES: O=C(Nc1ccc(Cl)c(-c2ccccn2)c1)c1cccc(S(=O)(=O)N2CCOCC2)c1]

Procedure H was performed to couple 3-(chlorosulfonyl) benzoic acid with morpholine to produce 3-(morpholinosulfamoyl)benzoic acid which was purified by reverse phase HPLC.

Procedure G was used to couple 3-(morpholinosulfamoyl) benzoic acid with 4-chloro-3-(pyridin-2-yl)aniline (25 mg) to yield N-(4-chloro-3-(pyridin-2-yl)phenyl)-3-(4-morpholinylsulfonyl)-benzamide. MS (Q1) 458.1 (M)+.

Example 34

N-(4-chloro-3-(pyridin-2-yl)phenyl)-4-[(2-hydroxyethyl)amino]sulfonyl]-benzamide

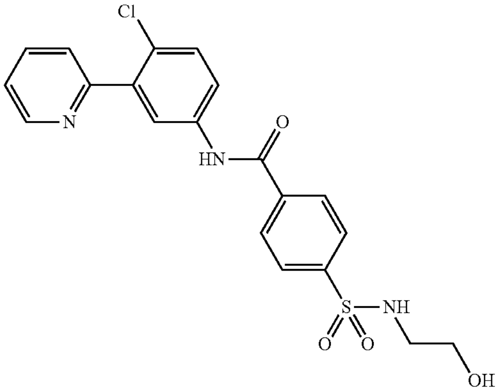 [SMILES: O=C(Nc1ccc(Cl)c(-c2ccccn2)c1)c1ccc(S(=O)(=O)NCCO)cc1]

Procedure H was performed to couple 4-(chlorosulfonyl) benzoic acid with ethanolamine to produce 4-(2-hydroxyethylsulfamoyl)benzoic acid which was purified by reverse phase HPLC.

Procedure G was used to couple 4-(2-hydroxyethylsulfamoyl)benzoic acid with 4-chloro-3-(pyridin-2-yl)aniline (42 mg) to yield N-(4-chloro-3-(pyridin-2-yl)phenyl)-4-[(2-hydroxyethyl)amino]sulfonyl]-benzamide. MS (Q1) 431.9 $(M)^+$.

Example 35

N-(4-chloro-3-(pyridin-2-yl)phenyl)-3-[(2-hydroxyethyl)amino]sulfonyl]-benzamide

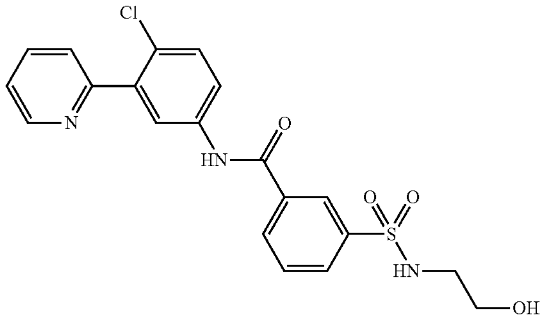 [SMILES: O=C(Nc1ccc(Cl)c(-c2ccccn2)c1)c1cccc(S(=O)(=O)NCCO)c1]

Procedure H was performed to couple 3-(chlorosulfonyl) benzoic acid with ethanolamine to produce 3-(2-hydroxyethylsulfamoyl)benzoic acid which was purified by reverse phase HPLC.

Procedure G was used to couple 3-(2-hydroxyethylsulfamoyl)benzoic acid with 4-chloro-3-(pyridin-2-yl)aniline (42 mg) to yield N-(4-chloro-3-(pyridin-2-yl)phenyl)-3-[(2-hydroxyethyl)amino]sulfonyl]-benzamide. MS (Q1) 432.0 $(M)^+$.

Example 36

N-(4-chloro-3-(pyridin-2-yl)phenyl)-3-(4-morpholinylsulfonyl)-benzamide

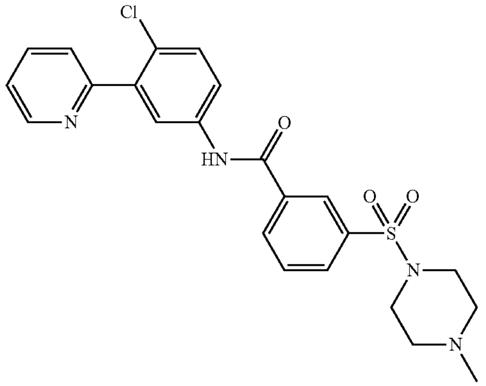 [SMILES: CN1CCN(S(=O)(=O)c2cccc(C(=O)Nc3ccc(Cl)c(-c4ccccn4)c3)c2)CC1]

Procedure H was performed to couple 3-(chlorosulfonyl) benzoic acid with piperazine to produce 3-(N-methylpiperazinosulfamoyl)benzoic acid which was purified by reverse phase HPLC.

Procedure G was used to couple 3-(N-methylpiperazinosulfamoyl)benzoic acid with 4-chloro-3-(pyridin-2-yl) aniline (50 mg) to yield N-(4-chloro-3-(pyridin-2-yl)phenyl)-3-(4-morpholinylsulfonyl)-benzamide. MS (Q1) 471.0 $(M)^+$.

Example 37

2-chloro-N-(4-chloro-3-(pyridin-2-yl)phenyl)-4-(methylsulfonyl)benzamide

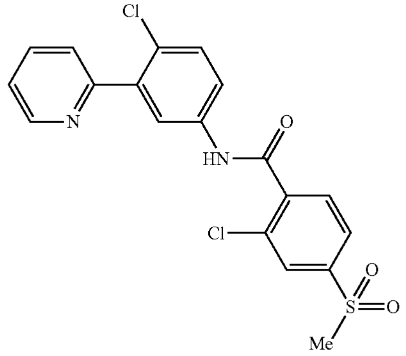 [SMILES: CS(=O)(=O)c1ccc(C(=O)Nc2ccc(Cl)c(-c3ccccn3)c2)c(Cl)c1]

Procedure G was used to couple 4-chloro-3-(pyridin-2-yl) aniline (50 mg) and 2-chloro-4-methylsulfonylbenzoic acid to produce 2-chloro-N-(4-chloro-3-(pyridin-2-yl)phenyl)-4-(methylsulfonyl)benzamide. MS (Q1) 421.0 $(M)^+$. The product was then dissolved in 1 N HCl solution followed by freebasing with 0.5 N NaOH solution (pH to 11). The resulting precipitate was filtered and vacuum-dry.

Procedure D may also be used to couple 4-chloro-3-(pyridin-2-yl)aniline and 2-chloro-4-(methylsulfonyl)benzoyl chloride to produce 2-chloro-N-(4-chloro-3-(pyridin-2-yl) phenyl)-4-(methylsulfonyl)benzamide which is collected by suction filtration and the HCl salt is washed with $Et_2O$ (or alternatively with MTBE). This material is freebased using EtOAc/aq $NaHCO_3$ and the organics are dried and concentrated to the solid freebase. This material is then crystallized from acetone:EtOAc (80:20, approx 10 mL/g) which is then finally recrystallized from hot slurry of iPrOAc. 2-chloro-N-(4-chloro-3-(pyridin-2-yl)phenyl)-4-(methylsulfonyl)benzamide HCl salt may also be dissolved in distilled water followed by freebasing with 0.5 N NaOH solution (pH to 11) and filtering and vacuum drying the precipitate.

Example 38

N-(4-chloro-3-(pyridin-2-yl)phenyl)-6-(1H-1,2,4-triazol-1-yl)pyridine-3-carboxamide

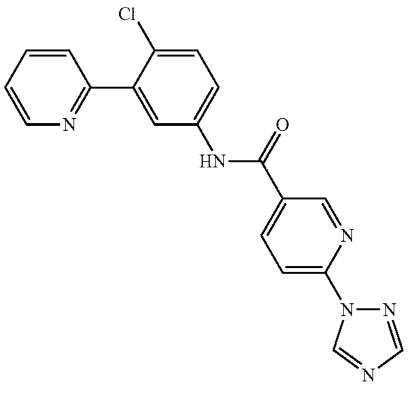 [SMILES: O=C(Nc1ccc(Cl)c(-c2ccccn2)c1)c1ccc(-n2cncn2)nc1]

Procedure G was used to couple 4-chloro-3-(pyridin-2-yl) aniline (40 mg) and 6-(1H-1,2,4-triazol-1-yl)pyridine-3-carboxylic acid to produce N-(4-chloro-3-(pyridin-2-yl)phenyl)-6-(1H-1,2,4-triazol-1-yl)pyridine-3-carboxamide. MS (Q1) 377.0 (M)+.

Example 39

N-(4-chloro-3-(pyridin-2-yl)phenyl)-4-[(dimethylamino)sulfonyl]-benzamide

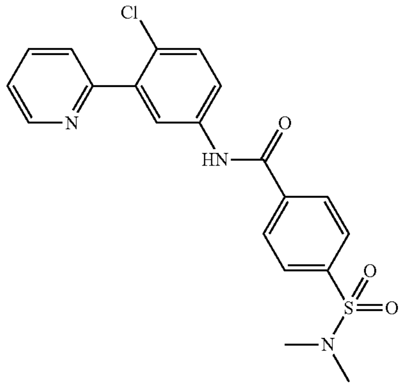 [SMILES: CN(C)S(=O)(=O)c1ccc(C(=O)Nc2ccc(Cl)c(-c3ccccn3)c2)cc1]

Procedure G was used to couple 4-chloro-3-(pyridin-2-yl) aniline (50 mg) and 4-[(dimethylamino)sulfonyl]benzoic acid to produce N-(4-chloro-3-(pyridin-2-yl)phenyl)-4-[(dimethylamino)sulfonyl]-benzamide. MS (Q1) 416.0 (M)+.

Example 40

N-(4-chloro-3-(pyridin-2-yl)phenyl)-5-(methylsulfonyl)thiophene-2-carboxamide

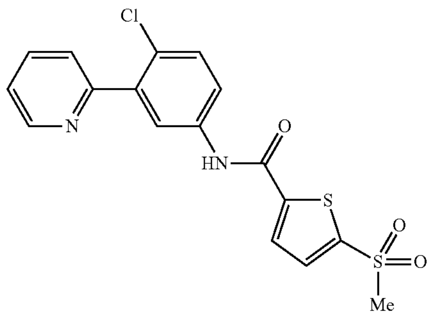 [SMILES: CS(=O)(=O)c1ccc(C(=O)Nc2ccc(Cl)c(-c3ccccn3)c2)s1]

Procedure G was used to couple 4-chloro-3-(pyridin-2-yl) aniline (40 mg) and 5-(methylsulfonyl)thiophene-2-carboxylic acid to produce N-(4-chloro-3-(pyridin-2-yl)phenyl)-5-(methylsulfonyl)thiophene-2-carboxamide. MS (Q1) 393.0 (M)+.

Example 41

N-(4-chloro-3-(pyridin-2-yl)phenyl)-4-(aminosulfonyl)-benzamide

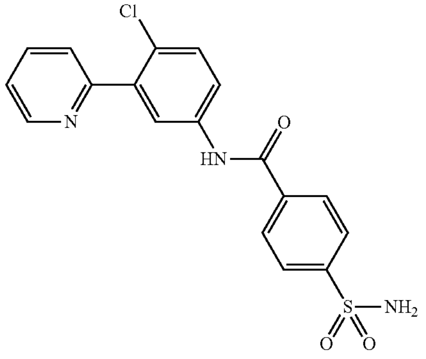 [SMILES: NS(=O)(=O)c1ccc(C(=O)Nc2ccc(Cl)c(-c3ccccn3)c2)cc1]

Procedure G was used to couple 4-chloro-3-(pyridin-2-yl) aniline (30 mg) and 4-carboxybenzenesulfonamide to produce N-(4-chloro-3-(pyridin-2-yl)phenyl)-4-(aminosulfonyl)-benzamide. MS (Q1) 388.0 (M)+.

Example 42

2,6-dichloro-N-(4-chloro-3-(pyridin-2-yl)phenyl) pyridine-3-carboxamide

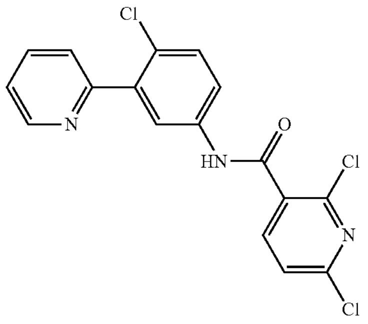 [SMILES: O=C(Nc1ccc(Cl)c(-c2ccccn2)c1)c1ccc(Cl)nc1Cl]

Procedure G was used to couple 4-chloro-3-(pyridin-2-yl) aniline (50 mg) and 2,6-dichloronicotinic acid to produce 2,6-dichloro-N-(4-chloro-3-(pyridin-2-yl)phenyl)pyridine-3-carboxamide. MS (Q1) 378.1 (M)+.

Example 43

2-chloro-N-(4-chloro-3-(pyridin-2-yl)phenyl)benzamide

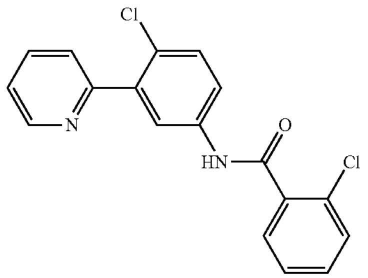 [SMILES: O=C(Nc1ccc(Cl)c(-c2ccccn2)c1)c1ccccc1Cl]

Procedure G was used to couple 4-chloro-3-(pyridin-2-yl) aniline (50 mg) and 2-chlorobenzoic acid to produce 2-chloro-N-(4-chloro-3-(pyridin-2-yl)phenyl)benzamide. MS (Q1) 343.1 (M)$^+$.

Example 44

N-(4-chloro-3-(pyridin-2-yl)phenyl)-2-fluoropyridine-3-carboxamide

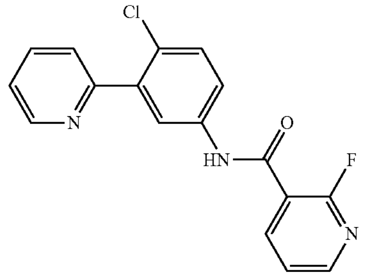 [SMILES: O=C(Nc1ccc(Cl)c(-c2ccccn2)c1)c1cccnc1F]

Procedure G was used to couple 4-chloro-3-(pyridin-2-yl) aniline (50 mg) and 2-fluoronicotinic acid to produce N-(4-chloro-3-(pyridin-2-yl)phenyl)-2-fluoropyridine-3-carboxamide. MS (Q1) 328.1 (M)$^+$.

Example 45

N-(4-chloro-3-(pyridin-2-yl)phenyl)-3-methylthiophene-2-carboxamide

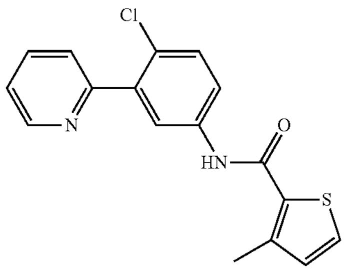 [SMILES: Cc1ccsc1C(=O)Nc1ccc(Cl)c(-c2ccccn2)c1]

Procedure G was used to couple 4-chloro-3-(pyridin-2-yl) aniline (50 mg) and 3-methyl-2-thiophenecarboxylic acid to produce N-(4-chloro-3-(pyridin-2-yl)phenyl)-3-methylthiophene-2-carboxamide. MS (Q1) 329.0 (M)$^+$.

Example 46

2-chloro-N-(4-chloro-3-(pyridin-2-yl)phenyl)-5-(methylsulfonyl)benzamide

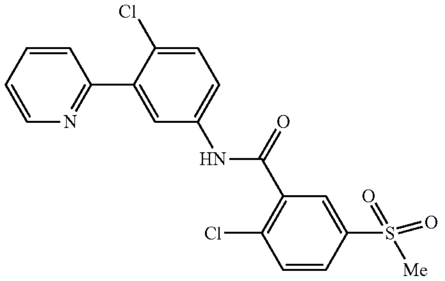 [SMILES: CS(=O)(=O)c1ccc(Cl)c(C(=O)Nc2ccc(Cl)c(-c3ccccn3)c2)c1]

Procedure G was used to couple 4-chloro-3-(pyridin-2-yl) aniline and 2-chloro-5-(methanesulfonyl)benzoic acid to produce 2-chloro-N-(4-chloro-3-(pyridin-2-yl)phenyl)-5-(methylsulfonyl)benzamide. MS (Q1) 420.95 (M)$^+$.

Example 47

N-(4-chloro-3-(pyridin-2-yl)phenyl)-3-(methylsulfonyl)benzamide

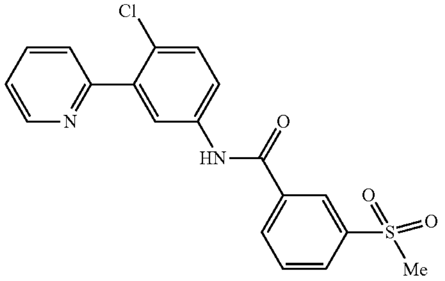 [SMILES: CS(=O)(=O)c1cccc(C(=O)Nc2ccc(Cl)c(-c3ccccn3)c2)c1]

Procedure G was used to couple 4-chloro-3-(pyridin-2-yl) aniline and 3-(methanesulfonyl)benzoic acid to produce N-(4-chloro-3-(pyridin-2-yl)phenyl)-3-(methylsulfonyl) benzamide. MS (Q1) 387.2 (M)$^+$.

Example 48

2-amino-N-(4-chloro-3-(pyridin-2-yl)phenyl)pyridine-3-carboxamide

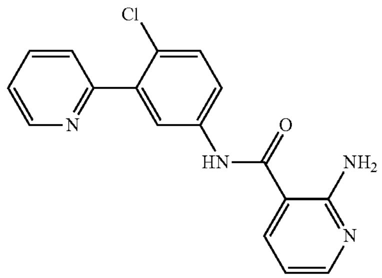 [SMILES: Nc1ncccc1C(=O)Nc1ccc(Cl)c(-c2ccccn2)c1]

Procedure G was used to couple 4-chloro-3-(pyridin-2-yl) aniline (50 mg) and 2-aminonicotinic acid to produce 2-amino-N-(4-chloro-3-(pyridin-2-yl)phenyl)pyridine-3-carboxamide. MS (Q1) 325.2 $(M)^+$.

Example 49

N-(4-chloro-3-(pyridin-2-yl)phenyl)-4-methoxybenzamide

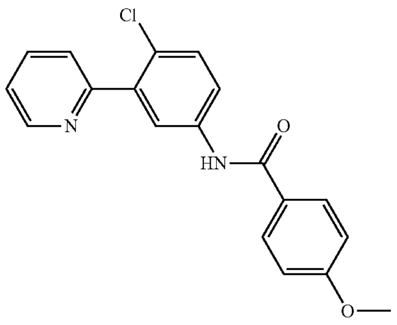 [SMILES: COc1ccc(C(=O)Nc2ccc(Cl)c(-c3ccccn3)c2)cc1]

Procedure G was used to couple 4-chloro-3-(pyridin-2-yl)aniline and 4-methoxylbenzoic acid to produce N-(4-chloro-3-(pyridin-2-yl)phenyl)-4-methoxybenzamide. MS (Q1) 341.2 $(M)^+$.

Example 50

N-benzyl-5-chloro-4-(pyridin-2-yl)thiazol-2-amine

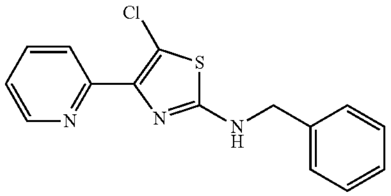 [SMILES: Clc1sc(NCc2ccccc2)nc1-c1ccccn1]

A solution of 2-(Bromoacetyl)pyridine hydrobromide (100 mg, 0.36 mmol) in ethanol (2 mL) was treated with 1-benzyl-2-thiourea (90 mg, 0.54 mmol). The resulting yellow solution was concentrated, and the crude residue was purified on reverse phase HPLC to produce N-benzyl-4-(pyridin-2-yl)thiazol-2-amine.

A solution of N-benzyl-4-(pyridin-2-yl)thiazol-2-amine (60 mg, 0.23 mmol) in DMF (2 mL) was cooled to 0° C. and treated with N-chlorosuccinimide (33 mg, 0.25 mmol), and the reaction mixture was allowed to warm to room temperature. The solvent was evaporated, and the product was purified on reverse phase HPLC to produce N-benzyl-5-chloro-4-(pyridin-2-yl)thiazol-2-amine. MS (Q1) 302.2 $(M)^+$.

Example 51

4-chloro-N-(3,5-dimethoxyphenyl)-3-(pyridin-2-yl)benzamide

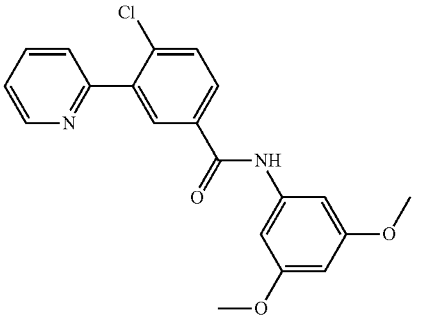 [SMILES: COc1cc(NC(=O)c2ccc(Cl)c(-c3ccccn3)c2)cc(OC)c1]

A solution of 3-bromo-4-chlorobenzoic acid (250 mg, 1.1 mmol) in DMF (2 mL) was treated with PyBop (550 mg, 1.1 mmol) and DIPEA (370 uL, 2.1 mmol). After stirring the reaction mixture for 5 min. 3,5-dimethoxy analine (105 mg, 0.69 mmol) was added and the reaction was stirred for 16 h. The reaction mixture was diluted with ethyl acetate and washed with 0.1 N HCl, 0.1 N sodium hydroxide and Brine, successively. The organic layer was dried ($MgSO_4$) and concentrated, and crude 3-bromo-4-chloro-N-(3,5-dimethoxyphenyl)benzamide was used without further purification.

3-bromo-4-chloro-N-(3,5-dimethoxyphenyl)benzamide was dissolved in 0.5 M 2-pyridylzincbromide (2.5 mL) and treated with $Pd(PPh)_3)_4$ (20 mg, 0.02 mmol). The reaction mixture was heated to 155° C. in a sealed tube for 20 min. in a microwave reactor. The resultant solution was diluted with Ethyl acetate and washed with 0.1 N sodium hydroxide and then brine. The organic layer was dried ($MgSO_4$) and concentrated, and the crude residue was partially purified by silica gel chromatography. Pure 4-chloro-N-(3,5-dimethoxyphenyl)-3-(pyridin-2-yl)benzamide was obtained by a second purification on reverse phase HPLC. MS (Q1) 369.1 $(M)^+$.

Example 52

N-(3-(3,5-bis(trifluoromethyl)phenyl)propyl)-4-chloro-3-(pyridin-2-yl)benzenamine

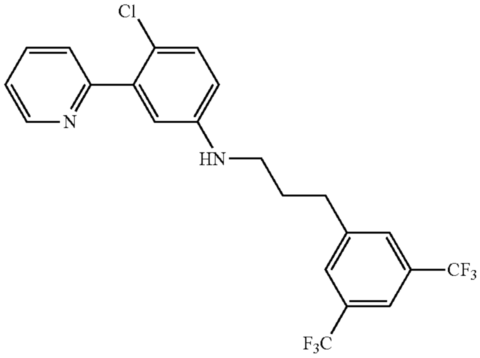 [SMILES: FC(F)(F)c1cc(CCCNc2ccc(Cl)c(-c3ccccn3)c2)cc(C(F)(F)F)c1]

A solution of 3,5-bis(trifluoromethyl)hydrocinnamic acid (1.0 g, 3.5 mmol) and TEA (0.46 g, 4.5 mmol) in THF (16 mL) was cooled to −40° C. (ethanol-water/dry ice bath). To this mixture was dropwise added isobutyl chloroformate (0.56 g, 4.1 mmol) and stirring was continued for another 1.5 hours while the temperature of the cooling bath was maintained between −40° C. and −20° C. Solid $NaBH_4$ (0.53 g, 14 mmol) was added, followed by $H_2O$ (1.3 mL). The cloudy mixture was stirred overnight while warming to room temperature. After concentrating in vacuo, the residue was partitioned between ethyl acetate and water. The aqueous layer was acidified to pH 1 with 37% HCl and extracted with ethyl acetate. The combined organic layers were washed sequentially with saturated $NaHCO_3$, and brine, then dried ($MgSO_4$) and concentrated. The resulting oil was purified by flash silica gel chromatography (6:4 ethyl ether-hexane) to yield 3-[3',5'-bis(trifluoromethyl)phenyl]-1-propanol.

3-[3',5'-bis(trifluoromethyl)phenyl]-1-propanol (0.88 g, 3.2 mmol) and $CBr_4$ (1.3 g, 4.0 mmol) were dissolved in $CH_2Cl_2$ (5 mL) and cooled to 0° C. Triphenylphosphine (1.3 g, 4.8 mmol) was added in three portions over 0.5 h. The mixture was stirred at 0° C. for 10 min., then diluted with pentane (30 mL) and sat. $NaHCO_3$ (30 mL). The aqueous layer was separated and washed with ethyl ether, and the combined organic layers were dried ($MgSO_4$) and concentrated. The residue was purified by silica gel flash chromatography (99:1 ethyl ether-hexane) to yield 0.8 g, (74%) of the 3-[3',5'-bis(trifluoromethyl)phenyl]-1-bromopropane.

4-chloro-3-(2'-pyridyl)aniline (10 mg, 0.05 mmol), 3-[3',5'-bis(trifluoromethyl)phenyl]-1-bromopropane (34 mg, 0.1 mmol) and $K_2CO_3$ (14 mg, 0.1 mmol) in DMF (1 mL) was stirred at 100° C. overnight. The reaction mixture was acidified with 1N HCl (aq.) and extracted with ethyl acetate. The combined organic layers were washed with brine, dried ($MgSO_4$) and concentrated. The crude was purified by preparative HPLC to yield N-(3-(3,5-bis(trifluoromethyl)phenyl)propyl)-4-chloro-3-(pyridin-2-yl)benzenamine.

Example 53

N-(4-chloro-3-(5-(trifluoromethyl)pyridin-2-yl)phenyl)-2-methyl-6-(trifluoromethyl)nicotinamide

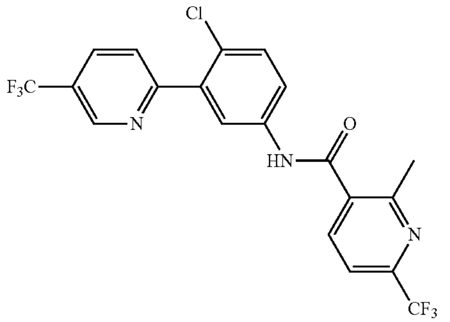 [SMILES: Cc1nc(C(F)(F)F)ccc1C(=O)Nc1ccc(Cl)c(-c2ccc(C(F)(F)F)cn2)c1]

N-(4-chloro-3-(4,4,5,5-tetramethyl-1,3,2-dioxaborolan-2-yl)phenyl)-2-methyl-6-(trifluoromethyl)nicotinamide (~0.5 mmol) was used in Procedure A with 5-trifluoromethyl-2-bromopyridine (113 mg, 0.5 mmol). Purified by silica gel chromatography (5-50% ethyl acetate/hexanes) to yield N-(4-chloro-3-(5-(trifluoromethyl)pyridin-2-yl)phenyl)-2-methyl-6-(trifluoromethyl)nicotinamide as a white foam: TLC $R_f$=0.30 (15% ethyl acetate/hexanes); MS (Q1) 460 $(M)^+$.

Example 54

N-(4-chloro-3-(5-(trifluoromethyl)pyridin-2-yl)phenyl)-4-(methylsulfonyl)benzamide

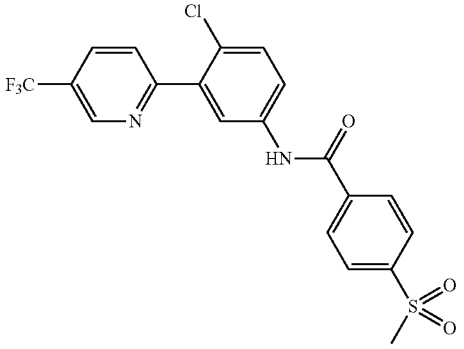 [SMILES: CS(=O)(=O)c1ccc(C(=O)Nc2ccc(Cl)c(-c3ccc(C(F)(F)F)cn3)c2)cc1]

N-(4-chloro-3-(4,4,5,5-tetramethyl-1,3,2-dioxaborolan-2-yl)phenyl)-4-(methylsulfonyl)benzamide (~1.0 mmol) was used in Procedure A with 5-trifluoromethyl-2-bromopyridine (226 mg, 1 mmol). Purified by silica gel chromatography (0-10% acetone/dichloromethane) to yield N-(4-chloro-3-(5-(trifluoromethyl)pyridin-2-yl)phenyl)-4-(methylsulfonyl)benzamide as a white solid: MS (Q1) 455 $(M)^+$.

Example 55

N-(4-chloro-3-(5-chloropyridin-2-yl)phenyl)-2-methyl-6-(trifluoromethyl)nicotinamide

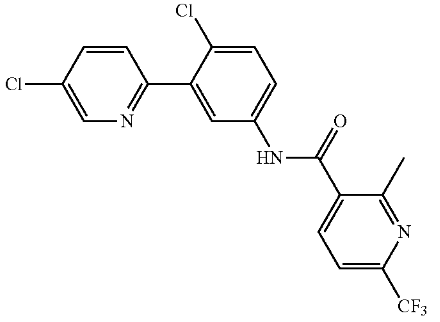 [SMILES: Cc1nc(C(F)(F)F)ccc1C(=O)Nc1ccc(Cl)c(-c2ccc(Cl)cn2)c1]

5-chloropyridin-2-yl trifluoromethanesulfonate (4.12 mmol) was used in Procedure I with trimethyltin chloride to yield 5-chloro-2-(trimethylstannyl)pyridine. The crude material (~4 mmol) was used in Procedure K with N-(4-chloro-3-iodophenyl)-2-methyl-6-(trifluoromethyl)nicotinamide (2 mmol). Purified by silica gel chromatography (0-50% ethyl acetate/hexane) to yield N-(4-chloro-3-(5-chloropyridin-2- yl)phenyl)-2-methyl-6-(trifluoromethyl)nicotinamide as a white solid: TLC $R_f$=0.48 (25% ethyl acetate/hexanes); MS (Q1) 427 $(M)^+$.

Example 56

N-(4-chloro-3-(6-chloropyridin-2-yl)phenyl)-2-methyl-6-(trifluoromethyl)nicotinamide

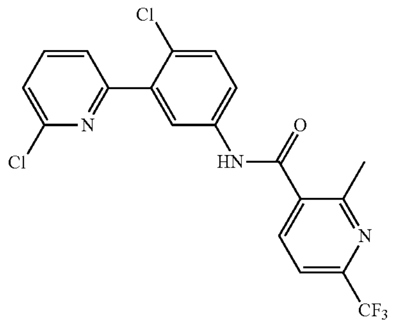 [SMILES: Cc1nc(C(F)(F)F)ccc1C(=O)Nc1ccc(Cl)c(-c2cccc(Cl)n2)c1]

6-chloropyridin-2-yl trifluoromethanesulfonate (4.12 mmol) was used in Procedure I with trimethyltin chloride to yield 2-chloro-6-(trimethylstannyl)pyridine. The crude material (~4 mmol) was used in Procedure K with N-(4-chloro-3-iodophenyl)-2-methyl-6-(trifluoromethyl)nicotinamide (2 mmol). Purified by silica gel chromatography (5-45% ethyl acetate/hexane) to yield N-(4-chloro-3-(6-chloropyridin-2-yl)phenyl)-2-methyl-6-(trifluoromethyl)nicotinamide as a white solid: TLC $R_f$=0.45 (25% ethyl acetate/hexanes); MS (Q1) 426 $(M)^+$.

Example 57

N-(4-chloro-3-(5-hydroxypyridin-2-yl)phenyl)-2-methyl-6-(trifluoromethyl)nicotinamide

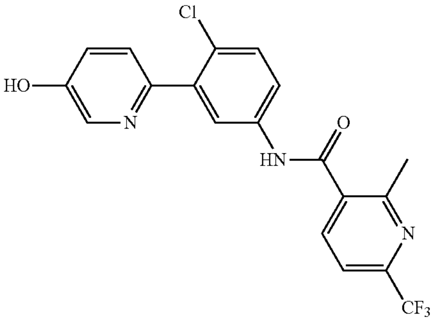 [SMILES: Cc1nc(C(F)(F)F)ccc1C(=O)Nc1ccc(Cl)c(-c2ccc(O)cn2)c1]

3-(triisopropylsilyloxy)pyridine (2.66 mmol) was used in Procedure J with hexamethyldistannane to yield 5-(triisopropylsilyloxy)-2-(trimethylstannyl)pyridine. The crude material (~0.55 mmol) was used in Procedure K with N-(4-chloro-3-iodophenyl)-2-methyl-6-(trifluoromethyl)nicotinamide (0.17 mmol). Purified by silica gel chromatography (0-40% ethyl acetate/hexane) to yield N-(4-chloro-3-(5-(triisopropylsilyloxy)pyridin-2-yl)phenyl)-2-methyl-6-(trifluoromethyl)nicotinamide as a yellow oil. N-(4-chloro-3-(5-(triisopropylsilyloxy)pyridin-2-yl)phenyl)-2-methyl-6-(trifluoromethyl)nicotinamide (1 mmol) was treated with TBAF (2 mL, 1 M in THF) in THF (1 mL) at 23° C. for thirty minutes, concentrated, redissolved in ethyl acetate, washed with brine, dried ($MgSO_4$), and concentrated. The crude solid was purified by silica gel chromatography (0-10% isopropanol/dichloromethane) to yield N-(4-chloro-3-(5-hydroxypyridin-2-yl)phenyl)-2-methyl-6-(trifluoromethyl)nicotinamide as a white solid: TLC $R_f$=0.59 (10% ethyl acetate/hexanes); MS (Q1) 408 $(M)^+$.

Example 58

N-(4-chloro-3-(5-methoxypyridin-2-yl)phenyl)-2-methyl-6-(trifluoromethyl)nicotinamide

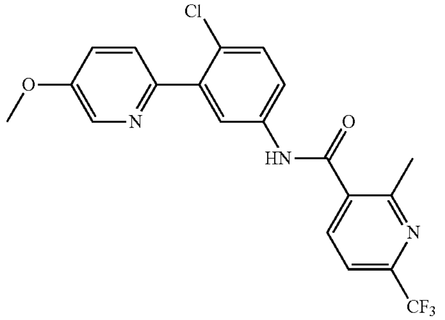 [SMILES: COc1ccc(-c2cc(NC(=O)c3ccc(C(F)(F)F)nc3C)ccc2Cl)nc1]

N-(4-chloro-3-(5-hydroxypyridin-2-yl)phenyl)-2-methyl-6-(trifluoromethyl)nicotinamide (0.12 mmol) was used in Procedure L with excess iodomethane. Purified by silica gel chromatography (0-100% ethyl acetate/hexane) to yield N-(4-chloro-3-(5-methoxypyridin-2-yl)phenyl)-2-methyl-6-(trifluoromethyl)nicotinamide as a white solid: TLC $R_f$=0.57 (50% ethyl acetate/hexanes); MS (Q1) 423$(M)^+$.

Example 59

N-(4-chloro-3-(5-ethoxypyridin-2-yl)phenyl)-2-methyl-6-(trifluoromethyl)nicotinamide

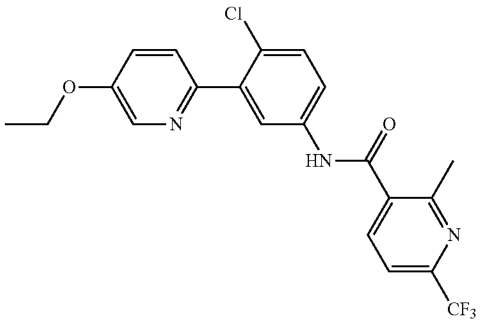 [SMILES: CCOc1ccc(-c2cc(NC(=O)c3ccc(C(F)(F)F)nc3C)ccc2Cl)nc1]

N-(4-chloro-3-(5-hydroxypyridin-2-yl)phenyl)-2-methyl-6-(trifluoromethyl)nicotinamide (0.05 mmol) was used in Procedure L with excess iodoethane. Purified by silica gel chromatography (0-100% ethyl acetate/hexane) to yield N-(4-chloro-3-(5-ethoxypyridin-2-yl)phenyl)-2-methyl-6-

(trifluoromethyl)nicotinamide as a white solid: TLC $R_f$=0.64 (50% ethyl acetate/hexanes); MS (Q1) 436 $(M)^+$.

Example 60

N-(4-chloro-3-(5-(2,2,2-trifluoroethoxy)pyridin-2-yl)phenyl)-2-methyl-6-(trifluoromethyl)nicotinamide

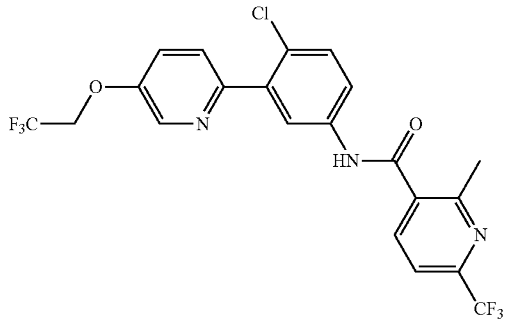 [SMILES: Cc1nc(C(F)(F)F)ccc1C(=O)Nc1ccc(Cl)c(-c2ccc(OCC(F)(F)F)cn2)c1]

N-(4-chloro-3-(5-hydroxypyridin-2-yl)phenyl)-2-methyl-6-(trifluoromethyl)nicotinamide (0.12 mmol) was used in Procedure L with excess trifluoroethyl iodide. Purified by silica gel chromatography (0-40% ethyl acetate/hexane) to yield N-(4-chloro-3-(5-(2,2,2-trifluoroethoxy)pyridin-2-yl)phenyl)-2-methyl-6-(trifluoromethyl)nicotinamide as a white solid: TLC $R_f$=0.64 (40% ethyl acetate/hexanes); MS (Q1) 490 $(M)^+$.

Example 61

N-(4-chloro-3-(4-ethylpyridin-2-yl)phenyl)-2-methyl-6-(trifluoromethyl)nicotinamide

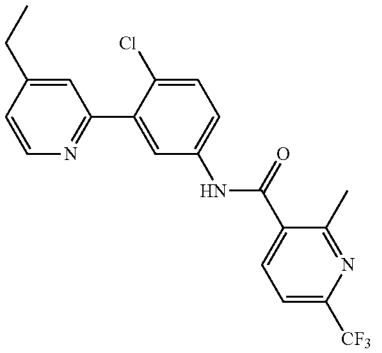 [SMILES: CCc1ccnc(-c2cc(NC(=O)c3ccc(C(F)(F)F)nc3C)ccc2Cl)c1]

N-(4-chloro-3-(4,4,5,5-tetramethyl-1,3,2-dioxaborolan-2-yl)phenyl)-2-methyl-6-(trifluoromethyl)nicotinamide (~1 mmol) was used in Procedure A with 4-ethyl-2-bromopyridine (1 mmol). Purified by silica gel chromatography (0-60% ethyl acetate/hexanes) to yield N-(4-chloro-3-(4-ethylpyridin-2-yl)phenyl)-2-methyl-6-(trifluoromethyl)nicotinamide as a tan solid: MS (Q1) 419 $(M)^+$.

Example 62

N-(4-chloro-3-(5-fluoropyridin-2-yl)phenyl)-2-methyl-6-(trifluoromethyl)nicotinamide

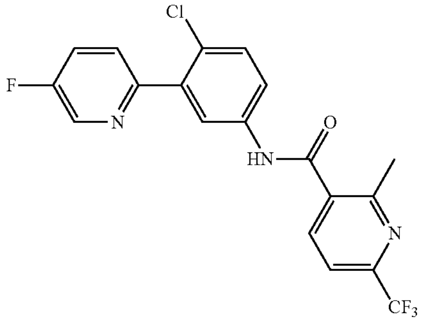 [SMILES: Cc1nc(C(F)(F)F)ccc1C(=O)Nc1ccc(Cl)c(-c2ccc(F)cn2)c1]

N-(4-chloro-3-(4,4,5,5-tetramethyl-1,3,2-dioxaborolan-2-yl)phenyl)-2-methyl-6-(trifluoromethyl)nicotinamide (~1 mmol) was used in Procedure A with 5-fluoro-2-bromopyridine (1 mmol). Purified by silica gel chromatography (5-45% ethyl acetate/hexanes) to yield N-(4-chloro-3-(5-fluoropyridin-2-yl)phenyl)-2-methyl-6-(trifluoromethyl)nicotinamide as a tan solid: MS (Q1) 409 $(M)^+$.

Example 63

N-(4-chloro-3-(5-phenylpyridin-2-yl)phenyl)-2-methyl-6-(trifluoromethyl)-nicotinamide

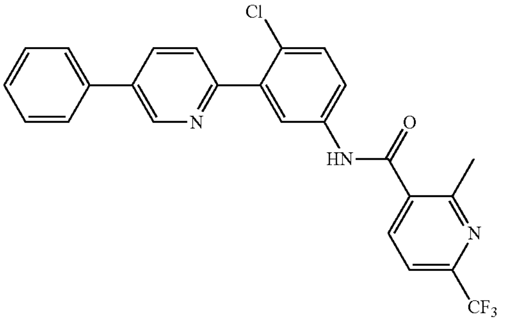 [SMILES: Cc1nc(C(F)(F)F)ccc1C(=O)Nc1ccc(Cl)c(-c2ccc(-c3ccccc3)cn2)c1]

5-phenylpyridin-2-yl trifluoromethanesulfonate (1.5 mmol) was used in Procedure J with trimethyltin chloride to yield 5-phenyl-2-(trimethylstannyl)pyridine. The crude material (~1.25 mmol) was used in Procedure K with N-(4-chloro-3-iodophenyl)-2-methyl-6-(trifluoromethyl)nicotinamide (1 mmol). Purified by silica gel chromatography (1% acetone/methylene chloride) to yield N-(4-chloro-3-(5-phenylpyridin-2-yl)phenyl)-2-methyl-6-(trifluoromethyl)nicotinamideas a tan solid: TLC $R_f$=0.15 (1% acetone/methylene chloride); MS (Q1) 467 $(M)^+$.

Example 64

(S)—N-(4-chloro-3-(pyridin-2-yl)phenyl)-6-(3-methylpiperazin-1-yl)nicotinamide

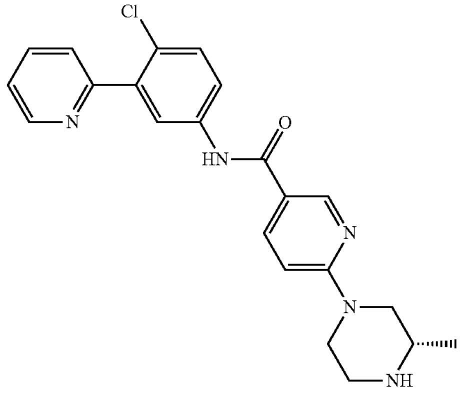 [SMILES: C[C@H]1CN(c2ccc(C(=O)Nc3ccc(Cl)c(-c4ccccn4)c3)cn2)CCN1]

Procedure F was performed using N-(4-chloro-3-(pyridin-2-yl)phenyl)-6-chloro-3-carboxamide (50 mg) and 75 mg of (S)-2-methylpiperazine in 0.75 mL of butanol at 160° C. for 60 min. Purification by reverse phase HPLC yielded (S)—N-(4-chloro-3-(pyridin-2-yl)phenyl)-6-(3-methylpiperazin-1-yl)nicotinamide. MS (Q1) 408 $(M)^+$.

Example 65

(R)—N-(4-chloro-3-(pyridin-2-yl)phenyl)-6-(3-methylpiperazin-1-yl)nicotinamide

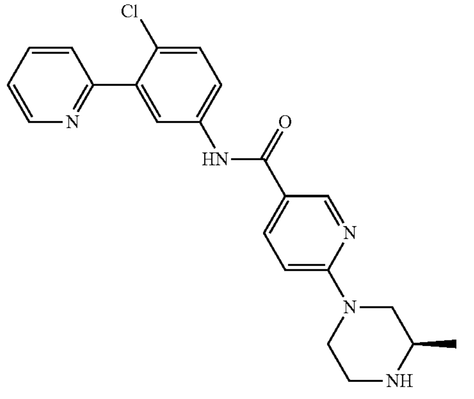

Procedure F was performed using N-(4-chloro-3-(pyridin-2-yl)phenyl)-6-chloro-3-carboxamide (50 mg) and 75 mg of (R)-2-methylpiperazine in 0.75 mL of butanol at 160° C. for 60 min. Purification by reverse phase HPLC yielded (R)—N-(4-chloro-3-(pyridin-2-yl)phenyl)-6-(3-methylpiperazin-1-yl)nicotinamide. MS (Q1) 408 $(M)^+$.

Example 66

N-(4-chloro-3-(pyridin-2-yl)phenyl)-6-((3S,5R)-3,5-dimethylpiperazin-1-yl)nicotinamide

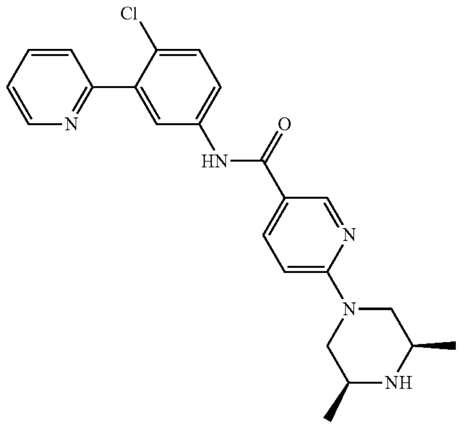 [SMILES: C[C@@H]1CN(c2ccc(C(=O)Nc3ccc(Cl)c(-c4ccccn4)c3)cn2)C[C@H](C)N1]

Procedure F was performed using N-(4-chloro-3-(pyridin-2-yl)phenyl)-6-chloro-3-carboxamide (75 mg) and 114 mg of 2,6-dimethylpiperazine in 1 mL of butanol at 160° C. for 60 min. Purification by reverse phase HPLC yielded N-(4-chloro-3-(pyridin-2-yl)phenyl)-6-((3S,5R)-3,5-dimethylpiperazin-1-yl)nicotinamide. MS (Q1) 422.1 $(M)^+$.

Example 67

$N^1$-(4-chloro-3-(pyridin-2-yl)phenyl)-$N^4$-(pyridin-3-yl)terephthalamide

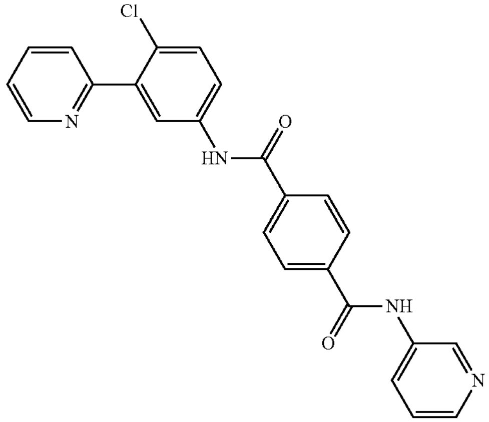 [SMILES: O=C(Nc1cccnc1)c1ccc(C(=O)Nc2ccc(Cl)c(-c3ccccn3)c2)cc1]

320 mg of 4-chloro-3-(pyridin-2-yl)aniline was coupled to 400 mg of 4-(methoxycarbonyl)benzoic acid via Procedure G to give methyl 4-(4-chloro-3-(pyridin-2-yl)phenylcarbamoyl)benzoate. 4-(4-chloro-3-(pyridin-2-yl)phenylcarbamoyl)benzoate was then hydrolyzed via Prodedure M to give 550 mg of 4-(4-chloro-3-(pyridin-2-yl)phenylcarbamoyl) benzoic acid. 50 mg of 4-(4-chloro-3-(pyridin-2-yl)phenylcarbamoyl)benzoic acid was coupled to 3-aminopyridine via Procedure G. The organic layer was evaporated to dryness and purified on reverse phase HPLC to yield $N^1$-(4-chloro-3-(pyridin-2-yl)phenyl)-$N^4$-(pyridin-3-yl)terephthalamide. MS (Q1) 429 $(M)^+$.

Example 68

$N^1$-(4-chloro-3-(pyridin-2-yl)phenyl)-$N^4$-(6-methoxypyridin-3-yl)terephthalamide

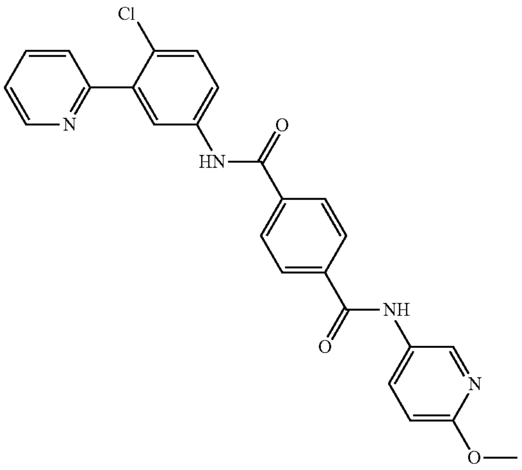 [SMILES: COc1ccc(NC(=O)c2ccc(C(=O)Nc3ccc(Cl)c(-c4ccccn4)c3)cc2)cn1]

50 mg of 4-(4-chloro-3-(pyridin-2-yl)phenylcarbamoyl) benzoic acid was coupled to 2-methoxy-5-aminopyridine via Procedure G. The product was purified on reverse phase HPLC to yield $N^1$-(4-chloro-3-(pyridin-2-yl)phenyl)-$N^4$-(6-methoxypyridin-3-yl)terephthalamide. MS (Q1) 459 $(M)^+$.

Example 69

$N^1$-(6-aminopyridin-3-yl)-$N^4$-(4-chloro-3-(pyridin-2-yl)phenyl)terephthalamide

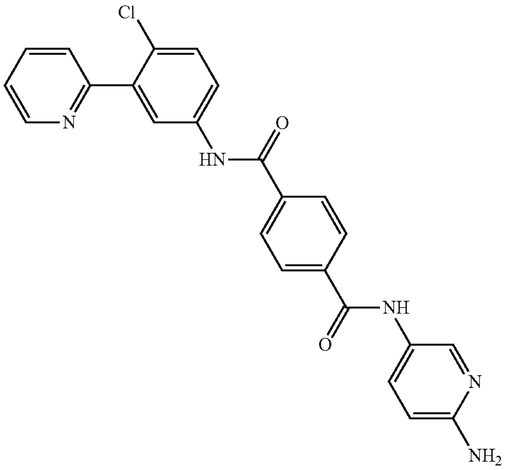 [SMILES: Nc1ccc(NC(=O)c2ccc(C(=O)Nc3ccc(Cl)c(-c4ccccn4)c3)cc2)cn1]

50 mg of 4-(4-chloro-3-(pyridin-2-yl)phenylcarbamoyl) benzoic acid was coupled to 2,5-diaminopyridine via Procedure G. The product was purified on reverse phase HPLC to yield $N^1$-(6-aminopyridin-3-yl)-$N^4$-(4-chloro-3-(pyridin-2-yl)phenyl)terephthalamide. MS (Q1) 444 $(M)^+$.

Example 70

$N^1$-(4-chloro-3-(pyridin-2-yl)phenyl)-$N^4$-(pyridin-2-ylmethyl)terephthalamide

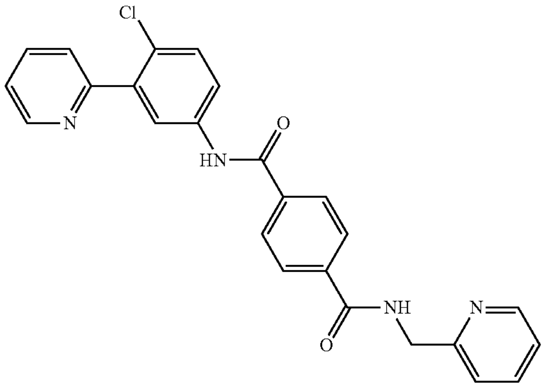

50 mg of 4-(4-chloro-3-(pyridin-2-yl)phenylcarbamoyl) benzoic acid was coupled to 2-(aminomethyl)pyridine via Procedure G. The product was purified on reverse phase HPLC to yield $N^1$-(4-chloro-3-(pyridin-2-yl)phenyl)-$N^4$-(pyridin-2-ylmethyl)terephthalamide. MS (Q1) 443 $(M)^+$.

Example 71

$N^1$-(4-chloro-3-(pyridin-2-yl)phenyl)-$N^4$-isopropyl-terephthalamide

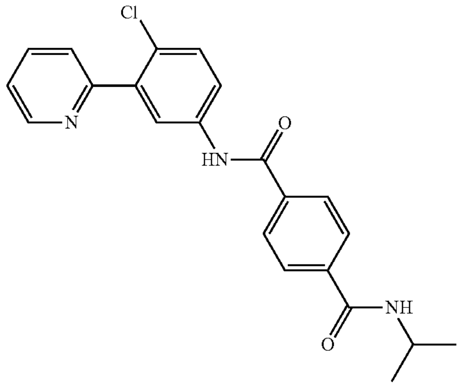 [SMILES: CC(C)NC(=O)c1ccc(C(=O)Nc2ccc(Cl)c(-c3ccccn3)c2)cc1]

50 mg of 4-(4-chloro-3-(pyridin-2-yl)phenylcarbamoyl) benzoic acid was coupled to isopropylamine via Procedure G. The product was purified on reverse phase HPLC to yield $N^1$-(4-chloro-3-(pyridin-2-yl)phenyl)-$N^4$-isopropylterephthalamide. MS (Q1) 394 $(M)^+$.

Example 72

N[1]-tert-butyl-N[4]-(4-chloro-3-(pyridin-2-yl)phenyl)terephthalamide

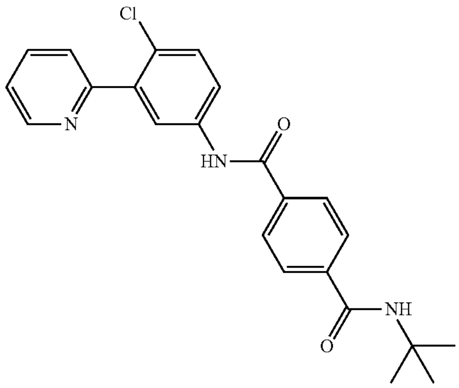 [SMILES: CC(C)(C)NC(=O)c1ccc(C(=O)Nc2ccc(Cl)c(-c3ccccn3)c2)cc1]

50 mg of 4-(4-chloro-3-(pyridin-2-yl)phenylcarbamoyl)benzoic acid was coupled to tert-butylamine via Procedure G. The product was purified on reverse phase HPLC to yield $N^1$-tert-butyl-$N^4$-(4-chloro-3-(pyridin-2-yl)phenyl)terephthalamide. MS (Q1) 408 $(M)^+$.

Example 73

N[4]-tert-butyl-2-chloro-N[1]-(4-chloro-3-(pyridin-2-yl)phenyl)terephthalamide

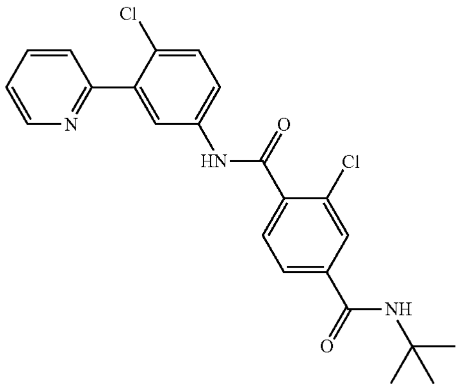 [SMILES: CC(C)(C)NC(=O)c1ccc(C(=O)Nc2ccc(Cl)c(-c3ccccn3)c2)c(Cl)c1]

67 mL of 2-chloro-1,4-dimethylbenzene and 356 g of Potassium Permanganate were refluxed in 1.5 L of $H_2O$ for several hours and monitored for disappearance of starting material by TLC. The Potassium Permanganate was filtered and the reaction mixture was acidified and filtered to yield 2-chloroterephthalic acid. 46.8 g of 2-chloroterephthalic acid was treated with a saturated HCl gas solution in MeOH overnight at room temperature. The reaction mixture was concentrated, subjected to basic workup and dried to yield the dimethyl 2-chloroterephthalate. 20 g of dimethyl 2-chloroterephthalate was cooled to 0° C. in DCM and 87 mL of a 1M in DCM solution of $BBr_3$ was added dropwise over several hours. The reaction mixture was subsequently warmed to room temperature and stirred until complete. Following basic workup, 2-chloro-4-(methoxycarbonyl)benzoic acid was purified by ISCO Combi-Flash. 959 mg of 2-chloro-4-(methoxycarbonyl)benzoic acid was coupled to 750 mg of 4-chloro-3-(pyridin-2-yl)aniline via procedure G. 1 g of methyl 3-chloro-4-(4-chloro-3-(pyridin-2-yl)phenylcarbamoyl)benzoate was hydrolyzed via Procedure M to give 3-chloro-4-(4-chloro-3-(pyridin-2-yl)phenylcarbamoyl)benzoic acid. 50 mg of 3-chloro-4-(4-chloro-3-(pyridin-2-yl)phenylcarbamoyl)benzoic acid was coupled to tert-butylamine via Procedure G. The product was purified on reverse phase HPLC to yield $N^4$-tert-butyl-2-chloro-$N^1$-(4-chloro-3-(pyridin-2-yl)phenyl)terephthalamide. MS (Q1) 443.2 $(M)^+$.

Example 74

2-chloro-N-(4-chloro-3-(pyridin-2-yl)phenyl)-4-(4-(2-hydroxyethyl)piperazine-1-carbonyl)benzamide

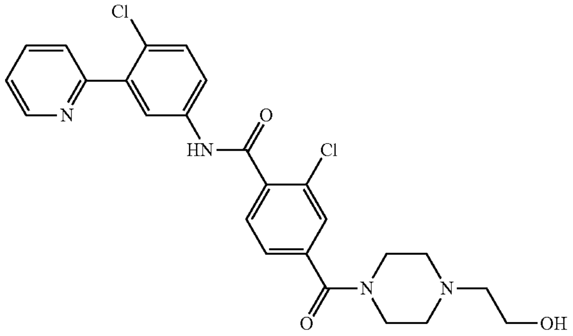 [SMILES: O=C(Nc1ccc(Cl)c(-c2ccccn2)c1)c1ccc(C(=O)N2CCN(CCO)CC2)cc1Cl]

50 mg of 3-chloro-4-(4-chloro-3-(pyridin-2-yl)phenylcarbamoyl)benzoic acid was coupled to N-(2-hydroxyethyl)piperazine via Procedure G. The product was purified on reverse phase HPLC to yield 2-chloro-N-(4-chloro-3-(pyridin-2-yl)phenyl)-4-(4-(2-hydroxyethyl)piperazine-1-carbonyl)benzamide. MS (Q1) 499 $(M)^+$.

Example 75

2-chloro-N-(4-chloro-3-(pyridin-2-yl)phenyl)-4-(4-methylpiperazine-1-carbonyl)benzamide

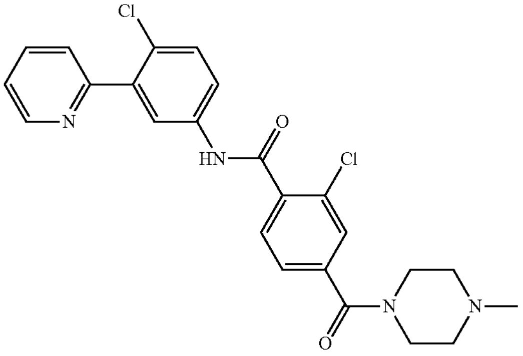 [SMILES: CN1CCN(C(=O)c2ccc(C(=O)Nc3ccc(Cl)c(-c4ccccn4)c3)c(Cl)c2)CC1]

50 mg of 3-chloro-4-(4-chloro-3-(pyridin-2-yl)phenylcarbamoyl)benzoic acid was coupled to 1-methylpiperazine via Procedure G. The product was purified on reverse phase HPLC to yield 2-chloro-N-(4-chloro-3-(pyridin-2-yl)phenyl)-4-(4-methylpiperazine-1-carbonyl)benzamide. MS (Q1) 469 (M)$^+$.

Example 76

4-(4-acetylpiperazine-1-carbonyl)-2-chloro-N-(4-chloro-3-(pyridin-2-yl)phenyl)benzamide

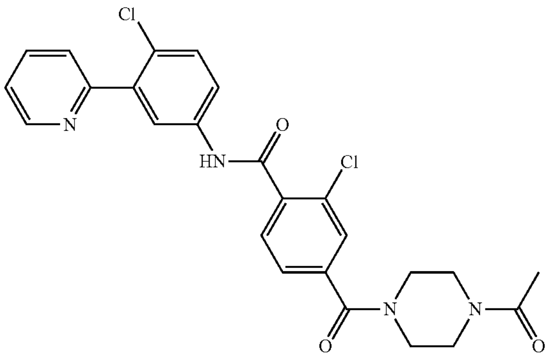 [SMILES: CC(=O)N1CCN(C(=O)c2ccc(C(=O)Nc3ccc(Cl)c(-c4ccccn4)c3)c(Cl)c2)CC1]

50 mg of 3-chloro-4-(4-chloro-3-(pyridin-2-yl)phenylcarbamoyl)benzoic acid was coupled to 1-acetylpiperazine via Procedure G. The product was purified on reverse phase HPLC to yield 4-(4-acetylpiperazine-1-carbonyl)-2-chloro-N-(4-chloro-3-(pyridin-2-yl)phenyl)benzamide. MS (Q1) 497 (M)$^+$.

Example 77

2-chloro-N-(4-chloro-3-(pyridin-2-yl)phenyl)-4-(4-(methylsulfonyl)piperazine-1-carbonyl)benzamide

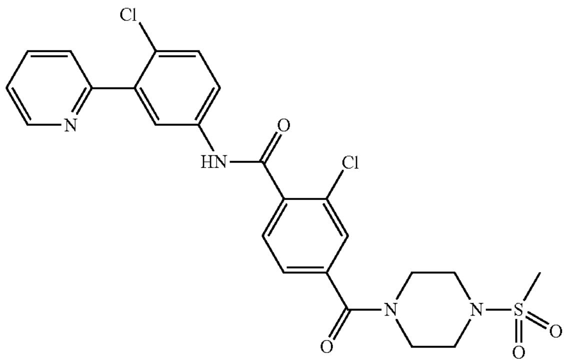 [SMILES: CS(=O)(=O)N1CCN(C(=O)c2ccc(C(=O)Nc3ccc(Cl)c(-c4ccccn4)c3)c(Cl)c2)CC1]

50 mg of 3-chloro-4-(4-chloro-3-(pyridin-2-yl)phenylcarbamoyl)benzoic acid was coupled to 1-sulfonylpiperazine via Procedure G. The product was purified on reverse phase HPLC to yield 2-chloro-N-(4-chloro-3-(pyridin-2-yl)phenyl)-4-(4-(methylsulfonyl)piperazine-1-carbonyl)benzamide. MS (Q1) 533 (M)$^+$.

Example 78

2-chloro-N-(4-chloro-3-(pyridin-2-yl)phenyl)-4-(morpholine-4-carbonyl)benzamide

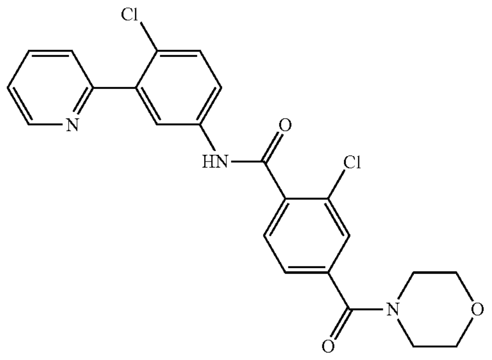 [SMILES: O=C(Nc1ccc(Cl)c(-c2ccccn2)c1)c1ccc(C(=O)N2CCOCC2)cc1Cl]

50 mg of 3-chloro-4-(4-chloro-3-(pyridin-2-yl)phenylcarbamoyl)benzoic acid was coupled to morpholine via Procedure G. The product was purified on reverse phase HPLC to yield 2-chloro-N-(4-chloro-3-(pyridin-2-yl)phenyl)-4-(morpholine-4-carbonyl)benzamide. MS (Q1) 456 (M)$^+$.

Example 79

2-chloro-N-(4-chloro-3-(pyridin-2-yl)phenyl)-4-(3,5-dimethylpiperazine-1-carbonyl)benzamide

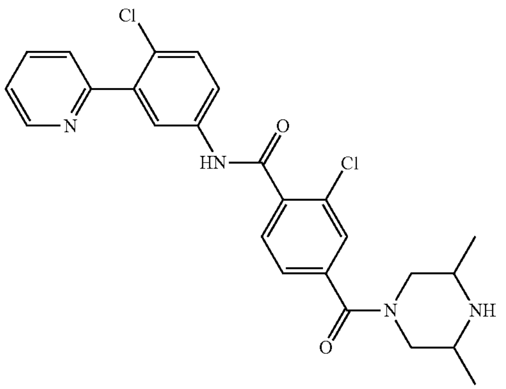 [SMILES: CC1CN(C(=O)c2ccc(C(=O)Nc3ccc(Cl)c(-c4ccccn4)c3)c(Cl)c2)CC(C)N1]

50 mg of 3-chloro-4-(4-chloro-3-(pyridin-2-yl)phenylcarbamoyl)benzoic acid was coupled to 2,6-dimethylpiperazine via Procedure G. The product was purified on reverse phase HPLC to yield 2-chloro-N-(4-chloro-3-(pyridin-2-yl)phenyl)-4-(3,5-dimethylpiperazine-1-carbonyl)benzamide. MS (Q1) 483 $(M)^+$.

Example 80

2-chloro-$N^1$-(4-chloro-3-(pyridin-2-yl)phenyl)-$N^4$-(pyridin-3-ylmethyl)terephthalamide

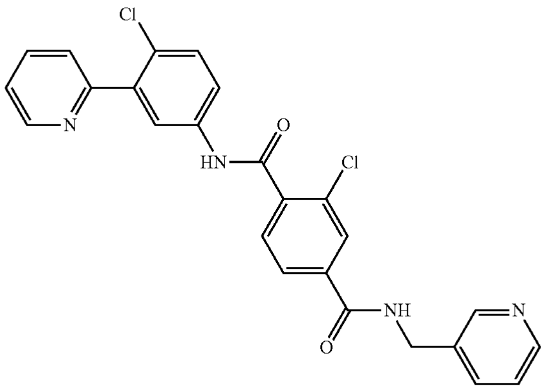 [SMILES: O=C(NCc1cccnc1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 3-(aminomethyl)pyridine via Procedure G. The product was purified on reverse phase HPLC to yield 2-chloro-$N^1$-(4-chloro-3-(pyridin-2-yl)phenyl)-$N^4$-(pyridin-3-ylmethyl)terephthalamide. MS (Q1) 477 $(M)^+$.

Example 81

2-chloro-$N^1$-(4-chloro-3-(pyridin-2-yl)phenyl)-$N^4$-(pyridin-2-ylmethyl)terephthalamide

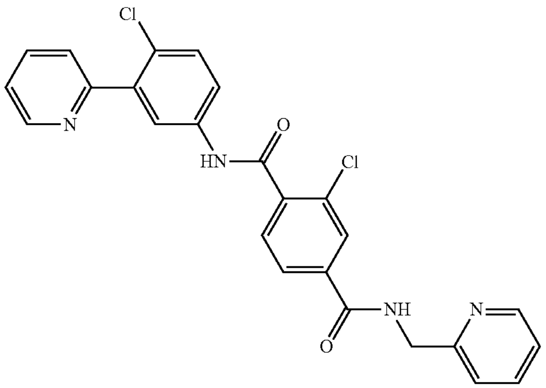 [SMILES: O=C(NCc1ccccn1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 2-(aminomethyl)pyridine via Procedure G. The product was purified on reverse phase HPLC to yield 2-chloro-$N^1$-(4-chloro-3-(pyridin-2-yl)phenyl)-$N^4$-(pyridin-2-ylmethyl)terephthalamide. MS (Q1) 477 $(M)^+$.

Example 82

2-chloro-$N^1$-(4-chloro-3-(pyridin-2-yl)phenyl)-$N^4$-(pyridin-4-yl)terephthalamide

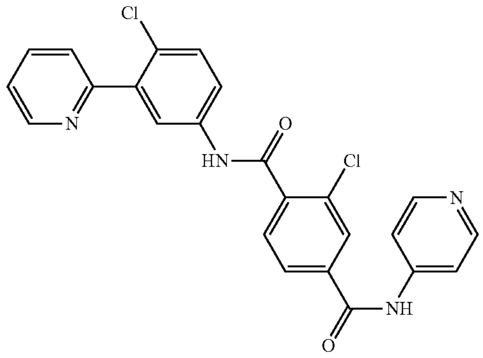 [SMILES: O=C(Nc1ccncc1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 4-aminopyridine via Procedure G. The product was purified on reverse phase HPLC to yield 2-chloro-$N^1$-(4-chloro-3-(pyridin-2-yl)phenyl)-$N^4$-(pyridin-4-yl)terephthalamide. MS (Q1) 463 $(M)^+$.

Example 83

2-chloro-$N^1$-(4-chloro-3-(pyridin-2-yl)phenyl)-$N^4$-(pyridin-3-yl)terephthalamide

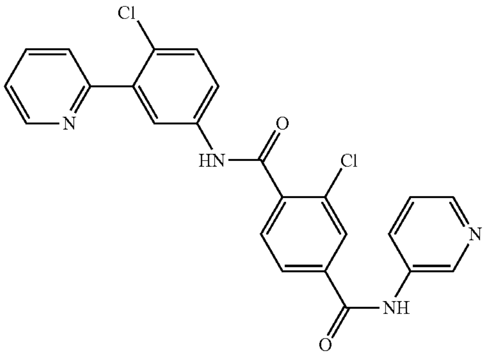 [SMILES: O=C(Nc1cccnc1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 3-aminopyridine via Procedure G. The product was purified on reverse phase HPLC to yield 2-chloro-N[1]-(4-chloro-3-(pyridin-2-yl)phenyl)-N[4]-(pyridin-3-yl)terephthalamide. MS (Q1) 463 $(M)^+$.

Example 84

2-chloro-N-(4-chloro-3-(pyridin-2-yl)phenyl)-4-(thiomorpholine-4-carbonyl)benzamide (S-oxidized thiomorpholine)

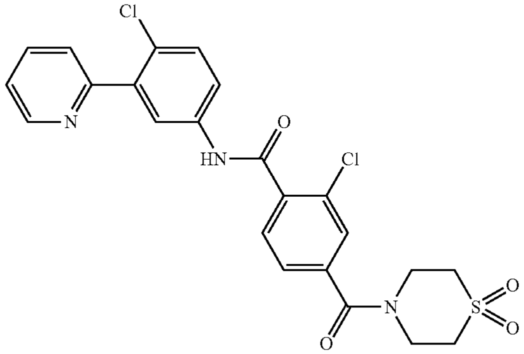 [SMILES: O=C(Nc1ccc(Cl)c(-c2ccccn2)c1)c1ccc(C(=O)N2CCS(=O)(=O)CC2)cc1Cl]

100 mg of 3-chloro-4-(4-chloro-3-(pyridin-2-yl)phenylcarbamoyl)benzoic acid was coupled to thiomorpholine via Procedure G. Crude 2-chloro-N-(4-chloro-3-(pyridin-2-yl)phenyl)-4-(thiomorpholine-4-carbonyl)benzamide was reacted via Procedure R to oxidize the thiomorpholine sulfur and purified via reverse phase HPLC to yield 2-chloro-N-(4-chloro-3-(pyridin-2-yl)phenyl)-4-(thiomorpholine-4-carbonyl)benzamide (in which the thiomorpholline sulfur is oxidized to $SO_2$). MS (Q1) 504 $(M)^+$.

Example 85

2-chloro-N-(4-chloro-3-(pyridin-2-yl)phenyl)-4-(thiazolidine-3-carbonyl)benzamide (S-oxidized thiazolidine)

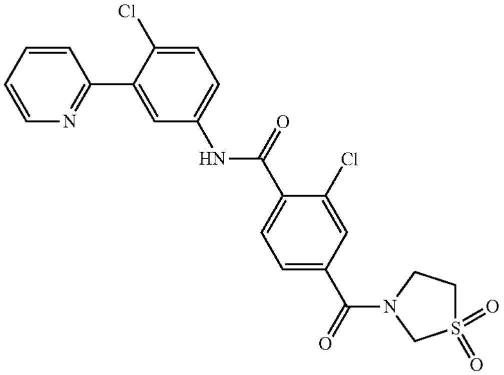 [SMILES: O=C(Nc1ccc(Cl)c(-c2ccccn2)c1)c1ccc(C(=O)N2CCS(=O)(=O)C2)cc1Cl]

100 mg of 3-chloro-4-(4-chloro-3-(pyridin-2-yl)phenylcarbamoyl)benzoic acid was coupled to thiazolidine via Procedure G. Crude 2-chloro-N-(4-chloro-3-(pyridin-2-yl)phenyl)-4-(thiazolidine-3-carbonyl)benzamide was reacted via Procedure R and purified via reverse phase HPLC to yield 2-chloro-N-(4-chloro-3-(pyridin-2-yl)phenyl)-4-(thiazolidine-3-carbonyl)benzamide (in which the thiazolidine sulfur is oxidized to $SO_2$). MS (Q1) 490 $(M)^+$.

Example 86

2-chloro-N[1]-(4-chloro-3-(pyridin-2-yl)phenyl)-N[4]-(1-methyl-1H-pyrazol-5-yl)terephthalamide

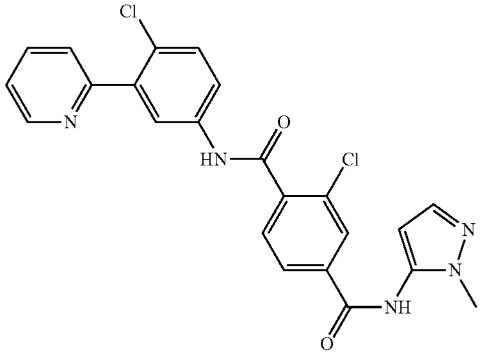 [SMILES: Cn1nccc1NC(=O)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 5-amino-1-methylpyrazole via Procedure G. The product was purified on reverse phase HPLC to yield 2-chloro-N[1]-(4-chloro-3-(pyridin-2-yl)phenyl)-N[4]-(1-methyl-1H-pyrazol-5-yl)terephthalamide. MS (Q1) 466 $(M)^+$.

Example 87

2-chloro-N[1]-(4-chloro-3-(pyridin-2-yl)phenyl)-N[4]-(isoxazol-5-yl)terephthalamide

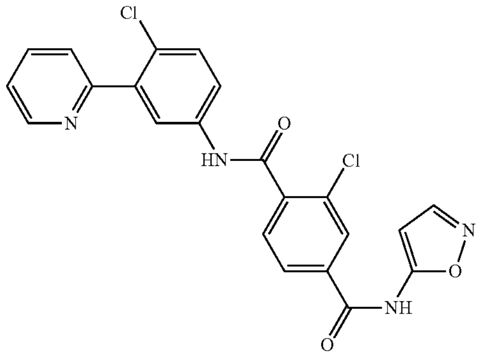 [SMILES: O=C(Nc1ccno1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 5-aminoisoxazole via Procedure G. The product was purified on reverse phase HPLC to yield 2-chloro-N$^1$-(4-chloro-3-(pyridin-2-yl)phenyl)-N$^4$-(isoxazol-5-yl)terephthalamide. MS (Q1) 463 (M)$^+$.

Example 88

2-chloro-N$^1$-(4-chloro-3-(pyridin-2-yl)phenyl)-N$^4$-(4,5-dihydrothiazol-2-yl)terephthalamide

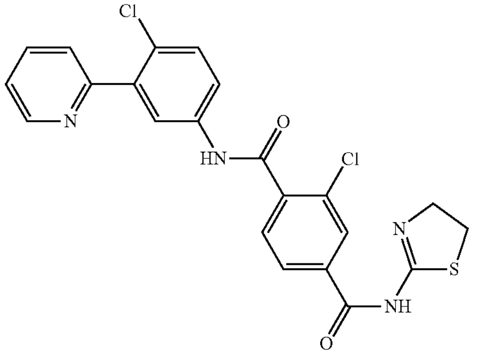

50 mg of 3-chloro-4-(4-chloro-3-(pyridin-2-yl)phenylcarbamoyl)benzoic acid was coupled to 2-amino-4,5-dihydrothiazole via Procedure G. The product was purified on reverse phase HPLC to yield 2-chloro-N$^1$-(4-chloro-3-(pyridin-2-yl)phenyl)-N$^4$-(4,5-dihydrothiazol-2-yl)terephthalamide. MS (Q1) 471 (M)$^+$.

Example 89

2-chloro-N$^1$-(4-chloro-3-(pyridin-2-yl)phenyl)-N$^4$-(1H-imidazol-2-yl)terephthalamide

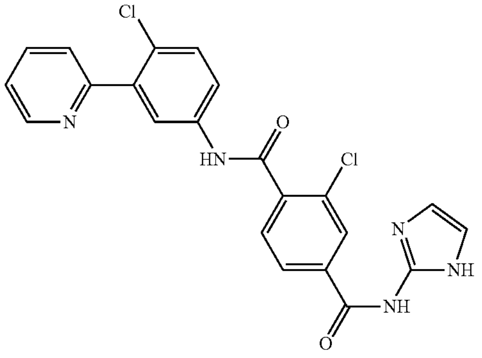

50 mg of 3-chloro-4-(4-chloro-3-(pyridin-2-yl)phenylcarbamoyl)benzoic acid was coupled to 2-aminoimidazole via Procedure G. The product was purified on reverse phase HPLC to yield 2-chloro-N$^1$-(4-chloro-3-(pyridin-2-yl)phenyl)-N$^4$-(1H-imidazol-2-yl)terephthalamide. MS (Q1) 452 (M)$^+$.

Example 90

2-chloro-N$^1$-(4-chloro-3-(pyridin-2-yl)phenyl)-N$^4$-(4H-1,2,4-triazol-4-yl)terephthalamide

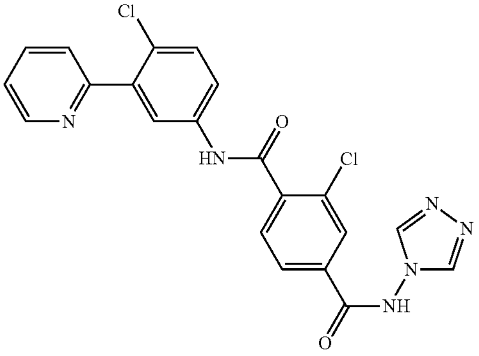 [SMILES: O=C(Nn1cnnc1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 4-amino-1,2,4-triazole via Procedure G. The product was purified on reverse phase HPLC to yield 2-chloro-N$^1$-(4-chloro-3-(pyridin-2-yl)phenyl)-N$^4$-(4H-1,2,4-triazol-4-yl)terephthalamide. MS (Q1) 453 (M)$^+$.

Example 91

2-chloro-N$^1$-(4-chloro-3-(pyridin-2-yl)phenyl)-N$^4$-(thiazol-2-yl)terephthalamide

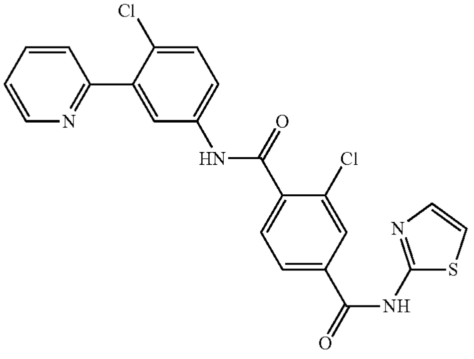 [SMILES: O=C(Nc1nccs1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 2-aminothiazole via Procedure G. The product was purified on reverse phase HPLC to yield 2-chloro-N[1]-(4-chloro-3-(pyridin-2-yl)phenyl)-N[4]-(thiazol-2-yl)terephthalamide. MS (Q1) 469 (M)$^+$.

Example 92

2-chloro-N[1]-(4-chloro-3-(pyridin-2-yl)phenyl)-N[4]-(1H-1,2,4-triazol-5-yl)terephthalamide

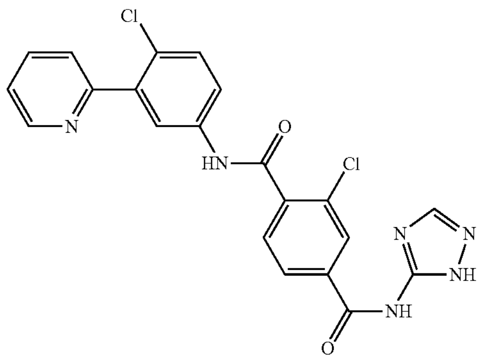 [SMILES: O=C(Nc1ncn[nH]1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 3-amino-1,2,4-triazole via Procedure G. The product was purified on reverse phase HPLC to yield 2-chloro-N[1]-(4-chloro-3-(pyridin-2-yl)phenyl)-N[4]—(H-1,2,4-triazol-5-yl)terephthalamide. MS (Q1) 453 (M)$^+$.

Example 93

2-chloro-N-(4-chloro-3-(pyridin-2-yl)phenyl)-4-(thiazolidine-3-carbonyl)benzamide

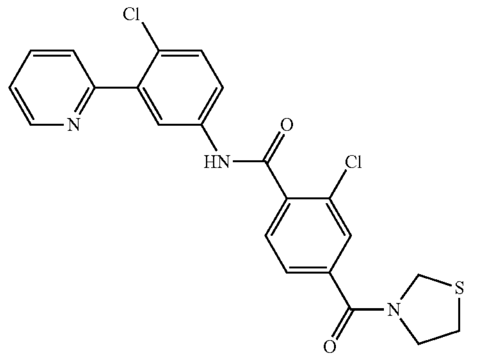 [SMILES: O=C(Nc1ccc(Cl)c(-c2ccccn2)c1)c1ccc(C(=O)N2CCSC2)cc1Cl]

50 mg of 3-chloro-4-(4-chloro-3-(pyridin-2-yl)phenylcarbamoyl)benzoic acid was coupled to thiazoline via Procedure G. The product was purified on reverse phase HPLC to yield 2-chloro-N-(4-chloro-3-(pyridin-2-yl)phenyl)-4-(thiazolidine-3-carbonyl)benzamide. MS (Q1) 459 (M)$^+$.

Example 94

2-chloro-N[1]-(4-chloro-3-(pyridin-2-yl)phenyl)-N[4]-(4,5-dihydrooxazol-2-yl)terephthalamide

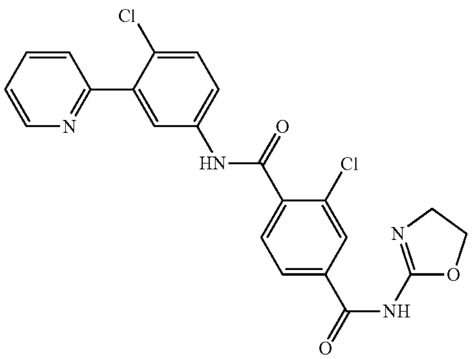 [SMILES: O=C(NC1=NCCO1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 2-amino-4,5-dihydrooxazole via Procedure G. The product was purified on reverse phase HPLC to yield 2-chloro-N[1]-(4-chloro-3-(pyridin-2-yl)phenyl)-N[4]-(4,5-dihydrooxazol-2-yl)terephthalamide. MS (Q1) 456 (M)$^+$.

Example 95

2-chloro-N-(4-chloro-3-(pyridin-2-yl)phenyl)-4-(1,4,5,6-tetrahydropyrimidine-1-carbonyl)benzamide

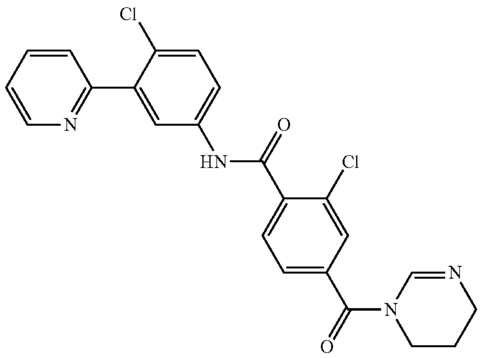 [SMILES: O=C(Nc1ccc(Cl)c(-c2ccccn2)c1)c1ccc(C(=O)N2C=NCCC2)cc1Cl]

50 mg of 3-chloro-4-(4-chloro-3-(pyridin-2-yl)phenylcarbamoyl)benzoic acid was coupled to 1,4,5,6-tetrahydropyrimidine via Procedure G. The product was purified on reverse phase HPLC to yield 2-chloro-N-(4-chloro-3-(pyridin-2-yl)phenyl)-4-(1,4,5,6-tetrahydropyrimidine-1-carbonyl)benzamide. MS (Q1) 454 $(M)^+$.

Example 96

2-chloro-N-(4-chloro-3-(pyridin-2-yl)phenyl)-4-(3-oxopiperazine-1-carbonyl)benzamide

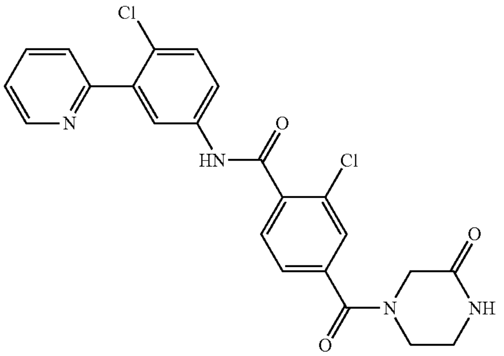 [SMILES: O=C1CN(C(=O)c2ccc(C(=O)Nc3ccc(Cl)c(-c4ccccn4)c3)c(Cl)c2)CCN1]

50 mg of 3-chloro-4-(4-chloro-3-(pyridin-2-yl)phenylcarbamoyl)benzoic acid was coupled to 3-oxopiperazine via Procedure G. The product was purified on reverse phase HPLC to yield 2-chloro-N-(4-chloro-3-(pyridin-2-yl)phenyl)-4-(3-oxopiperazine-1-carbonyl)benzamide. MS (Q1) 470 $(M)^+$.

Example 97

2-chloro-$N^1$-(4-chloro-3-(pyridin-2-yl)phenyl)-$N^4$-methoxyterephthalamide

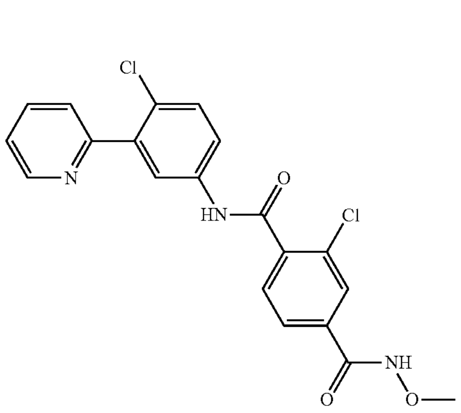 [SMILES: CONC(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to N-methylhydroxylamine hydrochloride via Procedure G. The product was purified on reverse phase HPLC to yield 2-chloro-$N^1$-(4-chloro-3-(pyridin-2-yl)phenyl)-$N^4$-methoxyterephthalamide. MS (Q1) 417 $(M)^+$.

Example 98

2-chloro-$N^1$-(4-chloro-3-(pyridin-2-yl)phenyl)-$N^4$-hydroxyterephthalamide

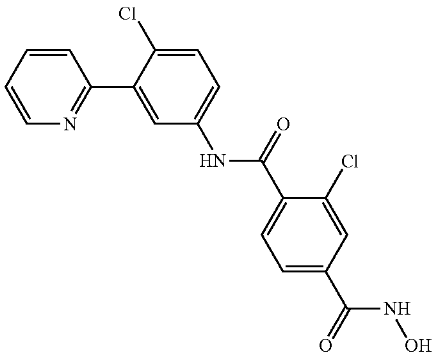 [SMILES: O=C(NO)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to hydroxylamine hydrochloride via Procedure G. The product was purified on reverse phase HPLC to yield 2-chloro-$N^1$-(4-chloro-3-(pyridin-2-yl)phenyl)-$N^4$-hydroxyterephthalamide. MS (Q1) 403 $(M)^+$.

Example 99

2-chloro-N-(4-chloro-3-(pyridin-2-yl)phenyl)-4-(pyrrolidine-1-carbonyl)benzamide

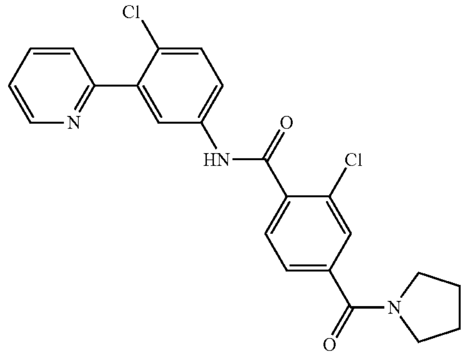 [SMILES: O=C(Nc1ccc(Cl)c(-c2ccccn2)c1)c1ccc(C(=O)N2CCCC2)cc1Cl]

75 mg of 3-chloro-4-(4-chloro-3-(pyridin-2-yl)phenylcarbamoyl)benzoic acid was coupled to pyrrolidine via Procedure G. The product was purified on reverse phase HPLC to yield 2-chloro-N-(4-chloro-3-(pyridin-2-yl)phenyl)-4-(pyrrolidine-1-carbonyl)benzamide. MS (Q1) 441 $(M)^+$.

Example 100

N-(4-chloro-3-(pyridin-2-yl)phenyl)-4-(ethylsulfonylmethyl)benzamide

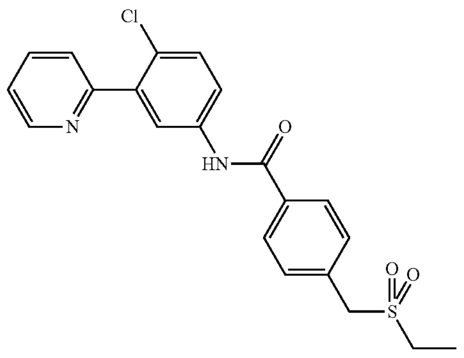 [SMILES: CCS(=O)(=O)Cc1ccc(C(=O)Nc2ccc(Cl)c(-c3ccccn3)c2)cc1]

Ethanesulfonyl chloride was reduced to sodium ethanesulfinate according to the procedure in J. Med. Chem. 1989, vol. 32, no. 11, p 2436. Briefly, 2.5 ml of ethanesulfonyl chloride was added dropwise to a solution of 3.67 g of sodium carbonate and 5.51 g of sodium sulfate in 13 mL of water. After completion of the reaction the water was evaporated and the solids were suspended in ethanol and heated to 80° C. for 1 h prior to filtering the solids. The filtrate was then evaporated to give 2.5 grams of the sodium ethanesulfinate. 293 mg of the sodium ethansulfinate was combined with 230 mg of methyl (4-bromoethyl)benzoate in 2 mL of DMF and heated to 120 C for 5 min in a microwave reactor. The reaction was then extracted with Ethyl Acetate and Brine to give 250 mg of methyl 4-(ethylsulfonylmethyl)benzoate after evaporation of the organic layer. 200 mg of methyl 4-(ethylsulfonylmethyl)benzoate was hydrolyzed via Procedure M to give 119 mg of 4-(ethylsulfonylmethyl)benzoic acid.

50 mg of 4-(ethylsulfonylmethyl)benzoic acid was coupled with 67 mg of 4-chloro-3-(pyridin-2-yl)aniline via Procedure G. This product was recrystallized from methanol to yield N-(4-chloro-3-(pyridin-2-yl)phenyl)-4-(ethylsulfonylmethyl)benzamide. MS (Q1) 415 $(M)^+$.

Example 101

N-(4-chloro-3-(pyridin-2-yl)phenyl)-4-(isopropylsulfonylmethyl)benzamide

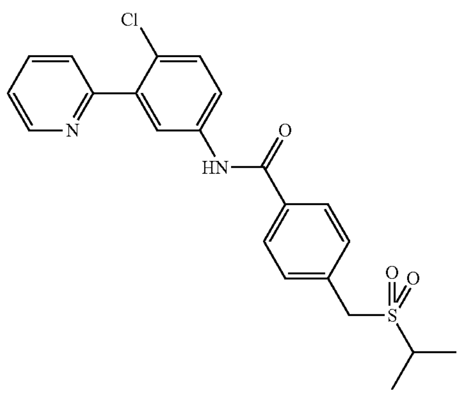 [SMILES: CC(C)S(=O)(=O)Cc1ccc(C(=O)Nc2ccc(Cl)c(-c3ccccn3)c2)cc1]

N-(4-chloro-3-(pyridin-2-yl)phenyl)-4-(isopropylsulfonylmethyl)benzamide was prepared using the same procedure as N-(4-chloro-3-(pyridin-2-yl)phenyl)-4-(ethylsulfonylmethyl)benzamide except propane-2-sulfonyl chloride was substituted for ethanesulfonyl chloride. The product was purified on reverse phase HPLC to yield N-(4-chloro-3-(pyridin-2-yl)phenyl)-4-(isopropylsulfonylmethyl)benzamide. MS (Q1) 429 $(M)^+$.

Example 102

2-chloro-$N^1$-(4-chloro-3-(pyridin-2-yl)phenyl)-$N^4$-ethylterephthalamide

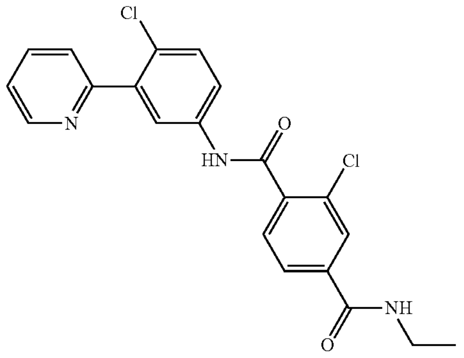 [SMILES: CCNC(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to ethylamine via Procedure G. The product was purified on reverse phase HPLC to yield 2-chloro-$N^1$-(4-chloro-3-(pyridin-2-yl)phenyl)-$N^4$-ethylterephthalamide. MS (Q1) 415 $(M)^+$.

Example 103

(S)-2-chloro-$N^1$-(4-chloro-3-(pyridin-2-yl)phenyl)-$N^4$-((tetrahydrofuran-2-yl)methyl)terephthalamide

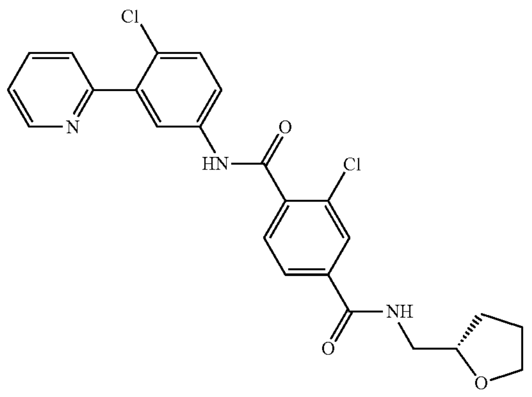 [SMILES: O=C(NC[C@@H]1CCCO1)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to (S)-(+)-tetrahydrofurylamine via Procedure G. The product was purified on reverse phase HPLC to yield (S)-2-chloro-N[1]-(4-chloro-3-(pyridin-2-yl)phenyl)-N[4]-((tetrahydrofuran-2-yl)methyl)terephthalamide. MS (Q1) 471 (M)+.

Example 104

2-chloro-N[1]-(4-chloro-3-(pyridin-2-yl)phenyl)-N[4]-(3-methoxypropyl)terephthalamide

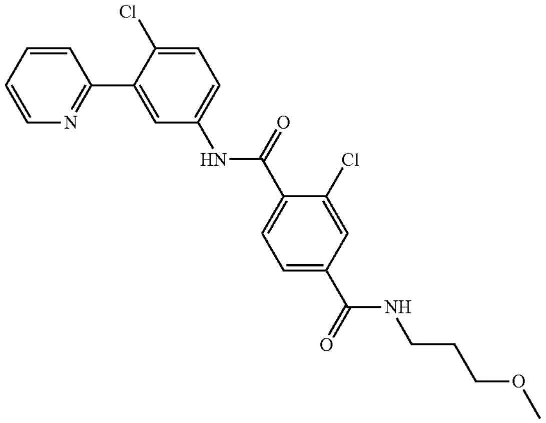 [SMILES: COCCCNC(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to 3-methoxypropylamine via Procedure G. The product was purified on reverse phase HPLC to yield 2-chloro-N[1]-(4-chloro-3-(pyridin-2-yl)phenyl)-N[4]-(3-methoxypropyl)terephthalamide. MS (Q1) 459 (M)+.

Example 105

2-chloro-N[1]-(4-chloro-3-(pyridin-2-yl)phenyl)-N[4]-(3-hydroxypropyl)terephthalamide

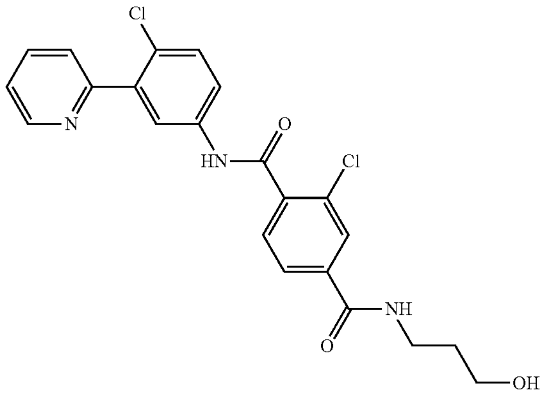 [SMILES: O=C(NCCCO)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to 3-hydroxypropylamine via Procedure G. The product was purified on reverse phase HPLC to yield 2-chloro-N[1]-(4-chloro-3-(pyridin-2-yl)phenyl)-N[4]-(3-hydroxypropyl)terephthalamide. MS (Q1) 445 (M)+.

Example 106

(S)-2-chloro-N[1]-(4-chloro-3-(pyridin-2-yl)phenyl)-N[4]-(1-hydroxypropan-2-yl)terephthalamide

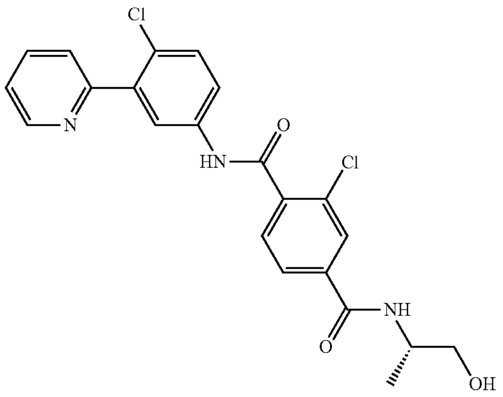 [SMILES: C[C@@H](CO)NC(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to (S)-2-amino-1-propanol via Procedure G. The product was purified on reverse phase HPLC to yield (S)-2-chloro-N[1]-(4-chloro-3-(pyridin-2-yl)phenyl)-N[4]-(1-hydroxypropan-2-yl)terephthalamide. MS (Q1) 445 (M)+.

Example 107

(S)-2-chloro-N[1]-(4-chloro-3-(pyridin-2-yl)phenyl)-N[4]-(1-methoxypropan-2-yl)terephthalamide

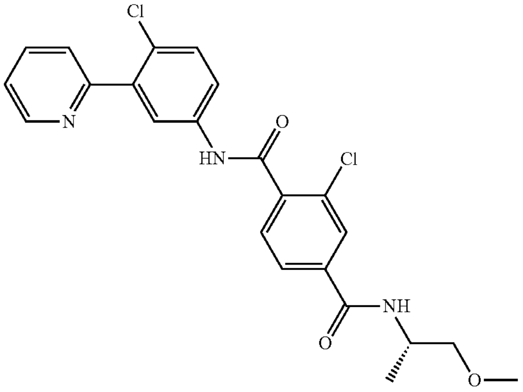 [SMILES: COC[C@H](C)NC(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to (S)-1-methoxy-2-propylamine via Procedure G. The product was purified on reverse phase HPLC to yield (S)-2-chloro-N[1]-(4-chloro-3-

(pyridin-2-yl)phenyl)-$N^4$-(1-methoxypropan-2-yl)terephthalamide. MS (Q1) 459 $(M)^+$.

Example 108

N4-(3-(1H-imidazol-1-yl)propyl)-2-chloro-N1-(4-chloro-3-(pyridin-2-yl)phenyl)terephthalamide

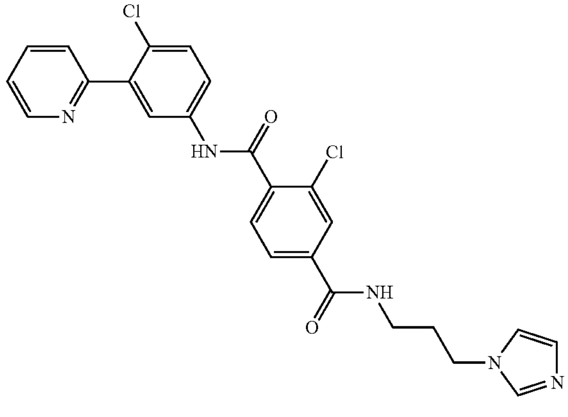 [SMILES: O=C(NCCCn1ccnc1)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to 1-(3-aminopropyl)imidazole via Procedure G. The product was purified on reverse phase HPLC to yield $N^4$-(3-(1H-imidazol-1-yl)propyl)-2-chloro-$N^1$-(4-chloro-3-(pyridin-2-yl)phenyl)terephthalamide. MS (Q1) 495 $(M)^+$.

Example 109

N4-(2-(1H-imidazol-4-yl)ethyl)-2-chloro-N1-(4-chloro-3-(pyridin-2-yl)phenyl)terephthalamide

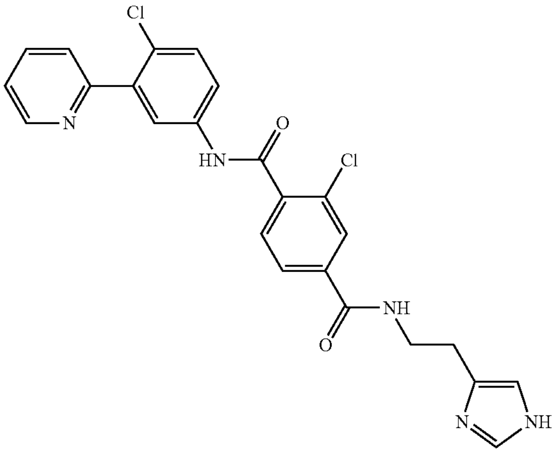 [SMILES: O=C(NCCc1c[nH]cn1)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to hystamine via Procedure G. The product was purified on reverse phase HPLC to yield $N^4$-(2-(1H-imidazol-4-yl)ethyl)-2-chloro-$N^1$-(4-chloro-3-(pyridin-2-yl)phenyl)terephthalamide. MS (Q1) 481 $(M)^+$.

Example 110

2-chloro-N1-(4-chloro-3-(pyridin-2-yl)phenyl)-N4-methylterephthalamide

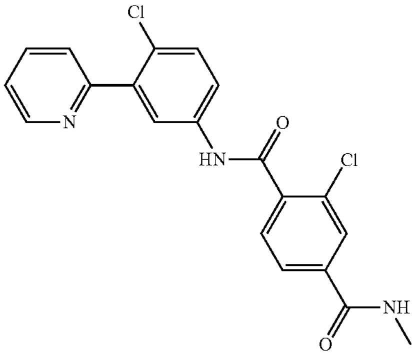 [SMILES: CNC(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to methylamine hydrochloride via Procedure G. The product was purified on reverse phase HPLC to yield 2-chloro-$N^1$-(4-chloro-3-(pyridin-2-yl)phenyl)-$N^4$-methylterephthalamide. MS (Q1) 401 $(M)^+$.

Example 111

2-chloro-N1-(4-chloro-3-(pyridin-2-yl)phenyl)-N4,N4-diethylterephthalamide

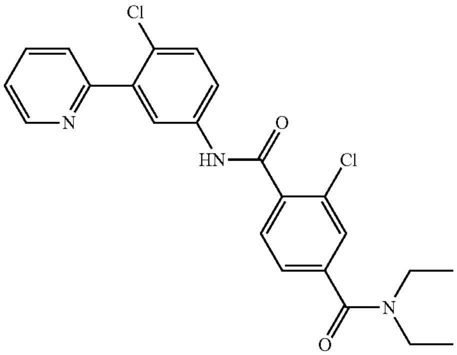 [SMILES: CCN(CC)C(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to diethylamine hydrochloride via Procedure G. The product was purified on reverse phase HPLC to yield 2-chloro-$N^1$-(4-chloro-3-(pyridin-2-yl)phenyl)-$N^4$,$N^4$-diethylterephthalamide. MS (Q1) 443 $(M)^+$ Example 112

(S)-2-chloro-N1-(4-chloro-3-(pyridin-2-yl)phenyl)-N4-(2-hydroxypropyl)-terephthalamide

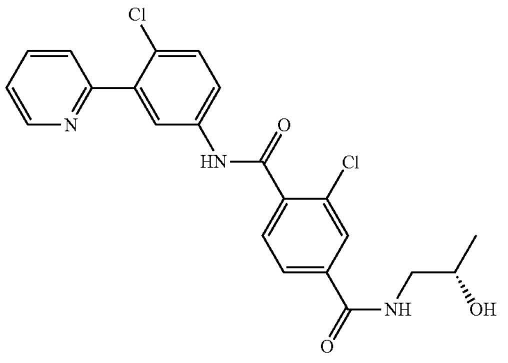 [SMILES: C[C@H](O)CNC(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to (S)-1-amino-2-propanol via Procedure G. The product was purified on reverse phase HPLC to yield (S)-2-chloro-N1-(4-chloro-3-(pyridin-2-yl)phenyl)-N4-(2-hydroxypropyl)terephthalamide. MS (Q1) 444 $(M)^+$.

Example 113

2-chloro-$N^1$-(4-chloro-3-(pyridin-2-yl)phenyl)-$N^4$-(2-methoxyethyl)terephthalamide

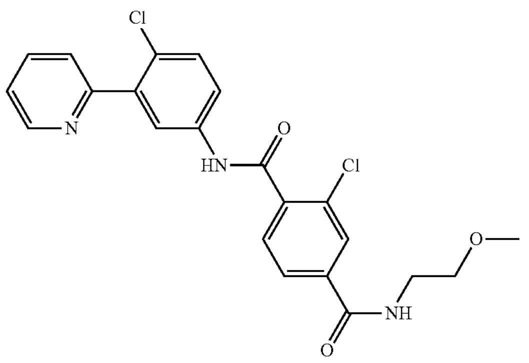 [SMILES: COCCNC(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to 2-methoxyethanamine via Procedure G. The product was purified on reverse phase HPLC to yield 2-chloro-$N^1$-(4-chloro-3-(pyridin-2-yl)phenyl)-$N^4$-(2-methoxyethyl)terephthalamide. MS (Q1) 444 $(M)^+$.

Example 114

2-chloro-$N^1$-(4-chloro-3-(pyridin-2-yl)phenyl)-$N^4$-(1-methylpiperidin-4-yl)terephthalamide

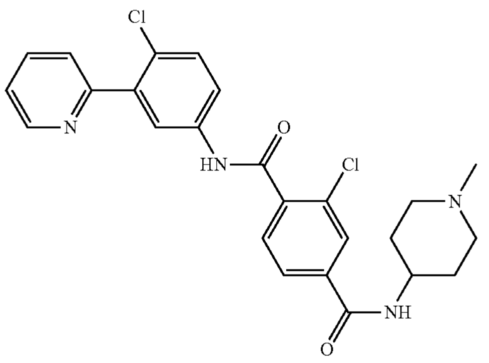 [SMILES: CN1CCC(NC(=O)c2ccc(C(=O)Nc3ccc(Cl)c(-c4ccccn4)c3)c(Cl)c2)CC1]

75 mg of 3-chloro-4-(4-chloro-3-(pyridin-2-yl)phenylcarbamoyl)benzoic acid was coupled to 4-amino-1-methylpiperidine via Procedure G. The product was purified on reverse phase HPLC to yield 2-chloro-$N^1$-(4-chloro-3-(pyridin-2-yl)phenyl)-$N^4$-(1-methylpiperidin-4-yl)terephthalamide. MS (Q1) 483 $(M)^+$.

Example 115

2-chloro-$N^1$-(4-chloro-3-(pyridin-2-yl)phenyl)-$N^4$-(3-(diethylamino)propyl)terephthalamide

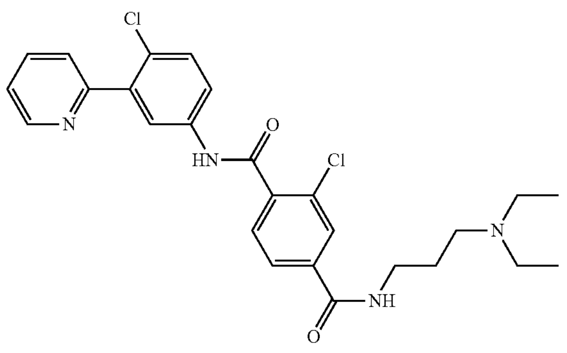 [SMILES: CCN(CC)CCCNC(=O)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to N,N-diethylpropylenediamine via Procedure G. The product was purified on reverse phase HPLC to yield 2-chloro-N$^1$-(4-chloro-3-(pyridin-2-yl)phenyl)-N-(3-(diethylamino)propyl)terephthalamide. MS (Q1) 499 $(M)^+$.

Example 116

2-chloro-N$^1$-(4-chloro-3-(pyridin-2-yl)phenyl)-N$^4$-(2-(pyrrolidin-1-yl)ethyl)terephthalamide

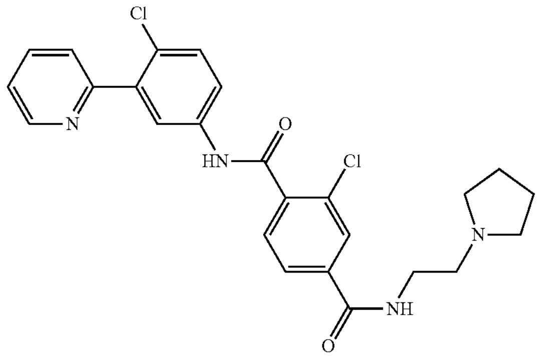 [SMILES: O=C(NCCN1CCCC1)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to N-(2-aminoethyl)pyrrolidine via Procedure G. The product was purified on reverse phase HPLC to yield 2-chloro-N$^1$-(4-chloro-3-(pyridin-2-yl)phenyl)-N$^4$-(2-(pyrrolidin-1-yl)ethyl)terephthalamide. MS (Q1) 483 $(M)^+$.

Example 117

N$^1$-(4-chloro-3-(pyridin-2-yl)phenyl)-N$^4$,N$^4$,2-trimethylterephthalamide

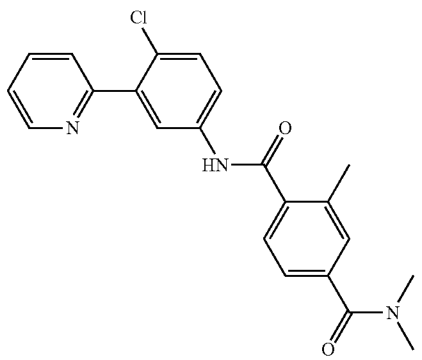 [SMILES: Cc1cc(C(=O)N(C)C)ccc1C(=O)Nc1ccc(Cl)c(-c2ccccn2)c1]

In a sealed tube, 1.94 g of dimethyl 2-bromoterephthalate was dissolved in 4 mL of HMPA and degassed with nitrogen prior to adding 1.1 mL of tetramethyl tin and 0.077 g of palladium tetrakistriphenylphosphene. After sealing the tube, the reaction was heated to 65° C. for 16 h. The reaction was then partitioned into ethylether and water and extracted. The organic layers were washed with 5% ammonium hydroxide, 1N HCl, again with 5% ammonium hydroxide, and finally with water. Filtration of the solvent through sodium sulfate and evaporation gave 1.44 g of crude dimethyl 2-methylterephthalate. 210 mg of dimethyl 2-methylterephthalate was hydrolyzed via Procedure M to give 4-(methoxycarbonyl)-3-methylbenzoic acid. Silica gel chromatography was performed (0% to 70% EtOAc gradient in Hexanes) to yield 115 mg of 4-(methoxycarbonyl)-3-methylbenzoic acid. 4-(methoxycarbonyl)-3-methylbenzoic acid was then coupled to dimethylamine hydrochloride via Procedure G. The crude methyl 4-(dimethylcarbamoyl)-2-methylbenzoate was then hydrolyzed via Procedure M to give 110 mg of 4-(dimethylcarbamoyl)-2-methylbenzoic acid. 4-chloro-3-(pyridin-2-yl)aniline was coupled to 110 mg of 4-(dimethylcarbamoyl)-2-methylbenzoic acid via Procedure G to yield N$^1$-(4-chloro-3-(pyridin-2-yl)phenyl)-N$^4$,N$^4$,2-trimethylterephthalamide. MS (Q1) 394 $(M)^+$.

Example 118

2-chloro-N$^1$-(4-chloro-3-(pyridin-2-yl)phenyl)-N$^4$-propylterephthalamide

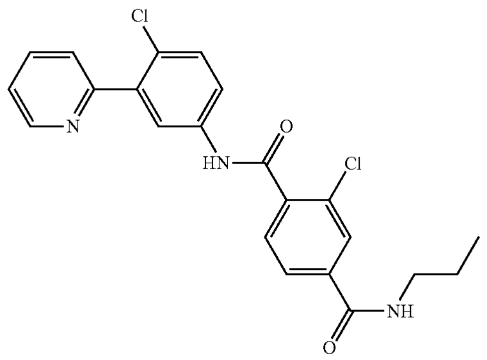 [SMILES: CCCNC(=O)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to propylamine via Procedure G. The product was purified on reverse phase HPLC to yield 2-chloro-N$^1$-(4-chloro-3-(pyridin-2-yl)phenyl)-N$^4$-propylterephthalamide. MS (Q1) 430 $(M)^+$.

Example 119

2-chloro-N$^1$-(4-chloro-3-(pyridin-2-yl)phenyl)-N$^4$-(2-hydroxyethyl)terephthalamide

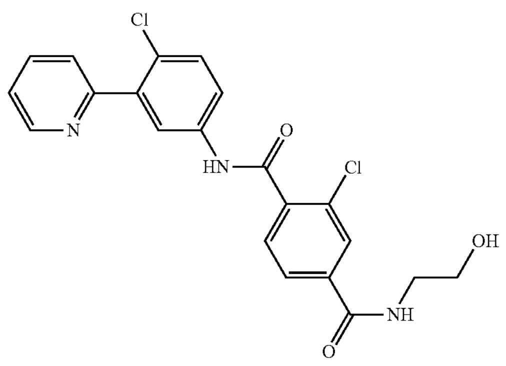 [SMILES: O=C(NCCO)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to propanolamine via Procedure G. The product was purified on reverse phase HPLC to yield 2-chloro-$N^1$-(4-chloro-3-(pyridin-2-yl)phenyl)-$N^4$-(2-hydroxyethyl)terephthalamide. MS (Q1) 428 $(M)^+$.

Example 120

2-chloro-$N^1$-(4-chloro-3-(pyridin-2-yl)phenyl) terephthalamide

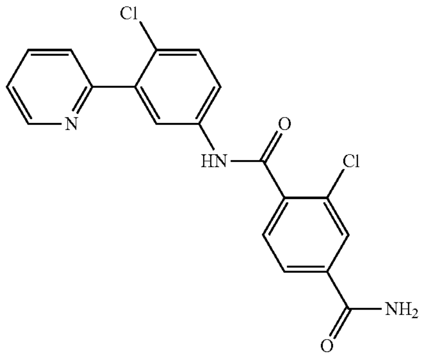 [SMILES: NC(=O)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to ammonium chloride via Procedure G. The product was purified on reverse phase HPLC to yield 2-chloro-$N^1$-(4-chloro-3-(pyridin-2-yl)phenyl)terephthalamide. MS (Q1) 386 $(M)^+$.

Example 121

N-(4-chloro-3-(pyridin-2-yl)phenyl)-4-(1H-tetrazol-1-yl)benzamide

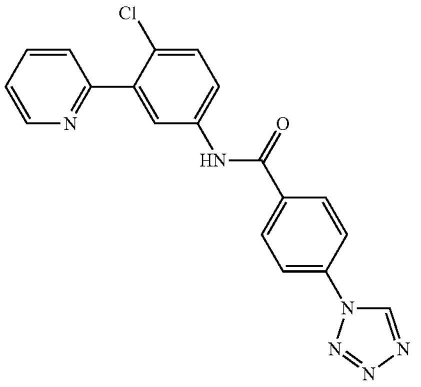 [SMILES: O=C(Nc1ccc(Cl)c(-c2ccccn2)c1)c1ccc(-n2cnnn2)cc1]

Procedure G was used to couple 4-chloro-3-(pyridin-2-yl) aniline (50 mg) and 4-(1H-tetrazol-1-yl)benzoic acid to yield N-(4-chloro-3-(pyridin-2-yl)phenyl)-4-(1H-tetrazol-1-yl) benzamide. MS (Q1) 421.0 $(M)^+$.

Example 122

2-chloro-N-(4-chloro-3-(pyridin-2-yl)phenyl)-4-(4-ethylpiperazine-1-carbonyl)benzamide

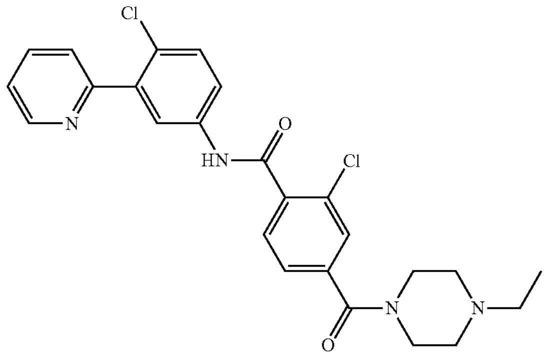 [SMILES: CCN1CCN(C(=O)c2ccc(C(=O)Nc3ccc(Cl)c(-c4ccccn4)c3)c(Cl)c2)CC1]

50 mg of 3-chloro-4-(4-chloro-3-(pyridin-2-yl)phenylcarbamoyl)benzoic acid was coupled to 1-ethylpiperazine via Procedure G. The product was purified on reverse phase HPLC to yield 2-chloro-N-(4-chloro-3-(pyridin-2-yl)phenyl)-4-(4-ethylpiperazine-1-carbonyl)benzamide. MS (Q1) 483 $(M)^+$.

Example 123

2-chloro-N-(4-chloro-3-(pyridin-2-yl)phenyl)-4-(piperazine-1-carbonyl)benzamide

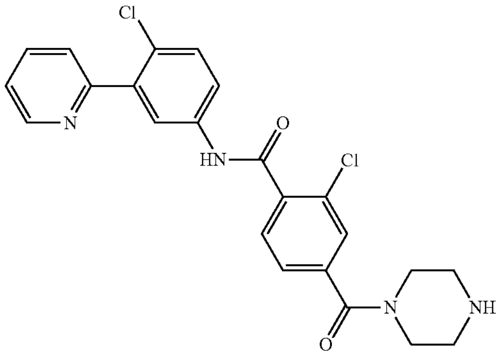 [SMILES: O=C(Nc1ccc(Cl)c(-c2ccccn2)c1)c1ccc(C(=O)N2CCNCC2)cc1Cl]

50 mg 3-chloro-4-(4-chloro-3-(pyridin-2-yl)phenylcarbamoyl)benzoic acid was coupled to Boc-piperazine via Procedure G. The organic layer was evaporated to dryness and treated with TFA. After 1 h the TFA was removed and the crude was purified on reverse phase HPLC to yield 2-chloro- N-(4-chloro-3-(pyridin-2-yl)phenyl)-4-(piperazine-1-carbonyl)benzamide. MS (Q1) 455 $(M)^+$.

Example 124

2-chloro-$N^1$-(4-chloro-3-(pyridin-2-yl)phenyl)-$N^4$-(2,2,2-trifluoroethyl)terephthalamide

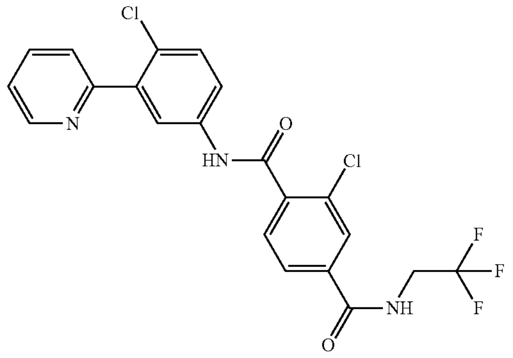 [SMILES: O=C(NCC(F)(F)F)c1ccc(C(=O)Nc2ccc(Cl)c(-c3ccccn3)c2)c(Cl)c1]

75 mg of 3-chloro-4-(4-chloro-3-(pyridin-2-yl)phenylcarbamoyl)benzoic acid was coupled to 2,2,2-trifluoroethylamine via Procedure G. The product was purified on reverse phase HPLC to yield 2-chloro-$N^1$-(4-chloro-3-(pyridin-2-yl)phenyl)-$N^4$-(2,2,2-trifluoroethyl)terephthalamide. MS (Q1) 469 $(M)^+$.

Example 125

6-(2-(1H-imidazol-5-yl)ethylamino)-N-(4-chloro-3-(pyridin-2-yl)phenyl)nicotinamide

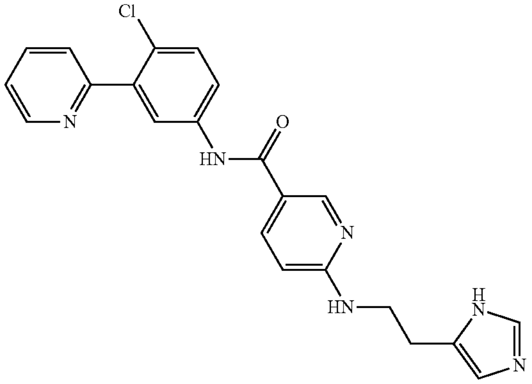 [SMILES: O=C(Nc1ccc(Cl)c(-c2ccccn2)c1)c1ccc(NCCc2cnc[nH]2)nc1]

Procedure F was performed using N-(4-chloro-3-(pyridin-2-yl)phenyl)-6-chloro-3-carboxamide (50 mg) and 100 mg of hystamine in butanol (0.5 mL). The crude reaction was purified by reverse phase HPLC to yield 6-(2-(1H-imidazol-5-yl)ethylamino)-N-(4-chloro-3-(pyridin-2-yl)phenyl)nicotinamide. MS (Q1) 419 $(M)^+$.

Example 126

6-(4-acetylpiperazin-1-yl)-N-(4-chloro-3-(pyridin-2-yl)phenyl)nicotinamide

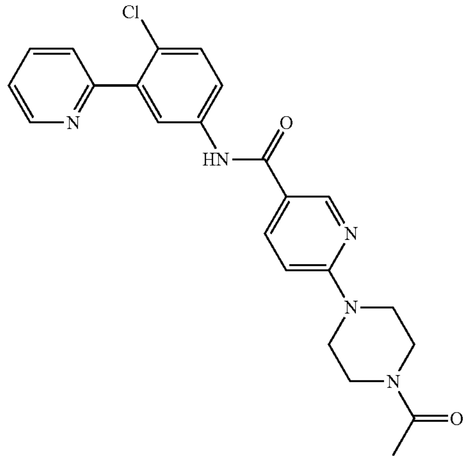 [SMILES: CC(=O)N1CCN(c2ccc(C(=O)Nc3ccc(Cl)c(-c4ccccn4)c3)cn2)CC1]

Procedure F was performed using N-(4-chloro-3-(pyridin-2-yl)phenyl)-6-chloro-3-carboxamide (50 mg) and 0.12 mL of acetylpiperazine in butanol (0.5 mL). The crude reaction was purified by reverse phase HPLC to yield 6-(4-acetylpiperazin-1-yl)-N-(4-chloro-3-(pyridin-2-yl)phenyl)nicotinamide. MS (Q1) 436 $(M)^+$.

Example 127

6-(3-(1H-imidazol-1-yl)propylamino)-N-(4-chloro-3-(pyridin-2-yl)phenyl)nicotinamide

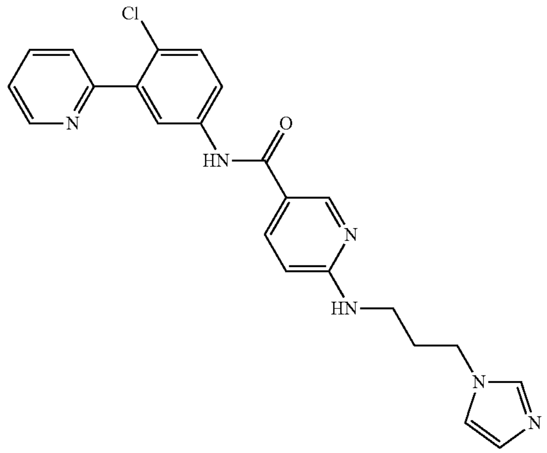 [SMILES: O=C(Nc1ccc(Cl)c(-c2ccccn2)c1)c1ccc(NCCCn2ccnc2)nc1]

Procedure F was performed using N-(4-chloro-3-(pyridin-2-yl)phenyl)-6-chloro-3-carboxamide (50 mg) and 125 mg of 1-(3-aminopropyl)imidazole in butanol (0.5 mL). The crude reaction was purified by reverse phase HPLC to yield 6-(3-

(1H-imidazol-1-yl)propylamino)-N-(4-chloro-3-(pyridin-2-yl)phenyl)nicotinamide. MS (Q1) 433 $(M)^+$.

Example 128

N-(4-chloro-3-(pyridin-2-yl)phenyl)-6-(3-(2-oxopyrrolidin-1-yl)propylamino)nicotinamide

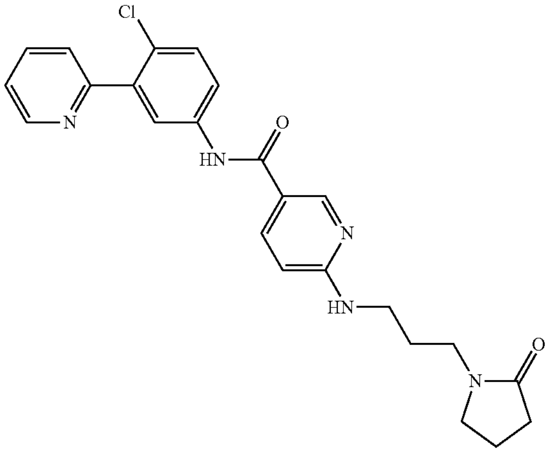 [SMILES: O=C(Nc1ccc(Cl)c(-c2ccccn2)c1)c1ccc(NCCCN2CCCC2=O)nc1]

Procedure F was performed using N-(4-chloro-3-(pyridin-2-yl)phenyl)-6-chloro-3-carboxamide (50 mg) and 0.42 mL of 1-(3-aminopropyl)-2-pyrrolidinone in butanol (0.5 mL). The crude reaction was purified by reverse phase HPLC to yield N-(4-chloro-3-(pyridin-2-yl)phenyl)-6-(3-(2-oxopyrrolidin-1-yl)propylamino)nicotinamide. MS (Q1) 450 $(M)^+$.

Example 129

N-(4-chloro-3-(pyridin-2-yl)phenyl)-6-(3-morpholinopropylamino)nicotinamide

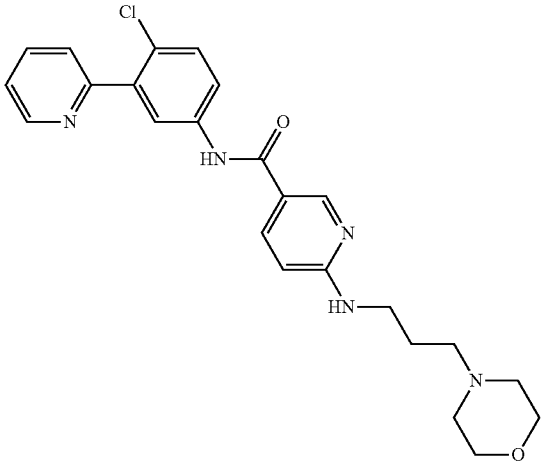 [SMILES: O=C(Nc1ccc(Cl)c(-c2ccccn2)c1)c1ccc(NCCCN2CCOCC2)nc1]

Procedure F was performed using N-(4-chloro-3-(pyridin-2-yl)phenyl)-6-chloro-3-carboxamide (50 mg) and 0.14 mL of N-(3-aminopropyl)morpholine in butanol (0.5 mL). The crude reaction was purified by reverse phase HPLC to yield N-(4-chloro-3-(pyridin-2-yl)phenyl)-6-(3-morpholinopropylamino)nicotinamide. MS (Q1) 452 $(M)^+$.

Example 130

N-(4-chloro-3-(pyridin-2-yl)phenyl)benzo[d][1,2,3]thiadiazole-5-carboxamide

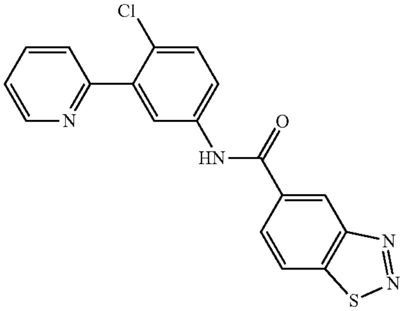 [SMILES: O=C(Nc1ccc(Cl)c(-c2ccccn2)c1)c1ccc2snnc2c1]

50 mg of 4-chloro-3-(pyridin-2-yl)aniline was coupled to benzo-1,2,3-thiadiazole-5-carboxylic acid via Procedure G. The crude product was purified via reverse phase HPLC to yield N-(4-chloro-3-(pyridin-2-yl)phenyl)benzo[d][1,2,3]thiadiazole-5-carboxamide. MS (Q1) 367 $(M)^+$.

Example 131

2-chloro-$N^1$-(4-chloro-3-(pyridin-2-yl)phenyl)-$N^4$-((1S,2R)-2-hydroxy-2,3-dihydro-1H-inden-1-yl)terephthalamide

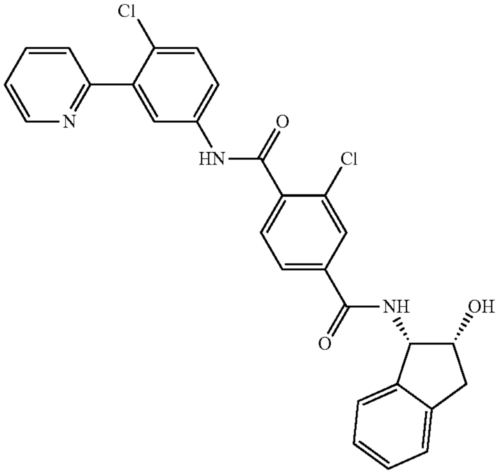 [SMILES: O=C(N[C@H]1c2ccccc2C[C@H]1O)c1ccc(C(=O)Nc2ccc(Cl)c(-c3ccccn3)c2)c(Cl)c1]

60 mg of 3-chloro-4-(4-chloro-3-(pyridin-2-yl)phenylcarbamoyl)benzoic acid was coupled to (1S,2R)-1-amino-2,3-dihydro-1H-inden-2-ol via Procedure G. The crude product was purified on reverse phase HPLC to yield 2-chloro-$N^1$-(4- chloro-3-(pyridin-2-yl)phenyl)-$N^4$-((1S,2R)-2-hydroxy-2,3-dihydro-1H-inden-1-yl)terephthalamide. MS (Q1) 518.2 $(M)^+$.

Example 132

2-chloro-$N^1$-(4-chloro-3-(pyridin-2-yl)phenyl)-$N^4$-((1R,2S)-2-hydroxy-2,3-dihydro-1H-inden-1-yl) terephthalamide

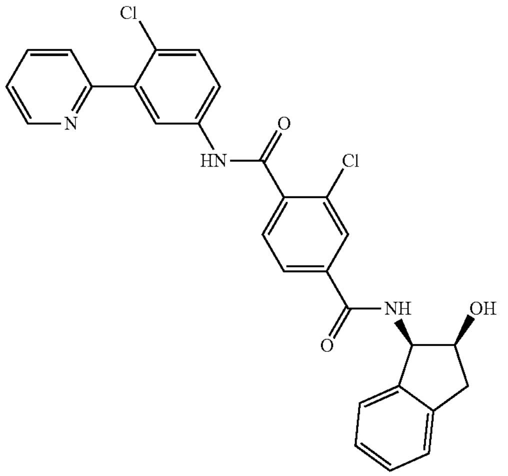 [SMILES: O=C(N[C@@H]1c2ccccc2C[C@@H]1O)c1ccc(C(=O)Nc2ccc(Cl)c(-c3ccccn3)c2)c(Cl)c1]

60 mg of 3-chloro-4-(4-chloro-3-(pyridin-2-yl)phenylcarbamoyl)benzoic acid was coupled to (1R,2S)-1-amino-2,3-dihydro-1H-inden-2-ol via Procedure G. The crude product was purified on reverse phase HPLC to yield 2-chloro-$N^1$-(4-chloro-3-(pyridin-2-yl)phenyl)-$N^4$-((1R,2S)-2-hydroxy-2,3-dihydro-1H-inden-1-yl)terephthalamide. MS (Q1) 518.2 $(M)^+$.

Example 133

$N^4$-benzyl-2-chloro-$N^1$-(4-chloro-3-(pyridin-2-yl) phenyl)-$N^4$-(2-hydroxyethyl)-terephthalamide

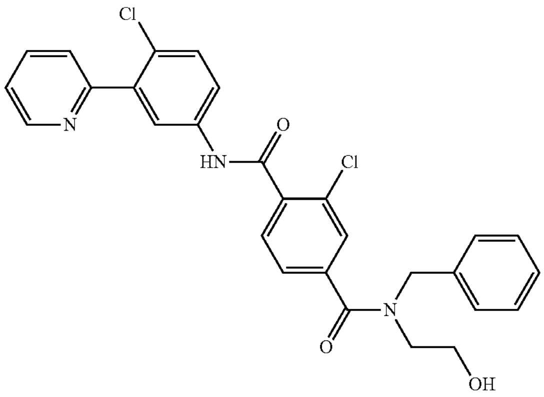 [SMILES: O=C(Nc1ccc(Cl)c(-c2ccccn2)c1)c1ccc(C(=O)N(CCO)Cc2ccccc2)cc1Cl]

40 mg of 3-chloro-4-(4-chloro-3-(pyridin-2-yl)phenylcarbamoyl)benzoic acid was coupled to 2-(benzylamino)ethanol via Procedure G. The crude product was purified on reverse phase HPLC to yield $N^4$-benzyl-2-chloro-$N^1$-(4-chloro-3-(pyridin-2-yl)phenyl)-$N^4$-(2-hydroxyethyl)terephthalamide. MS (Q1) 520 $(M)^+$.

Example 134

2-chloro-$N^1$-(4-chloro-3-(pyridin-2-yl)phenyl)-$N^4$-methyl-$N^4$-(pyridin-2-ylmethyl)terephthalamide

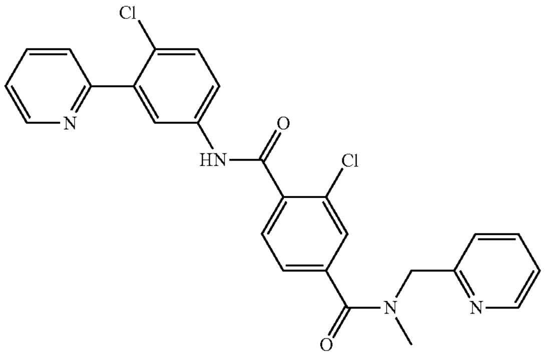 [SMILES: CN(Cc1ccccn1)C(=O)c1ccc(C(=O)Nc2ccc(Cl)c(-c3ccccn3)c2)c(Cl)c1]

40 mg of 3-chloro-4-(4-chloro-3-(pyridin-2-yl)phenylcarbamoyl)benzoic acid was coupled to N-methyl-1-(pyridin-2-yl)methanamine via Procedure G. The crude product was purified on reverse phase HPLC to yield 2-chloro-$N^1$-(4-chloro-3-(pyridin-2-yl)phenyl)-$N^4$-methyl-$N^4$-(pyridin-2-ylmethyl)terephthalamide. MS (Q1) 491 $(M)^+$.

Example 135

$N^4$-benzyl-2-chloro-$N^1$-(4-chloro-3-(pyridin-2-yl) phenyl)-$N^4$-methylterephthalamide

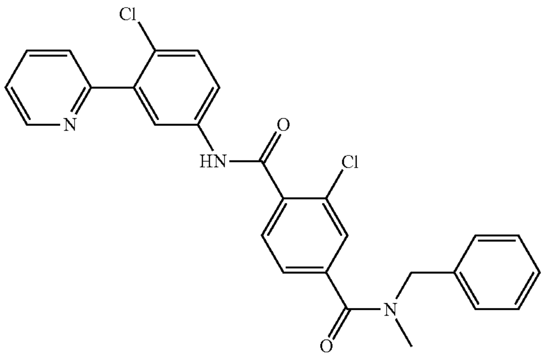 [SMILES: CN(Cc1ccccc1)C(=O)c1ccc(C(=O)Nc2ccc(Cl)c(-c3ccccn3)c2)c(Cl)c1]

40 mg of 3-chloro-4-(4-chloro-3-(pyridin-2-yl)phenylcarbamoyl)benzoic acid was coupled to N-methyl-1-phenylmethanamine via Procedure G. The crude product was purified on reverse phase HPLC to yield $N^4$-benzyl-2-chloro-$N^1$-

(4-chloro-3-(pyridin-2-yl)phenyl)-$N^4$-methylterephthalamide. MS (Q1) 490.1 $(M)^+$.

Example 136

$N^4$-(2-aminobenzyl)-2-chloro-$N^1$-(4-chloro-3-(pyridin-2-yl)phenyl)terephthalamide

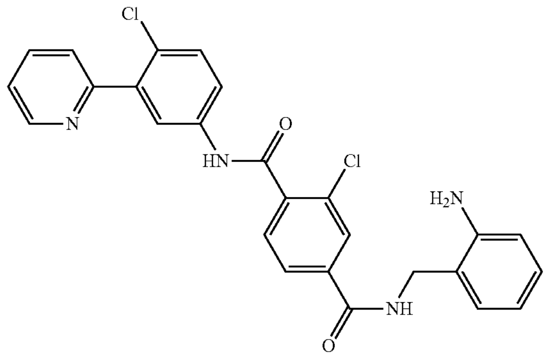 [SMILES: Nc1ccccc1CNC(=O)c1ccc(C(=O)Nc2ccc(Cl)c(-c3ccccn3)c2)c(Cl)c1]

60 mg of 3-chloro-4-(4-chloro-3-(pyridin-2-yl)phenylcarbamoyl)benzoic acid was coupled to N'-phenylethane-1,2-diamine via Procedure G. The crude product was purified on reverse phase HPLC to yield $N^4$-(2-aminobenzyl)-2-chloro-$N^1$-(4-chloro-3-(pyridin-2-yl)phenyl)terephthalamide. MS (Q1) 491 $(M)^+$.

Example 137

$N^4$-benzyl-2-chloro-$N^1$-(4-chloro-3-(pyridin-2-yl)phenyl)terephthalamide

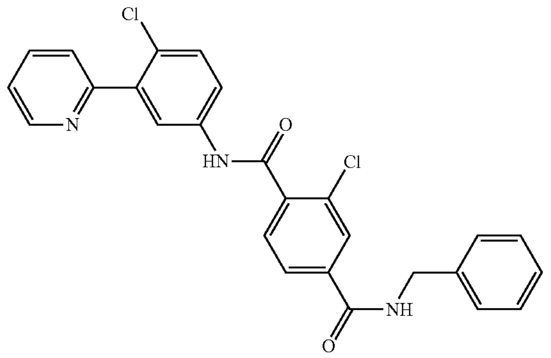 [SMILES: O=C(NCc1ccccc1)c1ccc(C(=O)Nc2ccc(Cl)c(-c3ccccn3)c2)c(Cl)c1]

60 mg of 3-chloro-4-(4-chloro-3-(pyridin-2-yl)phenylcarbamoyl)benzoic acid was coupled to benzylamine via Procedure G. The crude product was purified on reverse phase HPLC to yield $N^4$-benzyl-2-chloro-$N^1$-(4-chloro-3-(pyridin-2-yl)phenyl)terephthalamide. MS (Q1) 476 $(M)^+$.

Example 138

(R)-2-chloro-$N^1$-(4-chloro-3-(pyridin-2-yl)phenyl)-$N^4$-(2-hydroxy-1-phenylethyl)terephthalamide

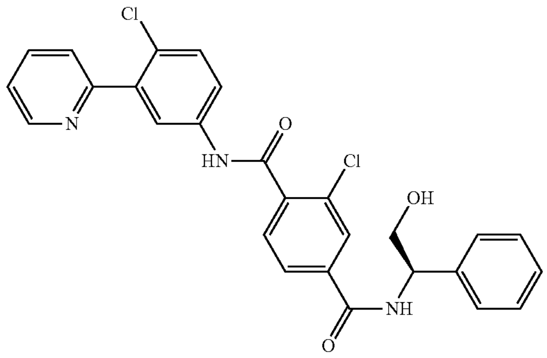 [SMILES: O=C(N[C@@H](CO)c1ccccc1)c1ccc(C(=O)Nc2ccc(Cl)c(-c3ccccn3)c2)c(Cl)c1]

60 mg of 3-chloro-4-(4-chloro-3-(pyridin-2-yl)phenylcarbamoyl)benzoic acid was coupled to (R)-2-amino-2-phenylethanol via Procedure G. The crude product was purified on reverse phase HPLC to yield (R)-2-chloro-$N^1$-(4-chloro-3-(pyridin-2-yl)phenyl)-$N^4$-(2-hydroxy-1-phenylethyl)terephthalamide. MS (Q1) 506 $(M)^+$.

Example 139

N-(4-chloro-3-(pyridin-2-yl)phenyl)-6-(4-methyl-1,4-diazepan-1-yl)nicotinamide

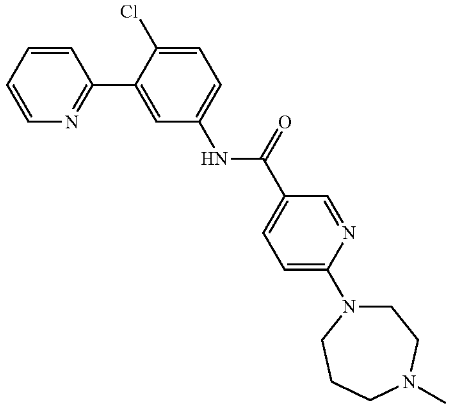 [SMILES: CN1CCCN(c2ccc(C(=O)Nc3ccc(Cl)c(-c4ccccn4)c3)cn2)CC1]

50 mg of 6-chloro-N-(4-chloro-3-(pyridin-2-yl)phenyl)nicotinamide was reacted with 1-methyl-1,4-diazepane via Procedure F. The reaction was evaporated to dryness and purified on reverse phase HPLC to yield N-(4-chloro-3-(pyridin-2-yl)phenyl)-6-(4-methyl-1,4-diazepan-1-yl)nicotinamide. MS (Q1) 422 (M)$^+$.

Example 140

N-(4-chloro-3-(pyridin-2-yl)phenyl)-6-(1,4-diazepan-1-yl)nicotinamide

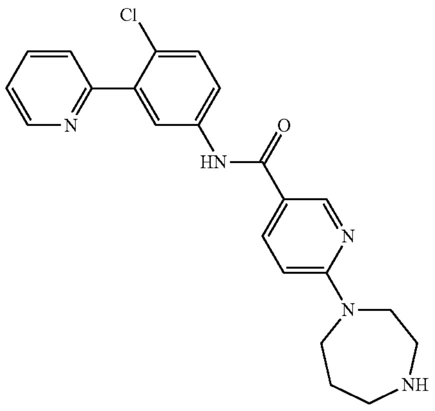 [SMILES: O=C(Nc1ccc(Cl)c(-c2ccccn2)c1)c1ccc(N2CCCNCC2)nc1]

50 mg of 6-chloro-N-(4-chloro-3-(pyridin-2-yl)phenyl)nicotinamide was reacted with 1,4-diazepane via Procedure F. The reaction was evaporated to dryness and purified on reverse phase HPLC to yield N-(4-chloro-3-(pyridin-2-yl)phenyl)-6-(1,4-diazepan-1-yl)nicotinamide. MS (Q1) 408 (M)$^+$.

Example 141

2-chloro-N$^1$-(4-chloro-3-(pyridin-2-yl)phenyl)-N$^4$-(2-(phenylamino)ethyl)terephthalamide

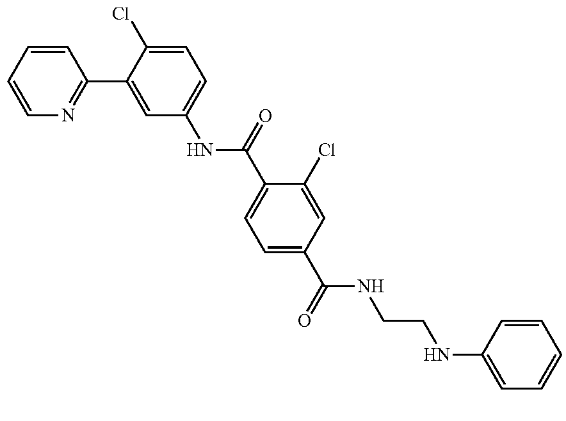 [SMILES: O=C(NCCNc1ccccc1)c1ccc(C(=O)Nc2ccc(Cl)c(-c3ccccn3)c2)c(Cl)c1]

62 mg of 3-chloro-4-(4-chloro-3-(pyridin-2-yl)phenylcarbamoyl)benzoic acid was coupled to N'-phenylethane-1,2-diamine via Procedure G. The crude product was purified on reverse phase HPLC to yield 2-chloro-N$^1$-(4-chloro-3-(pyridin-2-yl)phenyl)-N$^4$-(2-(phenylamino)ethyl)terephthalamide. MS (Q1) 505.1 (M)$^+$.

Example 142

(S)-2-chloro-N$^1$-(4-chloro-3-(pyridin-2-yl)phenyl)-N$^4$-(2-hydroxy-1-phenylethyl)terephthalamide

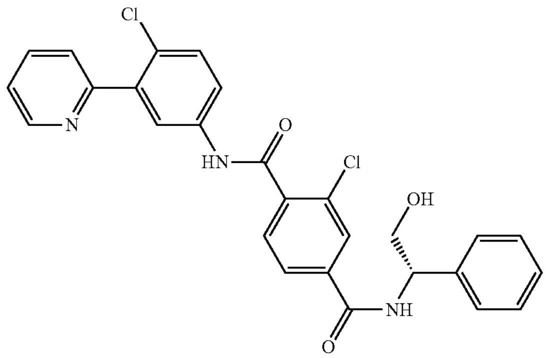 [SMILES: O=C(N[C@H](CO)c1ccccc1)c1ccc(C(=O)Nc2ccc(Cl)c(-c3ccccn3)c2)c(Cl)c1]

62 mg of 3-chloro-4-(4-chloro-3-(pyridin-2-yl)phenylcarbamoyl)benzoic acid was coupled to (S)-2-amino-2-phenylethanol via Procedure G. The crude product was purified on reverse phase HPLC to yield (S)-2-chloro-N$^1$-(4-chloro-3-(pyridin-2-yl)phenyl)-N$^4$-(2-hydroxy-1-phenylethyl)terephthalamide. MS (Q1) 506 (M)$^+$.

Example 143

2-chloro-N$^1$-(4-chloro-3-(pyridin-2-yl)phenyl)-N$^4$-(1-phenylethyl)terephthalamide

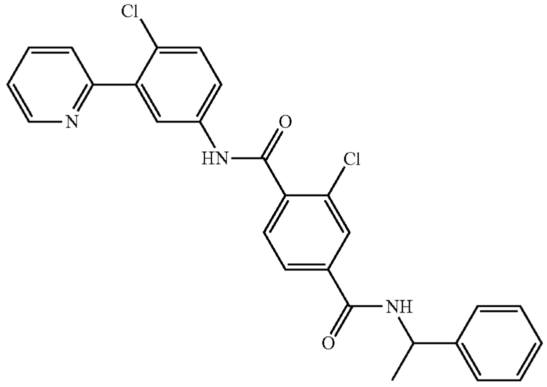 [SMILES: CC(NC(=O)c1ccc(C(=O)Nc2ccc(Cl)c(-c3ccccn3)c2)c(Cl)c1)c1ccccc1]

62 mg of 3-chloro-4-(4-chloro-3-(pyridin-2-yl)phenylcarbamoyl)benzoic acid was coupled to 1-phenylethanamine via Procedure G. The crude product was purified on reverse phase HPLC to yield 2-chloro-$N^1$-(4-chloro-3-(pyridin-2-yl)phenyl)-$N^4$-(1-phenylethyl)terephthalamide. MS (Q1) 490.1 $(M)^+$.

Example 144

2-chloro-$N^1$-(4-chloro-3-(pyridin-2-yl)phenyl)-$N^4$-(4-(methylsulfonyl)benzyl)-terephthalamide

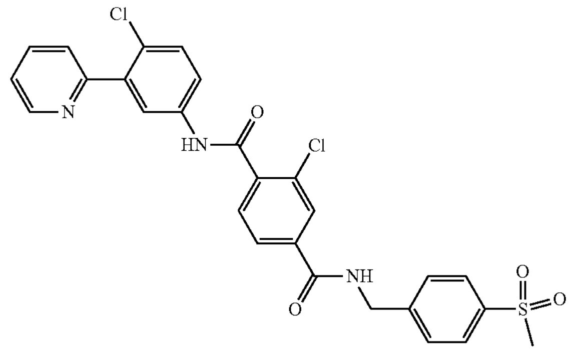 [SMILES: CS(=O)(=O)c1ccc(CNC(=O)c2ccc(C(=O)Nc3ccc(Cl)c(-c4ccccn4)c3)c(Cl)c2)cc1]

62 mg of 3-chloro-4-(4-chloro-3-(pyridin-2-yl)phenylcarbamoyl)benzoic acid was coupled to (4-(methylsulfonyl)phenyl)methanamine via Procedure G. The crude product was purified on reverse phase HPLC to yield 2-chloro-$N^1$-(4-chloro-3-(pyridin-2-yl)phenyl)-$N^4$-(4-(methylsulfonyl)benzyl)terephthalamide. MS (Q1) 554 $(M)^+$.

Example 145

N-(3-chloro-4-(4-chloro-3-(pyridin-2-yl)phenylcarbamoyl)benzyl)picolinamide

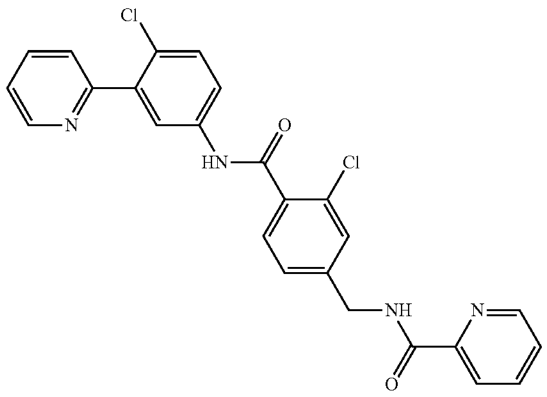 [SMILES: O=C(NCc1ccc(C(=O)Nc2ccc(Cl)c(-c3ccccn3)c2)c(Cl)c1)c1ccccn1]

75 mg of 4-chloro-3-(pyridin-2-yl)aniline was coupled to 4-((tert-butoxycarbonylamino)methyl)-2-chlorobenzoic acid via Procedure G to yield tert-butyl 3-chloro-4-(4-chloro-3-(pyridin-2-yl)phenylcarbamoyl)benzylcarbamate. Tert-butyl 3-chloro-4-(4-chloro-3-(pyridin-2-yl)phenylcarbamoyl)benzylcarbamate was subsequently treated with 4N HCl in Dioxane to remove the Boc protecting group and form the HCl salt of 4-(aminomethyl)-2-chloro-N-(4-chloro-3-(pyridin-2-yl)phenyl)benzamide. 54 mg of the crude HCl salt of 4-(aminomethyl)-2-chloro-N-(4-chloro-3-(pyridin-2-yl)phenyl)benzamide was coupled to picolinic acid via Procedure G. The crude product was purified by reverse phase HPLC to yield N-(3-chloro-4-(4-chloro-3-(pyridin-2-yl)phenylcarbamoyl)benzyl)picolinamide. MS (Q1) 477.3 $(M)^+$.

Example 146

N-(4-(4-chloro-3-(pyridin-2-yl)phenylcarbamoyl)benzyl)picolinamide

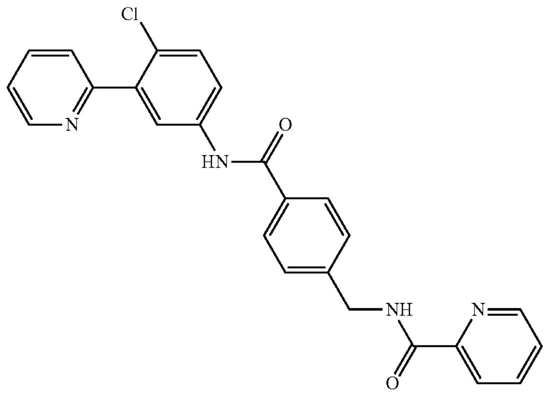 [SMILES: O=C(Nc1ccc(Cl)c(-c2ccccn2)c1)c1ccc(CNC(=O)c2ccccn2)cc1]

75 mg of 4-chloro-3-(pyridin-2-yl)aniline was coupled to 4-((tert-butoxycarbonylamino)methyl)benzoic acid via Procedure G to yield tert-butyl 4-(4-chloro-3-(pyridin-2-yl)phenylcarbamoyl)benzylcarbamate. Tert-butyl 4-(4-chloro-3-(pyridin-2-yl)phenylcarbamoyl)benzylcarbamate was subsequently treated with 4N HCl in Dioxane to remove the Boc protecting group and form the HCl salt of 4-(aminomethyl)-N-(4-chloro-3-(pyridin-2-yl)phenyl)benzamide. 50 mg of the crude HCl salt of 4-(aminomethyl)-N-(4-chloro-3-(pyridin-2-yl)phenyl)benzamide was coupled to picolinic acid via Procedure G. The crude product was purified by reverse phase HPLC to yield N-(4-(4-chloro-3-(pyridin-2-yl)phenylcarbamoyl)benzyl)picolinamide. MS (Q1) 443.3 $(M)^+$.

Example 147

$N^5$-(4-chloro-3-(pyridin-2-yl)phenyl)-$N^2$-isopropylpyridine-2,5-dicarboxamide

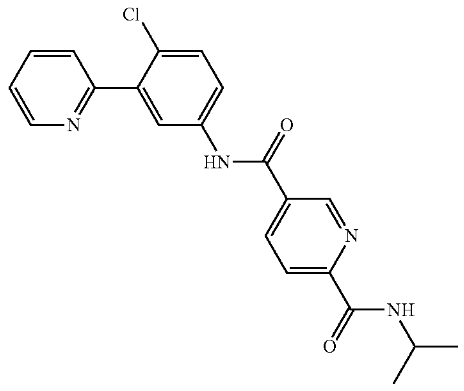 [SMILES: CC(C)NC(=O)c1ccc(C(=O)Nc2ccc(Cl)c(-c3ccccn3)c2)cn1]

250 mg of 5-(methoxycarbonyl)picolinic acid was coupled to isopropylamine via Procedure G. Crude methyl 6-(isopropylcarbamoyl)nicotinate was hydrolyzed via Procedure M to yield 227 mg of 6-(isopropylcarbamoyl)nicotinic acid. 60 mg of 4-chloro-3-(pyridin-2-yl)aniline was coupled to 6-(isopropylcarbamoyl)nicotinic acid via Procedure G. The crude product was purified by reverse phase HPLC to yield $N^5$-(4-chloro-3-(pyridin-2-yl)phenyl)-$N^2$-isopropylpyridine-2,5-dicarboxamide. MS (Q1) 395.1 $(M)^+$.

Example 148

$N^2$-tert-butyl-$N^5$-(4-chloro-3-(pyridin-2-yl)phenyl) pyridine-2,5-dicarboxamide

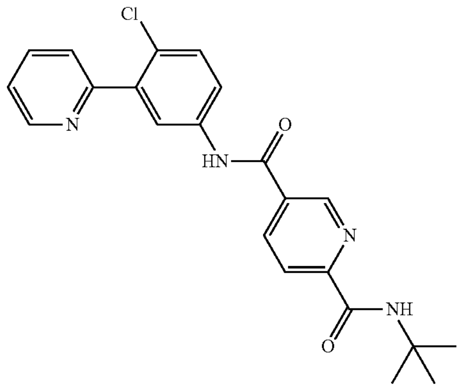 [SMILES: CC(C)(C)NC(=O)c1ccc(C(=O)Nc2ccc(Cl)c(-c3ccccn3)c2)cn1]

250 mg of 5-(methoxycarbonyl)picolinic acid was coupled to tert-butylamine via Procedure G. Crude methyl 6-(tert-butylcarbamoyl)nicotinate was hydrolyzed via Procedure M to yield 250 mg of 6-(tert-butylcarbamoyl)nicotinic acid. 60 mg of 4-chloro-3-(pyridin-2-yl)aniline was coupled to 6-(tert-butylcarbamoyl)nicotinic acid via Procedure G. The crude product was purified by reverse phase HPLC to yield $N^2$-tert-butyl-$N^5$-(4-chloro-3-(pyridin-2-yl)phenyl)pyridine-2,5-dicarboxamide. MS (Q1) 409 $(M)^+$.

Example 149

$N^5$-(4-chloro-3-(pyridin-2-yl)phenyl)-$N^2$-(pyridin-2-ylmethyl)pyridine-2,5-dicarboxamide

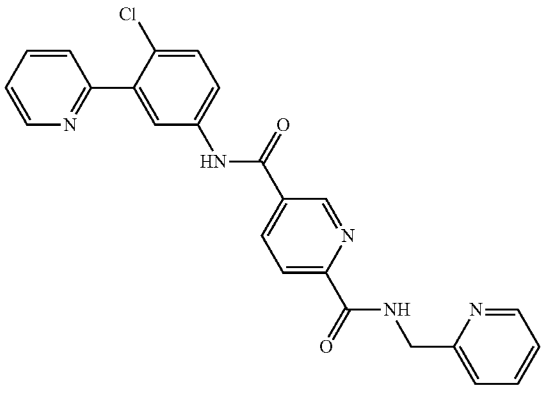

250 mg of 5-(methoxycarbonyl)picolinic acid was coupled to pyridin-2-ylmethanamine via Procedure G. Crude methyl 6-(pyridin-2-ylmethylcarbamoyl)nicotinate was hydrolyzed via Procedure M to yield 250 mg of 6-(pyridin-2-ylmethylcarbamoyl)nicotinic acid. 60 mg of 4-chloro-3-(pyridin-2-yl) aniline was coupled to 6-(pyridin-2-ylmethylcarbamoyl) nicotinic acid via Procedure G. The crude product was purified by reverse phase HPLC to yield $N^5$-(4-chloro-3-(pyridin-2-yl)phenyl)-$N^2$-(pyridin-2-ylmethyl)pyridine-2,5-dicarboxamide. MS (Q1) 444.1 $(M)^+$.

Example 150

$N^2$-benzyl-$N^5$-(4-chloro-3-(pyridin-2-yl)phenyl)pyridine-2,5-dicarboxamide

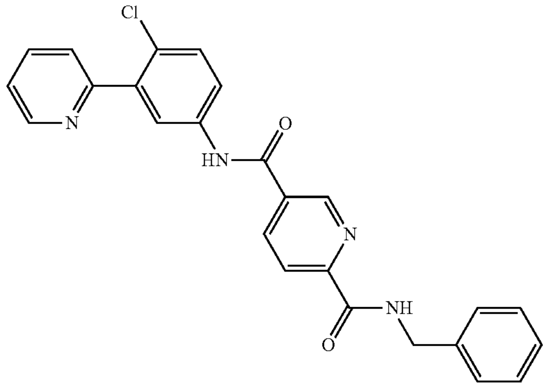 [SMILES: O=C(Nc1ccc(Cl)c(-c2ccccn2)c1)c1ccc(C(=O)NCc2ccccn2)nc1]

250 mg of 5-(methoxycarbonyl)picolinic acid was coupled to benzylamine via Procedure G. Crude methyl 6-(benzylcarbamoyl)nicotinate was hydrolyzed via Procedure M to yield 300 mg of 6-(benzylcarbamoyl)nicotinic acid. 60 mg of 4-chloro-3-(pyridin-2-yl)aniline was coupled to 6-(benzylcarbamoyl)nicotinic acid via Procedure G. The crude product was purified by reverse phase HPLC to yield-benzyl-$N^5$-(4-chloro-3-(pyridin-2-yl)phenyl)pyridine-2,5-dicarboxamide. MS (Q1) 443.1 $(M)^+$.

Example 151

$N^5$-(4-chloro-3-(pyridin-2-yl)phenyl)-$N^2$-(6-methoxypyridin-3-yl)pyridine-2,5-dicarboxamide

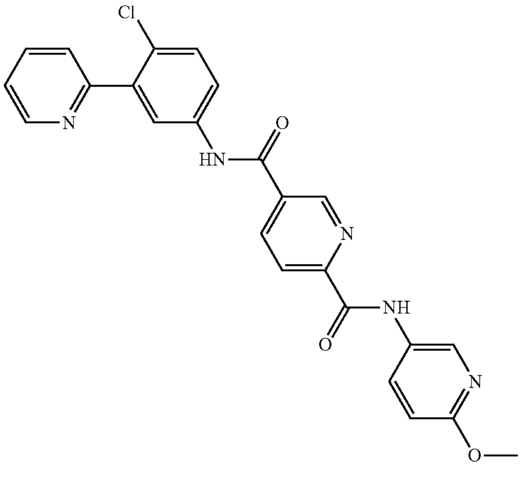 [SMILES: COc1ccc(NC(=O)c2ccc(C(=O)Nc3ccc(Cl)c(-c4ccccn4)c3)cn2)cn1]

250 mg of 5-(methoxycarbonyl)picolinic acid was coupled to 6-methoxypyridin-3-amine via Procedure G. Crude methyl 6-(6-methoxypyridin-3-ylcarbamoyl)nicotinate was hydrolyzed via Procedure M to yield 196 mg of 6-(6-methoxypyridin-3-ylcarbamoyl)nicotinic acid. 60 mg of 4-chloro-3-(pyridin-2-yl)aniline was coupled to 6-(6-methoxypyridin-3-ylcarbamoyl)nicotinic acid via Procedure G. The crude product was recrystallized to yield pure $N^5$-(4-chloro-3-(pyridin-2-yl)phenyl)-$N^2$-(6-methoxypyridin-3-yl)pyridine-2,5-dicarboxamide. MS (Q1) 460 $(M)^+$.

Example 152

2-chloro-$N^1$-(4-chloro-3-(pyridin-2-yl)phenyl)-$N^4$-((6-methylpyridin-2-yl)methyl)-terephthalamide

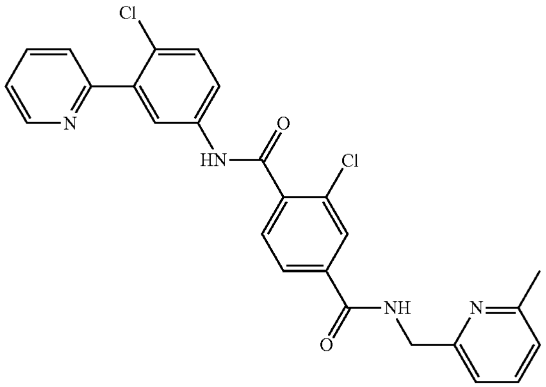 [SMILES: Cc1cccc(CNC(=O)c2ccc(C(=O)Nc3ccc(Cl)c(-c4ccccn4)c3)c(Cl)c2)n1]

2.5 mL of Diisopropylazodicarboxylate in 1.5 mL of THF was added dropwise to a solution of 250 mg of (6-methylpyridin-2-yl)methanol, 2.8 g of Triphenylphosphine and 1.6 g of isoindoline-1,3-dione in anhydrous THF at room temperature. The reaction was stirred for 2 hours and monitored by TLC. Upon complection, the solvent was concentrated, the crude material was extracted in water and Chloroform 3 times and dried over Magnesium Sulfate. The crude was purified via ISCO Combi-Flash to yield 2-((6-methylpyridin-2-yl)methyl)isoindoline-1,3-dione. 350 mg of 2-((6-methylpyridin-2-yl)methyl)isoindoline-1,3-dione was treated with 440 μL of Hydrazine Monohydrate in EtOH and refluxed for several hours to yield (6-methylpyridin-2-yl)methanamine. The crude (6-methylpyridin-2-yl)methanamine was evaporated and directly coupled to 50 mg of 3-chloro-4-(4-chloro-3-(pyridin-2-yl)phenylcarbamoyl)benzoic acid via Procedure G. The crude product was purified on reverse phase HPLC to yield 2-chloro-$N^1$-(4-chloro-3-(pyridin-2-yl)phenyl)-$N^4$-((6-methylpyridin-2-yl)methyl)terephthalamide. MS (Q1) 491.1 $(M)^+$.

Example 153

N-(4-chloro-3-(pyridin-2-yl)phenyl)-4-((2-hydroxypropylsulfonyl)methyl)benzamide

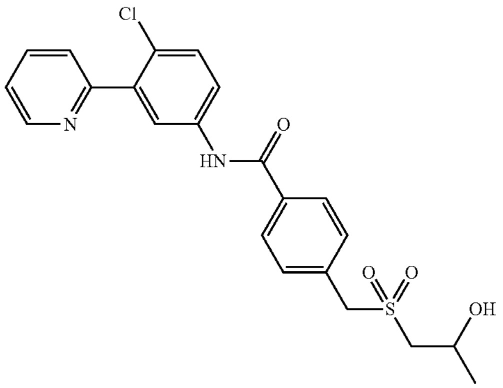 [SMILES: CC(O)CS(=O)(=O)Cc1ccc(C(=O)Nc2ccc(Cl)c(-c3ccccn3)c2)cc1]

1 g of methyl 4-(bromomethyl)benzoate was reacted with 1-mercaptopropan-2-ol via Procedure Q. 1 g of methyl 4-((2-hydroxypropylthio)methyl)benzoate was oxidized with 2 g of MCPBA in DCM at −78° C. to form crude methyl 4-((2-hydroxypropylsulfonyl)methyl)benzoate. The reaction was evaporated and purified by ISCO Combi-Flash to yield 567 mg of pure methyl 4-((2-hydroxypropylsulfonyl)methyl)benzoate which was subsequently hydrolyzed via Procedure M to give 328 mg of 4-((2-hydroxypropylsulfonyl)methyl)benzoic acid. 50 mg of 4-chloro-3-(pyridin-2-yl)aniline was coupled to 4-((2-hydroxypropylsulfonyl)methyl)benzoic acid via Procedure G. The crude product was purified on reverse phase HPLC to yield N-(4-chloro-3-(pyridin-2-yl)phenyl)-4-((2-hydroxypropylsulfonyl)methyl)benzamide. MS (Q1) 445.3 $(M)^+$.

Example 154

(R)-2-chloro-$N^1$-(4-chloro-3-(pyridin-2-yl)phenyl)-$N^4$-(2-hydroxypropyl)terephthalamide

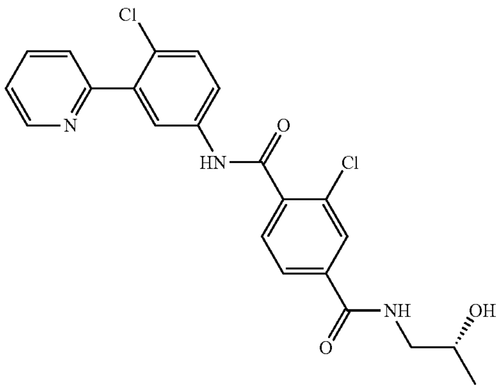 [SMILES: C[C@@H](O)CNC(=O)c1ccc(C(=O)Nc2ccc(Cl)c(-c3ccccn3)c2)c(Cl)c1]

100 mg of 3-chloro-4-(4-chloro-3-(pyridin-2-yl)phenylcarbamoyl)benzoic acid was coupled to (R)-2-amino-2-phenylethanol via Procedure G. The crude product was purified on reverse phase HPLC to yield (R)-2-chloro-$N^1$-(4-chloro-3-(pyridin-2-yl)phenyl)-$N^4$-(2-hydroxypropyl)terephthalamide. MS (Q1) 444.3 $(M)^+$.

Example 155

N-(4-chloro-3-(pyridin-2-yl)phenyl)-4-((2-(dimethylamino)ethylsulfonyl)methyl)-benzamide

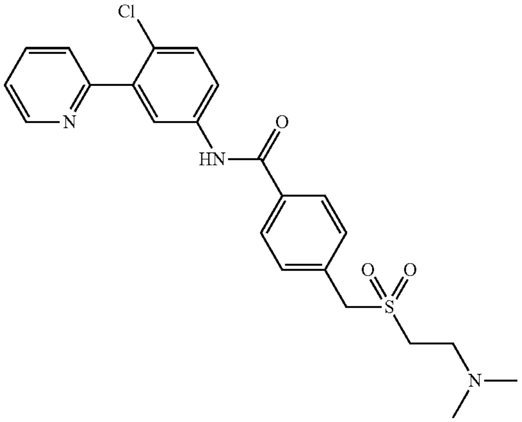 [SMILES: CN(C)CCS(=O)(=O)Cc1ccc(C(=O)Nc2ccc(Cl)c(-c3ccccn3)c2)cc1]

500 mg of 4-chloro-3-(pyridin-2-yl)aniline was coupled to 4-(bromomethyl)benzoic acid via Procedure E. 170 mg of 4-(bromomethyl)-N-(4-chloro-3-(pyridin-2-yl)phenyl)benzamide was reacted with 2-(dimethylamino)ethanethiol hydrochloride via Procedure Q. 140 mg of crude N-(4-chloro-3-(pyridin-2-yl)phenyl)-4-((2-(dimethylamino)ethylthio)methyl)benzamide was reacted with oxone via Procedure R. The crude product was purified by reverse phase HPLC to yield N-(4-chloro-3-(pyridin-2-yl)phenyl)-4-((2-(dimethylamino)ethylsulfonyl)methyl)benzamide. MS (Q1) 458.3 $(M)^+$.

Example 156

2-chloro-$N^1$-(4-chloro-3-(pyridin-2-yl)phenyl)-$N^4$-(6-methoxypyridin-3-yl)terephthalamide

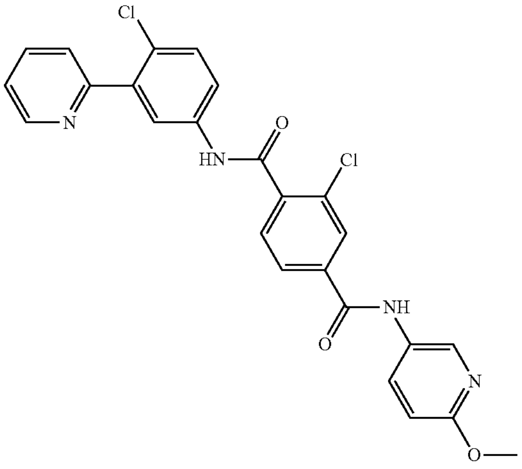 [SMILES: COc1ccc(NC(=O)c2ccc(C(=O)Nc3ccc(Cl)c(-c4ccccn4)c3)c(Cl)c2)cn1]

50 mg of 3-chloro-4-(4-chloro-3-(pyridin-2-yl)phenylcarbamoyl)benzoic acid was coupled to 6-methoxypyridin-3-amine via Procedure G. The crude product was purified on reverse phase HPLC to yield 2-chloro-$N^1$-(4-chloro-3-(pyridin-2-yl)phenyl)-$N^4$-(6-methoxypyridin-3-yl)terephthalamide. MS (Q1) 493 $(M)^+$.

Example 157

$N^4$-(6-aminopyridin-3-yl)-2-chloro-$N^1$-(4-chloro-3-(pyridin-2-yl)phenyl)-terephthalamide

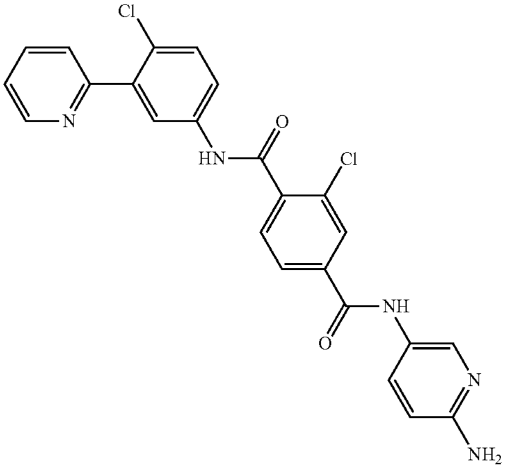 [SMILES: Nc1ccc(NC(=O)c2ccc(C(=O)Nc3ccc(Cl)c(-c4ccccn4)c3)c(Cl)c2)cn1]

50 mg of 3-chloro-4-(4-chloro-3-(pyridin-2-yl)phenylcarbamoyl)benzoic acid was coupled to pyridine-2,5-diamine via Procedure G. The crude product was purified on reverse phase HPLC to yield $N^4$-(6-aminopyridin-3-yl)-2-chloro-$N^1$-(4-chloro-3-(pyridin-2-yl)phenyl)terephthalamide. MS (Q1) 478 $(M)^+$.

Example 158

2-chloro-$N^1$-(4-chloro-3-(pyridin-2-yl)phenyl)-$N^4$-(6-chloropyridin-3-yl)terephthalamide

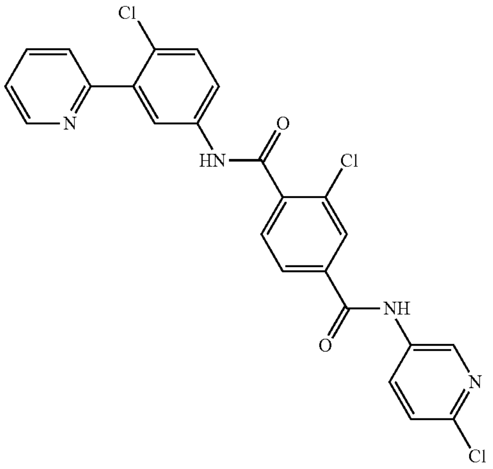 [SMILES: O=C(Nc1ccc(Cl)nc1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 6-chloropyridin-3- amine via Procedure G. The crude product was purified on reverse phase HPLC to yield 2-chloro-N[1]-(4-chloro-3-(pyridin-2-yl)phenyl)-N[4]-(6-chloropyridin-3-yl)terephthalamide. MS (Q1) 497 (M)+.

Example 159

2-chloro-N[1]-(4-chloro-3-(pyridin-2-yl)phenyl)-N[4]-(pyridin-2-yl)terephthalamide

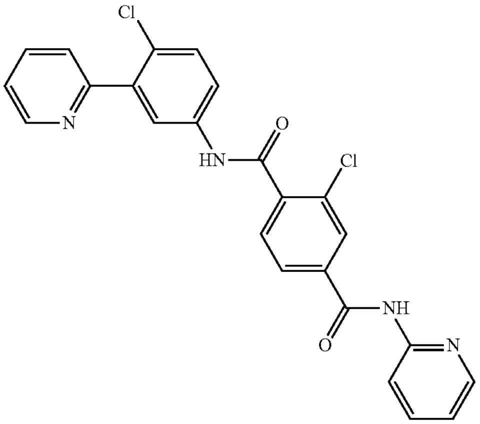 [SMILES: O=C(Nc1ccccn1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to pyridin-2-amine via Procedure G. The crude product was purified on reverse phase HPLC to yield 2-chloro-N[1]-(4-chloro-3-(pyridin-2-yl)phenyl)-N[4]-(pyridin-2-yl)terephthalamide. MS (Q1) 463 (M)+.

Example 160

2-chloro-N[1]-(4-chloro-3-(pyridin-2-yl)phenyl)-N[4]-(piperidin-4-ylmethyl)terephthalamide

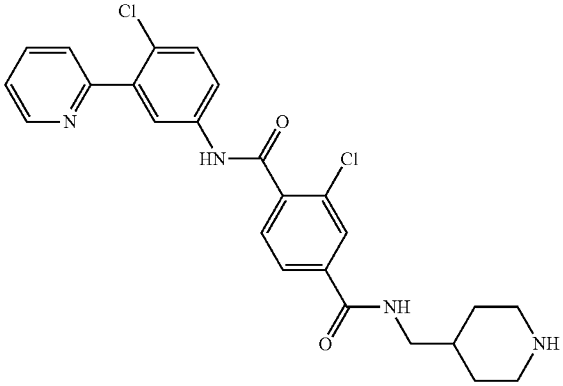 [SMILES: O=C(NCC1CCNCC1)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to piperidin-4-ylmethanamine via Procedure G. The crude product was purified on reverse phase HPLC to yield 2-chloro-N[1]-(4-chloro-3-(pyridin-2-yl)phenyl)-N[4]-(piperidin-4-ylmethyl)terephthalamide. MS (Q1) 483 (M)+.

Example 161

2-chloro-N[1]-(4-chloro-3-(pyridin-2-yl)phenyl)-N[4]-(1,3-dimethyl-1H-pyrazol-5-yl)terephthalamide

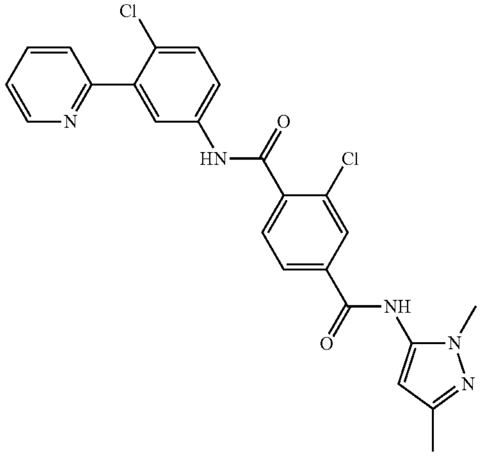 [SMILES: Cc1cc(NC(=O)c2ccc(C(=O)Nc3ccc(Cl)c(-c4ccccn4)c3)c(Cl)c2)n(C)n1]

50 mg of 3-chloro-4-(4-chloro-3-(pyridin-2-yl)phenylcarbamoyl)benzoic acid was coupled to 1,3-dimethyl-1H-pyrazol-5-amine via Procedure G. The crude product was purified on reverse phase HPLC to yield 2-chloro-N[1]-(4-chloro-3-(pyridin-2-yl)phenyl)-N[4]-(1,3-dimethyl-1H-pyrazol-5-yl)terephthalamide. MS (Q1) 480 (M)+.

Example 162

2-chloro-N[1]-(4-chloro-3-(pyridin-2-yl)phenyl)-N[4]-(2-(methylsulfonyl)ethyl)-terephthalamide

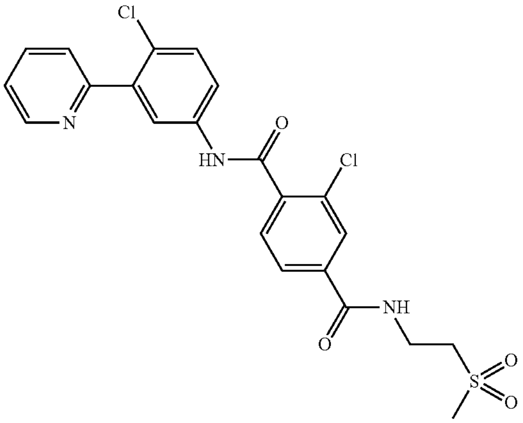 [SMILES: CS(=O)(=O)CCNC(=O)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to 2-(methylsulfonyl)ethanamine via Procedure G. The crude product was purified on reverse phase HPLC to yield 2-chloro-N$^1$-(4-chloro-3-(pyridin-2-yl)phenyl)-N$^4$-(2-(methylsulfonyl)ethyl)terephthalamide. MS (Q1) 492 (M)$^+$.

Example 163

2-chloro-N$^1$-(4-chloro-3-(pyridin-2-yl)phenyl)-N$^4$-isopropylterephthalamide

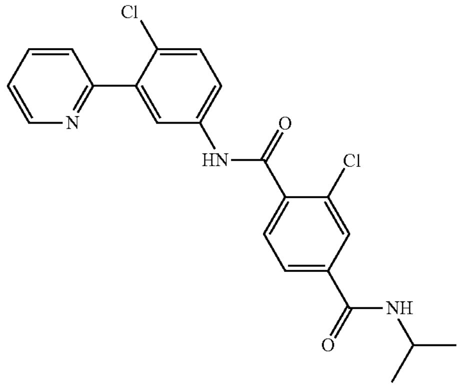 [SMILES: CC(C)NC(=O)c1ccc(C(=O)Nc2ccc(Cl)c(-c3ccccn3)c2)c(Cl)c1]

50 mg of 3-chloro-4-(4-chloro-3-(pyridin-2-yl)phenylcarbamoyl)benzoic acid was coupled to isopropylamine via Procedure G. The crude product was purified on reverse phase HPLC to yield 2-chloro-N$^1$-(4-chloro-3-(pyridin-2-yl)phenyl)-N$^4$-isopropylterephthalamide. MS (Q1) 428 (M)$^+$.

Example 164

2-chloro-N-(4-chloro-3-(pyridin-2-yl)phenyl)-4-(N-(2-methoxyethyl)methyl-sulfonamido)benzamide

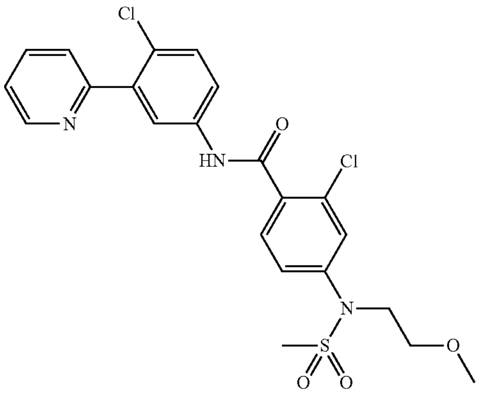 [SMILES: COCCN(c1ccc(C(=O)Nc2ccc(Cl)c(-c3ccccn3)c2)c(Cl)c1)S(C)(=O)=O]

To 5 g of methyl 2-chloro-4-nitrobenzoate in 100 mL of EtOH was added 20 g of Tin (II) Chloride in portions. The reaction was heated to 55° C. and monitored by TLC until complete. Solvent was concentrated and extraction was performed in Ethyl Acetate and water with TEA to reduce emulsions. The organic layer was dried over Magnesium Sulfate, filtered and concentrated to give 3.9 g of methyl 4-amino-2-chlorobenzoate. 1 g of methyl 4-amino-2-chlorobenzoate was cooled to 0° C. in DCM with 485 μL of Pyridine before Methanesulfonyl Chloride was added dropwise. The reaction was allowed to warm to room temperature and stir overnight.

Solvent was concentrated and the crude material was dissolved in Ethyl Acetate and extracted with saturated bicarbonate solution and then brine. The crude material was dried over Magnesium Sulfate, filtered and concentrated to give 1.54 g of methyl 2-chloro-4-(methylsulfonamido)benzoate. 107 μL of 1-bromo-2-methoxyethane and 556 mg of Cesium Carbonate were added to 150 mg of methyl 2-chloro-4-(methylsulfonamido)benzoate in DMF and stirred at room temperature for 16 hours. The reaction mixture was extracted in Ethyl Acetate twice with saturated bicarbonate and once with brine, dried over Magnesium Sulfate, filtered and concentrated to give methyl 2-chloro-4-(N-(2-methoxyethyl)methylsulfonamido)benzoate. 182 mg of methyl 2-chloro-4-(N-(2-methoxyethyl)methylsulfonamido)benzoate was hydrolyzed via Procedure M to yield 169 mg of crude 2-chloro-4-(N-(2-methoxyethyl)methylsulfonamido)benzoic acid. 65 mg of 4-chloro-3-(pyridin-2-yl)aniline was coupled to 2-chloro-4-(N-(2-methoxyethyl)methylsulfonamido)benzoic acid via Procedure G. The crude product was purified by reverse phase HPLC to yield 2-chloro-N-(4-chloro-3-(pyridin-2-yl)phenyl)-4-(N-(2-methoxyethyl)methylsulfonamido)benzamide. MS (Q1) 494 (M)$^+$.

Example 165

4-(N-(2-(1H-pyrrol-1-yl)ethyl)methylsulfonamido)-2-chloro-N-(4-chloro-3-(pyridin-2-yl)phenyl)benzamide

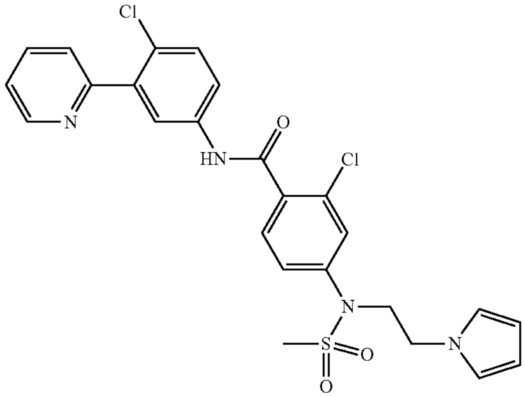 [SMILES: CS(=O)(=O)N(CCn1cccc1)c1ccc(C(=O)Nc2ccc(Cl)c(-c3ccccn3)c2)c(Cl)c1]

200 μL of 1-(2-bromoethyl)-1H-pyrrole and 556 mg of Cesium Carbonate were added to 150 mg of methyl 2-chloro-4-(methylsulfonamido)benzoate in DMF and stirred at room temperature for 16 hours. The reaction mixture was extracted in Ethyl Acetate twice with saturated bicarbonate and once with brine, dried over Magnesium Sulfate, filtered and concentrated to give methyl 4-(N-(2-(1H-pyrrol-1-yl)ethyl)methylsulfonamido)-2-chlorobenzoate. 230 mg of methyl 4-(N-(2-(1H-pyrrol-1-yl)ethyl)methylsulfonamido)-2-chlorobenzoate was hydrolyzed via Procedure M to yield 221 mg of crude 4-(N-(2-(1H-pyrrol-1-yl)ethyl)methylsulfonamido)-2-chlorobenzoic acid.

64 mg of 4-chloro-3-(pyridin-2-yl)aniline was coupled to 4-(N-(2-(1H-pyrrol-1-yl)ethyl)methylsulfonamido)-2-chlorobenzoic acid via Procedure G. The crude product was purified by reverse phase HPLC to yield 4-(N-(2-(1H-pyrrol-1-yl)ethyl)methylsulfonamido)-2-chloro-N-(4-chloro-3-(pyridin-2-yl)phenyl)benzamide. MS (Q1) 529 (M)$^+$.

Example 166

2-chloro-N-(4-chloro-3-(pyridin-2-yl)phenyl)-4-(N-isobutylmethylsulfonamido)-benzamide

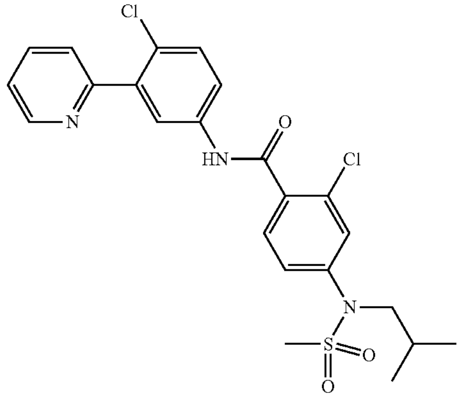 [SMILES: CC(C)CN(c1ccc(C(=O)Nc2ccc(Cl)c(-c3ccccn3)c2)c(Cl)c1)S(C)(=O)=O]

175 μL of 1-iodo-2-methylpropane and 740 mg of Cesium Carbonate were added to 200 mg of methyl 2-chloro-4-(methylsulfonamido)benzoate in 2 mL of DMF and stirred in the microwave at 140° C. for 30 minutes. The reaction mixture was extracted in Ethyl Acetate twice with water, dried over Magnesium Sulfate, filtered, concentrated and purified on ISCO Combi-Flash to give methyl 2-chloro-4-(N-isobutylmethylsulfonamido)benzoate. 120 mg of methyl 2-chloro-4-(N-isobutylmethylsulfonamido)benzoate was hydrolyzed via Procedure M to yield 110 mg of crude 2-chloro-4-(N-isobutylmethylsulfonamido)benzoic acid. 75 mg of 4-chloro-3-(pyridin-2-yl)aniline was coupled to 2-chloro-4-(N-isobutylmethylsulfonamido)benzoic acid via Procedure G. The crude product was purified by reverse phase HPLC to yield 2-chloro-N-(4-chloro-3-(pyridin-2-yl)phenyl)-4-(N-isobutylmethylsulfonamido)benzamide. MS (Q1) 492 $(M)^+$.

Example 167

2-chloro-N-(4-chloro-3-(pyridin-2-yl)phenyl)-4-(N-(2-morpholinoethyl)methyl-sulfonamido)benzamide

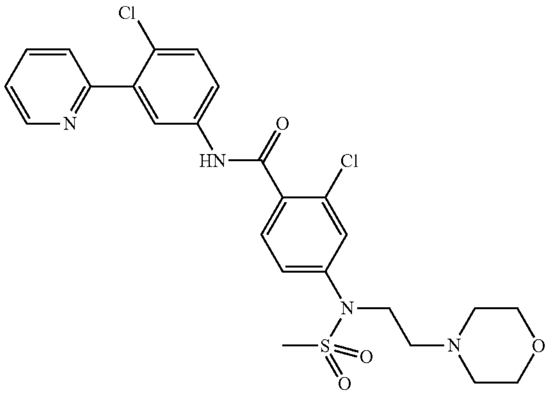 [SMILES: CS(=O)(=O)N(CCN1CCOCC1)c1ccc(C(=O)Nc2ccc(Cl)c(-c3ccccn3)c2)c(Cl)c1]

1.2 g of 4-(2-chloroethyl)morpholine and 2.5 g of Cesium Carbonate were added to 334 mg of methyl 2-chloro-4-(methylsulfonamido)benzoate in 7 mL of DMF and stirred in the microwave at 150° C. for 30 minutes. The reaction mixture was extracted in Ethyl Acetate twice with water, dried over Magnesium Sulfate, filtered, concentrated to give crude methyl 2-chloro-4-(N-(2-morpholinoethyl)methylsulfonamido)benzoate. 476 mg of methyl 2-chloro-4-(N-(2-morpholinoethyl)methylsulfonamido)benzoate was hydrolyzed via Procedure M and purified by reverse phase HPLC to yield 460 mg of crude 2-chloro-4-(N-(2-morpholinoethyl)methylsulfonamido)benzoic acid. 100 mg of 4-chloro-3-(pyridin-2-yl)aniline was coupled to 2-chloro-4-(N-(2-morpholinoethyl)methylsulfonamido)benzoic acid via Procedure G. The crude product was purified by reverse phase HPLC to yield 2-chloro-N-(4-chloro-3-(pyridin-2-yl)phenyl)-4-(N-(2-morpholinoethyl)methylsulfonamido)benzamide. MS (Q1) 549 $(M)^+$.

Example 168

N-(4-chloro-3-(pyridin-2-yl)phenyl)-2-methyl-4-(methylsulfonylmethyl)benzamide

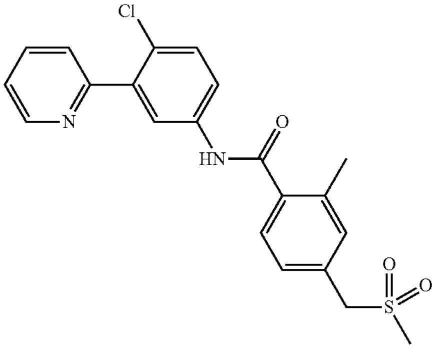 [SMILES: Cc1cc(CS(C)(=O)=O)ccc1C(=O)Nc1ccc(Cl)c(-c2ccccn2)c1]

410 mg of dimethyl 2-methylterephthalate was hydrolyzed via Procedure M and purified by ISCO Combi-Flash to afford 4-(methoxycarbonyl)-3-methylbenzoic acid. 255 mg of 4-(methoxycarbonyl)-3-methylbenzoic acid was cooled to 0° C. in 2 mL of THF before a solution of 2.6 mL of 1M $BH_3$-THF complex in THF was added dropwise. The ice bath was subsequently removed and the reaction was stirred at room temperature until reaction stalled out at ~50% complete by TLC. The reaction was re-cooled to 0° C. and another 2.6 mL of $BH_3$-THF was added dropwise before the ice bath was removed. Upon completion, the reaction was re-cooled to 0° C. and quenched with 3N HCl dropwise. The aqueous layer was extracted 2 times with Ethyl Acetate and the organic layer was then extracted once with bicarbonate solution and brine, dried over Magnesium Sulfate, filtered and concentrated to give methyl 4-(hydroxymethyl)-2-methylbenzoate. 220 mg of methyl 4-(hydroxymethyl)-2-methylbenzoate was cooled to 0° C. in 5 mL of DCM before adding 260 mg of Triphenylphosphine and 395 mg of NBS. The reaction was concentrated and directly purified via ISCO Combi-Flash to give pure methyl 4-(bromomethyl)-2-methylbenzoate. 255 mg of methyl 4-(bromomethyl)-2-methylbenzoate was reacted via Procedure O to give methyl 2-methyl-4-(methylsulfonylmethyl)benzoate. 250 mg of methyl 2-methyl-4-(methylsulfonylmethyl)benzoate was then hydrolyzed upon heating to 45° C. for 1 hour via Procedure M to give 2-methyl-4-(methylsulfonylmethyl)benzoic acid. 202 mg of 4-chloro-3-(pyridin-2-yl)aniline was coupled to 2-methyl-4-(methylsulfonylmethyl)benzoic acid via Procedure G. The crude product was purified by reverse phase HPLC to yield N-(4-chloro-3-(pyridin-2-yl)phenyl)-2-methyl-4-(methylsulfonylmethyl)benzamide. MS (Q1) 415 $(M)^+$.

Example 169

2-chloro-N-(4-chloro-3-(pyridin-2-yl)phenyl)-4-(N-methylmethyl-sulfonamido)benzamide

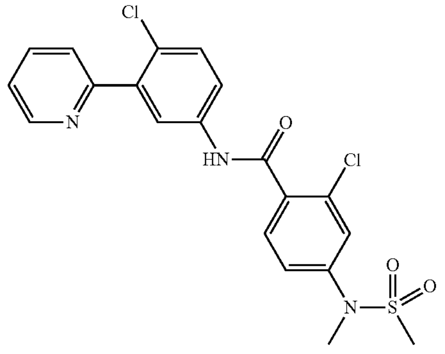 [SMILES: CN(c1ccc(C(=O)Nc2ccc(Cl)c(-c3ccccn3)c2)c(Cl)c1)S(C)(=O)=O]

78 μL of iodomethane and 447 mg of Cesium Carbonate were added to 300 mg of methyl 2-chloro-4-(methylsulfonamido)benzoate in 3 mL of DMF and stirred at room temperature for 16 hours. The reaction mixture was extracted in Ethyl Acetate twice with saturated bicarbonate and once with brine, dried over Magnesium Sulfate, filtered and concentrated to give crude methyl 2-chloro-4-(N-methylmethylsulfonamido) benzoate. 295 mg of methyl 2-chloro-4-(N-methylmethylsulfonamido)benzoate was hydrolyzed via Procedure M to yield 249 mg of 2-chloro-4-(N-methylmethylsulfonamido)benzoic acid.

100 mg of 4-chloro-3-(pyridin-2-yl)aniline was coupled to 2-chloro-4-(N-methylmethylsulfonamido)benzoic acid via Procedure G. The crude product was purified by reverse phase HPLC to yield 2-chloro-N-(4-chloro-3-(pyridin-2-yl)phenyl)-4-(N-methylmethylsulfonamido)benzamide. MS (Q1) 450 $(M)^+$.

Example 170

N-(4-chloro-3-(pyridin-2-yl)phenyl)-4-((2-oxopiperazin-1-yl)methyl)benzamide

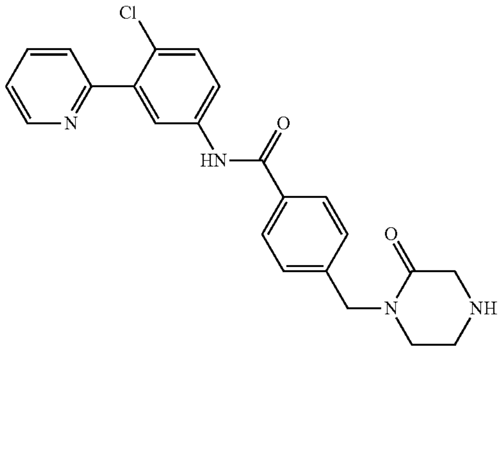 [SMILES: O=C(Nc1ccc(Cl)c(-c2ccccn2)c1)c1ccc(CN2CCNCC2=O)cc1]

500 mg of methyl 4-(bromomethyl)benzoate was reacted with 480 mg of tert-butyl 3-oxopiperazine-1-carboxylate and 1 g of Cesium Carbonate in 9 mL of DMF at 45° C. Upon completion, the reaction was extracted in Ethyl Acetate 2 times saturated bicarbonate, dried over Magnesium Sulfate, filtered and concentrated to give tert-butyl 4-(4-(methoxycarbonyl)benzyl)-3-oxopiperazine-1-carboxylate. 613 mg of tert-butyl 4-(4-(methoxycarbonyl)benzyl)-3-oxopiperazine-1-carboxylate was hydrolyzed via Procedure M to give 4-((4-(tert-butoxycarbonyl)-2-oxopiperazin-1-yl)methyl)benzoic acid. 200 mg of 4-chloro-3-(pyridin-2-yl)aniline was coupled to 4-((4-(tert-butoxycarbonyl)-2-oxopiperazin-1-yl)methyl) benzoic acid via Procedure G. The crude product was extracted twice with saturated bicarbonate in Ethyl Acetate, dried over Magnesium Sulfate, filtered and concentrated to give crude tert-butyl 4-(4-(4-chloro-3-(pyridin-2-yl)phenylcarbamoyl)benzyl)-3-oxopiperazine-1-carboxylate. 4N HCl was subsequently added to crude tert-butyl 4-(4-(4-chloro-3-(pyridin-2-yl)phenylcarbamoyl)benzyl)-3-oxopiperazine-1-carboxylate and concentrated to give the HCl salt of N-(4-chloro-3-(pyridin-2-yl)phenyl)-4-((2-oxopiperazin-1-yl) methyl)benzamide. The reaction was purified by reverse phase HPLC to give pure N-(4-chloro-3-(pyridin-2-yl)phenyl)-4-((2-oxopiperazin-1-yl)methyl)benzamide. MS (Q1) 421.3 $(M)^+$.

Example 171

N-(4-chloro-3-(pyridin-2-yl)phenyl)-4-((4-methyl-2-oxopiperazin-1-yl)methyl)benzamide

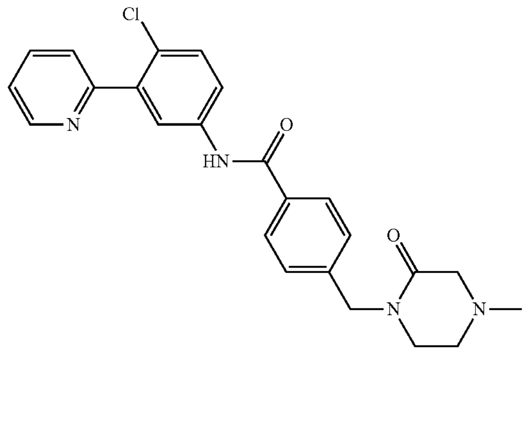 [SMILES: CN1CCN(Cc2ccc(C(=O)Nc3ccc(Cl)c(-c4ccccn4)c3)cc2)C(=O)C1]

To 200 mg of the HCl salt of N-(4-chloro-3-(pyridin-2-yl) phenyl)-4-((2-oxopiperazin-1-yl)methyl)benzamide was added 55 mg of Paraformaldehyde and 185 mg of Sodium Triacetoxyborohydride in 1 mL of 2% AcOH in DMF. After completion, the reaction is extracted once with bicarbonate and brine in Ethyl Acetate, dried over Magnesium Sulfate, concentrated and purified by reverse phase HPLC to give pure N-(4-chloro-3-(pyridin-2-yl)phenyl)-4-((4-methyl-2-oxopiperazin-1-yl)methyl)benzamide. MS (Q1) 435.3 (M)+.

Example 172

2-chloro-N-(4-chloro-3-(pyridin-2-yl)phenyl)-4-((4,5-dihydro-1H-imidazol-2-ylamino)methyl)benzamide

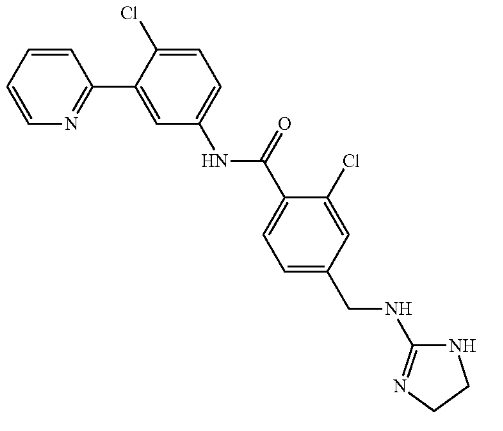 [SMILES: O=C(Nc1ccc(Cl)c(-c2ccccn2)c1)c1ccc(CNC2=NCCN2)cc1Cl]

100 mg of the crude HCl salt of 4-(aminomethyl)-2-chloro-N-(4-chloro-3-(pyridin-2-yl)phenyl)benzamide was reacted with 72 mg of 1-(4,5-dihydro-1H-imidazol-2-yl)-3,5-dimethyl-1H-pyrazole and 100 μL of DIPEA in 500 μL of DMF in the microwave at 150° C. for 5 minutes. The crude product was concentrated to dryness and purified by reverse phase HPLC to yield 2-chloro-N-(4-chloro-3-(pyridin-2-yl)phenyl)-4-((4,5-dihydro-1H-imidazol-2-ylamino)methyl)benzamide. MS (Q1) 440 (M)+.

Example 173

N-(4-chloro-3-(pyridin-2-yl)phenyl)-4-((4,5-dihydro-1H-imidazol-2-ylamino)methyl)benzamide

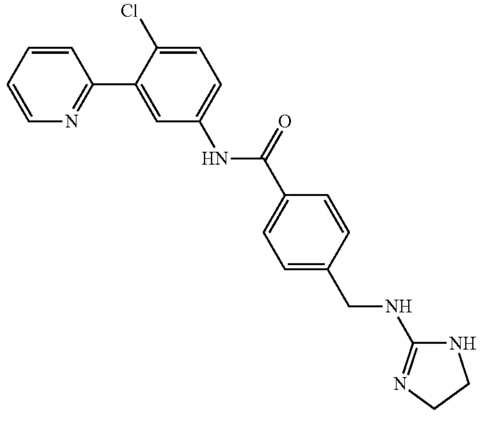 [SMILES: O=C(Nc1ccc(Cl)c(-c2ccccn2)c1)c1ccc(CNC2=NCCN2)cc1]

100 mg of the crude HCl salt of 4-(aminomethyl)-N-(4-chloro-3-(pyridin-2-yl)phenyl)benzamide was reacted with 80 mg of 1-(4,5-dihydro-1H-imidazol-2-yl)-3,5-dimethyl-1H-pyrazole and 110 μL of DIPEA in 1 mL of DMF in the microwave at 150° C. for 5 minutes. The crude product was concentrated to dryness and purified by reverse phase HPLC to yield N-(4-chloro-3-(pyridin-2-yl)phenyl)-4-((4,5-dihydro-1H-imidazol-2-ylamino)methyl)benzamide. MS (Q1) 406 (M)+.

Example 174

N-(4-chloro-3-(pyridin-2-yl)phenyl)-4-((pyridin-2-ylsulfonyl)methyl)benzamide

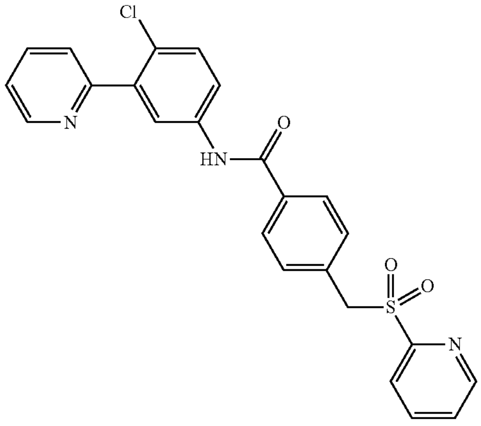 [SMILES: O=C(Nc1ccc(Cl)c(-c2ccccn2)c1)c1ccc(CS(=O)(=O)c2ccccn2)cc1]

500 mg of methyl 4-(bromomethyl)benzoate was reacted with pyridine-2-thiol via Procedure Q. 260 mg of methyl 4-((pyridin-2-ylthio)methyl)benzoate was reacted via Procedure R to give methyl 4-((pyridin-2-ylsulfonyl)methyl)benzoate. 275 mg of methyl 4-((pyridin-2-ylsulfonyl)methyl) benzoate was hydrolyzed via Procedure M to give 4-((pyridin-2-ylsulfonyl)methyl)benzoic acid. 75 mg of 4-chloro-3-(pyridin-2-yl)aniline was coupled to 4-((pyridin-2-ylsulfonyl)methyl)benzoic acid via Procedure G. The crude product was purified by reverse phase HPLC to yield pure N-(4-chloro-3-(pyridin-2-yl)phenyl)-4-((pyridin-2-ylsulfonyl)methyl)benzamide. MS (Q1) 464.1 (M)+.

Example 175

N-(4-chloro-3-(pyridin-2-yl)phenyl)-4-(N-methylmethylsulfonamido)benzamide

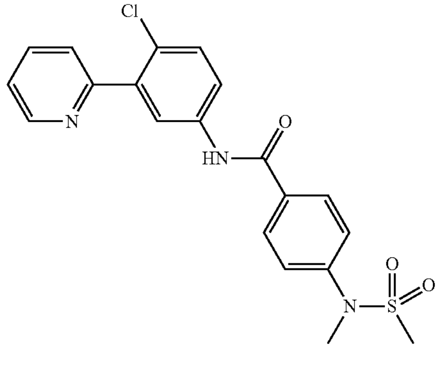 [SMILES: CN(c1ccc(C(=O)Nc2ccc(Cl)c(-c3ccccn3)c2)cc1)S(C)(=O)=O]

500 mg of methyl 4-(methylamino)benzoate was cooled to 0° C. in DCM with 270 μL of Pyridine before 260 μL Methanesulfonyl Chloride was added dropwise. Reaction was allowed to warm to room temperature and stir overnight. Solvent was concentrated and the crude material was dissolved in Ethyl Acetate and extracted with 0.1N NaOH solution twice. Crude material was dried over Magnesium Sulfate, filtered and concentrated to give methyl 4-(N-methylmethylsulfonamido)benzoate. 698 mg of methyl 4-(N-methylmethylsulfonamido)benzoate was hydrolyzed via Procedure M to give 4-(N-methylmethylsulfonamido) benzoic acid. 100 mg of 4-chloro-3-(pyridin-2-yl)aniline was coupled to 4-(N-methylmethylsulfonamido)benzoic acid via Procedure G. The crude product was purified by reverse phase HPLC to yield pure N-(4-chloro-3-(pyridin-2-yl)phenyl)-4-(N-methylmethylsulfonamido)benzamide. MS (Q1) 416.3 (M)+.

Example 176

2-bromo-N-(4-chloro-3-(pyridin-2-yl)phenyl)-4-(methylsulfonylmethyl)benzamide

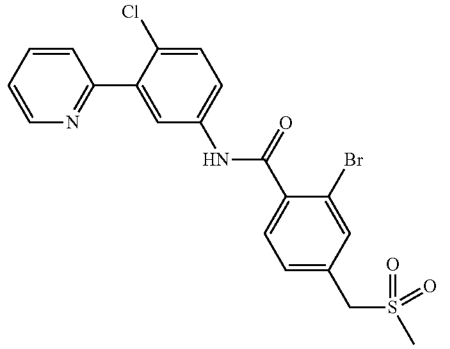 [SMILES: CS(=O)(=O)Cc1ccc(C(=O)Nc2ccc(Cl)c(-c3ccccn3)c2)c(Br)c1]

1.2 g of 2-bromo-4-methylbenzoic acid was brominated via Procedure N. 100 mg of 4-chloro-3-(pyridin-2-yl)aniline was coupled to 160 mg of 2-bromo-4-(bromomethyl)benzoic acid via Procedure E. 213 mg of 2-bromo-4-(bromomethyl)-N-(4-chloro-3-(pyridin-2-yl)phenyl)benzamide was reacted via Procedure O to give 2-bromo-N-(4-chloro-3-(pyridin-2-yl)phenyl)-4-(methylsulfonylmethyl)benzamide which was purified by reverse phase HPLC to afford pure 2-bromo-N-(4-chloro-3-(pyridin-2-yl)phenyl)-4-(methylsulfonylmethyl)benzamide. MS (Q1) 481.2 (M)+.

Example 177

4-((4H-1,2,4-triazol-3-ylsulfinyl)methyl)-N-(4-chloro-3-(pyridin-2-yl)phenyl)benzamide

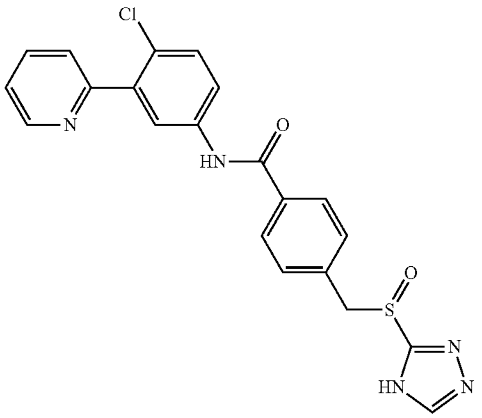 [SMILES: O=C(Nc1ccc(Cl)c(-c2ccccn2)c1)c1ccc(CS(=O)c2nnc[nH]2)cc1]

500 mg of methyl 4-(bromomethyl)benzoate was reacted with 4H-1,2,4-triazole-3-thiol via Procedure Q. 542 mg of methyl 4-((4H-1,2,4-triazol-3-ylthio)methyl)benzoate was subsequently reacted via Procedure R to give an approximate 1:9 mixture of methyl 4-((4H-1,2,4-triazol-3-ylsulfinyl)methyl)benzoate and methyl 4-((4H-1,2,4-triazol-3-ylsulfonyl)methyl)benzoate. The mixture of 467 mg was hydrolyzed via Procedure M to give 4-((4H-1,2,4-triazol-3-ylsulfinyl)methyl)benzoic acid and 4-((4H-1,2,4-triazol-3-ylsulfonyl)methyl)benzoic acid. 107 mg of the mixture of 4-((4H-1,2,4-triazol-3-ylsulfinyl)methyl)benzoic acid and 4-((4H-1,2,4-triazol-3-ylsulfonyl)methyl)benzoic acid was coupled to 75 mg of 4-chloro-3-(pyridin-2-yl)aniline via Procedure G. The mixture was separated on reverse phase HPLC to give 4-((4H-1,2,4-triazol-3-ylsulfinyl)methyl)-N-(4-chloro-3-(pyridin-2-yl)phenyl)benzamide. MS (Q1) 438.1 (M)+.

Example 178

4-((4H-1,2,4-triazol-3-ylsulfonyl)methyl)-N-(4-chloro-3-(pyridin-2-yl)phenyl)-benzamide

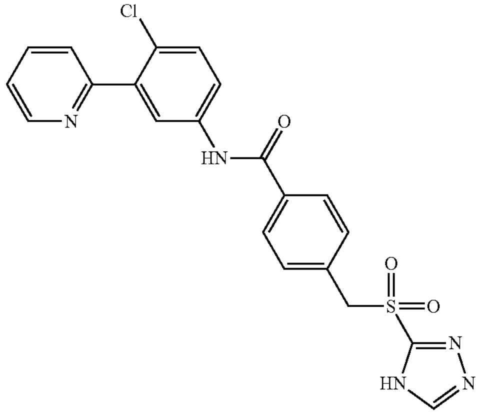 [SMILES: O=C(Nc1ccc(Cl)c(-c2ccccn2)c1)c1ccc(CS(=O)(=O)c2nnc[nH]2)cc1]

107 mg of a mixture of 4-((4H-1,2,4-triazol-3-ylsulfinyl)methyl)benzoic acid and 4-((4H-1,2,4-triazol-3-ylsulfonyl)methyl)benzoic acid was coupled to 75 mg of 4-chloro-3-(pyridin-2-yl)aniline via Procedure G. The mixture was separated on reverse phase HPLC to give 4-((4H-1,2,4-triazol-3-ylsulfonyl)methyl)-N-(4-chloro-3-(pyridin-2-yl)phenyl)benzamide. MS (Q1) 454.3 (M)+.

Example 179

N-(4-chloro-3-(pyridin-2-yl)phenyl)-4-((4-methyl-4H-1,2,4-triazol-3-ylsulfinyl)-methyl)benzamide

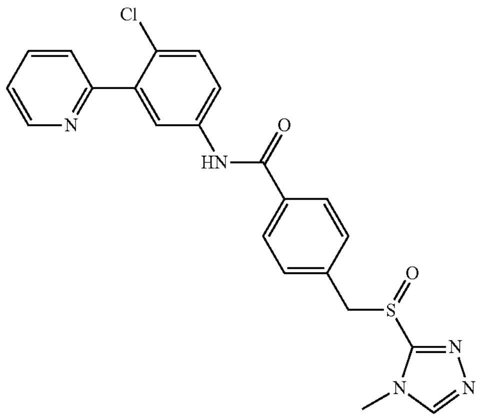 [SMILES: Cn1cnnc1S(=O)Cc1ccc(C(=O)Nc2ccc(Cl)c(-c3ccccn3)c2)cc1]

500 mg of methyl 4-(bromomethyl)benzoate was reacted with 4-methyl-4H-1,2,4-triazole-3-thiol via Procedure Q. 804 mg of methyl 4-((4-methyl-4H-1,2,4-triazol-3-ylthio)

methyl)benzoate was subsequently reacted via Procedure R to give an approximate 1:9 mixture of methyl 4-((4-methyl-4H-1,2,4-triazol-3-ylsulfinyl)methyl)benzoate and methyl 4-((4-methyl-4H-1,2,4-triazol-3-ylsulfonyl)methyl)benzoate. The mixture of 740 mg was hydrolyzed via Procedure M to give 4-((4-methyl-4H-1,2,4-triazol-3-ylsulfinyl)methyl)benzoic acid and 4-((4-methyl-4H-1,2,4-triazol-3-ylsulfonyl)methyl)benzoic acid. 114 mg of the mixture of 4-((4-methyl-4H-1,2,4-triazol-3-ylsulfinyl)methyl)benzoic acid and 4-((4-methyl-4H-1,2,4-triazol-3-ylsulfonyl)methyl)benzoic acid was coupled to 75 mg of 4-chloro-3-(pyridin-2-yl)aniline via Procedure G. The mixture was separated on reverse phase HPLC to give N-(4-chloro-3-(pyridin-2-yl)phenyl)-4-((4-methyl-4H-1,2,4-triazol-3-ylsulfinyl)methyl)benzamide. MS (Q1) 452.3 (M)$^+$.

Example 180

N-(4-chloro-3-(pyridin-2-yl)phenyl)-4-((4-methyl-4H-1,2,4-triazol-3-ylsulfonyl)-methyl)benzamide

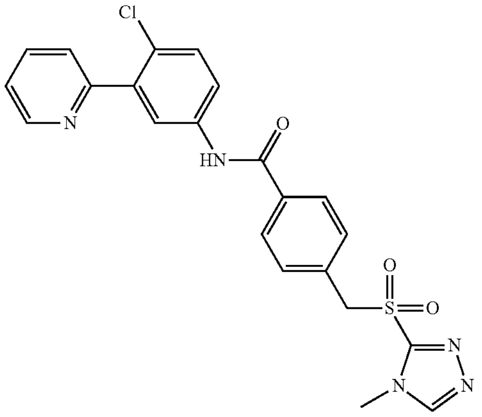 [SMILES: Cn1cnnc1S(=O)(=O)Cc1ccc(C(=O)Nc2ccc(Cl)c(-c3ccccn3)c2)cc1]

114 mg of the mixture of 4-((4-methyl-4H-1,2,4-triazol-3-ylsulfinyl)methyl)benzoic acid and 4-((4-methyl-4H-1,2,4-triazol-3-ylsulfonyl)methyl)benzoic acid was coupled to 75 mg of 4-chloro-3-(pyridin-2-yl)aniline via Procedure G. The mixture was separated on reverse phase HPLC to give N-(4-chloro-3-(pyridin-2-yl)phenyl)-4-((4-methyl-4H-1,2,4-triazol-3-ylsulfonyl)methyl)benzamide. MS (Q1) 468.1 (M)$^+$.

Example 181

N-(4-chloro-3-(pyridin-2-yl)phenyl)-3-(methylsulfonylmethyl)benzamide

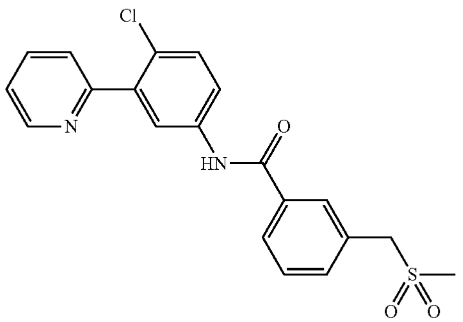 [SMILES: CS(=O)(=O)Cc1cccc(C(=O)Nc2ccc(Cl)c(-c3ccccn3)c2)c1]

300 mg of methyl 3-(bromomethyl)benzoate was reacted via Procedure O to give methyl 3-(methylsulfonylmethyl)benzoate. 230 mg of methyl 3-(methylsulfonylmethyl)benzoate was reacted via Procedure M to give 3-(methylsulfonylmethyl)benzoic acid. 75 mg of 4-chloro-3-(pyridin-2-yl)aniline was coupled to 3-(methylsulfonylmethyl)benzoic acid via Procedure G. The crude product was purified by reverse phase HPLC to yield pure N-(4-chloro-3-(pyridin-2-yl)phenyl)-3-(methylsulfonylmethyl)benzamide. MS (Q1) 401 (M)$^+$.

Example 182

N-(4-chloro-3-(pyridin-2-yl)phenyl)-2-methoxy-4-(methylsulfonylmethyl)benzamide

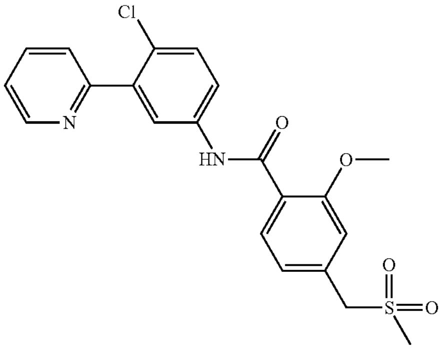 [SMILES: COc1cc(CS(C)(=O)=O)ccc1C(=O)Nc1ccc(Cl)c(-c2ccccn2)c1]

900 mg of 2-methoxy-4-methylbenzoic acid was brominated via Procedure N to afford 4-(bromomethyl)-2-methoxybenzoic acid. 100 mg of 4-chloro-3-(pyridin-2-yl)aniline was coupled to 132 mg of 4-(bromomethyl)-2-methoxybenzoic acid via Procedure E. 211 mg of 4-(bromomethyl)-N-(4-chloro-3-(pyridin-2-yl)phenyl)-2-methoxybenzamide was reacted via Procedure O and purified by reverse phase HPLC to yield pure N-(4-chloro-3-(pyridin-2-yl)phenyl)-2-methoxy-4-(methylsulfonylmethyl)benzamide. MS (Q1) 431 (M)$^+$.

Example 183

N-(4-chloro-3-(pyridin-2-yl)phenyl)-4-(1-(methylsulfonyl)ethyl)benzamide

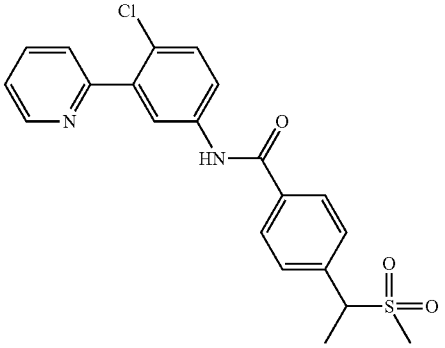 [SMILES: CC(c1ccc(C(=O)Nc2ccc(Cl)c(-c3ccccn3)c2)cc1)S(C)(=O)=O]

75 mg of 4-chloro-3-(pyridin-2-yl)aniline was coupled to 93 mg of 4-(1-bromoethyl)benzoic acid via Procedure E. 153 mg of 4-(1-bromoethyl)-N-(4-chloro-3-(pyridin-2-yl)phenyl)benzamide was reacted via Procedure O and purified by reverse phase HPLC to give pure N-(4-chloro-3-(pyridin-2-yl)phenyl)-4-(1-(methylsulfonyl)ethyl)benzamide. MS (Q1) 415.3 (M)$^+$.

Example 184 ethyl 4-(4-chloro-3-(pyridin-2-yl)phenylcarbamoyl)benzyl(methyl)phosphinate

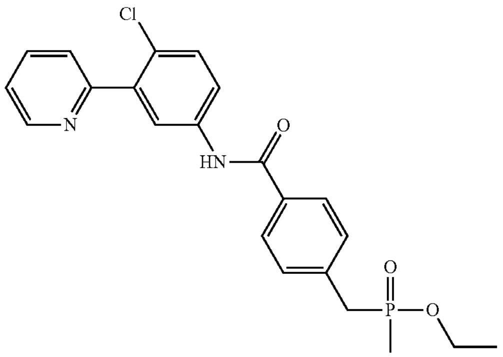 [SMILES: CCOP(C)(=O)Cc1ccc(C(=O)Nc2ccc(Cl)c(-c3ccccn3)c2)cc1]

90 mg of 4-(bromomethyl)-N-(4-chloro-3-(pyridin-2-yl)phenyl)benzamide was reacted with 45 μL of diethyl methylphosphonite in the microwave at 120° C. for 5 minutes. The reaction was evaporated to dryness and purified by reverse phase HPLC to give pure ethyl 4-(4-chloro-3-(pyridin-2-yl)phenylcarbamoyl)benzyl(methyl)phosphinate. MS (Q1) 429 (M)$^+$.

Example 185

N-(4-chloro-3-(5-(hydroxymethyl)pyridin-2-yl)phenyl)-4-(methylsulfonyl-methyl)benzamide

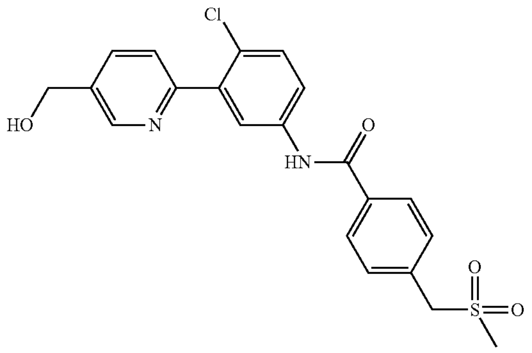 [SMILES: CS(=O)(=O)Cc1ccc(C(=O)Nc2ccc(Cl)c(-c3ccc(CO)cn3)c2)cc1]

75 mL of (5-methylpyridin-2-yl)zinc(II) bromide was reacted with 4 g of 1-chloro-2-iodo-4-nitrobenzene via Procedure B. To 935 mg of 2-(2-chloro-5-nitrophenyl)-5-methylpyridine in 5 mL of Sulfuric Acid was slowly added 2.25 g of Chromium (III) Oxide and the reaction was stirred for several hours at room temperature until complete. Icewater was added to dilute the reaction and the aqueous layer was extracted 3 times with Ethyl Acetate. The organic layers were combined, dried over Magnesium Sulfate, filtered and concentrated to give 6-(2-chloro-5-nitrophenyl)nicotinic acid. 704 mg of 6-(2-chloro-5-nitrophenyl)nicotinic acid was esterified with 3.1 mL of 4N HCl in Dioxane in 20 mL of MeOH. The reaction was concentrated and subjected to basic workup, dried over Magnesium Sulfate, filtered and concentrated to give methyl 6-(2-chloro-5-nitrophenyl)nicotinate. 681 mg of methyl 6-(2-chloro-5-nitrophenyl)nicotinate was treated with 2.1 g of Tin (II) Chloride and 1 mL of HCl in 25 mL of EtOH. Upon completion, EtOH was concentrated and the reaction was extracted with Ethyl Acetate and water with TEA to decrease emulsions. The organic layer was dried over Magnesium Sulfate, filtered and concentrated to give crude methyl 6-(5-amino-2-chlorophenyl)nicotinate. 296 mg of methyl 6-(5-amino-2-chlorophenyl)nicotinate was coupled to 266 mg of 4-(methylsulfonylmethyl)benzoic acid via Procedure G. To 518 mg of methyl 6-(2-chloro-5-(4-(methylsulfonylmethyl)benzamido)phenyl)nicotinate at 0° C. in 20 mL of EtOH was slowly added 640 mg of Sodium Borohydride. The reaction was subsquently refluxed for 1 hour until complete, quenched with water and extracted with Ethyl Acetate. The organic layer was dried over Magnesium Sulfate, filtered, concentrated and purified by reverse phase HPLC to give pure N-(4-chloro-3-(5-(hydroxymethyl)pyridin-2-yl)phenyl)-4-(methylsulfonylmethyl)benzamide. MS (Q1) 431.1 (M)$^+$.

Example 186

6-(2-chloro-5-(2-methyl-6-(trifluoromethyl)nicotinamido)phenyl)nicotinate

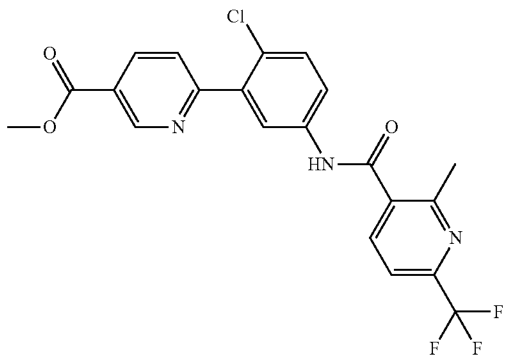 [SMILES: COC(=O)c1ccc(-c2cc(NC(=O)c3ccc(C(F)(F)F)nc3C)ccc2Cl)nc1]

200 mg of methyl 6-(5-amino-2-chlorophenyl)nicotinate was treated with 255 μL of 2-methyl-6-(trifluoromethyl)nicotinoyl chloride via Procedure D and purified by reverse phase HPLC to give pure 6-(2-chloro-5-(2-methyl-6-(trifluoromethyl)nicotinamido)phenyl)nicotinate. MS (Q1) 450 (M)$^+$.

Example 187

N-(4-chloro-3-(5-(hydroxymethyl)pyridin-2-yl)phenyl)-2-methyl-6-(trifluoromethyl)nicotinamide

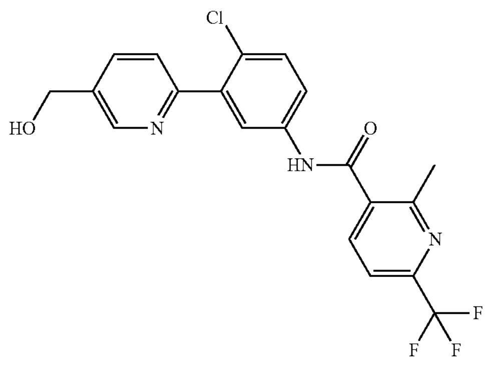 [SMILES: Cc1nc(C(F)(F)F)ccc1C(=O)Nc1ccc(Cl)c(-c2ccc(CO)cn2)c1]

To 110 mg of methyl 6-(2-chloro-5-(2-methyl-6-(trifluoromethyl)nicotinamido)phenyl)nicotinate at 0° C. in 5 mL of EtOH was slowly added 148 mg of Sodium Borohydride. The reaction was subsquently refluxed for 1 hour until complete, quenched with water and extracted with Ethyl Acetate. The organic layer was dried over Magnesium Sulfate, filtered, concentrated and purified by reverse phase HPLC to give pure N-(4-chloro-3-(5-(hydroxymethyl)pyridin-2-yl)phenyl)-2-methyl-6-(trifluoromethyl)nicotinamide. MS (Q1) 422.1 $(M)^+$.

Example 188

N-(4-chloro-3-(5-(methylcarbamoyl)pyridin-2-yl)phenyl)-2-methyl-6-(trifluoromethyl)nicotinamide

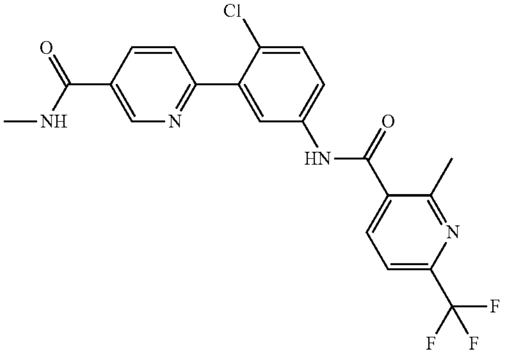 [SMILES: CNC(=O)c1ccc(-c2cc(NC(=O)c3ccc(C(F)(F)F)nc3C)ccc2Cl)nc1]

120 mg of 6-(2-chloro-5-(2-methyl-6-(trifluoromethyl)nicotinamido)phenyl)nicotinate was hydrolyzed via Procedure M. 112 mg of 6-(2-chloro-5-(2-methyl-6-(trifluoromethyl)nicotinamido)phenyl)nicotinic acid was coupled to Methylamine Hydrochloride via Procedure G and purified by reverse phase HPLC to give pure N-(4-chloro-3-(5-(methylcarbamoyl)pyridin-2-yl)phenyl)-2-methyl-6-(trifluoromethyl)nicotinamide. MS (Q1) 449 $(M)^+$.

Example 189

2-chloro-N-(4-chloro-3-(pyridin-2-yl)phenyl)-4-((2,2,2-trifluoroethylamino)methyl)benzamide

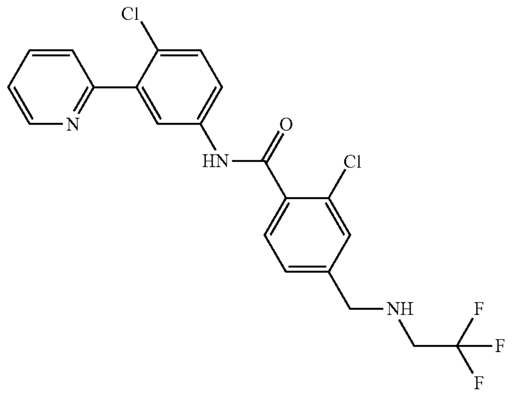 [SMILES: O=C(Nc1ccc(Cl)c(-c2ccccn2)c1)c1ccc(CNCC(F)(F)F)cc1Cl]

To 24.9 g of 2-chloro-4-(methoxycarbonyl)benzoic acid and 2 mL of Sulfuric Acid in 350 mL of DCM was added isobutylene gas at −78° C. until the solvent was saturated and capped off securely. Let go several days at room temperature and re-cool to −78° C. before removing cap. Concentrate solvent, extract with Ethyl Acetate and bicarbonate, dry with Magnesium Sulfate, filter and concentrate to give 31.4 g of 1-tert-butyl 4-methyl 2-chloroterephthalate. 3.35 g of 1-tert-butyl 4-methyl 2-chloroterephthalate was hydrolyzed via Procedure M. 2.5 g of 4-(tert-butoxycarbonyl)-3-chlorobenzoic acid was cooled to 0° C. in 25 mL of THF before a solution of 19.5 mL of 1M $BH_3$-THF complex in THF was added dropwise. The ice bath was subsequently removed and the reaction was stirred at room temperature until reaction stalled out at ~50% complete by TLC. The reaction is re-cooled to 0° C. and another 19.5 mL of $BH_3$-THF is added dropwise before the ice bath is removed. Upon completion, the reaction is re-cooled to 0° C. and quenched with 3N HCl dropwise. The aqueous layer was extracted two times with Ethyl Acetate and the organic layer was then extracted once with bicarbonate solution and brine, dried over Magnesium Sulfate, filtered and concentrated to give tert-butyl 2-chloro-4-(hydroxymethyl)benzoate. 564 mg of tert-butyl 2-chloro-4-(hydroxymethyl)benzoate was cooled to 0° C. in 5 mL of DCM before adding 665 mg of Triphenylphosphine and 417 mg of NBS. Reaction was concentrated and directly purified via ISCO Combi-Flash to give pure tert-butyl 2-chloro-4-(hydroxymethyl)benzoate. 147 mg of tert-butyl 4-(bromomethyl)-2-chlorobenzoate was reacted with 2,2,2-trifluoroethanamine in DMSO via Procedure P. 141 mg of tert-butyl 2-chloro-4-((2,2,2-trifluoroethylamino)methyl)benzoate was treated with 4N HCl in Dioxane at 45° C. and concentrated to give 2-chloro-4-((2,2,2-trifluoroethylamino)methyl)benzoic acid. 50 mg of 4-chloro-3-(pyridin-2-yl)aniline was coupled to 75 mg of 2-chloro-4-((2,2,2-trifluoroethylamino)methyl)benzoic acid via Procedure G. The crude product was purified by reverse phase HPLC to give pure 2-chloro-N-(4-chloro-3-(pyridin-2-yl)phenyl)-4-((2,2,2-trifluoroethylamino)methyl)benzamide. MS (Q1) 454.6 $(M)^+$.

Example 190

2-chloro-N-(4-chloro-3-(pyridin-2-yl)phenyl)-4-(methylsulfonylmethyl)benzamide

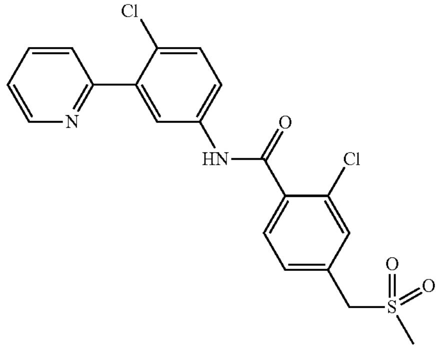 [SMILES: CS(=O)(=O)Cc1ccc(C(=O)Nc2ccc(Cl)c(-c3ccccn3)c2)c(Cl)c1]

3.01 g of tert-butyl 4-(bromomethyl)-2-chlorobenzoate was reacted via Procedure O to give tert-butyl 2-chloro-4-(methylsulfonylmethyl)benzoate. 1.2 g of tert-butyl 2-chloro-4-(methylsulfonylmethyl)benzoate was treated with 10 mL of 4N HCl in Dioxane at 45° C. and concentrated upon completion to give crude 2-chloro-4-(methylsulfonylmethyl)benzoic acid. 775 mg of 4-chloro-3-(pyridin-2-yl)aniline was coupled to 1 g of 2-chloro-4-(methylsulfonylmethyl)benzoic acid via Procedure G. The crude product was purified by reverse phase HPLC to give pure 2-chloro-N-(4-chloro-3-(pyridin-2-yl)phenyl)-4-(methylsulfonylmethyl) benzamide. MS (Q1) 435 $(M)^+$.

Example 191

N-(4-chloro-3-(pyridin-2-yl)phenyl)-6-(methylsulfonamido)nicotinamide

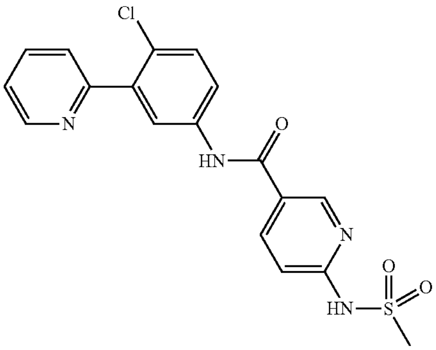 [SMILES: CS(=O)(=O)Nc1ccc(C(=O)Nc2ccc(Cl)c(-c3ccccn3)c2)cn1]

100 mg of 6-chloro-N-(4-chloro-3-(pyridin-2-yl)phenyl) nicotinamide was reacted with methanesulfonamide and 108 µL of 2-tert-Butylimino-2-diethylamino-1,3-dimethyl-perhydro-1,3,2-diazaphosphorine via Procedure F. The crude reaction was concentrated to dryness and purified by reverse phase HPLC to give pure N-(4-chloro-3-(pyridin-2-yl)phenyl)-6-(methylsulfonamido)nicotinamide. MS (Q1) 403 $(M)^+$.

Example 192

4-((1H-1,2,4-triazol-1-yl)methyl)-N-(4-chloro-3-(pyridin-2-yl)phenyl)benzamide

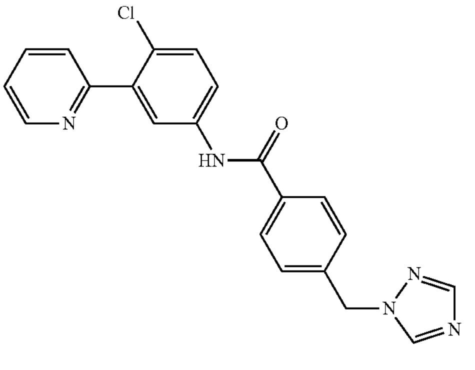 [SMILES: O=C(Nc1ccc(Cl)c(-c2ccccn2)c1)c1ccc(Cn2cncn2)cc1]

88 mg of 4-(bromomethyl)-N-(4-chloro-3-(pyridin-2-yl) phenyl)benzamide was coupled to 45 mg of 1H-1,2,4-triazole via Procedure P. The reaction was evaporated to dryness and purified by reverse phase HPLC to yield 4-((1H-1,2,4-triazol-1-yl)methyl)-N-(4-chloro-3-(pyridin-2-yl)phenyl)benzamide. MS (Q1) 390 $(M)^+$.

Example 193

4-((1H-1,2,3-triazol-1-yl)methyl)-N-(4-chloro-3-(pyridin-2-yl)phenyl)benzamide

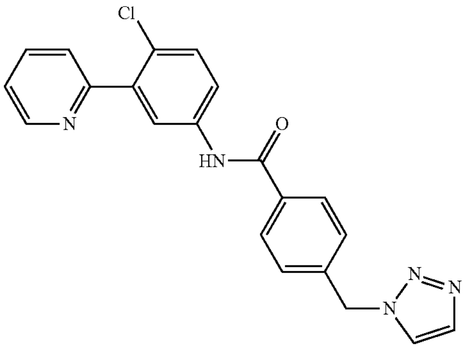 [SMILES: O=C(Nc1ccc(Cl)c(-c2ccccn2)c1)c1ccc(Cn2ccnn2)cc1]

88 mg of 4-(bromomethyl)-N-(4-chloro-3-(pyridin-2-yl) phenyl)benzamide was coupled to 40 µL of 1H-1,2,3-triazole via Procedure P. The reaction was evaporated to dryness and purified by reverse phase HPLC to yield 4-((1H-1,2,3-triazol-1-yl)methyl)-N-(4-chloro-3-(pyridin-2-yl)phenyl)benzamide. MS (Q1) 390.1 $(M)^+$.

Example 194

N-(4-chloro-3-(pyridin-2-yl)phenyl)-4-((3,5-dimethyl-1H-pyrazol-1-yl)methyl)benzamide

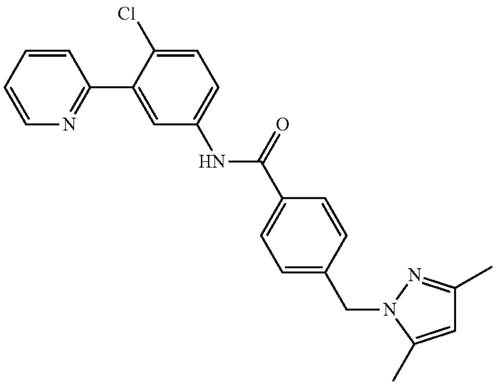 [SMILES: Cc1cc(C)n(Cc2ccc(C(=O)Nc3ccc(Cl)c(-c4ccccn4)c3)cc2)n1]

70 mg of 4-(bromomethyl)-N-(4-chloro-3-(pyridin-2-yl) phenyl)benzamide was coupled to 50 mg of 3,5-dimethyl-1H-pyrazole via Procedure P. The reaction was evaporated to dryness and purified by reverse phase HPLC to yield N-(4- chloro-3-(pyridin-2-yl)phenyl)-4-((3,5-dimethyl-1H-pyrazol-1-yl)methyl)benzamide. MS (Q1) 417.3 $(M)^+$.

Example 195

4-((1H-pyrazol-1-yl)methyl)-N-(4-chloro-3-(pyridin-2-yl)phenyl)benzamide

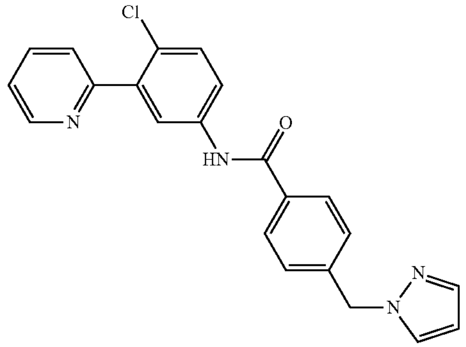 [SMILES: O=C(Nc1ccc(Cl)c(-c2ccccn2)c1)c1ccc(Cn2cccn2)cc1]

70 mg of 4-(bromomethyl)-N-(4-chloro-3-(pyridin-2-yl)phenyl)benzamide was coupled to 36 mg of 1H-pyrazole via Procedure P. The reaction was evaporated to dryness and purified by reverse phase HPLC to yield 4-((1H-pyrazol-1-yl)methyl)-N-(4-chloro-3-(pyridin-2-yl)phenyl)benzamide. MS (Q1) 389.3 $(M)^+$.

Example 196

N-(4-chloro-3-(pyridin-2-yl)phenyl)-6-(methylsulfonylmethyl)nicotinamide

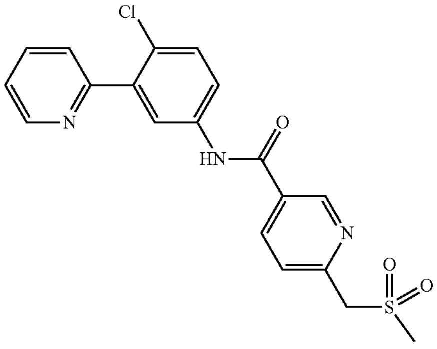 [SMILES: CS(=O)(=O)Cc1ccc(C(=O)Nc2ccc(Cl)c(-c3ccccn3)c2)cn1]

1.2 g of 6-methylnicotinic acid was brominated via Procedure N to give 6-(bromomethyl)nicotinic acid. 75 mg of 4-chloro-3-(pyridin-2-yl)aniline was coupled to 87 mg of 6-(bromomethyl)nicotinic acid via Procedure E. 145 mg of 6-(bromomethyl)-N-(4-chloro-3-(pyridin-2-yl)phenyl)nicotinamide was reacted via Procedure O and purified by reverse phase HPLC to yield pure N-(4-chloro-3-(pyridin-2-yl)phenyl)-6-(methylsulfonylmethyl)nicotinamide. MS (Q1) 402 $(M)^+$.

Example 197

N-(4-chloro-3-(pyridin-2-yl)phenyl)-4-(N-hydroxycarbamimidoyl)benzamide

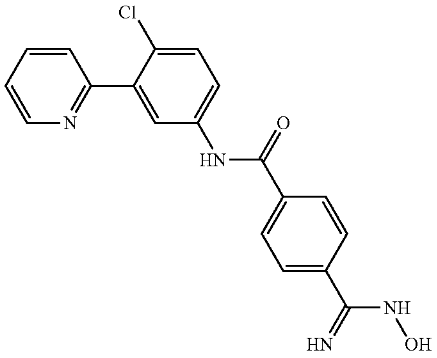 [SMILES: N=C(NO)c1ccc(C(=O)Nc2ccc(Cl)c(-c3ccccn3)c2)cc1]

240 mg of 4-chloro-3-(pyridin-2-yl)aniline was coupled to 207 mg of 4-cyanobenzoic acid via Procedure G. To 445 mg of N-(4-chloro-3-(pyridin-2-yl)phenyl)-4-cyanobenzamide and 2.5 mL of DIPEA in 10 mL of EtOH was added 793 mg Hydroxylamine Hydrochloride and heated to 60° C. until reaction was complete. The solvent was subsequently evaporated, extracted twice with water in Ethyl Acetate, dried with Magnesium Sulfate, filtered and concentrated. The crude product was purified by reverse phase HPLC to give pure N-(4-chloro-3-(pyridin-2-yl)phenyl)-4-(N-hydroxycarbamimidoyl)benzamide. MS (Q1) 367.4 $(M)^+$.

Example 198

N-(4-chloro-3-(pyridin-2-yl)phenyl)-4-(N-methoxycarbamimidoyl)benzamide

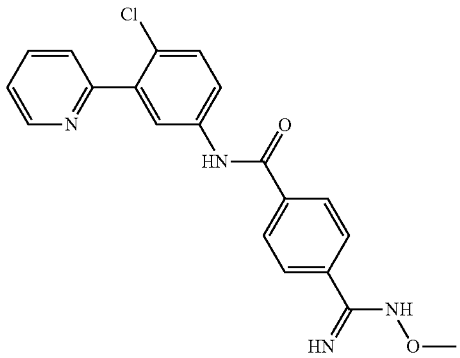 [SMILES: CONC(=N)c1ccc(C(=O)Nc2ccc(Cl)c(-c3ccccn3)c2)cc1]

100 mg of N-(4-chloro-3-(pyridin-2-yl)phenyl)-4-(N-hydroxycarbamimidoyl)benzamide was cooled to 0° C. in 1.5 mL of Dioxane. 5 mL of 2N NaOH was slowly added followed by dropwise addition of 33 μL of dimethylsulfate. The ice bath was removed and reaction was stirred at room temperature for 1 hour. The reaction was subsequently evaporated and extracted with water twice in Ethyl Acetate, dried with Magnesium Sulfate, filtered and concentrated to yield pure N-(4-chloro-3-(pyridin-2-yl)phenyl)-4-(N-methoxycarbamimidoyl)benzamide. MS (Q1) 381 $(M)^+$.

Example 199

N-(4-chloro-3-(4-(hydroxymethyl)pyridin-2-yl)phenyl)-2-methyl-6-(trifluoromethyl)nicotinamide

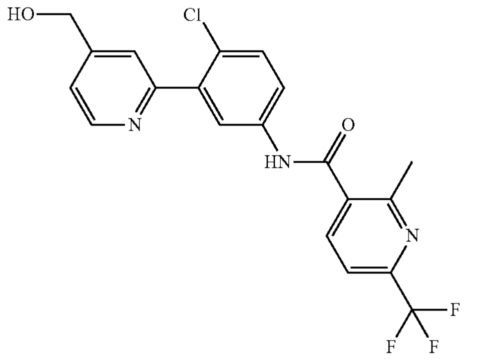 [SMILES: Cc1nc(C(F)(F)F)ccc1C(=O)Nc1ccc(Cl)c(-c2cc(CO)ccn2)c1]

75 mL of (4-methylpyridin-2-yl)zinc(II) bromide was reacted with 4 g of 1-chloro-2-iodo-4-nitrobenzene via Procedure B. To 300 mg of 2-(2-chloro-5-nitrophenyl)-4-methylpyridine in 1.5 mL of Sulfuric Acid was slowly added 362 mg of Chromium (III) Oxide and the reaction was stirred for several hours at room temperature until complete. Icewater was added to dilute the reaction and the aqueous layer was extracted 3 times with Ethyl Acetate. The organic layers were combined, dried over Magnesium Sulfate, filtered and concentrated to give 2-(2-chloro-5-nitrophenyl)isonicotinic acid. 300 mg of 2-(2-chloro-5-nitrophenyl)isonicotinic acid was esterified with 750 μL of 4N HCl in Dioxane in 10 mL of MeOH at 55° C. for 16 hours. The reaction was concentrated and subjected to basic workup, dried over Magnesium Sulfate, filtered and concentrated to give methyl 2-(2-chloro-5-nitrophenyl)isonicotinate. 259 mg of methyl 2-(2-chloro-5-nitrophenyl)isonicotinate was treated with 200 mg of Tin (II) Chloride and 500 μL of HCl in 10 mL of EtOH. Upon completion, EtOH was concentrated and the reaction was extracted with Ethyl Acetate and water with TEA to decrease emulsions. The organic layer was dried over Magnesium Sulfate, filtered and concentrated to give crude methyl 2-(5-amino-2-chlorophenyl)isonicotinate. 240 mg of methyl 2-(5-amino-2-chlorophenyl)isonicotinate was treated with 204 μL of 2-methyl-6-(trifluoromethyl)nicotinoyl chloride via Procedure D. To 100 mg of methyl 2-(2-chloro-5-(2-methyl-6-(trifluoromethyl)nicotinamido)phenyl)isonicotinate at 0° C. in 5 mL of EtOH was slowly added 135 mg of Sodium Borohydride. The reaction was subsequently refluxed for 1 hour until complete, quenched with water and extracted with Ethyl Acetate. The organic layer was dried over Magnesium Sulfate, filtered, concentrated and purified by reverse phase HPLC to give pure N-(4-chloro-3-(4-(hydroxymethyl)pyridin-2-yl)phenyl)-2-methyl-6-(trifluoromethyl)nicotinamide. MS (Q1) 422.1 $(M)^+$.

Example 200

N-(4-chloro-3-(pyridin-2-yl)phenyl)-4-(methylsulfonylamide)benzamide

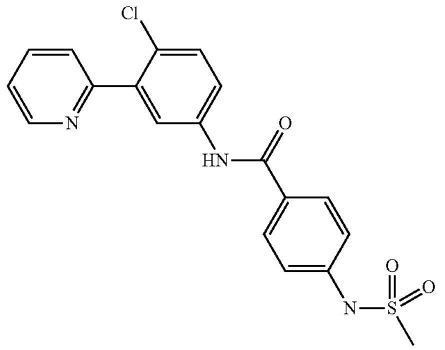 [SMILES: CS(=O)(=O)Nc1ccc(C(=O)Nc2ccc(Cl)c(-c3ccccn3)c2)cc1]

300 mg of 4-chloro-3-(pyridin-2-yl)aniline was coupled to 270 mg of 4-nitrobenzoic acid via Procedure G. To 520 mg of N-(4-chloro-3-(pyridin-2-yl)phenyl)-4-nitrobenzamide in 2.5 mL of HCl in 10 mL of EtOH was added 1.3 g of Tin (II) Chloride and stirred at 55° C. Upon completion, the reaction was concentratd and extracted with Ethyl Acetate in water with TEA to reduce emulsions. The organic layer was dried over Magnesium Sulfate, filtered and concentrated to give 4-amino-N-(4-chloro-3-(pyridin-2-yl)phenyl)benzamide. 100 mg of 4-amino-N-(4-chloro-3-(pyridin-2-yl)phenyl)benzamide was reacted with 30 μL of Methanesulfonyl Chloride and 90 μL DIPEA in 500 μL DCM. The reaction mixture was evaporated, subjected to basic workup conditions and purified by reverse phase HPLC to yield N-(4-chloro-3-(pyridin-2-yl)phenyl)-4-(methylsulfonylamide)benzamide. MS (Q1) 402 $(M)^+$.

Example 201

N-(4-chloro-3-(pyridin-2-yl)phenyl)-4-(1-methylethylsulfonamido)benzamide

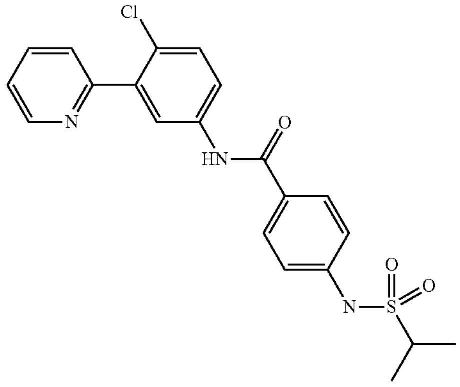 [SMILES: CC(C)S(=O)(=O)Nc1ccc(C(=O)Nc2ccc(Cl)c(-c3ccccn3)c2)cc1]

151 mg of 4-amino-N-(4-chloro-3-(pyridin-2-yl)phenyl) benzamide was reacted with 105 μL of propane-2-sulfonyl chloride and 205 μL DIPEA in 500 μL DCM. The reaction mixture was evaporated, subjected to basic workup conditions and purified by reverse phase HPLC to yield N-(4-chloro-3-(pyridin-2-yl)phenyl)-4-(1-methylethylsulfonamido)benzamide. MS (Q1) 430 $(M)^+$.

Example 202

N-(4-chloro-3-(pyridin-2-yl)phenyl)-4-(methylsulfonylmethyl)benzamide

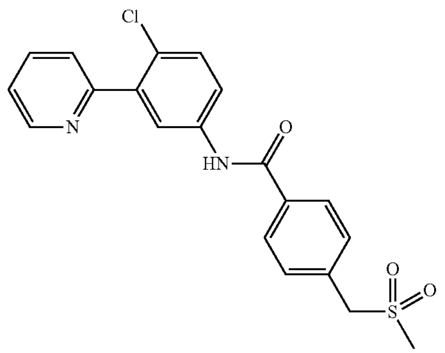 [SMILES: CS(=O)(=O)Cc1ccc(C(=O)Nc2ccc(Cl)c(-c3ccccn3)c2)cc1]

1 g of methyl 4-(bromomethyl)benzoate was reacted via Procedure O. 2.77 g of methyl 4-(methylsulfonylmethyl)benzoate was hydrolyzed via Procedure M. 1 g of 4-chloro-3-(pyridin-2-yl)aniline was coupled to 1.15 g of 4-(methylsulfonylmethyl)benzoic acid via Procedure G. The crude product was subjected to basic workup and recrystallized with 1:1 Ratio of Isopropylacetate and Ether to yield N-(4-chloro-3-(pyridin-2-yl)phenyl)-4-(methylsulfonylmethyl)benzamide. MS (Q1) 401 $(M)^+$.

Example 203

4-(4-acetylpiperazin-1-ylsulfonyl)-N-(4-chloro-3-(pyridin-2-yl)phenyl)benzamide

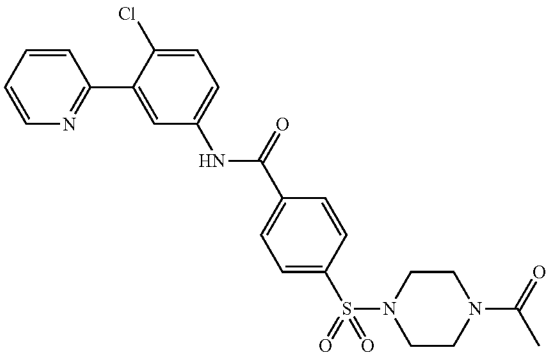 [SMILES: CC(=O)N1CCN(S(=O)(=O)c2ccc(C(=O)Nc3ccc(Cl)c(-c4ccccn4)c3)cc2)CC1]

1 g of 4-(chlorosulfonyl)benzoic acid was reacted with 646 μL of 1-(piperazin-1-yl)ethanone via Procedure H. 75 mg of 4-chloro-3-(pyridin-2-yl)aniline was coupled to 125 mg of 4-(4-acetylpiperazin-1-ylsulfonyl)benzoic acid via Procedure G and purified by reverse phase HPLC to yield 4-(4-acetylpiperazin-1-ylsulfonyl)-N-(4-chloro-3-(pyridin-2-yl)phenyl)benzamide. MS (Q1) 499.4 $(M)^+$.

Example 204

N-(4-chloro-3-(pyridin-2-yl)phenyl)-4-(4-(2-hydroxyethyl)piperazin-1-ylsulfonyl)benzamide

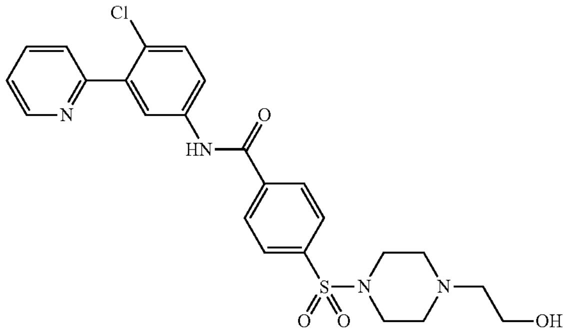 [SMILES: O=C(Nc1ccc(Cl)c(-c2ccccn2)c1)c1ccc(S(=O)(=O)N2CCN(CCO)CC2)cc1]

1 g of 4-(chlorosulfonyl)benzoic acid was reacted with 615 μL of 2-(piperazin-1-yl)ethanol via Procedure H. 75 mg of 4-chloro-3-(pyridin-2-yl)aniline was coupled to 125 mg of 4-(4-(3-hydroxypropyl)piperazin-1-ylsulfonyl)benzoic acid by Procedure G and purified by reverse phase HPLC to yield N-(4-chloro-3-(pyridin-2-yl)phenyl)-4-(4-(2-hydroxyethyl)piperazin-1-ylsulfonyl)benzamide. MS (Q1) 501.3 $(M)^+$.

Example 205

N-(4-chloro-3-(pyridin-2-yl)phenyl)-4-(4-hydroxypiperidin-1-ylsulfonyl)benzamide

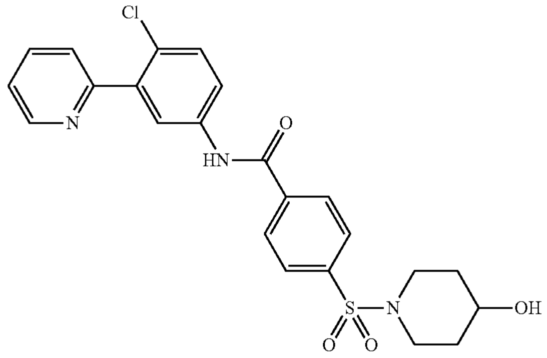 [SMILES: O=C(Nc1ccc(Cl)c(-c2ccccn2)c1)c1ccc(S(=O)(=O)N2CCC(O)CC2)cc1]

1 g of 4-(chlorosulfonyl)benzoic acid was reacted with 506 μL of piperidin-4-ol via Procedure H. 75 mg of 4-chloro-3-(pyridin-2-yl)aniline was coupled to 114 mg of 4-(4-hydroxypiperidin-1-ylsulfonyl)benzoic acid via Procedure G and purified by reverse phase HPLC to yield N-(4-chloro-3-(pyridin-2-yl)phenyl)-4-(4-hydroxypiperidin-1-ylsulfonyl)benzamide. MS (Q1) 472.3 $(M)^+$.

Example 206

N-(4-chloro-3-(pyridin-2-yl)phenyl)-4-(2,6-dimethylmorpholinosulfonyl)benzamide

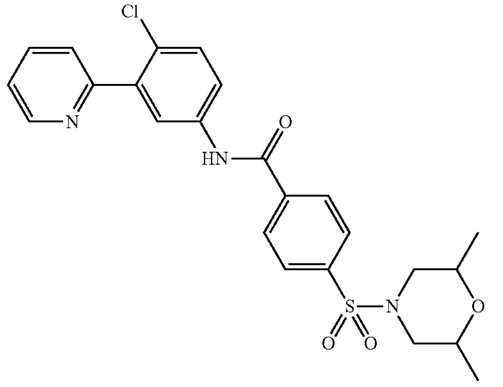 [SMILES: CC1CN(S(=O)(=O)c2ccc(C(=O)Nc3ccc(Cl)c(-c4ccccn4)c3)cc2)CC(C)O1]

1 g of 4-(chlorosulfonyl)benzoic acid was reacted with 616 μL of 2,6-dimethylmorpholine via Procedure H. 75 mg of 4-chloro-3-(pyridin-2-yl)aniline was coupled to 120 mg of 4-(2,6-dimethylmorpholinosulfonyl)benzoic acid via Procedure G and purified by reverse phase HPLC to yield N-(4-chloro-3-(pyridin-2-yl)phenyl)-4-(2,6-dimethylmorpholinosulfonyl)benzamide. MS (Q1) 486.3 $(M)^+$.

Example 207

N-(4-chloro-3-(pyridin-2-yl)phenyl)-4-(3,5-dimethylpiperazin-1-ylsulfonyl)benzamide

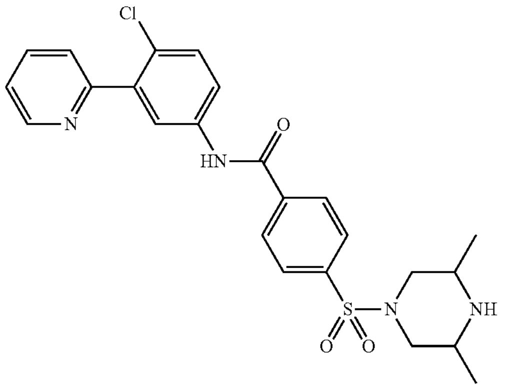 [SMILES: CC1CN(S(=O)(=O)c2ccc(C(=O)Nc3ccc(Cl)c(-c4ccccn4)c3)cc2)CC(C)N1]

1 g of 4-(chlorosulfonyl)benzoic acid was reacted with 570 mg of 2,6-dimethylpiperazine via Procedure H. 75 mg of 4-chloro-3-(pyridin-2-yl)aniline was coupled to 119 mg of 4-(3,5-dimethylpiperazin-1-ylsulfonyl)benzoic acid via Procedure G and purified by reverse phase HPLC to yield N-(4-chloro-3-(pyridin-2-yl)phenyl)-4-(3,5-dimethylpiperazin-1-ylsulfonyl)benzamide. MS (Q1) 485.4 $(M)^+$.

Example 208

N-(4-chloro-3-(pyridin-2-yl)phenyl)-4-(4-ethylpiperazin-1-ylsulfonyl)benzamide

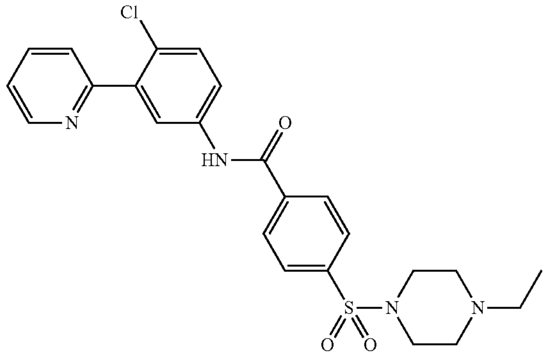 [SMILES: CCN1CCN(S(=O)(=O)c2ccc(C(=O)Nc3ccc(Cl)c(-c4ccccn4)c3)cc2)CC1]

1 g of 4-(chlorosulfonyl)benzoic acid was reacted with 570 mg of 1-ethylpiperazine via Procedure H. 75 mg of 4-chloro-3-(pyridin-2-yl)aniline was coupled to 4-(4-ethylpiperazin-1-ylsulfonyl)benzoic acid via Procedure G and purified by reverse phase HPLC to yield N-(4-chloro-3-(pyridin-2-yl)phenyl)-4-(4-ethylpiperazin-1-ylsulfonyl). MS (Q1) 485 $(M)^+$.

Example 209

N-(4-chloro-3-(pyridin-2-yl)phenyl)-4-(piperazin-1-ylsulfonyl)benzamide

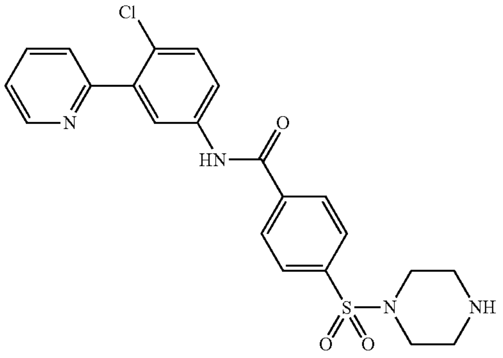 [SMILES: O=C(Nc1ccc(Cl)c(-c2ccccn2)c1)c1ccc(S(=O)(=O)N2CCNCC2)cc1]

1 g of 4-(chlorosulfonyl)benzoic acid was reacted with 931 mg of tert-butyl piperazine-1-carboxylate via Procedure H. 75 mg of 4-chloro-3-(pyridin-2-yl)aniline was coupled to 150 mg of 4-(4-(tert-butoxycarbonyl)piperazin-1-ylsulfonyl) benzoic acid via Procedure G. The crude product was subjected to basic workup conditions, treated with TFA to remove the Boc group and purified by reverse phase HPLC to yield N-(4-chloro-3-(pyridin-2-yl)phenyl)-4-(piperazin-1-ylsulfonyl)benzamide. MS (Q1) 457.1 $(M)^+$.

Example 210

N-(4-chloro-3-(pyridin-2-yl)phenyl)-4-(N-(2,2,2-trifluoroethyl)sulfamoyl)benzamide

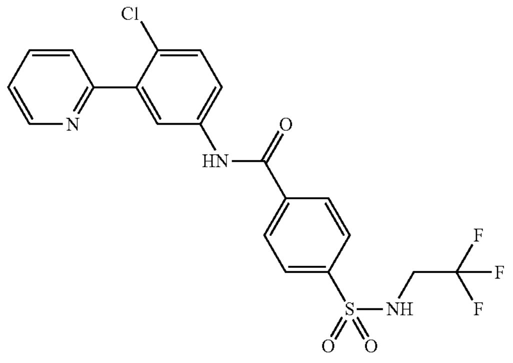 [SMILES: O=C(Nc1ccc(Cl)c(-c2ccccn2)c1)c1ccc(S(=O)(=O)NCC(F)(F)F)cc1]

1 g of 4-(chlorosulfonyl)benzoic acid was reacted with 500 μL of 2,2,2-trifluoroethanamine via Procedure H. 60 mg of 4-chloro-3-(pyridin-2-yl)aniline was coupled to 92 mg of 4-(N-(2,2,2-trifluoroethyl)sulfamoyl)benzoic acid by Procedure G and purified by reverse phase HPLC to yield N-(4-chloro-3-(pyridin-2-yl)phenyl)-4-(N-(2,2,2-trifluoroethyl)sulfamoyl)benzamide. MS (Q1) 470 $(M)^+$.

Example 211

2-chloro-N-(4-chloro-3-(pyridin-2-yl)phenyl)-4-sulfamoylbenzamide

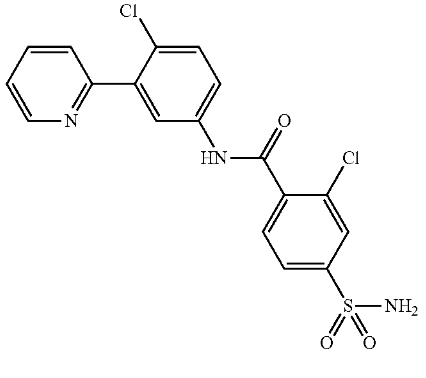 [SMILES: NS(=O)(=O)c1ccc(C(=O)Nc2ccc(Cl)c(-c3ccccn3)c2)c(Cl)c1]

A solution of 818 mg of Sodium Nitrite in 13 mL of water was added dropwise to a solution of 2 g of methyl 4-amino-2-chlorobenzoate in 5 mL of HCl and 15 mL of AcOH at 0° C. The reaction was removed from the ice bath and stirred at room temperature for 15 minutes. Simultaneously a solution of 460 mg of Copper II Chloride Dihydrate in 1 mL of water was added to a saturated solution of sulfur dioxide gas in 10 mL of AcOH at 0° C. The cooled solution containing Copper II Chloride and sulfur dioxide gas was slowly added to the re-cooled initial solution containing Sodium Nitrite. The reaction was warmed to room temperature and stirred until gas no longer evolved. The reaction was filtered through celite and poured into a beaker of stirred icewater until a yellow-orange solid crashed out. The icewater solution was filtered thru a Buchner funnel to collect the methyl 2-chloro-4-(chlorosulfonyl)benzoate precipitate and was dried for 24 hours under vacuum. 1 g of methyl 2-chloro-4-(chlorosulfonyl) benzoate was added to a solution of 2 mL of 2M solution of Ammonia in MeOH and 970 μL DIPEA in 5 mL MeOH. Upon completion the reaction was concentrated, extracted twice with saturated bicarbonate, dried with Magnesium Sulfate, filtered and concentrated to give methyl 2-chloro-4-sulfamoylbenzoate. 777 mg of methyl 2-chloro-4-sulfamoylbenzoate was hydrolyzed via Procedure M to yield crude 2-chloro-4-sulfamoylbenzoic acid. 75 mg of 4-chloro-3-(pyridin-2-yl)aniline was coupled to 91 mg of crude 2-chloro-4-sulfamoylbenzoic acid via Procedure G. The crude product was purified by reverse phase HPLC to yield 2-chloro-N-(4-chloro-3-(pyridin-2-yl)phenyl)-4-sulfamoylbenzamide. MS (Q1) 422 $(M)^+$.

Example 212

N-(4-chloro-3-(pyridin-2-yl)phenyl)-4-(piperidin-4-ylmethyl)benzamide

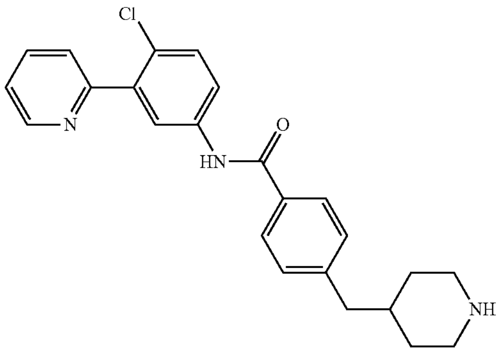 [SMILES: O=C(Nc1ccc(Cl)c(-c2ccccn2)c1)c1ccc(CC2CCNCC2)cc1]

75 mg of 4-chloro-3-(pyridin-2-yl)aniline was coupled to 125 mg of 4-((1-(tert-butoxycarbonyl)piperidin-4-yl)methyl) benzoic acid via Procedure G. The crude product was treated with 4N HCl in Dioxane, evaporated and purified by reverse phase HPLC to yield N-(4-chloro-3-(pyridin-2-yl)phenyl)-4-(piperidin-4-ylmethyl)benzamide. MS (Q1) 406.1 $(M)^+$.

Example 213

2-chloro-N-(4-chloro-3-(pyridin-2-yl)phenyl)-4-(methylsulfonamido)benzamide

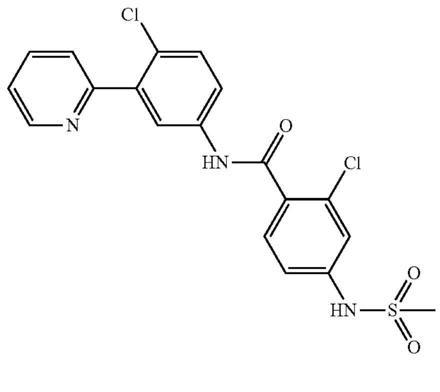 [SMILES: CS(=O)(=O)Nc1ccc(C(=O)Nc2ccc(Cl)c(-c3ccccn3)c2)c(Cl)c1]

4.2 g of methyl 2-chloro-4-(methylsulfonamido)benzoate was hydrolyzed via Procedure M. 1 g of 4-chloro-3-(pyridin-2-yl)aniline was coupled to 1.35 g of 2-chloro-4-(methylsulfonamido)benzoic acid via Procedure G. The crude product was purified by reverse phase HPLC to yield 2-chloro-N-(4-chloro-3-(pyridin-2-yl)phenyl)-4-(methylsulfonamido)benzamide. MS (Q1) 436.1 $(M)^+$.

Example 214

N-(4-chloro-3-(pyridin-2-yl)phenyl)-4-(1H-imidazol-1-yl)benzamide

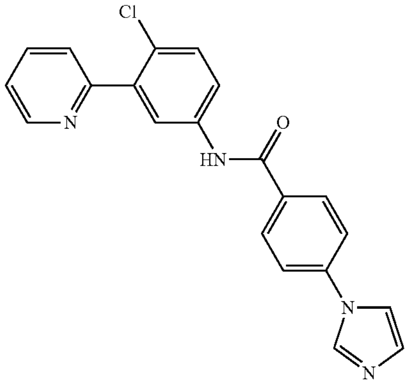 [SMILES: O=C(Nc1ccc(Cl)c(-c2ccccn2)c1)c1ccc(-n2ccnc2)cc1]

75 mg of 4-chloro-3-(pyridin-2-yl)aniline was coupled to 78 mg of 4-(1H-imidazol-1-yl)benzoic acid via Procedure G. The crude product was purified by reverse phase HPLC to yield N-(4-chloro-3-(pyridin-2-yl)phenyl)-4-(1H-imidazol-1-yl)benzamide. MS (Q1) 375.3 $(M)^+$.

Example 215

2-chloro-N-(4-chloro-3-(pyridin-2-yl)phenyl)-4-(2-hydroxy-2-methylpropylsulfonyl)-benzamide

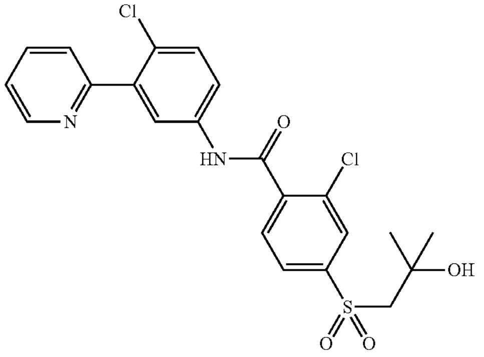 [SMILES: CC(C)(O)CS(=O)(=O)c1ccc(C(=O)Nc2ccc(Cl)c(-c3ccccn3)c2)c(Cl)c1]

8 g of methyl 4-amino-2-chlorobenzoate was dissolved in 16 mL of MeOH, 8 mL of $H_2O$ and 8 mL of concentrated hydrochloric acid and was then cooled to 0 C. A solution of 3.9 g of sodium nitrite in 15 mL of $H_2O$ was added dropwise over 30 min. The reaction was stirred at 0° C. for an additional 1 h. The cold diazonating mixture was added to a solution of 13.8 g of potassium ethyl xanthate in 10 mL of $H_2O$ at 50~60° C. The reaction was heated to 65° C. for 2 h and monitored by TLC until complete. The mixture was cooled to 25° C. and extracted with ethyl acetate. The combined organic extracts were washed with brine, dried ($MgSO_4$), and concentrated. Purified by silica gel chromatography (0-10% ethyl acetate/hexane) to afford methyl 2-chloro-4-(ethoxycarbonothioylthio)benzoate. A solution of 2.6 g of sodium hydroxide in 20 mL of $H_2O$ was added to 5.9 g of methyl 2-chloro-4-(ethoxycarbonothioylthio)benzoate in 40 mL of EtOH The reaction mixture was heated to 70° C. for 1 h. Upon completion, the mixture was cooled to 25° C., and then acidified to pH 3 by the addition of 10 N HCl. The solid was filtered and washed with $H_2O$ to give 2-chloro-4-mercaptobenzonic acid. 3.8 g of 2-chloro-4-mercaptobenzonic acid in 40 mL of 5% sulfuric acid-methanol was refluxed under nitrogen atmosphere for 3 h. After concentration of the reaction mixture, 10 mL of $H_2O$ was added and the resulting mixture was made alkaline with sodium hydrogen carbonate, and extracted with ethyl acetate. The organic layer was washed with brine, dried ($MgSO_4$), and evaporated to yield methyl 2-chloro-4-mercaptobenzoate. 80 mg of isobutylene oxide was reacted with methyl 2-chloro-4-mercaptobenzoate via Procedure S to afford methyl 2-chloro-4-(2-hydroxy-2-methylpropylthio)benzoate. 190 mg of methyl 2-chloro-4-(2-hydroxy-2-methylpropylthio)benzoate was hydrolyzed via Procedure M to give 2-chloro-4-(2-hydroxy-2-methylpropylthio)benzoic acid. 160 mg of 2-chloro-4-(2-hydroxy-2-methylpropylthio)benzoic acid was reacted via procedure R to give 2-chloro-4-(2-hydroxy-2-methylpropylsulfonyl)benzoic acid. 60 mg of 4-chloro-3-(pyridine-2-yl)aniline was coupled to 2-chloro-4-(2-hydroxy-2-methylpropylsulfonyl)benzoic acid via Procedure G. The product was purified on reverse phase HPLC to yield 2-chloro-N-(4-chloro-3-(pyridin-2-yl)phenyl)-4-(2-hydroxy-2-methylpropylsulfonyl)benzamide. MS (Q1) 479.1 $(M)^+$.

Example 216

(R)-2-chloro-N-(4-chloro-3-(pyridin-2-yl)phenyl)-4-(2-hydroxy-2-phenylethylsulfonyl)benzamide

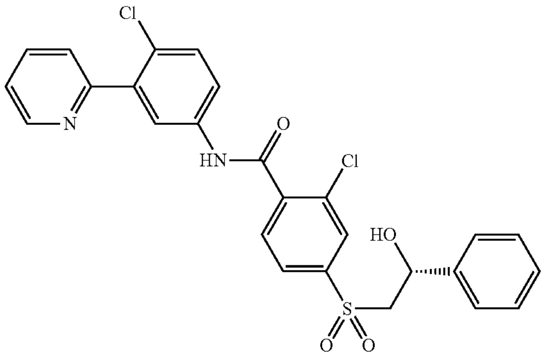 [SMILES: O=C(Nc1ccc(Cl)c(-c2ccccn2)c1)c1ccc(S(=O)(=O)C[C@H](O)c2ccccc2)cc1Cl]

150 mg of (R)-styrene oxide was reacted with methyl 2-chloro-4-mercaptobenzoate via Procedure S to afford (R)-methyl 2-chloro-4-(2-hydroxy-2-phenylethylthio)benzoate. 190 mg of (R)-methyl-2-chloro-4-(2-hydroxy-2-phenylethylthio)benzoate was hydrolyzed via Procedure M to give (R)-2-chloro-4-(2-hydroxy-2-phenylethylthio)benzoic acid. 170 mg of (R)-2-chloro-4-(2-hydroxy-2-phenylethylthio)benzoic acid was reacted via Procedure R to give (R)-2-chloro-4-(2-hydroxy-2-phenylethylsulfonyl)benzoic acid. 60 mg of 4-chloro-3-(pyridine-2-yl)aniline was coupled to (R)-2-chloro-4-(2-hydroxy-2-phenylethylsulfonyl)benzoic acid via Procedure G. The product was purified on reverse phase HPLC to yield (R)-2-chloro-N-(4-chloro-3-(pyridin-2-yl)phenyl)-4-(2-hydroxy-2-phenylethylsulfonyl)benzamide. MS (Q1) 527.2 $(M)^+$.

Example 217

(S)-2-chloro-N-(4-chloro-3-(pyridin-2-yl)phenyl)-4-(2-hydroxy-2-phenylethyl-sulfonyl)benzamide

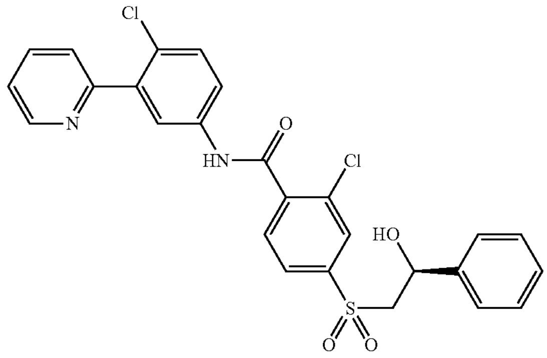 [SMILES: O=C(Nc1ccc(Cl)c(-c2ccccn2)c1)c1ccc(S(=O)(=O)C[C@@H](O)c2ccccc2)cc1Cl]

119 mg of (S)-styrene oxide was reacted with methyl 2-chloro-4-mercaptobenzoate via Procedure S to afford (S)-methyl 2-chloro-4-(2-hydroxy-2-phenylethylthio)benzoate. 230 mg of (S)-methyl-2-chloro-4-(2-hydroxy-2-phenylethylthio)benzoate was hydrolyzed via Procedure M to give (S)-2-chloro-4-(2-hydroxy-2-phenylethylthio)benzoic acid. 180 mg of (S)-2-chloro-4-(2-hydroxy-2-phenylethylthio) benzoic acid was reacted via Procedure R to give (S)-2-chloro-4-(2-hydroxy-2-phenylethylsulfonyl)benzoic acid. 60 mg of 4-chloro-3-(pyridine-2-yl)aniline was coupled to (S)-2-chloro-4-(2-hydroxy-2-phenylethylsulfonyl)benzoic acid via Procedure G. The product was purified on reverse phase HPLC to yield (S)-2-chloro-N-(4-chloro-3-(pyridin-2-yl)phenyl)-4-(2-hydroxy-2-phenylethylsulfonyl)benzamide. MS (Q1) 527.0 $(M)^+$.

Example 218

(R)-2-chloro-N-(4-chloro-3-(pyridin-2-yl)phenyl)-4-(2-hydroxypropylsulfonyl)-benzamide

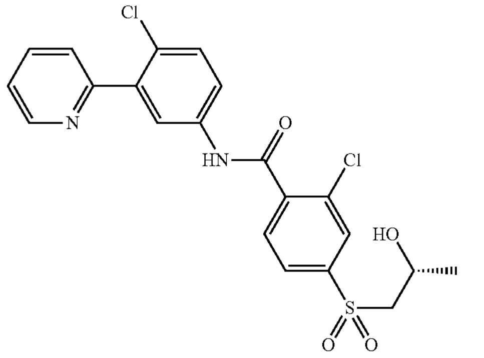 [SMILES: C[C@@H](O)CS(=O)(=O)c1ccc(C(=O)Nc2ccc(Cl)c(-c3ccccn3)c2)c(Cl)c1]

140 mg of (R)-propylene oxide was reacted with methyl 2-chloro-4-mercaptobenzoate via Procedure S to afford (R)-methyl 2-chloro-4-(2-hydroxypropylthio)benzoate. 435 mg of (R)-methyl-2-chloro-4-(2-hydroxypropylthio)benzoate was hydrolyzed via Procedure M to give (R)-2-chloro-4-(2-hydroxypropylthio)benzoic acid. 403 mg of (R)-2-chloro-4-(2-hydroxypropylthio)benzoic acid was reacted via Procedure R to give (R)-2-chloro-4-(2-hydroxypropylsulfonyl) benzoic acid. 298 mg of 4-chloro-3-(pyridine-2-yl)aniline was coupled to (R)-2-chloro-4-(2-hydroxypropylsulfonyl) benzoic acid via Procedure G. The product was purified on reverse phase HPLC to yield (R)-2-chloro-N-(4-chloro-3-(pyridin-2-yl)phenyl)-4-(2-hydroxypropylsulfonyl)benzamide. MS (Q1) 465.1 $(M)^+$.

Example 219

(S)-2-chloro-N-(4-chloro-3-(pyridin-2-yl)phenyl)-4-(2-hydroxypropylsulfonyl)-benzamide

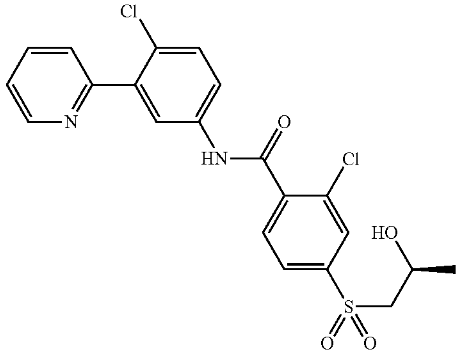 [SMILES: C[C@H](O)CS(=O)(=O)c1ccc(C(=O)Nc2ccc(Cl)c(-c3ccccn3)c2)c(Cl)c1]

86 mg of (S)-propylene oxide was reacted with methyl 2-chloro-4-mercaptobenzoate via Procedure S to afford (S)-methyl 2-chloro-4-(2-hydroxypropylthio)benzoate. 275 mg of (S)-methyl-2-chloro-4-(2-hydroxypropylthio)benzoate was hydrolyzed via Procedure M to give (S)-2-chloro-4-(2-hydroxypropylthio)benzoic acid. 220 mg of (S)-2-chloro-4-(2-hydroxypropylthio)benzoic acid was reacted via Procedure R to give (S)-2-chloro-4-(2-hydroxypropylsulfonyl) benzoic acid. 70 mg of 4-chloro-3-(pyridine-2-yl)aniline was coupled to (S)-2-chloro-4-(2-hydroxypropylsulfonyl)benzoic acid via Procedure G. The product was purified on reverse phase HPLC to yield (S)-2-chloro-N-(4-chloro-3-(pyridin-2-yl)phenyl)-4-(2-hydroxypropylsulfonyl)benzamide. MS (Q1) 465.0 $(M)^+$ Example 220

(R)—N-(4-chloro-3-(pyridin-2-yl)phenyl)-4-(2-hydroxypropylsulfonyl)benzamide

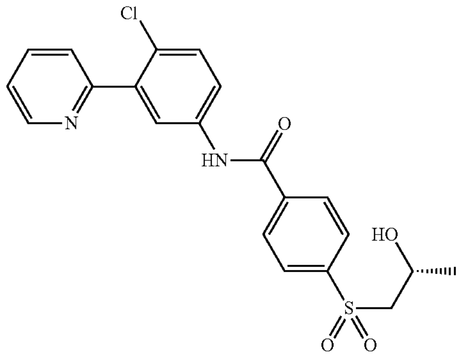 [SMILES: C[C@@H](O)CS(=O)(=O)c1ccc(C(=O)Nc2ccc(Cl)c(-c3ccccn3)c2)cc1]

100 mg of (R)-propylene oxide was reacted with methyl 4-mercaptobenzoate via Procedure S to afford (R)-methyl 4-(2-hydroxypropylthio)benzoate. 169 mg of (R)-methyl 4-(2-hydroxypropylthio)benzoate was reacted via Procedure R to give (R)-methyl 4-(2-hydroxypropylsulfonyl)benzoate. 179 mg of (R)-methyl 4-(2-hydroxypropylsulfonyl)benzoate was hydrolyzed via Procedure M to give (R)-4-(2-hydroxypropylsulfonyl)benzoic acid. 45 mg of 4-chloro-3-(pyridine-2-yl)aniline was coupled to (R)-4-(2-hydroxypropylsulfonyl)benzoic acid via Procedure G. The product was purified on reverse phase HPLC to yield (R)—N-(4-chloro-3-(pyridin-2-yl)phenyl)-4-(2-hydroxypropylsulfonyl)benzamide. MS (Q1) 431.2 $(M)^+$.

Example 221

(S)—N-(4-chloro-3-(pyridin-2-yl)phenyl)-4-(2-hydroxypropylsulfonyl)benzamide

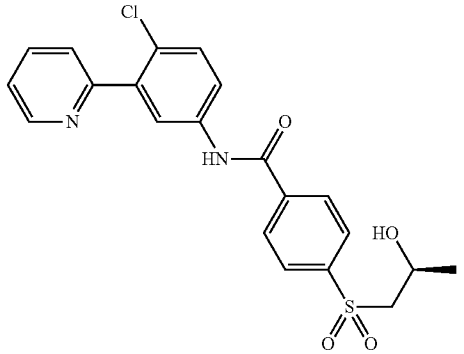 [SMILES: C[C@H](O)CS(=O)(=O)c1ccc(C(=O)Nc2ccc(Cl)c(-c3ccccn3)c2)cc1]

150 mg of (S)-propylene oxide was reacted with methyl 4-mercaptobenzoate via Procedure S to afford (S)-methyl 4-(2-hydroxypropylthio)benzoate. 650 mg of (S)-methyl 4-(2-hydroxypropylthio)benzoate was reacted via Procedure R to give (S)-methyl 4-(2-hydroxypropylsulfonyl)benzoate. 350 mg of (S)-methyl 4-(2-hydroxypropylsulfonyl)benzoate was hydrolyzed via Procedure M to give (S)-4-(2-hydroxypropylsulfonyl)benzoic acid. 45 mg of 4-chloro-3-(pyridine-2-yl)aniline was coupled to (S)-4-(2-hydroxypropylsulfonyl)benzoic acid via Procedure G. The product was purified on reverse phase HPLC to yield (S)—N-(4-chloro-3-(pyridin-2-yl)phenyl)-4-(2-hydroxypropylsulfonyl)benzamide. MS (Q1) 431.3 $(M)^+$.

Example 222

N-(4-chloro-3-(pyridin-2-yl)phenyl)-4-(pyridin-3-ylmethylsulfonyl)benzamide

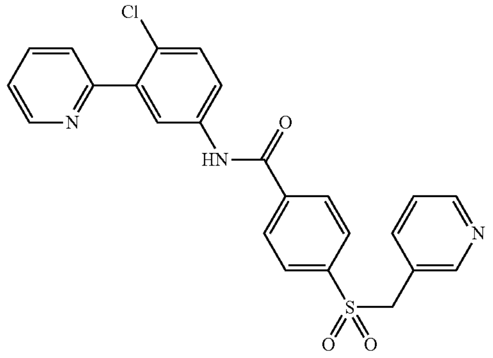 [SMILES: O=C(Nc1ccc(Cl)c(-c2ccccn2)c1)c1ccc(S(=O)(=O)Cc2cccnc2)cc1]

1 g of 3-(bromomethyl)pyridine hydrobromide was reacted with methyl 4-mercaptobenzoate via Procedure Q to afford methyl 4-(pyridin-3-ylmethylthio)benzoate. 980 mg of methyl 4-(pyridin-3-ylmethylthio)benzoate was reacted via Procedure R to give methyl 4-(pyridin-3-ylmethylsulfonyl)benzoate. 760 mg of methyl 4-(pyridin-3-ylmethylsulfonyl)benzoate was hydrolyzed via Procedure M to give 4-(pyridin-3-ylmethylsulfonyl)benzoic acid. 60 mg of 4-chloro-3-(pyridin-2-yl)aniline was coupled to 4-(pyridin-3-ylmethylsulfonyl)benzoic acid via Procedure G. The product was purified on reverse phase HPLC to yield N-(4-chloro-3-(pyridin-2-yl)phenyl)-4-(pyridin-3-ylmethylsulfonyl)benzamide. MS (Q1) 464.1 $(M)^+$.

Example 223

N-(4-chloro-3-(pyridin-2-yl)phenyl)-4-(pyridin-2-ylmethylsulfonyl)benzamide

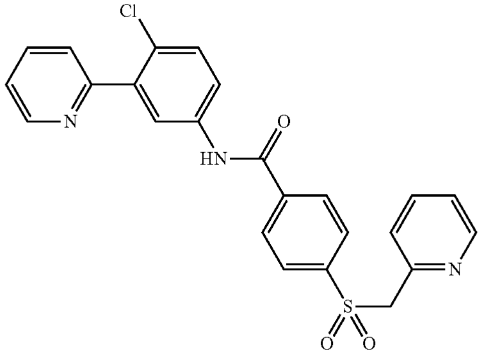 [SMILES: O=C(Nc1ccc(Cl)c(-c2ccccn2)c1)c1ccc(S(=O)(=O)Cc2ccccn2)cc1]

1 g of 2-(bromomethyl)pyridine hydrobromide was reacted with methyl 4-mercaptobenzoate via Procedure Q to afford methyl 4-(pyridin-2-ylmethylthio)benzoate. 500 mg of methyl 4-(pyridin-2-ylmethylthio)benzoate was reacted via Procedure R to give methyl 4-(pyridin-2-ylmethylsulfonyl)benzoate. 470 mg of methyl 4-(pyridin-2-ylmethylsulfonyl)benzoate was hydrolyzed via Procedure M to give 4-(pyridin-2-ylmethylsulfonyl)benzoic acid. 70 mg of 4-chloro-3-(pyridin-2-yl)aniline was coupled to 4-(pyridin-2-ylmethylsulfonyl)benzoic acid via Procedure G. The product was purified on reverse phase HPLC to yield N-(4-chloro-3-(pyridin-2-yl)phenyl)-4-(pyridin-2-ylmethylsulfonyl)benzamide. MS (Q1) 464.1 $(M)^+$.

Example 224

4-(2-amino-2-oxoethylsulfonyl)-N-(4-chloro-3-(pyridin-2-yl)phenyl)benzamide

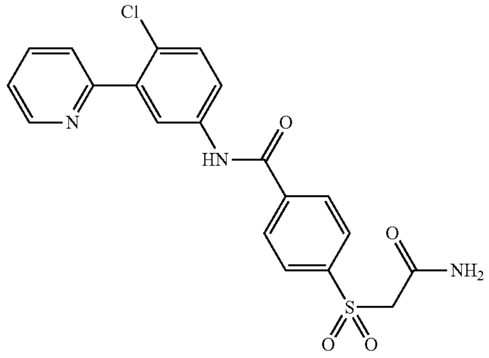 [SMILES: NC(=O)CS(=O)(=O)c1ccc(C(=O)Nc2ccc(Cl)c(-c3ccccn3)c2)cc1]

2.5 g of 2-bromoacetamide was reacted with methyl 4-mercaptobenzoate via Procedure Q to afford methyl 4-(2-amino-2-oxoethylthio)benzoate. 2.6 g of methyl 4-(2-amino-2-oxoethylthio)benzoate was reacted via Procedure R to give methyl 4-(2-amino-2-oxoethylsulfonyl)benzoate. 1 g of methyl 4-(2-amino-2-oxoethylsulfonyl)benzoate was hydrolyzed via Procedure M to give 4-(2-amino-2-oxoethylsulfonyl)benzoic acid. 150 mg of 4-chloro-3-(pyridin-2-yl)aniline was coupled to 4-(2-amino-2-oxoethylsulfonyl)benzoic acid via Procedure G. The product was purified on reverse phase HPLC to yield 4-(2-amino-2-oxoethylsulfonyl)-N-(4-chloro-3-(pyridin-2-yl)phenyl)benzamide. MS (Q1) 430.2 $(M)^+$.

Example 225

2-chloro-N-(4-chloro-3-(pyridin-2-yl)phenyl)-4-(2-hydroxypropylsulfonyl)benzamide

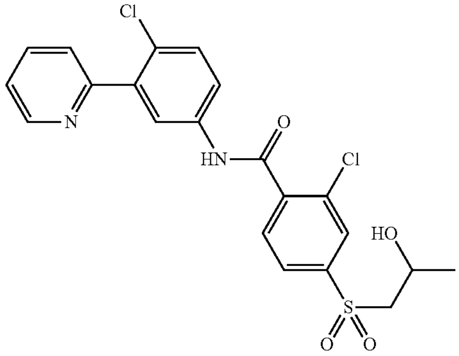

2 g of 2-chloro-4-fluorobenzonitrile was reacted with 1-mercapto-2-propanol via Procedure Q to afford 2-chloro-4-(2-hydroxypropylthio)benzonitrile. 2.5 g of 2-chloro-4-(2-hydroxypropylthio)benzonitrile was reacted via Procedure T to give 2-chloro-4-(2-hydroxypropylthio)benzoic acid. 2.1 g of 2-chloro-4-(2-hydroxypropylthio)benzoic acid was reacted via Procedure R to give 2-chloro-4-(2-hydroxypropylsulfonyl)benzoic acid. 70 mg of 4-chloro-3-(pyridin-2-yl) aniline was coupled to 2-chloro-4-(2-hydroxypropylsulfonyl)benzoic acid via Procedure G. The product was purified on reverse phase HPLC to yield 2-chloro-N-(4-chloro-3-(pyridin-2-yl)phenyl)-4-(2-hydroxypropylsulfonyl)benzamide. MS (Q1) 465.2 $(M)^+$.

Example 226

N-(4-chloro-3-(pyridin-2-yl)phenyl)-4-(2-hydroxypropylsulfonyl)-2-methylbenzamide

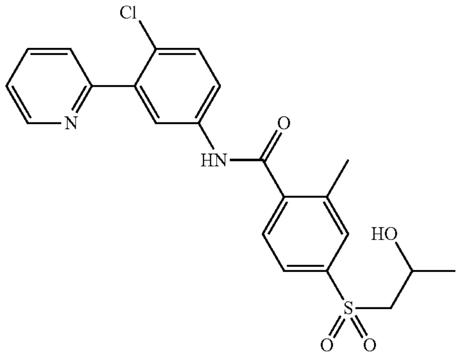

2 g of 4-bromo-2-methylbenzonitrile was reacted with 1-mercapto-2-propanol via Procedure Q to afford 4-(2-hydroxypropylthio)-2-methylbenzonitrile. 950 mg of 4-(2-hydroxypropylthio)-2-methylbenzonitrile was reacted via Procedure T to give 4-(2-hydroxypropylthio)-2-methylbenzoic acid. 1.0 g of 4-(2-hydroxypropylthio)-2-methylbenzoic acid was reacted via Procedure R to give 4-(2-hydroxypropylsulfonyl)-2-methylbenzoic acid. 100 mg of 4-chloro-3-(pyridin-2-yl)aniline was coupled to 4-(2-hydroxypropylsulfonyl)-2-methylbenzoic acid via Procedure G. The product was purified on reverse phase HPLC to yield N-(4-chloro-3-(pyridin-2-yl)phenyl)-4-(2-hydroxypropylsulfonyl)-2-methylbenzamide. MS (Q1) 445.3 $(M)^+$.

Example 227

N-(4-chloro-3-(pyridin-2-yl)phenyl)-4-(2-hydroxyethylsulfonyl)benzamide

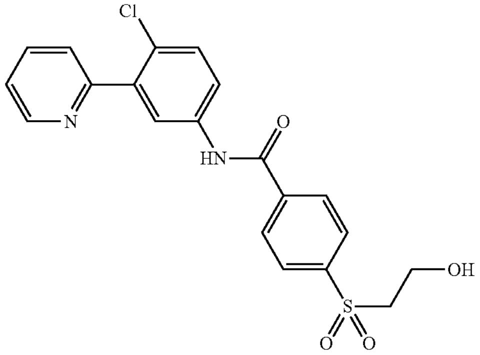 [SMILES: O=C(Nc1ccc(Cl)c(-c2ccccn2)c1)c1ccc(S(=O)(=O)CCO)cc1]

5 g of 4-fluorobenzonitrile was used in Procedure Q with 2-mercaptoethanol to afford 4-(2-hydroxyethylthio)benzonitrile. 900 mg of 4-(2-hydroxyethylthio)benzonitrile was reacted via Procedure T to give 4-(2-hydroxyethylthio)benzoic acid. 1.0 g of 4-(2-hydroxyethylthio)benzoic acid was reacted via Procedure R to give 4-(2-hydroxyethylsulfonyl) benzoic acid. 80 mg of 4-chloro-3-(pyridin-2-yl)aniline was coupled to 4-(2-hydroxyethylsulfonyl)benzoic acid via Procedure G. The product was purified on reverse phase HPLC to yield N-(4-chloro-3-(pyridin-2-yl)phenyl)-4-(2-hydroxyethylsulfonyl)benzamide. MS (Q1) 417.0 $(M)^+$.

Example 228

4-(2-(1H-imidazol-1-yl)ethylsulfonyl)-N-(4-chloro-3-(pyridin-2-yl)phenyl)benzamide

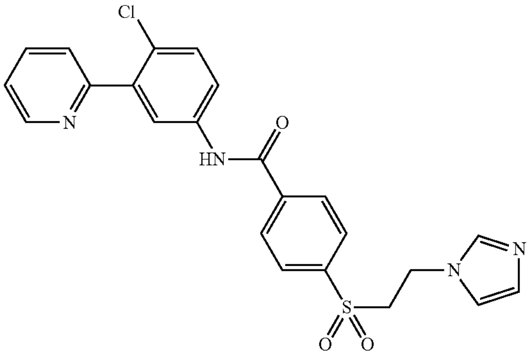 [SMILES: O=C(Nc1ccc(Cl)c(-c2ccccn2)c1)c1ccc(S(=O)(=O)CCn2ccnc2)cc1]

4 g of 4-(2-hydroxyethylthio)benzonitrile was reacted via Procedure R to yield 4-(2-hydroxyethylsulfonyl)benzonitrile. 3.0 g of triphenylphosphine was added to a solution of 2 g of 4-(2-hydroxyethylsulfonyl)benzonitrile and 4.7 g of carbon tetrabromide in dichloromethane at 0° C. The reaction mixture was allowed to warm to room temperature and stirred for 1 h. The mixture was diluted with dichloromethane, washed with $H_2O$, dried ($MgSO_4$) and evaporated. Purified by silica gel chromatography (0-70% ethyl acetate/hexane) to afford 4-(2-bromoethylsulfonyl)benzonitrile. 250 mg of 4-(2-bromoethylsulfonyl)benzonitrile was used in Procedure P with imidazole to give 4-(2-(1H-imidazol-1-yl)ethylsulfonyl)benzonitrile. 300 mg of 4-(2-(1H-imidazol-1-yl)ethylsulfonyl)benzonitrile was reacted via Procedure T to give 4-(2-(1H-imidazol-1-yl)ethylsulfonyl)benzoic acid. 60 mg of 4-chloro-3-(pyridin-2-yl)aniline was coupled to 4-(2-(1H-imidazol-1-yl)ethylsulfonyl)benzoic acid via Procedure G. The product was purified on reverse phase HPLC to yield 4-(2-(1H-imidazol-1-yl)ethylsulfonyl)-N-(4-chloro-3-(pyridin-2-yl)phenyl)benzamide. MS (Q1) 467.1 $(M)^+$.

Example 229

4-(2-(1H-pyrazol-1-yl)ethylsulfonyl)-N-(4-chloro-3-(pyridin-2-yl)phenyl)benzamide

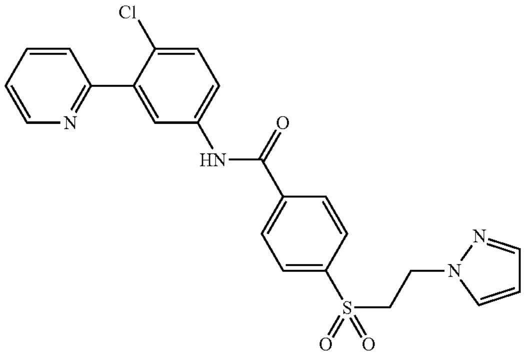 [SMILES: O=C(Nc1ccc(Cl)c(-c2ccccn2)c1)c1ccc(S(=O)(=O)CCn2cccn2)cc1]

250 mg of 4-(2-bromoethylsulfonyl)benzonitrile was used in Procedure P with pyrazole to yield 4-(2-(1H-pyrazole-1-yl)ethylsulfonyl)benzonitrile. 300 mg of 4-(2-(1H-pyrazole-1-yl)ethylsulfonyl)benzonitrile was reacted via Procedure T to give 4-(2-(1H-pyrazole-1-yl)ethylsulfonyl)benzoic acid. 75 mg of 4-chloro-3-(pyridin-2-yl)aniline was coupled to 4-(2-(1H-pyrazole-1-yl)ethylsulfonyl)benzoic acid via Procedure G. The product was purified on reverse phase HPLC to yield 4-(2-(1H-pyrazol-1-yl)ethylsulfonyl)-N-(4-chloro-3-(pyridin-2-yl)phenyl)benzamide. MS (Q1) 467.0 $(M)^+$.

Example 230

N-(4-chloro-3-(pyridin-2-yl)phenyl)-4-(2-(4-methyl-1H-imidazol-1-yl)ethylsulfonyl)benzamide

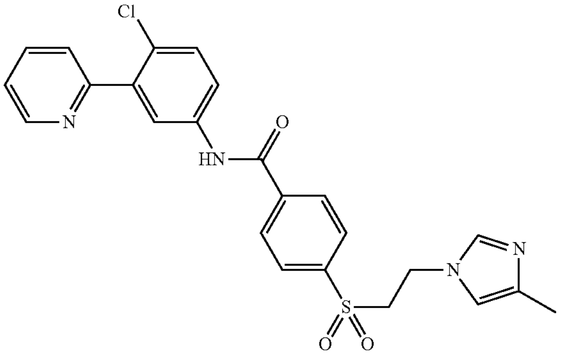 [SMILES: Cc1cn(CCS(=O)(=O)c2ccc(C(=O)Nc3ccc(Cl)c(-c4ccccn4)c3)cc2)cn1]

270 mg of 4-(2-bromoethylsulfonyl)benzonitrile was used in Procedure P with 4-methylimidazole to yield 4-(2-(4-methyl-1H-imidazole-1-yl)ethylsulfonyl)benzonitrile. 320 mg of 4-(2-(4-methyl-1H-imidazole-1-yl)ethylsulfonyl)benzonitrile was reacted via Procedure T to give 4-(2-(4-methyl-1H-imidazole-1-yl)ethylsulfonyl)benzoic acid.

70 mg of 4-chloro-3-(pyridin-2-yl)aniline was coupled to 4-(2-(4-methyl-1H-imidazole-1-yl)ethylsulfonyl)benzoic acid via Procedure G. The product was purified on reverse phase HPLC to yield N-(4-chloro-3-(pyridin-2-yl)phenyl)-4-(2-(4-methyl-1H-imidazol-1-yl)ethylsulfonyl)benzamide. MS (Q1) 481.0 $(M)^+$.

Example 231

N-(4-chloro-3-(pyridin-2-yl)phenyl)-4-(2-(3-methyl-1H-1,2,4-triazol-1-yl)ethylsulfonyl)benzamide

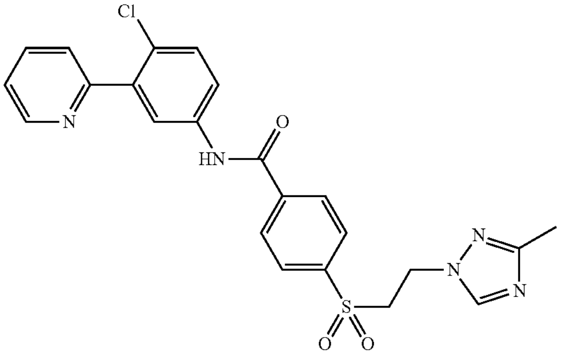 [SMILES: Cc1ncn(CCS(=O)(=O)c2ccc(C(=O)Nc3ccc(Cl)c(-c4ccccn4)c3)cc2)n1]

To a stirred suspension of 10 g of thiosemicarbazide in 100 mL of pyridine was slowly added 7.8 ml of acetyl chloride at 0° C. The temperature was maintained throughout the addition (0° C.-4° C.). The reaction mixture was allowed to warm to room temperature and stirred for 16 h. Evaporation gave 1-acetyl thiosemicarbazide. The crude 1-acetyl thiosemicarbazide was dissolved in 70 mL of MeOH and 12 g of sodium methoxide, and was refluxed for 10 h. The solvent was removed and the residue was dissolved in $H_2O$, then acidified to pH 2 by the addition of 1N HCl. The resulting solid was filtered and washed with $H_2O$ to give 3-methyl-1,2,4-triazole-5-thiol. 1 g of 3-methyl-1,2,4-triazole-5-thiol was added to a solution of 61 mg of sodium nitrite in 3 ml of nitric acid and 6 mL of $H_2O$ at 0° C. The reaction mixture was stirred for 1 h at 0° C., and basified with saturated sodium carbonate and concentrated. The residue was dissolved with MeOH and filtered. The filtrate was evaporated to give 3-methyl-1,2,4-triazole. 230 mg of 4-(2-bromoethylsulfonyl)benzonitrile was used in Procedure P with 3-methyl-1,2,4-triazole to yield 4-(2-(3-methyl-1H-1,2,4-triazole-1-yl)ethylsulfonyl)benzonitrile. 310 mg of 4-(2-(3-methyl-1H-1,2,4-triazole-1-yl)ethylsulfonyl)benzonitrile was reacted via Procedure T to give 4-(2-(3-methyl-1H-1,2,4-triazole-1-yl)ethylsulfonyl)benzoic acid.

60 mg of 4-chloro-3-(pyridin-2-yl)aniline was coupled to 4-(2-(3-methyl-1H-1,2,4-triazole-1-yl)ethylsulfonyl)benzoic acid via Procedure G. The product was purified on reverse phase HPLC to yield N-(4-chloro-3-(pyridin-2-yl)phenyl)-4-(2-(3-methyl-1H-1,2,4-triazol-1-yl)ethylsulfonyl)benzamide. MS (Q1) 482.1 $(M)^+$.

Example 232

N-(4-chloro-3-(pyridin-2-yl)phenyl)-4-(3-hydroxypropylsulfonyl)benzamide

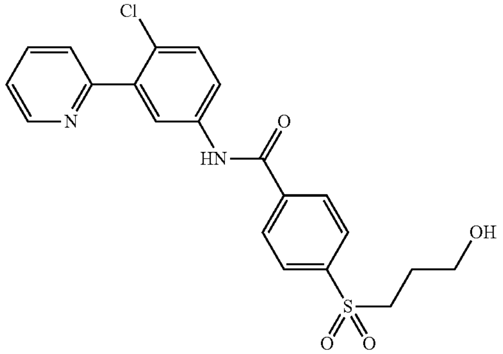 [SMILES: O=C(Nc1ccc(Cl)c(-c2ccccn2)c1)c1ccc(S(=O)(=O)CCCO)cc1]

5 g of 4-fluorobenzonitrile was used in Procedure Q with 3-mercapto-1-propanol to afford 4-(3-hydroxypropylthio)benzonitrile. 1.8 g of 4-(3-hydroxypropylthio)benzonitrile was reacted via Procedure T to give 4-(3-hydroxypropylthio)benzoic acid. 1.2 g of 4-(3-hydroxypropylthio)benzoic acid was reacted via Procedure R to give 4-(3-hydroxypropylsulfonyl)benzoic acid. 50 mg of 4-chloro-3-(pyridin-2-yl)aniline was coupled to 4-(3-hydroxypropylsulfonyl)benzoic acid via Procedure G. The product was purified on reverse phase HPLC to yield N-(4-chloro-3-(pyridin-2-yl)phenyl)-4-(3-hydroxypropylsulfonyl)benzamide. MS (Q1) 431.3 $(M)^+$.

Example 233

N-(4-chloro-3-(pyridin-2-yl)phenyl)-4-(2-methoxyethylsulfonyl)benzamide

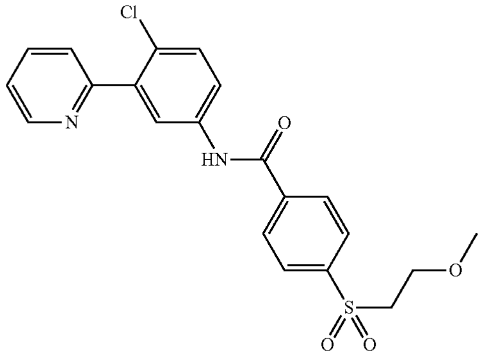 [SMILES: COCCS(=O)(=O)c1ccc(C(=O)Nc2ccc(Cl)c(-c3ccccn3)c2)cc1]

A mixture of 500 mg of methyl 4-mercaptobenzoate, 1.6 g of potassium carbonate, 1.2 g of 2-bromoethylmethylether and 329 mg of tetrabutylammonium iodide in 10 mL of acetone was refluxed for 16 h. The reaction mixture was diluted with ethyl acetate, washed with $H_2O$ and concentrated. Purified by silica gel chromatography (0-50% ethyl acetate/hexane) to yield 4-(2-methoxyethylthio)benzoate. 240 mg of 4-(2-methoxyethylthio)benzoate was reacted via Procedure R to give 4-(2-methoxyethylsulfonyl)benzoate. 120 mg of 4-(2-methoxyethylsulfonyl)benzoate was hydrolyzed via Procedure M to yield 4-(2-methoxyethylsulfonyl)benzoic acid. 50 mg of 4-chloro-3-(pyridin-2-yl)aniline was coupled to 4-(2-methoxyethylsulfonyl)benzoic acid via Procedure G. The product was purified on reverse phase HPLC to yield N-(4-chloro-3-(pyridin-2-yl)phenyl)-4-(2-methoxyethylsulfonyl)benzamide. MS (Q1) 431.0 $(M)^+$.

Example 234

N-(4-chloro-3-(pyridin-2-yl)phenyl)-4-(propylsulfonyl)benzamide

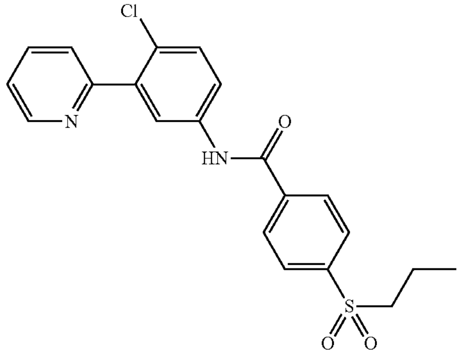 [SMILES: CCCS(=O)(=O)c1ccc(C(=O)Nc2ccc(Cl)c(-c3ccccn3)c2)cc1]

1 g of 4-fluorobenzonitrile was used in Procedure Q with 1-propanethiol to afford 4-(propylthio)benzonitrile. 860 mg of 4-(propylthio)benzonitrile was reacted via Procedure T to give 4-(propylthio)benzoic acid. 700 mg of 4-(propylthio)benzoic acid was reacted via Procedure R to give 4-(propylsulfonyl)benzoic acid. 60 mg of 4-chloro-3-(pyridin-2-yl)aniline was coupled to 4-(propylsulfonyl)benzoic acid via Procedure G. The product was purified on reverse phase HPLC to yield N-(4-chloro-3-(pyridin-2-yl)phenyl)-4-(propylsulfonyl)benzamide. MS (Q1) 415.0 $(M)^+$.

Example 235

2-chloro-N-(4-chloro-3-(pyridin-2-yl)phenyl)-4-(2-hydroxyethylsulfonyl)benzamide

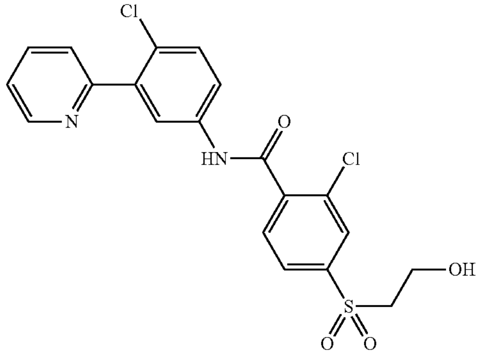 [SMILES: O=C(Nc1ccc(Cl)c(-c2ccccn2)c1)c1ccc(S(=O)(=O)CCO)cc1Cl]

4 g of 2-chloro-4-fluorobenzonitrile was used in Procedure Q with 2-mercaptoethanol to afford 2-chloro-4-(2-hydroxyethylthio)benzonitrile. 1 g of 2-chloro-4-(2-hydroxyethylthio)benzonitrile was reacted via Procedure T to give 2-chloro-4-(2-hydroxyethylthio)benzoic acid. 1 g of 2-chloro-4-(2-hydroxyethylthio)benzoic acid was reacted via Procedure R to yield 2-chloro-4-(2-hydroxyethylsulfonyl)benzoic acid. 50 mg of 4-chloro-3-(pyridin-2-yl)aniline was coupled to 2-chloro-4-(2-hydroxyethylsulfonyl)benzoic acid via Procedure G. The product was purified on reverse phase HPLC to yield 2-chloro-N-(4-chloro-3-(pyridin-2-yl)phenyl)-4-(2-hydroxyethylsulfonyl)benzamide. MS (Q1) 451.0 $(M)^+$.

Example 236

2-chloro-N-(4-chloro-3-(pyridin-2-yl)phenyl)-4-(3-hydroxypropylsulfonyl)benzamide

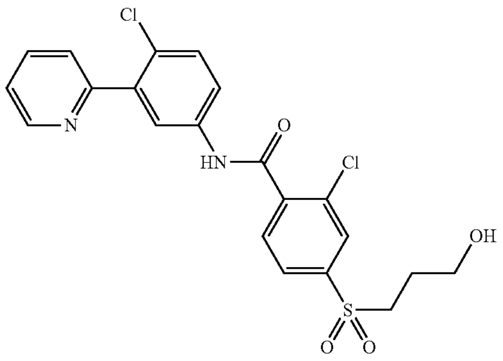 [SMILES: O=C(Nc1ccc(Cl)c(-c2ccccn2)c1)c1ccc(S(=O)(=O)CCCO)cc1Cl]

4 g of 2-chloro-4-fluorobenzonitrile was used in Procedure Q with 3-mercapto-1-propanol to afford 2-chloro-4-(3-hydroxypropylthio)benzonitrile. 1 g of 2-chloro-4-(3-hydroxypropylthio)benzonitrile was reacted via Procedure T to give 2-chloro-4-(3-hydroxypropylthio)benzoic acid. 1.2 g of 2-chloro-4-(3-hydroxypropylthio)benzoic acid was reacted via Procedure R to yield 2-chloro-4-(2-hydroxypropylsulfonyl)benzoic acid. 75 mg of 4-chloro-3-(pyridin-2-yl)aniline was coupled to 2-chloro-4-(2-hydroxypropylsulfonyl)benzoic acid via Procedure G. The product was purified on reverse phase HPLC to yield 2-chloro-N-(4-chloro-3-(pyridin-2-yl)phenyl)-4-(3-hydroxypropylsulfonyl)benzamide. MS (Q1) 465.0 $(M)^+$.

Example 237

4-(allylsulfonyl)-N-(4-chloro-3-(pyridin-2-yl)phenyl)benzamide

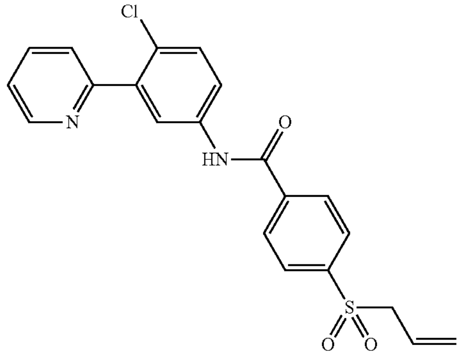 [SMILES: C=CCS(=O)(=O)c1ccc(C(=O)Nc2ccc(Cl)c(-c3ccccn3)c2)cc1]

7.3 g of 4-(3-hydroxypropylthio)benzonitrile was reacted via Procedure R to yield 4-(3-hydroxypropylsulfonyl)benzonitrile. 1.9 g of NBS was added to a solution of 2 g of 4-(3-hydroxypropylsulfonyl)benzonitrile and 2.8 g of triphenylphosphine in 10 mL of dichloromethane at 0° C. The reaction mixture was stirred at 0~5° C. for 1 h. The mixture was diluted with dichloromethane, washed with $H_2O$, dried ($MgSO_4$) and evaporated. Purified by silica gel chromatography (10-70% ethyl acetate/hexane) to afford 4-(3-bromopropylsulfonyl)benzonitrile. 300 mg of 4-(3-bromopropylsulfonyl)benzonitrile was reacted via Procedure T to give 4-(allylsulfonyl)benzoic acid. 40 mg of 4-chloro-3-(pyridin-2-yl)aniline was coupled to 4-(allylsulfonyl)benzoic acid via Procedure G. The product was purified on reverse phase HPLC to yield 4-(allylsulfonyl)-N-(4-chloro-3-(pyridin-2-yl)phenyl)benzamide. MS (Q1) 413.2 $(M)^+$.

Example 238

4-(allylsulfonyl)-2-chloro-N-(4-chloro-3-(pyridin-2-yl)phenyl)benzamide

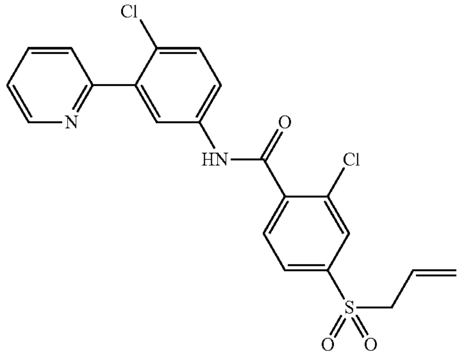 [SMILES: C=CCS(=O)(=O)c1ccc(C(=O)Nc2ccc(Cl)c(-c3ccccn3)c2)c(Cl)c1]

115 mg of NBS was added to a solution of 200 mg of 2-chloro-N-(4-chloro-3-(pyridin-2-yl)phenyl)-4-(3-hydroxypropylsulfonyl)benzamide and 169 mg of triphenylphosphine in 3 mL of dichloromethane at 0° C. The reaction mixture was stirred at 0~5° C. for 1 h. The mixture was diluted with dichloromethane, washed with $H_2O$, dried ($MgSO_4$) and evaporated. Purified by prep TLC plate (60% ethyl acetate/hexane) to afford 4-(3-bromopropylsulfonyl)-2-chloro-N-(4-chloro-3-(pyridin-2-yl)phenyl)benzamide. 60 mg of 4-(3-bromopropylsulfonyl)-2-chloro-N-(4-chloro-3-(pyridin-2-yl)phenyl)benzamide and 111 mg of cesium carbonate in 0.5 mL of DMF were heated to 100° C. in a sealed microwave reactor for 20 min. The reaction mixture was evaporated, and the product was purified on reverse phase HPLC to yield 4-(allylsulfonyl)-2-chloro-N-(4-chloro-3-(pyridin-2-yl)phenyl)benzamide. MS (Q1) 448.0 $(M)^+$.

Example 239

2-chloro-N-(4-chloro-3-(pyridin-2-yl)phenyl)-4-(3-morpholinopropylsulfonyl)-benzamide

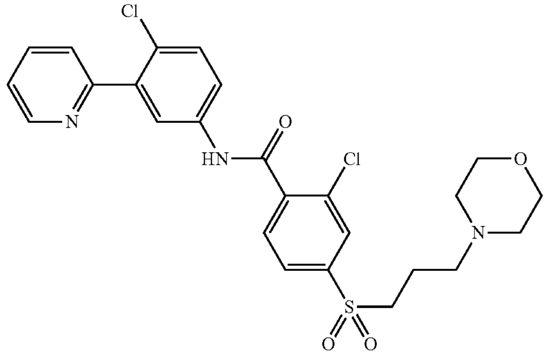 [SMILES: O=C(Nc1ccc(Cl)c(-c2ccccn2)c1)c1ccc(S(=O)(=O)CCCN2CCOCC2)cc1Cl]

120 mg of 4-(3-bromopropylsulfonyl)-2-chloro-N-(4-chloro-3-(pyridin-2-yl)phenyl)benzamide was used in Procedure P with morpholine to yield 2-chloro-N-(4-chloro-3-(pyridin-2-yl)phenyl)-4-(3-morpholinopropylsulfonyl) benzamide. MS (Q1) 534.0 (M)+.

Example 240

2-chloro-N-(4-chloro-3-(pyridin-2-yl)phenyl)-4-(2-oxopyrrolidin-1-yl)benzamide

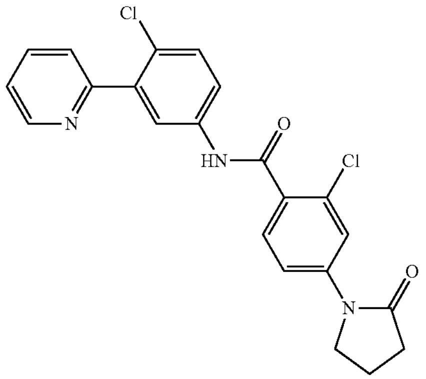 [SMILES: O=C(Nc1ccc(Cl)c(-c2ccccn2)c1)c1ccc(N2CCCC2=O)cc1Cl]

A mixture of 500 mg of 2-chloro-4-florobenzonitrile, 821 mg of 2-pyrrolidinone and 3 g of cesium carbonate in 5 mL of DMF was heated to 100° C. in a sealed microwave reactor for 15 min. The reaction mixture was diluted with ethyl acetate, washed with $H_2O$, dried ($MgSO_4$) and evaporated. Purified by silica gel chromatography (20-80% ethyl acetate/hexane) to afford 2-chloro-4-(2-oxopyrrolidin-1-yl)benzonitrile. 890 mg of 2-chloro-4-(2-oxopyrrolidin-1-yl)benzonitrile was reacted via Procedure T to give 2-chloro-4-(2-oxopyrrolidin-1-yl)benzoic acid. 80 mg of 4-chloro-3-(pyridin-2-yl)aniline was coupled to 2-chloro-4-(2-oxopyrrolidin-1-yl)benzoic acid via Procedure G. The product was purified on reverse phase HPLC to yield 2-chloro-N-(4-chloro-3-(pyridin-2-yl)phenyl)-4-(2-oxopyrrolidin-1-yl)benzamide. MS (Q1) 426.2 (M)+.

Example 241

N-(4-chloro-3-(pyridin-2-yl)phenyl)-4-(2-oxooxazolidin-3-yl)benzamide

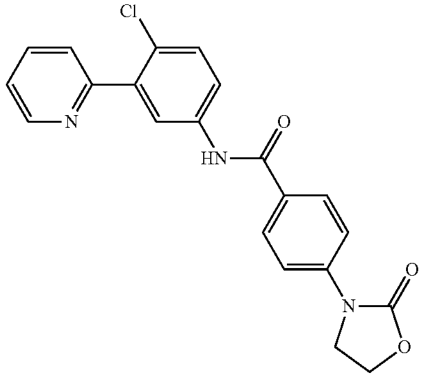 [SMILES: O=C(Nc1ccc(Cl)c(-c2ccccn2)c1)c1ccc(N2CCOC2=O)cc1]

A mixture of 1 g of methyl 4-iodobenzoate, 399 mg of 2-oxozolidone, 1.1 g of potassium carbonate, 34 mg of N,N'-dimethylethylenediamine and 73 mg of copper iodide in 10 mL of toluene was heated to 150° C. in a sealed microwave reactor for 2 h. The reaction mixture was diluted with ethyl acetate, washed with $H_2O$, dried ($MgSO_4$) and evaporated. Purified by silica gel chromatography (20-70% ethyl acetate/hexane) to afford methyl 4-(2-oxooxazolidin-3-yl)benzoate. 530 mg of methyl 4-(2-oxooxazolidin-3-yl)benzoate was hydrolyzed via Procedure M to give 4-(2-oxooxazolidin-3-yl)benzoic acid. 70 mg of 4-chloro-3-(pyridin-2-yl)aniline was coupled to 4-(2-oxooxazolidin-3-yl)benzoic acid via Procedure G. The product was purified on reverse phase HPLC to yield N-(4-chloro-3-(pyridin-2-yl)phenyl)-4-(2-oxooxazolidin-3-yl)benzamide. MS (Q1) 394.2 (M)+.

Example 242

N-(4-chloro-3-(pyridin-2-yl)phenyl)-4-(ethylsulfonyl)-2-methylbenzamide

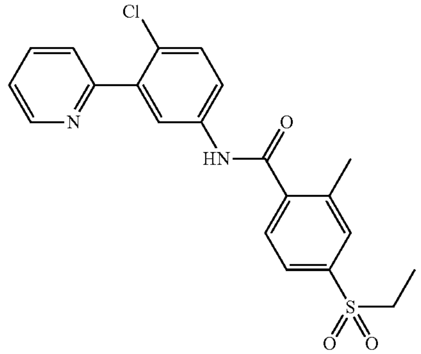 [SMILES: CCS(=O)(=O)c1ccc(C(=O)Nc2ccc(Cl)c(-c3ccccn3)c2)c(C)c1]

4 g of 4-bromo-2-methylbenzonitrile was used in Procedure Q with ethanethiol to afford 4-(ethylthio)-2-methylbenzonitrile. 2 g of 4-(ethylthio)-2-methylbenzonitrile was reacted via Procedure R to give 4-(ethylsulfonyl)-2-methylbenzonitrile. 2.5 g of 4-(ethylsulfonyl)-2-methylbenzonitrile was reacted via Procedure T to give 4-(ethylsulfonyl)-2-methylbenzoic acid. 75 mg of 4-chloro-3-(pyridin-2-yl)aniline was coupled to 4-(ethylsulfonyl)-2-methylbenzoic acid via Procedure G. The product was purified on reverse phase HPLC to yield N-(4-chloro-3-(pyridin-2-yl)phenyl)-4-(ethylsulfonyl)-2-methylbenzamide. MS (Q1) 415.0 (M)+.

Example 243

2-chloro-N-(4-chloro-3-(pyridin-2-yl)phenyl)-4-(ethylsulfonyl)benzamide

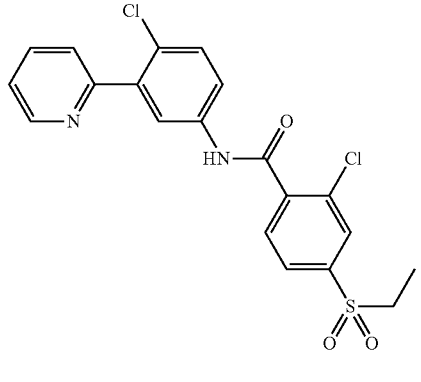 [SMILES: CCS(=O)(=O)c1ccc(C(=O)Nc2ccc(Cl)c(-c3ccccn3)c2)c(Cl)c1]

4 g of 2-chloro-4-fluorobenzonitrile was used in Procedure Q with ethanethiol to afford 2-chloro-4-(ethylthio)benzonitrile. 2 g of 2-chloro-4-(ethylthio)benzonitrile was reacted via Procedure T to give 2-chloro-4-(ethylthio)benzoic acid. 1.5 g of 2-chloro-4-(ethylthio)benzoic acid was reacted via Procedure R to yield 2-chloro-4-(ethylsulfonyl)benzoic acid. 75 mg of 4-chloro-3-(pyridin-2-yl)aniline was coupled to 2-chloro-4-(ethylsulfonyl)benzoic acid via Procedure G. The product was purified on reverse phase HPLC to yield 2-chloro-N-(4-chloro-3-(pyridin-2-yl)phenyl)-4-(ethylsulfonyl)benzamide. MS (Q1) 435.1 $(M)^+$.

Example 244

2-chloro-N-(4-chloro-3-(pyridin-2-yl)phenyl)-4-(isopropylsulfonyl)benzamide

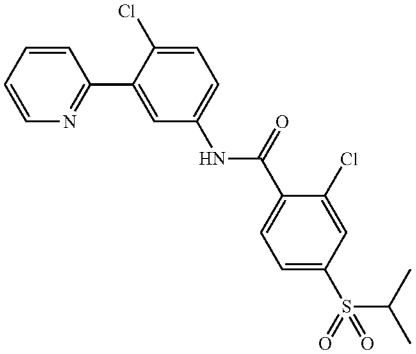 [SMILES: CC(C)S(=O)(=O)c1ccc(C(=O)Nc2ccc(Cl)c(-c3ccccn3)c2)c(Cl)c1]

2 g of 2-chloro-4-fluorobenzonitrile was used in Procedure Q with 2-propanethiol to afford 2-chloro-4-(isopropylthio)benzonitrile. 1.6 g of 2-chloro-4-(isopropythio)benzonitrile was reacted via Procedure T to give 2-chloro-4-(isopropylthio)benzoic acid. 1 g of 2-chloro-4-(isopropylthio)benzoic acid was reacted via Procedure R to give 2-chloro-4-(isopropylsulfonyl)benzoic acid. 75 mg of 4-chloro-3-(pyridin-2-yl)aniline was coupled to 2-chloro-4-(isopropylsulfonyl)benzoic acid via Procedure G. The product was purified on reverse phase HPLC to yield 2-chloro-N-(4-chloro-3-(pyridin-2-yl)phenyl)-4-(isopropylsulfonyl)benzamide. MS (Q1) 449.1 $(M)^+$.

Example 245

N-(4-chloro-3-(pyridin-2-yl)phenyl)-4-(isopropylsulfonyl)benzamide

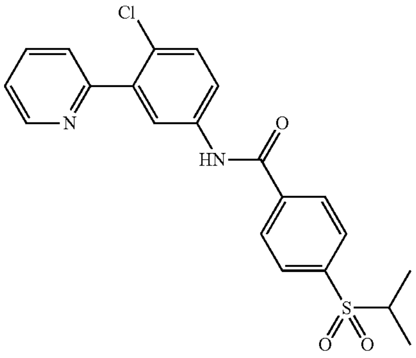 [SMILES: CC(C)S(=O)(=O)c1ccc(C(=O)Nc2ccc(Cl)c(-c3ccccn3)c2)cc1]

2 g of 4-fluorobenzonitrile was used in Procedure Q with 2-propanethiol to afford 4-(isopropylthio)benzonitrile. 900 mg of 4-(isopropythio)benzonitrile was reacted via Procedure T to give 4-(isopropylthio)benzoic acid. 730 mg of 4-(isopropylthio)benzoic acid was reacted via Procedure R to give 4-(isopropylsulfonyl)benzoic acid. 75 mg of 4-chloro-3-(pyridin-2-yl)aniline was coupled to 4-(isopropylsulfonyl)benzoic acid via Procedure G. The product was purified on reverse phase HPLC to yield N-(4-chloro-3-(pyridin-2-yl)phenyl)-4-(isopropylsulfonyl)benzamide. MS (Q1) 415.0 (M)

Example 246

N-(4-chloro-3-(pyridin-2-yl)phenyl)-2-methyl-4-(methylsulfonyl)benzamide

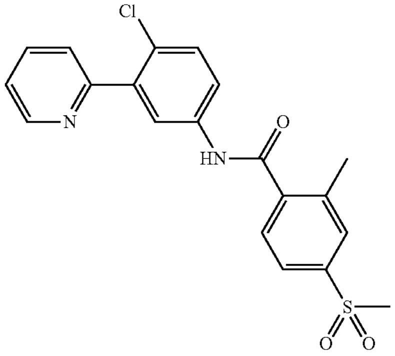

A solution of 500 mg of 4-bromo-2-methylbenzonitrile and 268 mg of sodium thiomethoxide in 3 mL of DMF was stirred for 1 h. The reaction mixture was diluted with ethyl acetate, washed with $H_2O$, dried ($MgSO_4$) and evaporated to afford 2-methyl-4-(methylthio)benzonitrile. 400 mg of 2-methyl-4-(methylthio)benzonitrile was reacted via Procedure T to give 2-methyl-4-(methylthio)benzoic acid. 430 mg of 2-methyl-4-(methylthio)benzoic acid was reacted via Procedure R to yield 2-methyl-4-(methylsulfonyl)benzoic acid. 60 mg of 4-chloro-3-(pyridin-2-yl)aniline was coupled to 2-methyl-4-(methylsulfonyl)benzoic acid via Procedure G. The product was purified on reverse phase HPLC to yield N-(4-chloro-3-(pyridin-2-yl)phenyl)-2-methyl-4-(methylsulfonyl)benzamide. MS (Q1) 401.0 $(M)^+$.

Example 247

N-(4-chloro-3-(pyridin-2-yl)phenyl)-6-(methylsulfonyl)nicotinamide

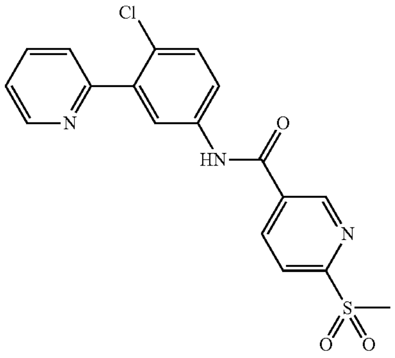 [SMILES: CS(=O)(=O)c1ccc(C(=O)Nc2ccc(Cl)c(-c3ccccn3)c2)cn1]

1 g of methyl 6-chloronicotinate was reacted via Procedure O to yield methyl 6-(methylsulfonyl)nicotinate. 1 g of methyl 6-(methylsulfonyl)nicotinate was hydrolyzed via Procedure M to give 6-(methylsulfonyl)nicotinic acid. 100 mg of 4-chloro-3-(pyridin-2-yl)aniline was coupled to 6-(methylsulfonyl)nicotinic acid via Procedure G. The product was purified on reverse phase HPLC to yield N-(4-chloro-3-(pyridin-2-yl)phenyl)-6-(methylsulfonyl)nicotinamide. MS (Q1) 388.1 $(M)^+$.

Example 248

N-(4-chloro-3-(pyridin-2-yl)phenyl)-2-methyl-4-phenylpyrimidine-5-carboxamide

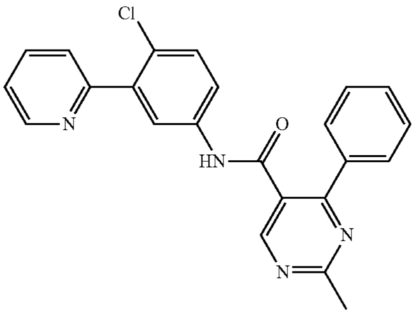 [SMILES: Cc1ncc(C(=O)Nc2ccc(Cl)c(-c3ccccn3)c2)c(-c2ccccc2)n1]

50 mg of 4-chloro-3-(pyridin-2-yl)aniline was coupled to 4-methyl-2-phenyl-5-pyrimidine carboxylic acid via Procedure G. The product was purified on reverse phase HPLC to yield N-(4-chloro-3-(pyridin-2-yl)phenyl)-2-methyl-4-phenylpyrimidine-5-carboxamide. MS (Q1) 401.1 $(M)^+$.

Example 249

N-(4-chloro-3-(pyridin-2-yl)phenyl)-1-(4-fluorophenyl)-5-methyl-1H-pyrazole-4-carboxamide

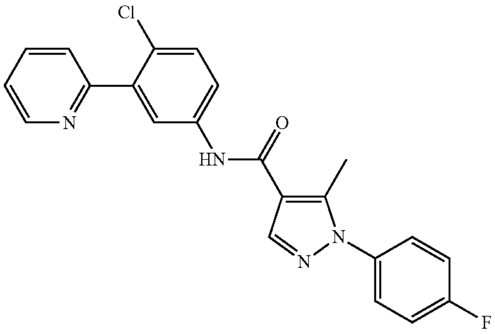 [SMILES: Cc1c(C(=O)Nc2ccc(Cl)c(-c3ccccn3)c2)cnn1-c1ccc(F)cc1]

50 mg of 4-chloro-3-(pyridin-2-yl)aniline was coupled to 1-(4-fluorophenyl)-5-methyl-1H-pyrazole-4-carboxylic acid via Procedure G. The product was purified on reverse phase HPLC to yield N-(4-chloro-3-(pyridin-2-yl)phenyl)-1-(4-fluorophenyl)-5-methyl-1H-pyrazole-4-carboxamide. MS (Q1) 407.0 $(M)^+$.

Example 250

6-chloro-N-(4-chloro-3-(pyridin-2-yl)phenyl)nicotinamide

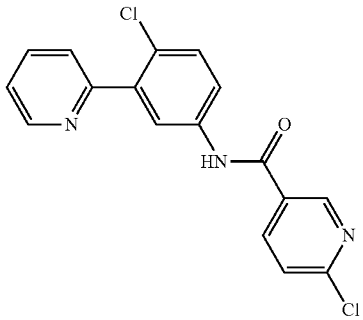 [SMILES: O=C(Nc1ccc(Cl)c(-c2ccccn2)c1)c1ccc(Cl)nc1]

A mixture of 450 mg of 4-chloro-3-(pyridin-2-yl)aniline, 427 mg of 6-chloronicotinyl chloride and 1.9 g of PS-DIEA in 10 mL of dichloromethane was shook on the shaker for 3 h. The reaction mixture was filtered and washed with dichloromethane. The filtrate was concentrated to yield 6-chloro-N-(4-chloro-3-(pyridin-2-yl)phenyl)nicotinamide. MS (Q1) 344.2 $(M)^+$.

Example 251

N-(4-chloro-3-(pyridin-2-yl)phenyl)-6-(4-ethylpiperazin-1-yl)nicotinamide

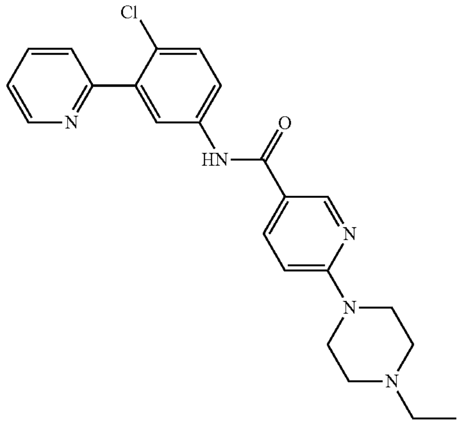 [SMILES: CCN1CCN(c2ccc(C(=O)Nc3ccc(Cl)c(-c4ccccn4)c3)cn2)CC1]

Procedure F was performed using 50 mg of 6-chloro-N-(4-chloro-3-(pyridin-2-yl)phenyl)nicotinamide and 93 μL of 1-ethylpiperazine in 0.5 mL of BuOH. Purified by reverse phase HPLC to yield N-(4-chloro-3-(pyridin-2-yl)phenyl)-6-(4-ethylpiperazin-1-yl)nicotinamide. MS (Q1) 422.0 $(M)^+$.

Example 252

N-(4-chloro-3-(pyridin-2-yl)phenyl)-6-(4-(2-hydroxyethyl)piperazin-1-yl)nicotinamide

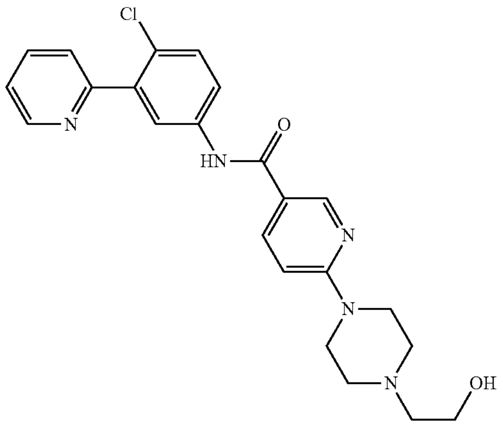 [SMILES: O=C(Nc1ccc(Cl)c(-c2ccccn2)c1)c1ccc(N2CCN(CCO)CC2)nc1]

Procedure F was performed using 50 mg of 6-chloro-N-(4-chloro-3-(pyridin-2-yl)phenyl)nicotinamide and 90 μL of 1-(2-hydroxyethyl)piperazine in 0.5 mL of BuOH. Purified by reverse phase HPLC to yield N-(4-chloro-3-(pyridin-2-yl)phenyl)-6-(4-(2-hydroxyethyl)piperazin-1-yl)nicotinamide. MS (Q1) 438.0 $(M)^+$.

Example 253

(R)—N-(4-chloro-3-(pyridin-2-yl)phenyl)-6-(2-hydroxypropylamino)nicotinamide

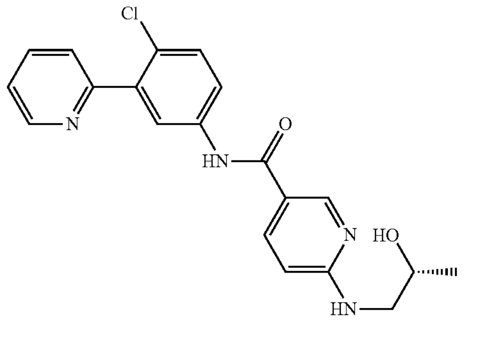 [SMILES: C[C@@H](O)CNc1ccc(C(=O)Nc2ccc(Cl)c(-c3ccccn3)c2)cn1]

Procedure F was performed using 50 mg of 6-chloro-N-(4-chloro-3-(pyridin-2-yl)phenyl)nicotinamide and 57 μL of R-1-Amino-2-propanol in 0.5 mL of BuOH. Purified by reverse phase HPLC to yield (R)—N-(4-chloro-3-(pyridin-2-yl)phenyl)-6-(2-hydroxypropylamino)nicotinamide. MS (Q1) 383.4 $(M)^+$.

Example 254

(S)—N-(4-chloro-3-(pyridin-2-yl)phenyl)-6-(2-hydroxypropylamino)nicotinamide

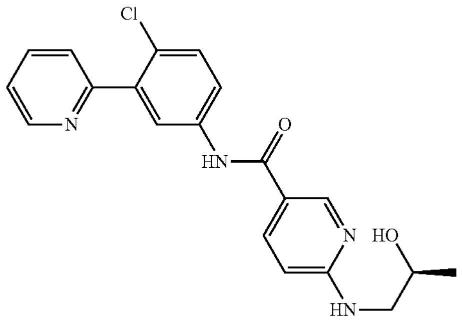 [SMILES: C[C@H](O)CNc1ccc(C(=O)Nc2ccc(Cl)c(-c3ccccn3)c2)cn1]

Procedure F was performed using 50 mg of 6-chloro-N-(4-chloro-3-(pyridin-2-yl)phenyl)nicotinamide and 57 μL of S-1-Amino-2-propanol in 0.5 mL of BuOH. Purified by reverse phase HPLC to yield (S)—N-(4-chloro-3-(pyridin-2-yl)phenyl)-6-(2-hydroxypropylamino)nicotinamide. MS (Q1) 383.4 $(M)^+$.

Example 255

N-(4-chloro-3-(pyridin-2-yl)phenyl)-6-(2,6-dimethylmorpholino)nicotinamide

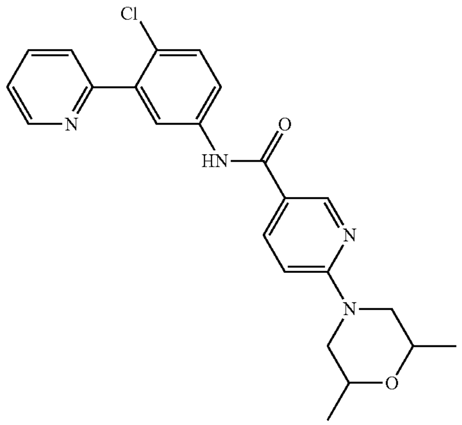 [SMILES: CC1CN(c2ccc(C(=O)Nc3ccc(Cl)c(-c4ccccn4)c3)cn2)CC(C)O1]

Procedure F was performed using 50 mg of 6-chloro-N-(4-chloro-3-(pyridin-2-yl)phenyl)nicotinamide and 90 μL of 2,6-dimethylmorpholine in 0.5 mL of BuOH. Purified by reverse phase HPLC to yield N-(4-chloro-3-(pyridin-2-yl)phenyl)-6-(2,6-dimethylmorpholino)nicotinamide. MS (Q1) 423.4 $(M)^+$.

Example 256

N-(4-chloro-3-(pyridin-2-yl)phenyl)-6-(4-hydroxypiperidin-1-yl)nicotinamide

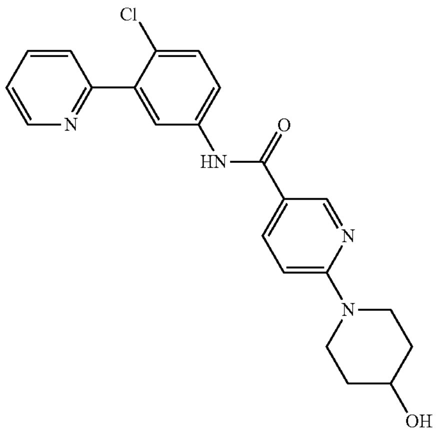 [SMILES: O=C(Nc1ccc(Cl)c(-c2ccccn2)c1)c1ccc(N2CCC(O)CC2)nc1]

Procedure F was performed using 50 mg of 6-chloro-N-(4-chloro-3-(pyridin-2-yl)phenyl)nicotinamide and 74 mg of 4-hydroxypiperidine in 0.5 mL of BuOH. Purified by reverse phase HPLC to yield N-(4-chloro-3-(pyridin-2-yl)phenyl)-6-(4-hydroxypiperidin-1-yl)nicotinamide. MS (Q1) 409.3 $(M)^+$.

Example 257

N-(4-chloro-3-(pyridin-2-yl)phenyl)-6-(3,5-dimethyl-1H-pyrazol-1-yl)nicotinamide

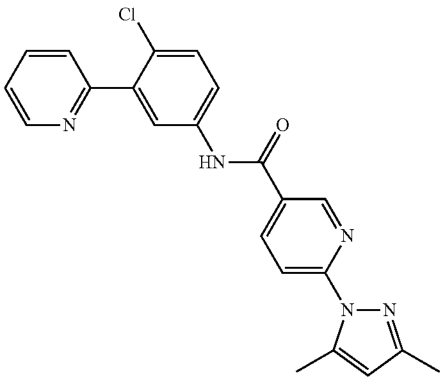 [SMILES: Cc1cc(C)n(-c2ccc(C(=O)Nc3ccc(Cl)c(-c4ccccn4)c3)cn2)n1]

21 mg of sodium hydride was added to a solution of 84 mg of 3,5-dimethylpyrazole in 2 mL of DMF. The reaction mixture was stirred for 10 min, and then added 100 mg of 6-chloro-N-(4-chloro-3-(pyridin-2-yl)phenyl)nicotinamide. The reaction was heated to 140° C. for 16 h. The mixture was quenched with MeOH and evaporated. The product was purified on reverse phase HPLC to yield N-(4-chloro-3-(pyridin-2-yl)phenyl)-6-(3,5-dimethyl-1H-pyrazol-1-yl)nicotinamide. MS (Q1) 404.3 $(M)^+$.

Example 258

N-(4-chloro-3-(pyridin-2-yl)phenyl)-6-(3-oxopiperidin-1-yl)nicotinamide

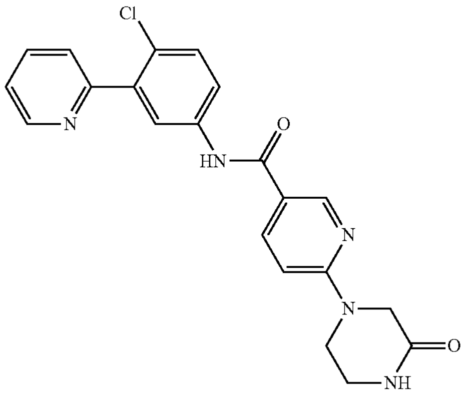 [SMILES: O=C1CN(c2ccc(C(=O)Nc3ccc(Cl)c(-c4ccccn4)c3)cn2)CCN1]

Procedure F was performed using 50 mg of 6-chloro-N-(4-chloro-3-(pyridin-2-yl)phenyl)nicotinamide and 29 mg of piperazin-2-one in 0.5 mL of BuOH. Purified by reverse phase HPLC to yield N-(4-chloro-3-(pyridin-2-yl)phenyl)-6-(3-oxopiperidin-1-yl)nicotinamide. MS (Q1) 408.3 $(M)^+$.

Example 259

N-(4-chloro-3-(pyridin-2-yl)phenyl)-4-(2-oxopiperazin-1-yl)benzamide

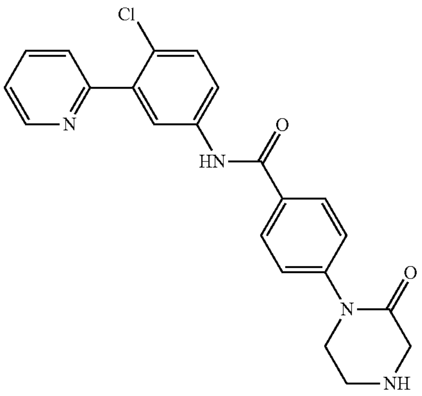 [SMILES: O=C(Nc1ccc(Cl)c(-c2ccccn2)c1)c1ccc(N2CCNCC2=O)cc1]

A mixture of 1 g of methyl 4-iodobenzoate, 920 mg of 4-Boc-piperazinone, 1.1 g of potassium carbonate, 32 mg of N,N'-dimethylethylenediamine and 70 mg of copper iodide in 10 mL of toluene was heated to 150° C. in a sealed microwave reactor for 3 h. The reaction mixture was diluted with ethyl acetate, washed with $H_2O$, dried ($MgSO_4$) and evaporated. Purified by silica gel chromatography (20-80% ethyl acetate/hexane) to afford tert-butyl 4-(4-(methoxycarbonyl)phenyl)-3-oxopiperazine-1-carboxylate. 500 mg of tert-butyl 4-(4-(methoxycarbonyl)phenyl)-3-oxopiperazine-1-carboxylate was hydrolyzed via Procedure M to give 4-(4-(tert-buthoxycarbonyl)-2-oxopiperazin-1-yl)benzoic acid. 100 mg of 4-chloro-3-(pyridin-2-yl)aniline was coupled to 4-(4-(tert-buthoxycarbonyl)-2-oxopiperazin-1-yl)benzoic acid via Procedure G. The reaction mixture was diluted with ethyl acetate, washed with 0.1 N sodium hydroxide and brine, dried ($MgSO_4$) and evaporated to afford tert-butyl 4-(4-(4-chloro- 3-(pyridin-2-yl)phenylcarbamoyl)phenyl)-3-oxopiperazine-1-carboxylate. 300 mg of crude tert-butyl 4-(4-(4-chloro-3-(pyridin-2-yl)phenylcarbamoyl)phenyl)-3-oxopiperazine-1-carboxylate was treated with TFA (2 mL) containing trace amounts of $H_2O$ for 1 h. The reaction mixture was evaporated and the crude product was purified by reverse phase HPLC to yield N-(4-chloro-3-(pyridin-2-yl)phenyl)-4-(2-oxopiperazin-1-yl)benzamide. MS (Q1) 407.3 $(M)^+$.

Example 260

N-(4-chloro-3-(pyridin-2-yl)phenyl)-4-(4-methyl-2-oxopiperazin-1-yl)benzamide

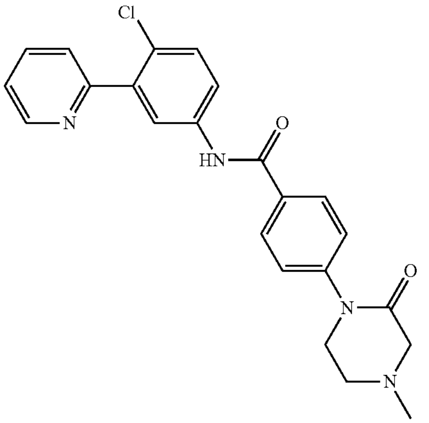 [SMILES: CN1CCN(c2ccc(C(=O)Nc3ccc(Cl)c(-c4ccccn4)c3)cc2)C(=O)C1]

120 mg of N-(4-chloro-3-(pyridin-2-yl)phenyl)-4-(2-oxopiperazin-1-yl)benzamide was dissolved in 2 mL of DMF and then treated with 53 mg of paraformaldehyde, 187 mg of sodium triacetoxyborohydride and 0.2 mL of AcOH. After stirring 16 h, the reaction mixture was evaporated and the crude product was purified by reverse phase HPLC to yield N-(4-chloro-3-(pyridin-2-yl)phenyl)-4-(4-methyl-2-oxopiperazin-1-yl)benzamide. MS (Q1) 421.3 $(M)^+$.

Example 261

2-amino-N-(4-chloro-3-(pyridin-2-yl)phenyl)-4-(methylsulfonyl)benzamide

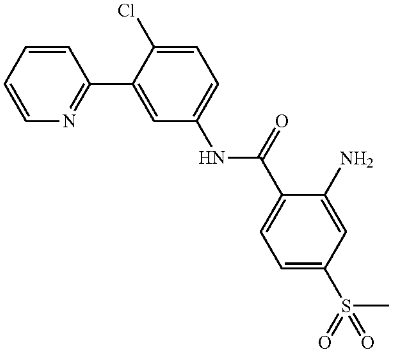

2.2 g of methyl 4-(methylsulfonyl)-2-nitrobenzoate was reacted via Procedure C to afford methyl 2-amino-4-(methylsulfonyl)benzoate. 500 mg of methyl 2-amino-4-(methylsulfonyl)benzoate was hydrolyzed via Procedure M to give 2-amino-4-(methylsulfonyl)benzoic acid. 100 mg of 4-chloro-3-(pyridin-2-yl)aniline was coupled to 2-amino-4-(methylsulfonyl)benzoic acid via Procedure G. The product was purified on reverse phase HPLC to yield 2-amino-N-(4-chloro-3-(pyridin-2-yl)phenyl)-4-(methylsulfonyl)benzamide. MS (Q1) 402.0 $(M)^+$.

Example 262

2-acetamido-N-(4-chloro-3-(pyridin-2-yl)phenyl)-4-(methylsulfonyl)benzamide

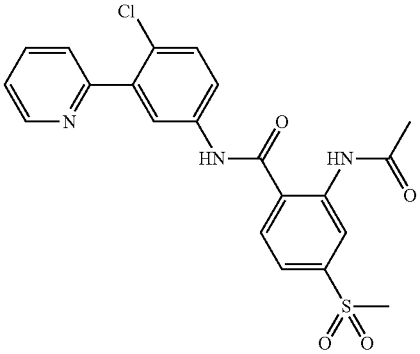 [SMILES: CC(=O)Nc1cc(S(C)(=O)=O)ccc1C(=O)Nc1ccc(Cl)c(-c2ccccn2)c1]

20 μL of acetyl chloride was added to a solution of 90 mg of 2-amino-N-(4-chloro-3-(pyridin-2-yl)phenyl)-4-(methylsulfonyl)benzamide in 2 mL of pyridine at 0° C. The reaction mixture was allowed to warm to room temperature and stirred for 2 h. The reaction was quenched with MeOH and evaporated. The product was purified on reverse phase HPLC to yield 2-acetamido-N-(4-chloro-3-(pyridin-2-yl)phenyl)-4-(methylsulfonyl)benzamide. MS (Q1) 444.0 $(M)^+$.

Example 263

N-(4-chloro-3-(pyridin-2-yl)phenyl)-2-iodo-4-(methylsulfonyl)benzamide

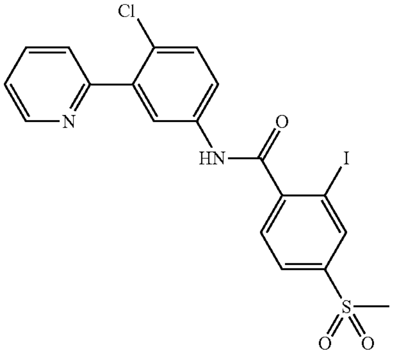 [SMILES: CS(=O)(=O)c1ccc(C(=O)Nc2ccc(Cl)c(-c3ccccn3)c2)c(I)c1]

600 mg of methyl 2-amino-4-(methylsulfonyl)benzoate was added to a solution of 4 mL of $H_2O$ and 1 mL of concentrated sulfuric acid. The solution was cooled to 0° C. and a solution of 206 mg of sodium nitrite in 1 mL of $H_2O$ was added slowly. The reaction mixture was stirred for 2 h and then a solution of 782 mg of potassium iodide in 2 mL of $H_2O$ was added dropwise at 0° C. The reaction was allowed to warm to room temperature and stirred for 5 h. The mixture was extracted with ethyl acetate. The combined organic extracts were washed with saturated $Na_2S_2O_3$, dried ($MgSO_4$) and evaporated. Purified by silica gel chromatography (5-50% ethyl acetate/hexane) to afford methyl 2-iodo-4-(methylsulfonyl)benzoate. 160 mg of methyl 2-iodo-4-(methylsulfonyl)benzoate was hydrolyzed via Procedure M to give 2-iodo-4-(methylsulfonyl)benzoic acid. 60 mg of 4-chloro-3-(pyridin-2-yl)aniline was coupled to 2-iodo-4-(methylsulfonyl)benzoic acid via Procedure G. The product was purified on reverse phase HPLC to yield N-(4-chloro-3-(pyridin-2-yl)phenyl)-2-iodo-4-(methylsulfonyl)benzamide. MS (Q1) 513.0 $(M)^+$.

Example 264

N-(4-chloro-3-(pyridin-2-yl)phenyl)-6-((3S,5R)-3,5-dimethylpiperazin-1-yl)-2-methylnicotinamide

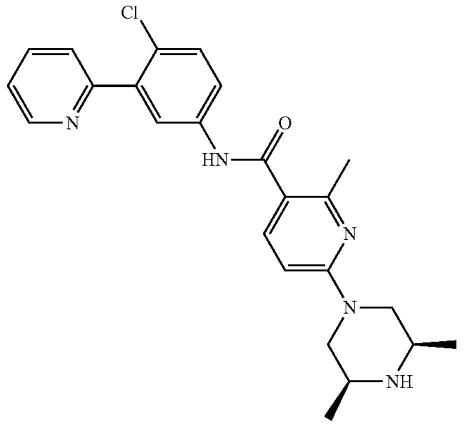 [SMILES: Cc1nc(N2C[C@@H](C)N[C@@H](C)C2)ccc1C(=O)Nc1ccc(Cl)c(-c2ccccn2)c1]

Stoichiometric amounts (0.04 mol) of methyl proplolate and ethyl 3-aminocrotonate were heated to 140° C. for 1 h. 1 g of the crude (2E,4Z)-methyl-4-(1-aminoethylidene)-5-oxooct-2-enoate in 4 mL of DMF was heated to 230° C. in a sealed microwave reactor for 40 min. The reaction mixture was diluted with ethyl acetate, washed with $H_2O$, dried ($MgSO_4$) and evaporated to afford crude ethyl 6-hydroxy-2-methylnicotinate. A mixture of 800 mg of crude ethyl 6-hydroxy-2-methylnicotinate in 4 mL of phosphorus oxychloride was heated to 150° C. in a sealed microwave reactor for 15 min. The reaction mixture was poured into ice/water, extracted with diethyl ether. The combined organic layers were dried ($MgSO_4$) and evaporated. Purified by silica gel chromatograph (0-20% ethyl acetate/hexane) to yield ethyl 6-chloro-2-methylnicotinate. 400 mg of ethyl 6-chloro-2-methylnicotinate was hydrolyzed via Procedure M to give 6-chloro-2-methylnicotinic acid. 300 mg of 4-chloro-3-(pyridin-2-yl)aniline was coupled to 6-chloro-2-methylnicotinic acid via Procedure G. The reaction mixture was diluted with ethyl acetate, washed with 0.1 N sodium hydroxide and brine, dried ($MgSO_4$) and evaporated to afford 6-chloro-N-(4-chloro-3-(pyridin-2-yl)phenyl)-2-methylnicotinamide. Procedure F was performed using 100 mg of 6-chloro-N-(4-chloro-3-(pyridin-2-yl)phenyl)-2-methylnicotinamide and 128 mg of 2,6-dimethylpiperazine in 1 mL of BuOH. Purified by reverse phase HPLC to yield N-(4-chloro-3-(pyridin-2-yl)phenyl)-6-((3S,5R)-3,5-dimethylpiperazin-1-yl)-2-methylnicotinamide. MS (Q1) 436.3 $(M)^+$.

Example 265

(S)—N-(4-chloro-3-(pyridin-2-yl)phenyl)-2-methyl-6-(3-methylpiperazin-1-yl)nicotinamide

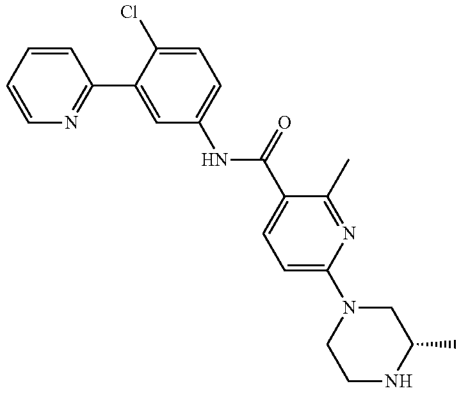 [SMILES: Cc1nc(N2CCN[C@@H](C)C2)ccc1C(=O)Nc1ccc(Cl)c(-c2ccccn2)c1]

Procedure F was performed using 100 mg of 6-chloro-N-(4-chloro-3-(pyridin-2-yl)phenyl)-2-methylnicotinamide and 112 mg of S-(−)-2-methylpiperizine in 1 mL of BuOH. Purified by reverse phase HPLC to yield (S)—N-(4-chloro-3-(pyridin-2-yl)phenyl)-2-methyl-6-(3-methylpiperazin-1-yl)nicotinamide. MS (Q1) 422.3 $(M)^+$.

Example 266

(R)—N-(4-chloro-3-(pyridin-2-yl)phenyl)-2-methyl-6-(3-methylpiperazin-1-yl)nicotinamide

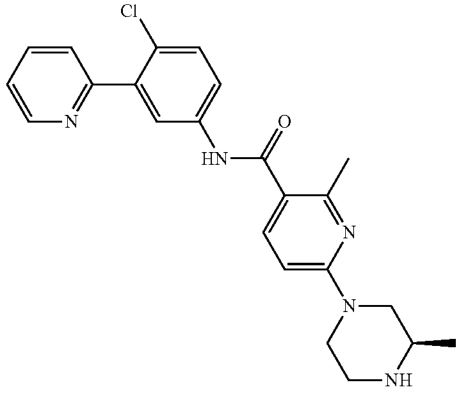 [SMILES: Cc1nc(N2CCN[C@H](C)C2)ccc1C(=O)Nc1ccc(Cl)c(-c2ccccn2)c1]

Procedure F was performed using 100 mg of 6-chloro-N-(4-chloro-3-(pyridin-2-yl)phenyl)-2-methylnicotinamide and 112 mg of R-(+)-2-methylpiperizine in 1 mL of BuOH. Purified by reverse phase HPLC to yield (R)—N-(4-chloro- 3-(pyridin-2-yl)phenyl)-2-methyl-6-(3-methylpiperazin-1-yl)nicotinamide. MS (Q1) 422.3 $(M)^+$.

Example 267

N-(4-chloro-3-(pyridin-2-yl)phenyl)-2-methyl-6-(3-methylpiperazin-1-yl)nicotinamide

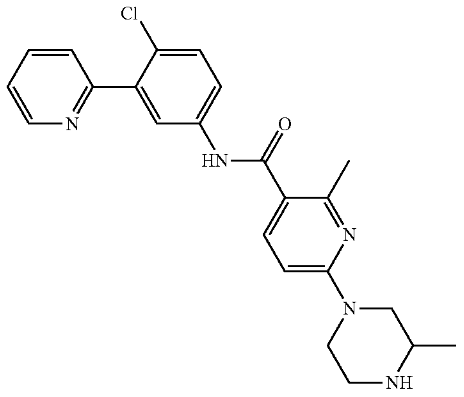 [SMILES: Cc1nc(N2CCNC(C)C2)ccc1C(=O)Nc1ccc(Cl)c(-c2ccccn2)c1]

Procedure F was performed using 100 mg of 6-chloro-N-(4-chloro-3-(pyridin-2-yl)phenyl)-2-methylnicotinamide and 112 mg of 2-methylpiperizine in 1 mL of BuOH. Purified by reverse phase HPLC to yield N-(4-chloro-3-(pyridin-2-yl)phenyl)-2-methyl-6-(3-methylpiperazin-1-yl)nicotinamide. MS (Q1) 422.3 $(M)^+$.

Example 268

N-(4-chloro-3-(pyridin-2-yl)phenyl)-6-(4-(2-hydroxyacetyl)piperazin-1-yl)-2-methylnicotinamide

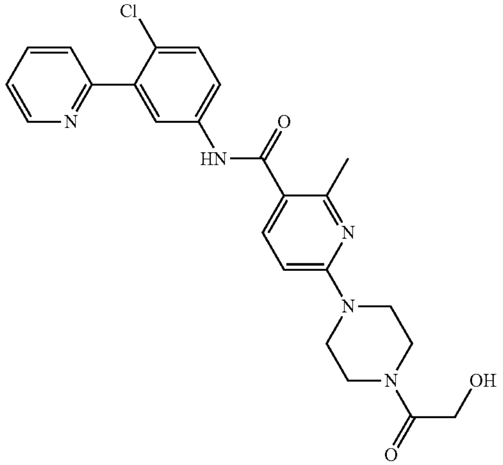 [SMILES: Cc1nc(N2CCN(C(=O)CO)CC2)ccc1C(=O)Nc1ccc(Cl)c(-c2ccccn2)c1]

100 mg of N-(4-chloro-3-(pyridin-2-yl)phenyl)-2-methyl-6-(piperazin-1-yl)nicotinamide was coupled to glycolic acid via Procedure G. The product was purified on reverse phase HPLC to yield N-(4-chloro-3-(pyridin-2-yl)phenyl)-6-(4-(2-hydroxyacetyl)piperazin-1-yl)-2-methylnicotinamide. MS (Q1) 466.3 $(M)^+$.

Example 269

N-(4-chloro-3-(pyridin-2-yl)phenyl)-2-methyl-6-(4-(methylsulfonyl)piperazin-1-yl)nicotinamide

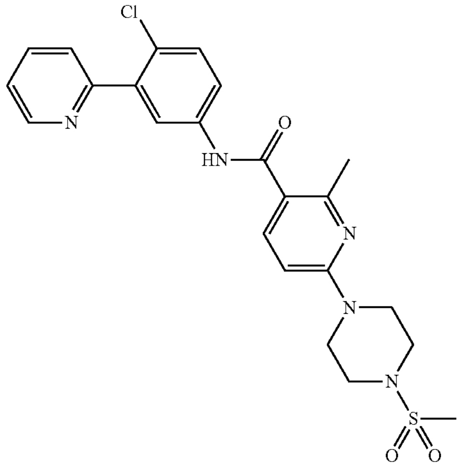 [SMILES: Cc1nc(N2CCN(S(C)(=O)=O)CC2)ccc1C(=O)Nc1ccc(Cl)c(-c2ccccn2)c1]

1.3 mL of methanesulfonyl chloride was slowly added to a solution of 2 g of 1-Boc-piperazine and 1.3 mL of pyridine in 6 mL of dichloromethane at 0° C. The reaction mixture was allowed to warm to room temperature and stirred for 2 h while being monitored by TLC. Upon completion, the mixture was diluted with dichloromethane, washed with $H_2O$, dried ($MgSO_4$) and evaporated. Purified by silica gel chromatograph (20-100% ethyl acetate/hexane) to afford tert-butyl-4-(methylsulfonyl)piperazine-1-carboxylate. 930 mg of tert-butyl-4-(methylsulfonyl)piperazine-1-carboxylate was treated with 4N HCl in dioxane for 2 h. The reaction mixture was evaporated to give the HCl salt of 1-(methylsulfonyl)piperazine. Procedure F was performed using 50 mg of 6-chloro-N-(4-chloro-3-(pyridin-2-yl)phenyl)-2-methylnicotinamide, 69 mg of 1-(methylsulfonyl)piperazine and DIEPA (1 eq) in 0.5 mL of BuOH. Purified by reverse phase HPLC to yield N-(4-chloro-3-(pyridin-2-yl)phenyl)-2-methyl-6-(4-(methylsulfonyl)piperazin-1-yl)nicotinamide. MS (Q1) 486.3 $(M)^+$.

Example 270

N-(4-chloro-3-(pyridin-2-yl)phenyl)-2-methyl-6-thiomorpholinonicotinamide

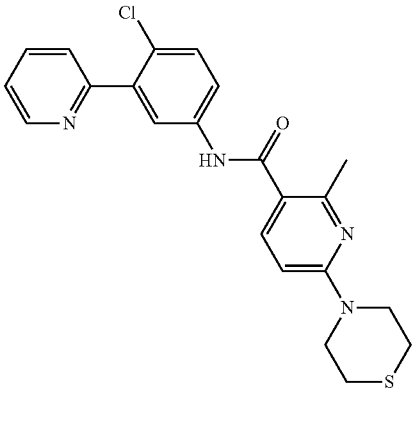 [SMILES: Cc1nc(N2CCSCC2)ccc1C(=O)Nc1ccc(Cl)c(-c2ccccn2)c1]

Procedure F was performed using 90 mg of 6-chloro-N-(4-chloro-3-(pyridin-2-yl)phenyl)-2-methylnicotinamide and 78 μL of thiomorpholine in 1 mL of BuOH. Purified by reverse phase HPLC to yield N-(4-chloro-3-(pyridin-2-yl)phenyl)-2-methyl-6-thiomorpholinonicotinamide. MS (Q1) 425.3 (M)$^+$.

Example 271

N-(4-chloro-3-(pyridin-2-yl)phenyl)-2-methyl-6-sulfonylmorpholinonicotinamide

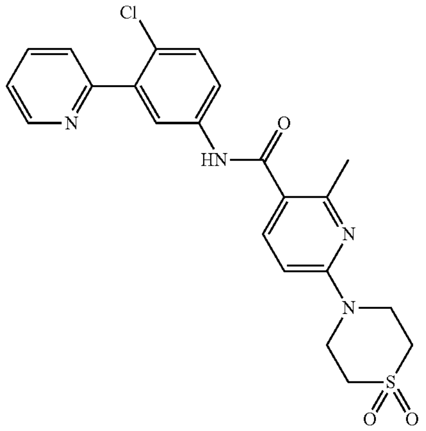 [SMILES: Cc1nc(N2CCS(=O)(=O)CC2)ccc1C(=O)Nc1ccc(Cl)c(-c2ccccn2)c1]

100 mg of N-(4-chloro-3-(pyridin-2-yl)phenyl)-2-methyl-6-thiomorpholinonicotinamide was reacted via produce R. The product was purified on reverse phase HPLC to yield N-(4-chloro-3-(pyridin-2-yl)phenyl)-2-methyl-6-sulfonylmorpholinonicotinamide. MS (Q1) 457.3 (M)$^+$.

Example 272

N-(4-chloro-3-(pyridin-2-yl)phenyl)-2-methyl-6-(2-(pyrrolidin-1-yl)ethylamino)-nicotinamide

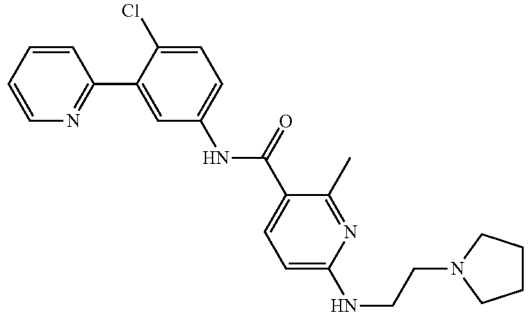 [SMILES: Cc1nc(NCCN2CCCC2)ccc1C(=O)Nc1ccc(Cl)c(-c2ccccn2)c1]

Procedure F was performed using 100 mg of 6-chloro-N-(4-chloro-3-(pyridin-2-yl)phenyl)-2-methylnicotinamide and 70 μL of 1-(2-aminoethyl)pyrrolidine in 1 mL of BuOH. Purified by reverse phase HPLC to yield N-(4-chloro-3-(pyridin-2-yl)phenyl)-2-methyl-6-(2-(pyrrolidin-1-yl)ethylamino)nicotinamide. MS (Q1) 436.0 (M)$^+$.

Example 273

N-(4-chloro-3-(pyridin-2-yl)phenyl)-6-((2-(dimethylamino)ethyl)(methyl)amino)-2-methylnicotinamide

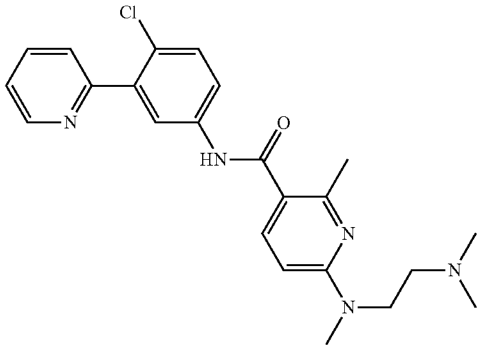 [SMILES: Cc1nc(N(C)CCN(C)C)ccc1C(=O)Nc1ccc(Cl)c(-c2ccccn2)c1]

Procedure F was performed using 60 mg of 6-chloro-N-(4-chloro-3-(pyridin-2-yl)phenyl)-2-methylnicotinamide and 66 μL of N,N,N'-trimethylethylenediamine in 0.5 mL of BuOH. Purified by reverse phase HPLC to yield N-(4-chloro-3-(pyridin-2-yl)phenyl)-6-((2-(dimethylamino)ethyl)(methyl)amino)-2-methylnicotinamide. MS (Q1) 424.0 (M)$^+$.

Example 274

N-(4-chloro-3-(pyridin-2-yl)phenyl)-2-methyl-6-(3-oxopiperazin-1-yl)nicotinamide

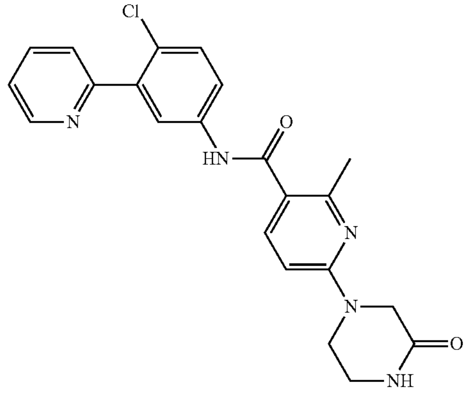 [SMILES: Cc1nc(N2CCNC(=O)C2)ccc1C(=O)Nc1ccc(Cl)c(-c2ccccn2)c1]

Procedure F was performed using 100 mg of 6-chloro-N-(4-chloro-3-(pyridin-2-yl)phenyl)-2-methylnicotinamide and 84 mg of piperazine-2-one in 1 mL of BuOH. Purified by reverse phase HPLC to yield N-(4-chloro-3-(pyridin-2-yl)phenyl)-2-methyl-6-(3-oxopiperazin-1-yl)nicotinamide. MS (Q1) 422.3 (M)$^+$.

Example 275

N-(4-chloro-3-(pyridin-2-yl)phenyl)-2-methyl-6-(3-methyl-1H-1,2,4-triazol-1-yl)nicotinamide

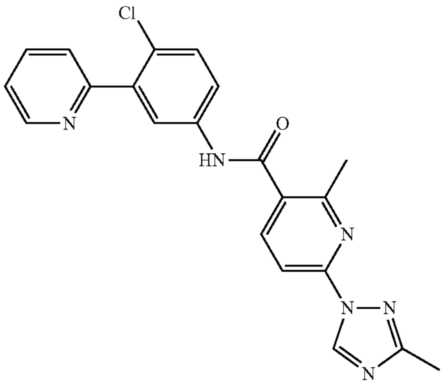 [SMILES: Cc1ncn(-c2ccc(C(=O)Nc3ccc(Cl)c(-c4ccccn4)c3)c(C)n2)n1]

A mixture of 57 mg of 3-methyl-1,2,4-triazol and 16 mg of sodium hydride in 2 mL of DMF was stirred for 10 min. 80 mg of 6-chloro-N-(4-chloro-3-(pyridin-2-yl)phenyl)-2-methylnicotinamide was added. The reaction was heated to 140° C. for 16 h. The reaction mixture was quenched with MeOH and evaporated. Purified by reverse phase HPLC to yield N-(4-chloro-3-(pyridin-2-yl)phenyl)-2-methyl-6-(3-methyl-1H-1,2,4-triazol-1-yl)nicotinamide. MS (Q1) 405.3 (M)$^+$.

Example 276

N-(4-chloro-3-(pyridin-2-yl)phenyl)-2-methyl-6-(1H-1,2,4-triazol-1-yl)nicotinamide

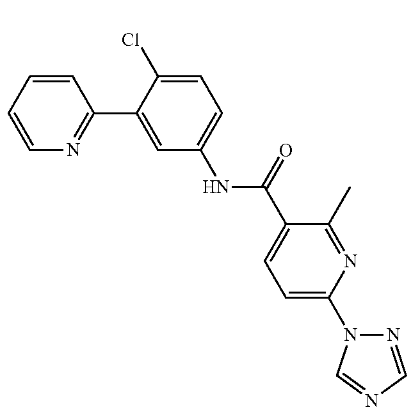 [SMILES: Cc1nc(-n2cncn2)ccc1C(=O)Nc1ccc(Cl)c(-c2ccccn2)c1]

A mixture of 41 mg of 1,2,4-triazol and 14 mg of sodium hydride in 2 mL of DMF was stirred for 10 min. 70 mg of 6-chloro-N-(4-chloro-3-(pyridin-2-yl)phenyl)-2-methylnicotinamide was added. The reaction was heated to 140° C. for 6 h. The reaction mixture was quenched with MeOH and evaporated. Purified by reverse phase HPLC to yield N-(4-chloro-3-(pyridin-2-yl)phenyl)-2-methyl-6-(1H-1,2,4-triazol-1-yl)nicotinamide. MS (Q1) 391.4 (M)$^+$.

Example 277

N-(4-chloro-3-(pyridin-2-yl)phenyl)-2-methyl-6-(1H-pyrazol-1-yl)nicotinamide

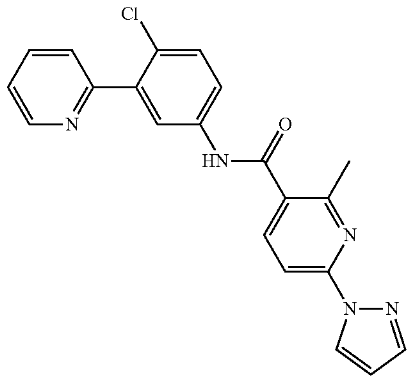 [SMILES: Cc1nc(-n2cccn2)ccc1C(=O)Nc1ccc(Cl)c(-c2ccccn2)c1]

A mixture of 52 mg of pyrazole and 18 mg of sodium hydride in 2 mL of DMF were stirred for 10 min. 90 mg of 6-chloro-N-(4-chloro-3-(pyridin-2-yl)phenyl)-2-methylnicotinamide was added. The reaction was heated to 140° C. for 5 h. The reaction mixture was quenched with MeOH and evaporated. Purified by reverse phase HPLC to yield N-(4-chloro-3-(pyridin-2-yl)phenyl)-2-methyl-6-(1H-pyrazol-1-yl)nicotinamide. MS (Q1) 390.0 (M)$^+$.

Example 278

N-(4-chloro-3-(pyridin-2-yl)phenyl)-2-methyl-6-(piperazin-1-yl)nicotinamide

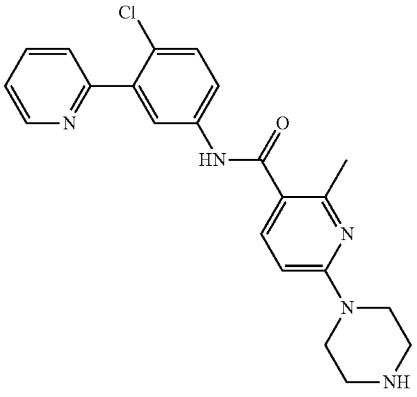 [SMILES: Cc1nc(N2CCNCC2)ccc1C(=O)Nc1ccc(Cl)c(-c2ccccn2)c1]

Procedure F was performed using 80 mg of 6-chloro-N-(4-chloro-3-(pyridin-2-yl)phenyl)-2-methylnicotinamide and 209 mg of 1-Boc-piperizine in 1 mL of BuOH. The reaction mixture was evaporated to afford tert-butyl 4-(5-(4-chloro-3-(pyridin-2-yl)phenylcarbamoyl)-6-methylpyridin-2-yl)piperazine-1-carboxylate. 150 mg of tert-butyl 4-(5-(4-chloro-3-(pyridin-2-yl)phenylcarbamoyl)-6-methylpyridin-2-yl)piperazine-1-carboxylate was treated with TFA (1 mL) containing trace amounts of $H_2O$ for 2 h. The reaction mixture was diluted with ethyl acetate, washed with 0.1N sodium hydroxide and brine, dried ($MgSO_4$) and evaporated. Purified by reverse phase HPLC to yield N-(4-chloro-3-(pyridin-2-yl)phenyl)-2-methyl-6-(piperazin-1-yl)nicotinamide. MS (Q1) 408.3 (M)$^+$.

Example 279

(R)—N-(4-chloro-3-(pyridin-2-yl)phenyl)-6-(2-hydroxypropylamino)-2-methylnicotinamide

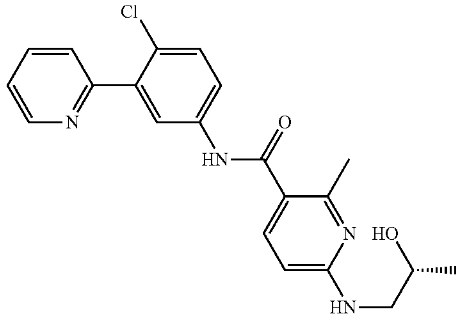 [SMILES: Cc1nc(NC[C@@H](C)O)ccc1C(=O)Nc1ccc(Cl)c(-c2ccccn2)c1]

Procedure F was performed using 60 mg of 6-chloro-N-(4-chloro-3-(pyridin-2-yl)phenyl)-2-methylnicotinamide and 116 μL of R-(−)-1-amino-2-propanol in 0.5 mL of BuOH. Purified by reverse phase HPLC to yield (R)—N-(4-chloro-3-(pyridin-2-yl)phenyl)-6-(2-hydroxypropylamino)-2-methylnicotinamide. MS (Q1) 397.4 (M)$^+$.

Example 280

(S)—N-(4-chloro-3-(pyridin-2-yl)phenyl)-6-(2-hydroxypropylamino)-2-methylnicotinamide

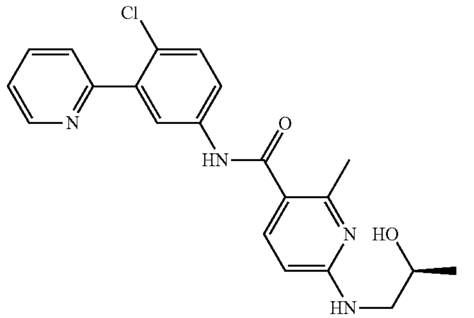 [SMILES: Cc1nc(NC[C@H](C)O)ccc1C(=O)Nc1ccc(Cl)c(-c2ccccn2)c1]

Procedure F was performed using 60 mg of 6-chloro-N-(4-chloro-3-(pyridin-2-yl)phenyl)-2-methylnicotinamide and 116 μL of S-(+)-1-amino-2-propanol in 0.5 mL of BuOH. Purified by reverse phase HPLC to yield (S)—N-(4-chloro-3-(pyridin-2-yl)phenyl)-6-(2-hydroxypropylamino)-2-methylnicotinamide. MS (Q1) 397.4 (M)$^+$.

Example 281

6-(2-(1H-imidazol-4-yl)ethylamino)-N-(4-chloro-3-(pyridin-2-yl)phenyl)-2-methylnicotinamide

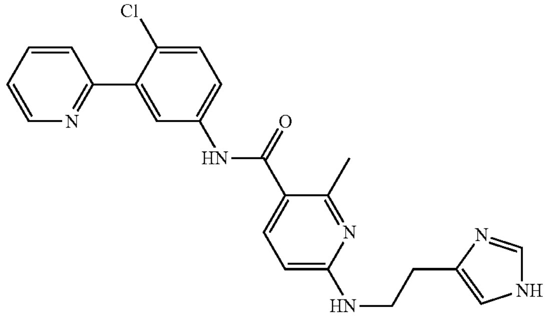 [SMILES: Cc1nc(NCCc2c[nH]cn2)ccc1C(=O)Nc1ccc(Cl)c(-c2ccccn2)c1]

Procedure F was performed using 60 mg of 6-chloro-N-(4-chloro-3-(pyridin-2-yl)phenyl)-2-methylnicotinamide and 93 mg of histamine in 0.5 mL of BuOH. Purified by reverse phase HPLC to yield 6-(2-(1H-imidazol-4-yl)ethylamino)-N-(4-chloro-3-(pyridin-2-yl)phenyl)-2-methylnicotinamide. MS (Q1) 433.0 (M)

Example 282

6-(4-acetylpiperazin-1-yl)-N-(4-chloro-3-(pyridin-2-yl)phenyl)-2-methylnicotinamide

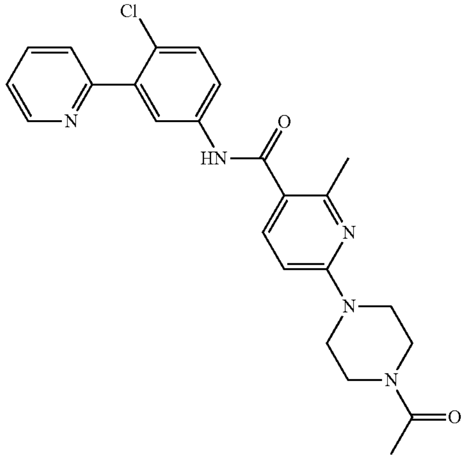 [SMILES: CC(=O)N1CCN(c2ccc(C(=O)Nc3ccc(Cl)c(-c4ccccn4)c3)c(C)n2)CC1]

Procedure F was performed using 55 mg of 6-chloro-N-(4-chloro-3-(pyridin-2-yl)phenyl)-2-methylnicotinamide and 99 mg of 1-acetylpiperazine in 0.5 mL of BuOH. Purified by reverse phase HPLC to yield 6-(4-acetylpiperazin-1-yl)-N-(4-chloro-3-(pyridin-2-yl)phenyl)-2-methylnicotinamide. MS (Q1) 450.4 (M)+.

Example 283

N-(4-chloro-3-(pyridin-2-yl)phenyl)-6-(2,6-dimethylmorpholino)-2-methylnicotinamide

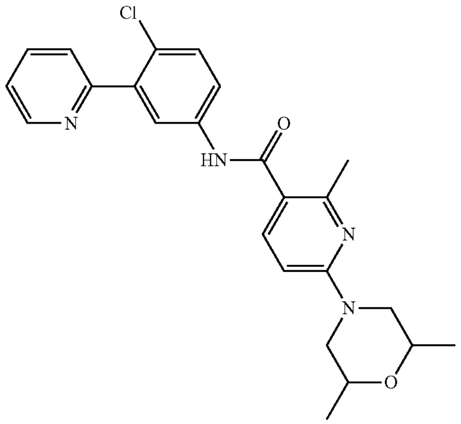 [SMILES: Cc1nc(N2CC(C)OC(C)C2)ccc1C(=O)Nc1ccc(Cl)c(-c2ccccn2)c1]

Procedure F was performed using 55 mg of 6-chloro-N-(4-chloro-3-(pyridin-2-yl)phenyl)-2-methylnicotinamide and 95 mg of 2,6-dimethylmorpholine in 0.5 mL of BuOH. Purified by reverse phase HPLC to yield N-(4-chloro-3-(pyridin-2-yl)phenyl)-6-(2,6-dimethylmorpholino)-2-methylnicotinamide. MS (Q1) 436.2 (M)+.

Example 284

N-(4-chloro-3-(pyridin-2-yl)phenyl)-6-(4-hydroxypiperidin-1-yl)-2-methylnicotinamide

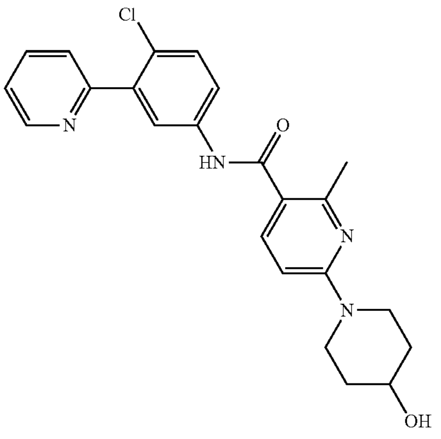 [SMILES: Cc1nc(N2CCC(O)CC2)ccc1C(=O)Nc1ccc(Cl)c(-c2ccccn2)c1]

Procedure F was performed using 55 mg of 6-chloro-N-(4-chloro-3-(pyridin-2-yl)phenyl)-2-methylnicotinamide and 78 mg of 4-hydropiperidine in 0.5 mL of BuOH. Purified by reverse phase HPLC to yield N-(4-chloro-3-(pyridin-2-yl)phenyl)-6-(4-hydroxypiperidin-1-yl)-2-methylnicotinamide. MS (Q1) 422.1 (M)+.

Example 285

6-(3-(1H-imidazol-1-yl)propylamino)-N-(4-chloro-3-(pyridin-2-yl)phenyl)-2-methylnicotinamide

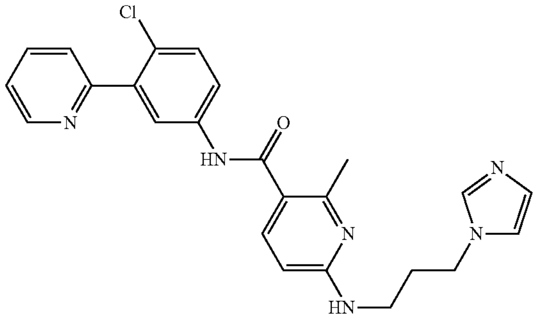 [SMILES: Cc1nc(NCCCn2ccnc2)ccc1C(=O)Nc1ccc(Cl)c(-c2ccccn2)c1]

Procedure F was performed using 55 mg of 6-chloro-N-(4-chloro-3-(pyridin-2-yl)phenyl)-2-methylnicotinamide and 92 μL of 1-(3-aminopropyl)-imidazole in 0.5 mL of BuOH. Purified by reverse phase HPLC to yield 6-(3-(1H-imidazol-1-yl)propylamino)-N-(4-chloro-3-(pyridin-2-yl)phenyl)-2-methylnicotinamide. MS (Q1) 446.1 (M)+.

Example 286

N-(4-chloro-3-(pyridin-2-yl)phenyl)-6-(isobutylamino)-2-methylnicotinamide

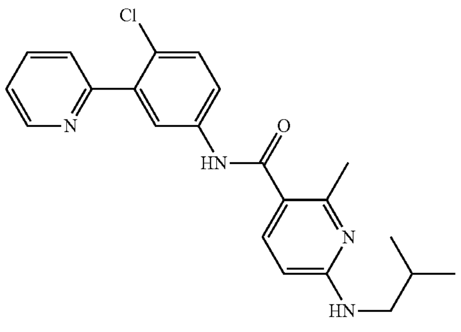 [SMILES: Cc1nc(NCC(C)C)ccc1C(=O)Nc1ccc(Cl)c(-c2ccccn2)c1]

Procedure F was performed using 50 mg of 6-chloro-N-(4-chloro-3-(pyridin-2-yl)phenyl)-2-methylnicotinamide and 70 μL of isobutylamine in 0.5 mL of BuOH. Purified by reverse phase HPLC to yield N-(4-chloro-3-(pyridin-2-yl)phenyl)-6-(isobutylamino)-2-methylnicotinamide. MS (Q1) 395.4 $(M)^+$.

Example 287

2-chloro-$N^1$-(4-chloro-3-(pyridin-2-yl)phenyl)-$N^4$,$N^4$-dimethylterephthalamide

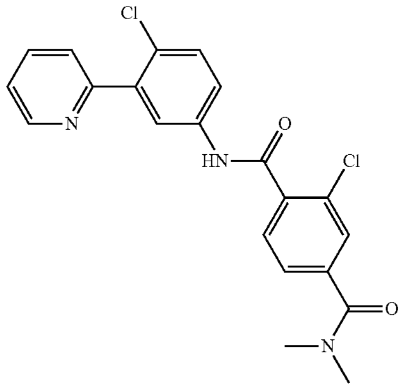 [SMILES: CN(C)C(=O)c1ccc(C(=O)Nc2ccc(Cl)c(-c3ccccn3)c2)c(Cl)c1]

290 mg of dimethylamine hydrochloride was coupled to 1 g of 4-(tert-butoxycarbonyl)-3-chlorobenzoic acid via Procedure G. The reaction mixture was diluted with ethyl acetate, washed with 0.1 N HCl, 0.1 N NaOH and brine, dried ($MgSO_4$) and evaporated to afford tert-butyl 2-chloro-4-(dimethylcarbamoyl)benzoate. 1.1 g of tert-butyl 2-chloro-4-(dimethylcarbamoyl)benzoate was treated with TFA (4 mL) containing trace amounts of $H_2O$ for 2 h. The reaction mixture was evaporated, and then added 0.1 N HCl. The resulting solid was filtered and washed with $H_2O$ to yield 2-chloro-4-(dimethylcarbamoyl)benzoic acid. 100 mg of 4-chloro-3-(pyridine-2-yl)aniline was coupled to 2-chloro-4-(dimethylcarbamoyl)benzoic acid via Procedure G. The product was purified on reverse phase HPLC to yield 2-chloro-$N^1$-(4-chloro-3-(pyridin-2-yl)phenyl)-$N^4$,$N^4$-dimethylterephthalamide. MS (Q1) 414.1 $(M)^+$.

Example 288

N-(4-chloro-3-(pyridin-2-yl)phenyl)-6-(morpholine-4-carbonyl)nicotinamide

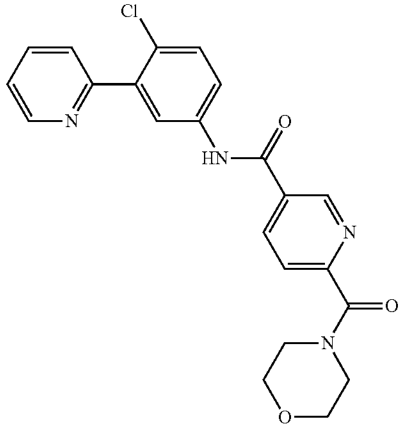 [SMILES: O=C(Nc1ccc(Cl)c(-c2ccccn2)c1)c1ccc(C(=O)N2CCOCC2)nc1]

63 mg of morpholine was coupled to 120 mg of 5-(methoxycarbonyl)pyridine-2-carboxylic acid via Procedure G. The reaction mixture was diluted with ethyl acetate, washed with saturated sodium bicarbonate and brine, dried ($MgSO_4$) and evaporated to afford methyl 6-(morpholine-4-carbonyl)nicotinate. 180 mg of methyl 6-(morpholine-4-carbonyl)nicotinate was hydrolyzed via Procedure M to give 6-(morpholine-4-carbonyl)nicotinic acid. 100 mg of 4-chloro-3-(pyridine-2-yl)aniline was coupled to 6-(morpholine-4-carbonyl)nicotinic acid via Procedure G. The product was purified on reverse phase HPLC to yield 2-chloro-N-(4-chloro-3-(pyridin-2-yl)phenyl)-6-(morpholine-4-carbonyl)nicotinamide. MS (Q1) 423.4 $(M)^+$.

Example 289

N-(4-Chloro-3-(pyridin-2-yl)phenyl)-3-hydroxy-4-(methylsulfonylmethyl)benzamide

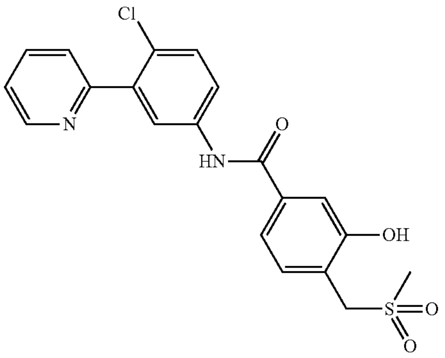 [SMILES: CS(=O)(=O)Cc1ccc(C(=O)Nc2ccc(Cl)c(-c3ccccn3)c2)cc1O]

3-Hydroxy-4-methylbenzoic acid (6.86 g, 45.1 mmol) was dissolved in methanol (200 ml). 4N HCl in 1,4-dioxane (34 ml, 0.135 mmol HCl) was added and the solution heated to 55° C. for 18 hours. The solvent was concentrated on a rotary evaporator, and then partitioned between water and ethyl acetate. The aqueous portion was extracted with ethyl acetate once, and the ethyl acetate extracts were combined and washed with water once, brine once, dried with $MgSO_4$, and evaporated to methyl 3-hydroxy-4-methylbenzoate as a crude tan solid (6.66 g) which was used without purification. Methyl 3-hydroxy-4-methylbenzoate (6.66 g, 40.1 mmol) was dissolved in dichloromethane (200 ml), treated with pyridine (4.3 ml, 60.2 mmol), and cooled in an ice water bath. Acetyl chloride (3.6 ml, 50.1 mmol) was added dropwise. The solution was allowed to warm to room temperature, with stirring, over 18 hours. The solution was washed with 1 N aqueous HCl twice, water once, brine once, dried with $MgSO_4$, and evaporated to methyl 3-acetoxy-4-methylbenzoate as a crude tan oil (6.93 g) which was used without purification. Methyl 3-acetoxy-4-methylbenzoate (6.38 g, 30.6 mmol) was dissolved in carbon tetrachloride (130 ml) and treated with benzoic peroxyanhydride (200 mg, 0.83 mmol) and NBS (5.45 g, 30.6 mmol), then heated to 85° C. for 3 hours. After cooling to room temperature, the solution was filtered through Celite 545 and evaporated to a crude yellow solid which was purified by silica gel flash chromatography (5% dichloromethane/hexanes increasing to 35% dichloromethane/hexanes) to yield methyl 3-acetoxy-4-(bromomethyl)benzoate as an off white solid (4.18 g). Methyl 3-acetoxy-4-(bromomethyl)benzoate (2.00 g, 6.97 mmol) was used in procedure O to afford methyl 3-acetoxy-4-(methylsulfonylmethyl)benzoate as a white solid (1.67 g) which was used without purification. Methyl 3-acetoxy-4-(methylsulfonylmethyl)benzoate (1.67 g, 5.83 mmol) was saponified via procedure M to afford 3-hydroxy-4-(methylsulfonylmethyl) benzoic acid as a white solid (1.05 g) which was used without purification. 3-Hydroxy-4-(methylsulfonylmethyl)benzoic acid (860 mg, 3.74 mmol) was dissolved in 1,4-dioxane (25 ml) and treated with thionyl chloride (8 ml) and DMF (5 drops), then heated to 50° C. for 2 hours. The reaction was cooled and evaporated to an oil. The oil residue was dissolved in dichloromethane (40 ml), cooled in an ice water bath, and treated dropwise with a solution of 4-chloro-3-(pyridin-2-yl) aniline (767 mg, 3.74 mmol) in dichloromethane (30 ml). The reaction was stirred 18 hours, allowing to warm to room temperature. The reaction was diluted with dichloromethane (40 ml) and stirred vigorously with water (50 ml) while acidifying to pH 6 with 1 M citric acid. The dichloromethane portion was separated, and enough methanol was added to dissolve precipitating solids. The solution was washed with water once, brine once, dried with $MgSO_4$, and evaporated to a solid which was triturated with dichloromethane, filtered, and air dried to yield 909 mg of crude product. A portion (20 mg) was purified on reverse phase HPLC to yield 16 mg of purified N-(4-chloro-3-(pyridin-2-yl)phenyl)-3-hydroxy-4-(methylsulfonylmethyl)benzamide as a white solid. MS (Q1) 417 $(M)^+$.

Example 290

N-(4-Chloro-3-(pyridin-2-yl)phenyl)-3-isobutoxy-4-(methylsulfonylmethyl)benzamide

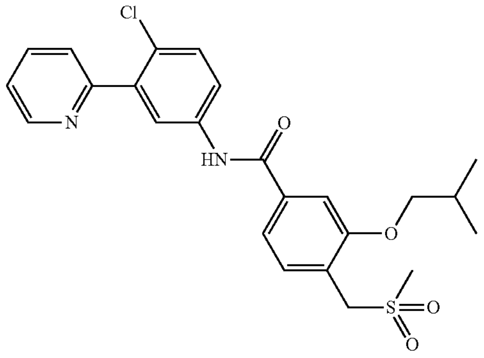 [SMILES: CC(C)COc1cc(C(=O)Nc2ccc(Cl)c(-c3ccccn3)c2)ccc1CS(C)(=O)=O]

N-(4-chloro-3-(pyridin-2-yl)phenyl)-3-hydroxy-4-(methylsulfonylmethyl)benzamide (50 mg, 0.12 mmol) was treated with 1-bromo-2-methylpropane (26 μl, 0.24 mmol) via procedure U to yield 19 mg of N-(4-chloro-3-(pyridin-2-yl)phenyl)-3-isobutoxy-4-(methylsulfonylmethyl)benzamide. MS (Q1) 473 $(M)^+$.

Example 291

N-(4-Chloro-3-(pyridin-2-yl)phenyl)-3-methoxy-4-(methylsulfonylmethyl)benzamide

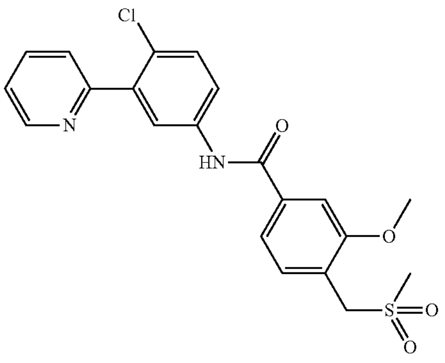 [SMILES: COc1cc(C(=O)Nc2ccc(Cl)c(-c3ccccn3)c2)ccc1CS(C)(=O)=O]

N-(4-Chloro-3-(pyridin-2-yl)phenyl)-3-hydroxy-4-(methylsulfonylmethyl)benzamide (50 mg, 0.12 mmol) was treated with iodomethane (7.5 μl, 0.12 mmol) via procedure U to yield 12 mg of N-(4-chloro-3-(pyridin-2-yl)phenyl)-3-methoxy-4-(methylsulfonylmethyl)benzamide. MS (Q1) 431 $(M)^+$.

Example 292

N-(4-Chloro-3-(pyridin-2-yl)phenyl)-3-ethoxy-4-(methylsulfonylmethyl)benzamide

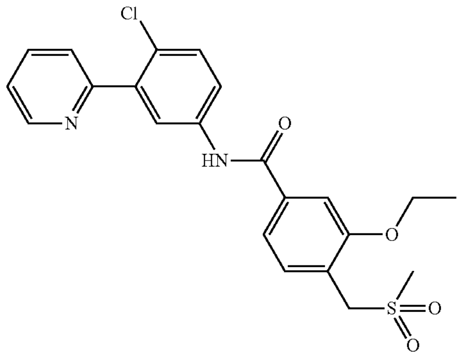 [SMILES: CCOc1cc(C(=O)Nc2ccc(Cl)c(-c3ccccn3)c2)ccc1CS(C)(=O)=O]

N-(4-Chloro-3-(pyridin-2-yl)phenyl)-3-hydroxy-4-(methylsulfonylmethyl)benzamide (50 mg, 0.12 mmol) was treated with iodoethane (10 μl, 0.12 mmol) via procedure U to yield 22 mg of N-(4-chloro-3-(pyridin-2-yl)phenyl)-3-ethoxy-4-(methylsulfonylmethyl)benzamide. MS (Q1) 445 $(M)^+$.

Example 293

N-(4-Chloro-3-(pyridin-2-yl)phenyl)-3-(2-(4-(methylsulfonyl)piperazin-1-yl)ethoxy)-4-(methylsulfonylmethyl)benzamide

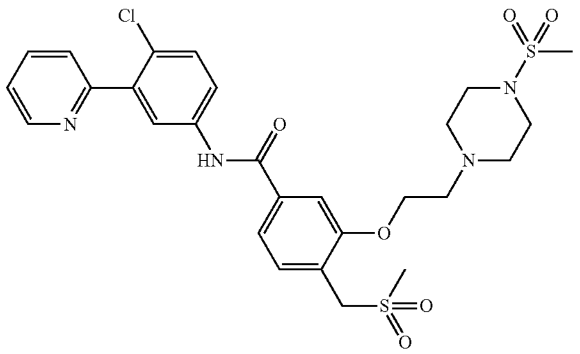 [SMILES: CS(=O)(=O)Cc1ccc(C(=O)Nc2ccc(Cl)c(-c3ccccn3)c2)cc1OCCN1CCN(S(C)(=O)=O)CC1]

N-(4-Chloro-3-(pyridin-2-yl)phenyl)-3-hydroxy-4-(methylsulfonylmethyl)benzamide (1.00 g, 2.40 mmol) was dissolved in DMF (20 ml). Cesium carbonate (1.56 g, 4.8 mmol) and 1,2-dibromoethane (0.83 ml, 9.6 mmol) were added, and the reaction was stirred at 50° C. for 18 hours. The reaction was quenched with water, basified with 10% aqueous NaOH, and extracted with ethyl acetate twice. The ethyl extracts were washed with water once, brine once, dried with $MgSO_4$, and evaporated to a crude oil which was purified by chromatography (25% hexanes in ethyl acetate) to yield 490 mg of 3-(2-bromoethoxy)-N-(4-chloro-3-(pyridin-2-yl)phenyl)-4-(methylsulfonylmethyl)benzamide as a yellow solid. 3-(2-Bromoethoxy)-N-(4-chloro-3-(pyridin-2-yl)phenyl)-4-(methylsulfonylmethyl)benzamide (100 mg, 0.19 mmol) was dissolved in DMF (2.0 ml), and potassium carbonate (32 mg, 0.23 mmol) and tert-butyl piperazine-1-carboxylate (38 mg, 0.21 mmol) were added. The reaction was stirred for 18 hours at room temperature, quenched in water, and extracted with ethyl acetate twice. The ethyl acetate extracts were washed with water once, brine once, dried with $MgSO_4$, and evaporated to a crude oil. The oil was dissolved in dichloromethane (1 ml) and treated with trifluoroacetic acid (3 ml) for 1 hour. The reaction was evaporated to dryness, and the crude solid was purified on reverse phase HPLC to yield 63 mg of N-(4-chloro-3-(pyridin-2-yl)phenyl)-4-(methylsulfonylmethyl)-3-(2-(piperazin-1-yl)ethoxy)benzamide as a white solid. N-(4-Chloro-3-(pyridin-2-yl)phenyl)-4-(methylsulfonylmethyl)-3-(2-(piperazin-1-yl)ethoxy)benzamide (30 mg, 0.047 mmol) was dissolved in dichloromethane (1.5 ml) and THF (1.0 ml). N-ethyl-N-isopropylpropan-2-amine (18 μl, 0.10 mmol) and methanesulfonyl chloride (4 μl, 0.051 mmol) were added, and the reaction stirred at room temperature for 72 hours. Additional N-ethyl-N-isopropylpropan-2-amine (9 μl, 0.051 mmol) and methanesulfonyl chloride (4 μl, 0.051 mmol) were added and the reaction stirred for 2 hours. After a further addition of methanesulfonyl chloride (4 μl, 0.051 mmol), the reaction was stirred for 2 hours and evaporated to a crude solid which was purified on reverse phase HPLC to yield 8 mg of N-(4-chloro-3-(pyridin-2-yl)phenyl)-3-(2-(4-(methylsulfonyl)piperazin-1-yl)ethoxy)-4-(methylsulfonylmethyl)benzamide. MS (Q1) 607 $(M)^+$.

Example 294

N-(4-Chloro-3-(pyridin-2-yl)phenyl)-4-(methylsulfonylmethyl)-3-(2-(3-oxopiperazin-1-yl)ethoxy)benzamide

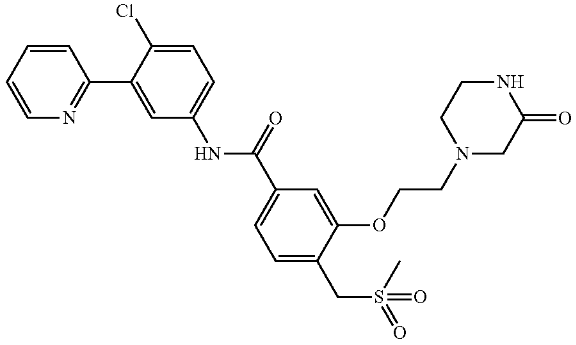 [SMILES: CS(=O)(=O)Cc1ccc(C(=O)Nc2ccc(Cl)c(-c3ccccn3)c2)cc1OCCN1CCNC(=O)C1]

3-(2-Bromoethoxy)-N-(4-chloro-3-(pyridin-2-yl)phenyl)-4-(methylsulfonylmethyl)benzamide (50 mg, 0.095 mmol) was dissolved in DMF (1.0 ml) and treated with potassium carbonate (18 mg, 0.13 mmol) and piperazin-2-one (11 mg, 0.11 mmol) for 18 hours. The reaction was heated for 2.0 hours at 50° C., then additional potassium carbonate (18 mg, 0.13 mmol) and piperazin-2-one (11 mg, 0.11 mmol) was added. After 2 hours, the reaction was quenched in 5% NaOH and extracted with ethyl acetate twice. The ethyl acetate extracts were washed with water once, brine once, dried with $MgSO_4$, and purified by reverse phase HPLC to yield 16 mg of N-(4-chloro-3-(pyridin-2-yl)phenyl)-4-(methylsulfonylmethyl)-3-(2-(3-oxopiperazin-1-yl)ethoxy)benzamide. MS (Q1) 558 $(M)^+$.

Example 295

3-(2-(4-Acetylpiperazin-1-yl)ethoxy)-N-(4-chloro-3-(pyridin-2-yl)phenyl)-4-(methylsulfonylmethyl)benzamide

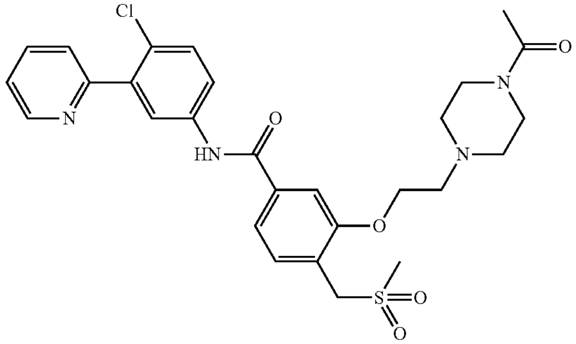 [SMILES: CC(=O)N1CCN(CCOc2cc(C(=O)Nc3ccc(Cl)c(-c4ccccn4)c3)ccc2CS(C)(=O)=O)CC1]

3-(2-Bromoethoxy)-N-(4-chloro-3-(pyridin-2-yl)phenyl)-4-(methylsulfonylmethyl)benzamide (50 mg, 0.095 mmol) was dissolved in DMF (1.0 ml) and treated with potassium carbonate (18 mg, 0.13 mmol) and 1-(piperazin-1-yl)ethanone (15 mg, 0.11 mmol) for 18 hours. The reaction was heated for 2.0 hours at 50° C., then additional potassium carbonate (18 mg, 0.13 mmol) and 1-(piperazin-1-yl)ethanone (15 mg, 0.11 mmol) was added. After 2 hours, the reaction was quenched in 5% NaOH and extracted with ethyl acetate twice. The ethyl acetate extracts were washed with water once, brine once, dried with $MgSO_4$, and purified by reverse phase HPLC to yield 18 mg of 3-(2-(4-acetylpiperazin-1-yl)ethoxy)-N-(4-chloro-3-(pyridin-2-yl)phenyl)-4-(methylsulfonylmethyl)benzamide. MS (Q1) 543 $(M)^+$.

Example 296

N-(4-Chloro-3-(pyridin-2-yl)phenyl)-3-(2-(2,6-dimethylmorpholino)ethoxy)-4-(methylsulfonylmethyl)benzamide

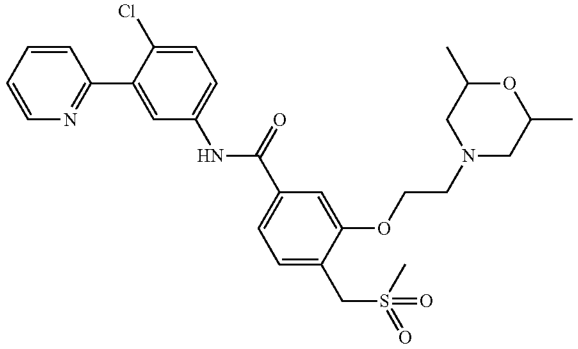 [SMILES: CC1CN(CCOc2cc(C(=O)Nc3ccc(Cl)c(-c4ccccn4)c3)ccc2CS(C)(=O)=O)CC(C)O1]

3-(2-Bromoethoxy)-N-(4-chloro-3-(pyridin-2-yl)phenyl)-4-(methylsulfonylmethyl)benzamide (50 mg, 0.095 mmol) was dissolved in DMF (1.0 ml) and treated with potassium carbonate (18 mg, 0.13 mmol) and 2,6-dimethylmorpholine (14 μl, 0.11 mmol), and stirred at room temperature for 18 hours. The reaction was quenched in 5% NaOH and extracted with ethyl acetate twice. The ethyl acetate extracts were washed with water once, brine once, dried with $MgSO_4$, and purified by reverse phase HPLC to yield 20 mg of N-(4-chloro-3-(pyridin-2-yl)phenyl)-3-(2-(2,6-dimethylmorpholino)ethoxy)-4-(methylsulfonylmethyl)benzamide. MS (Q1) 571 $(M)^+$.

Example 297

N-(4-Chloro-3-(pyridin-2-yl)phenyl)-4-(methylsulfonylmethyl)-3-(2-morpholinoethoxy)benzamide

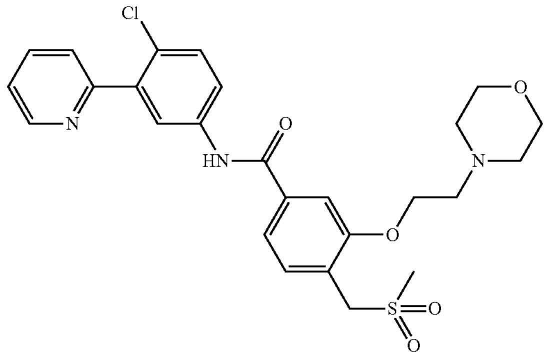 [SMILES: CS(=O)(=O)Cc1ccc(C(=O)Nc2ccc(Cl)c(-c3ccccn3)c2)cc1OCCN1CCOCC1]

3-(2-Bromoethoxy)-N-(4-chloro-3-(pyridin-2-yl)phenyl)-4-(methylsulfonylmethyl)benzamide (50 mg, 0.095 mmol) was dissolved in acetonitrile (1.0 ml) and DMF (1.0 ml), treated with potassium carbonate (16 mg, 0.12 mmol) and morpholine (10 μl, 0.11 mmol), and stirred 18 hours at room temperature. The reaction was heated to 50° C. for 8 hours, and then was allowed to stir 18 hours at room temperature. The reaction was quenched in water and extracted with ethyl acetate twice. The ethyl acetate extracts were washed with water once, brine once, dried with $MgSO_4$, and evaporated to an oil which was purified by reverse phase HPLC to yield 30 mg of N-(4-chloro-3-(pyridin-2-yl)phenyl)-4-(methylsulfonylmethyl)-3-(2-morpholinoethoxy)benzamide. MS (Q1) 530 $(M)^+$.

Example 298

N-(4-Chloro-3-(pyridin-2-yl)phenyl)-4-(methylsulfonylmethyl)-3-(2-(piperidin-1-yl)ethoxy)benzamide

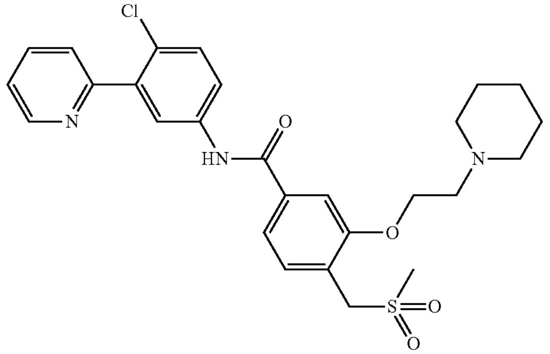 [SMILES: CS(=O)(=O)Cc1ccc(C(=O)Nc2ccc(Cl)c(-c3ccccn3)c2)cc1OCCN1CCCCC1]

3-(2-Bromoethoxy)-N-(4-chloro-3-(pyridin-2-yl)phenyl)-4-(methylsulfonylmethyl)benzamide (50 mg, 0.095 mmol) was dissolved in dichloromethane (1.0 ml), treated with triethylamine (20 μl, 0.15 mmol) and piperidine (11 μl, 0.11 mmol), and stirred 2.0 hours at room temperature. Acetonitrile (0.25 ml) and N-ethyl-N-isopropylpropan-2-amine (25 μl, 0.19 mmol) were added, and the reaction was stirred for an additional 45 hours. The reaction was quenched in water and extracted with dichloromethane twice. The dichloromethane extracts were washed with water once, brine once, dried with $MgSO_4$, and evaporated to an solid which was purified by reverse phase HPLC to yield 17 mg N-(4-chloro-3-(pyridin-2-yl)phenyl)-4-(methylsulfonylmethyl)-3-(2-(piperidin-1-yl)ethoxy)benzamide. MS (Q1) 528 $(M)^+$.

Example 299

N-(4-Chloro-3-(pyridin-2-yl)phenyl)-4-(methylsulfonylmethyl)-3-(2-(pyrrolidin-1-yl)ethoxy)benzamide

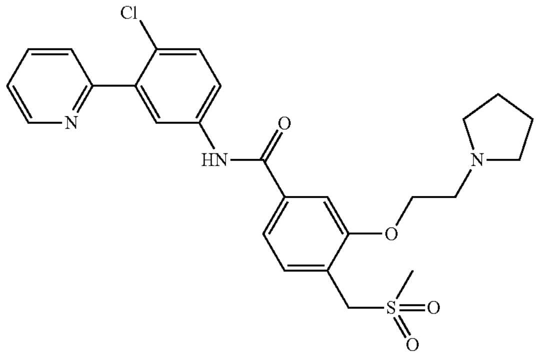 [SMILES: CS(=O)(=O)Cc1ccc(C(=O)Nc2ccc(Cl)c(-c3ccccn3)c2)cc1OCCN1CCCC1]

3-(2-Bromoethoxy)-N-(4-chloro-3-(pyridin-2-yl)phenyl)-4-(methylsulfonylmethyl)benzamide (40 mg, 0.076 mmol) was dissolved in acetonitrile (1.0 ml) and DMF (1.0 ml), treated with potassium carbonate (16 mg, 0.12 mmol) and pyrrolidine (7 μl, 0.084 mmol), and stirred 18 hours at room temperature. The reaction was quenched in water and extracted with ethyl acetate twice. The ethyl acetate extracts were washed with water once, brine once, dried with $MgSO_4$, and evaporated to an oil which was purified by reverse phase HPLC to yield 30 mg of N-(4-chloro-3-(pyridin-2-yl)phenyl)-4-(methylsulfonylmethyl)-3-(2-(pyrrolidin-1-yl)ethoxy)benzamide. MS (Q1) 514 $(M)^+$.

Example 300

3-Amino-N-(4-chloro-3-(pyridin-2-yl)phenyl)-4-(methylsulfonylmethyl)benzamide

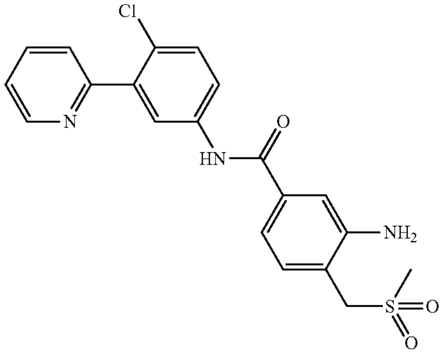

4-(Bromomethyl)-3-nitrobenzoic acid (2.00 g, 7.69 mmol) was dissolved in methanol (20 ml) and treated with 1 drop of concentrated sulfuric acid, then stirred 72 hours at room temperature. An additional 3 drops of concentrated sulfuric acid was added, and the reaction stirred at 50° C. for 24 hours. The solvent was concentrated on a rotary evaporator, diluted with ethyl acetate, and washed with water twice, saturated $NaHCO_3$ once, water once, brine once, dried with $MgSO_4$, and evaporated to a 1.82 g of a yellow oil, methyl 4-(bromomethyl)-3-nitrobenzoate and used without purification. Methyl 4-(bromomethyl)-3-nitrobenzoate (1.82 g, 6.64 mmol) was used in procedure O to afford 1.66 g of methyl 4-(methylsulfonylmethyl)-3-nitrobenzoate as a solid which was used without purification. Methyl 4-(methylsulfonylmethyl)-3-nitrobenzoate (1.66 g, 6.07 mmol) was saponified via procedure M to afford 1.21 g of 4-(methylsulfonylmethyl)-3-nitrobenzoic acid as an orange solid, which was used without purification. 4-(Methylsulfonylmethyl)-3-nitrobenzoic acid (639 mg, 2.46 mmol) was dissolved in 1,4-dioxane (15 ml), treated with thionyl chloride (1.0 ml) and DMF (1 drop), and stirred at room temperature for 18 hours, then at 50° C. for 8 hours, then at room temperature for 18 hours. After an additional 4.0 hours at 50° C., the solvents and excess thionyl chloride were removed via rotary evaporator, and the residue was dissolved dichloromethane (25.0 ml) and treated with N-ethyl-N-isopropylpropan-2-amine (1.7 ml, 9.8 mmol) and 4-chloro-3-(pyridin-2-yl)aniline (503 mg, 2.46 mmol) and stirred for 20 min at room temperature, over which time a solid precipitated. Water was added, and the mixture was filtered and air dried, to afford 797 mg of N-(4-chloro-3-(pyridin-2-yl)phenyl)-4-(methylsulfonylmethyl)-3-nitrobenzamide as a tan-yellow solid. N-(4-Chloro-3-(pyridin-2-yl)phenyl)-4-(methylsulfonylmethyl)-3-nitrobenzamide (786 mg, 1.76 mmol) was dissolved in ethanol (74 ml) and concentrated HCl (12 ml). Tin(II) chloride dihydrate (1.31 g, 5.82 mmol) was added and the reaction was heated to 55° C. for 2.5 hours. The reaction was cooled in an ice bath and triethylamine (10 ml) was added to basify the solution. The reaction was evaporated to a yellow solid which was slurried in ethyl acetate. The slurry was filtered through Celite 545, and the mother liquors were washed with water twice, brine once, dried with $MgSO_4$, and evaporated to 552 mg of as a crude yellow solid, 20 mg of which was purified by reverse phase HPLC to afford 13 mg of purified 3-amino-N-(4-chloro-3-(pyridin-2-yl)phenyl)-4-(methylsulfonylmethyl)benzamide. MS (Q1) 416 $(M)^+$.

Example 301

3-Acetamido-N-(4-chloro-3-(pyridin-2-yl)phenyl)-4-(methylsulfonylmethyl)benzamide

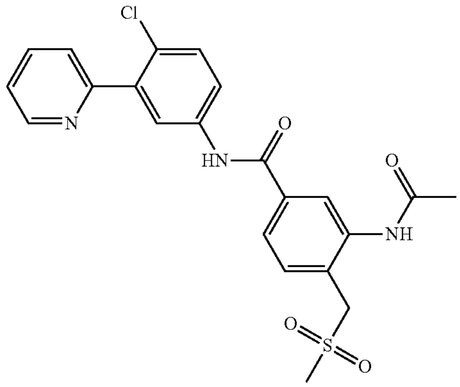 [SMILES: CC(=O)Nc1cc(C(=O)Nc2ccc(Cl)c(-c3ccccn3)c2)ccc1CS(C)(=O)=O]

3-Amino-N-(4-chloro-3-(pyridin-2-yl)phenyl)-4-(methylsulfonylmethyl)benzamide (30 mg, 0.072 mmol) was reacted with acetyl chloride (5.6 μl, 0.079 mol) via procedure V to afford 19 mg of 3-acetamido-N-(4-chloro-3-(pyridin-2-yl)phenyl)-4-(methylsulfonylmethyl)benzamide as a white solid. MS (Q1) 458 $(M)^+$.

Example 302

N-(5-(4-Chloro-3-(pyridin-2-yl)phenylcarbamoyl)-2-(methylsulfonylmethyl)phenyl)-2-methyl-6-(trifluoromethyl)nicotinamide

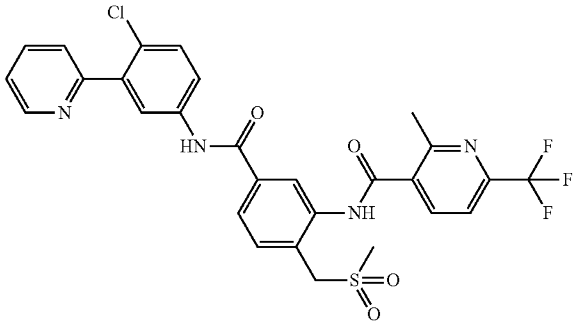 [SMILES: Cc1nc(C(F)(F)F)ccc1C(=O)Nc1cc(C(=O)Nc2ccc(Cl)c(-c3ccccn3)c2)ccc1CS(C)(=O)=O]

3-Amino-N-(4-chloro-3-(pyridin-2-yl)phenyl)-4-(methylsulfonylmethyl)benzamide (30 mg, 0.072 mmol) was reacted with 2-methyl-6-(trifluoromethyl)nicotinoyl chloride (19 mg, 0.079 mmol) via procedure V to afford 16 mg of N-(5-(4-chloro-3-(pyridin-2-yl)phenylcarbamoyl)-2-(methylsulfonylmethyl)phenyl)-2-methyl-6-(trifluoromethyl) nicotinamide as a white solid. MS (Q1) 603 $(M)^+$.

Example 303

3-Benzamido-N-(4-chloro-3-(pyridin-2-yl)phenyl)-4-(methylsulfonylmethyl)benzamide

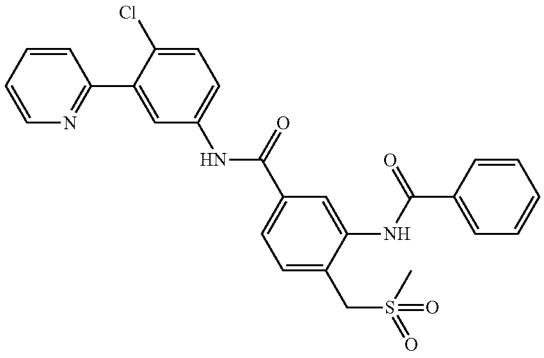 [SMILES: CS(=O)(=O)Cc1ccc(C(=O)Nc2ccc(Cl)c(-c3ccccn3)c2)cc1NC(=O)c1ccccc1]

3-Amino-N-(4-chloro-3-(pyridin-2-yl)phenyl)-4-(methylsulfonylmethyl)benzamide (30 mg, 0.072 mmol) was reacted with benzoyl chloride (9 µl, 0.079 mmol) via procedure V to afford 17 mg of 3-benzamido-N-(4-chloro-3-(pyridin-2-yl)phenyl)-4-(methylsulfonylmethyl)benzamide as a white solid. MS (Q1) 520 $(M)^+$.

Example 304

N-(4-Chloro-3-(pyridin-2-yl)phenyl)-4-(methylsulfonylmethyl)-3-(2-(pyrrolidin-1-yl)acetamido)benzamide

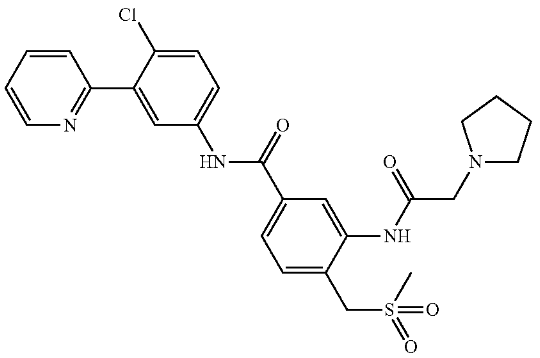 [SMILES: CS(=O)(=O)Cc1ccc(C(=O)Nc2ccc(Cl)c(-c3ccccn3)c2)cc1NC(=O)CN1CCCC1]

3-Amino-N-(4-chloro-3-(pyridin-2-yl)phenyl)-4-(methylsulfonylmethyl)benzamide (100 mg, 0.24 mmol) was dissolved in 1,4-dioxane (5.0 ml), treated with triethylamine (274 µl, 1.97 mmol) and 2-bromoacetyl bromide (121 µl, 1.39 mmol). The reaction was heated to reflux for 10 minutes, and stirred at room temperature for 18 hours. The reaction was quenched with water, and extracted twice with ethyl acetate. The ethyl acetate extracts were filtered, washed with water once, brine once, dried with $MgSO_4$, evaporated to 158 mg of a crude brown oil, 3-(2-bromoacetamido)-N-(4-chloro-3-(pyridin-2-yl)phenyl)-4-(methylsulfonylmethyl)benzamide, which was used without further purification. Crude 3-(2-bromoacetamido)-N-(4-chloro-3-(pyridin-2-yl)phenyl)-4-(methylsulfonyl-methyl)benzamide (158 mg) was dissolved in DMF, treated with N-ethyl-N-isopropylpropan-2-amine (61 µl, 0.35 mmol) and pyrrolidine (27 µl, 0.32 mmol), and stirred at room temperature for 18 hours. The reaction was quenched with water and extracted with ethyl acetate twice. The ethyl acetate extracts were washed with water once, brine once, dried with $MgSO_4$, evaporated to a tan solid which was purified by reverse phase HPLC to afford 27 mg of N-(4-chloro-3-(pyridin-2-yl)phenyl)-4-(methylsulfonylmethyl)-3-(2-(pyrrolidin-1-yl)acetamido)benzamide as a white powder. MS (Q1) 527 $(M)^+$.

Example 305

4-(N-(3-(1H-Imidazol-4-yl)propyl)carbamimidoyl)-N-(4-chloro-3-(pyridin-2-yl)phenyl)benzamide

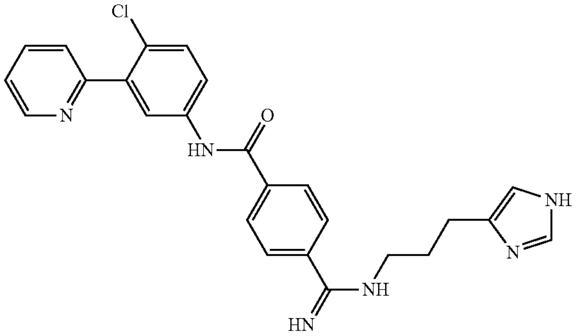 [SMILES: N=C(NCCCc1c[nH]cn1)c1ccc(C(=O)Nc2ccc(Cl)c(-c3ccccn3)c2)cc1]

4-Chloro-3-(pyridin-2-yl)aniline (687 mg, 3.36 mmol) was dissolved in dichloromethane (8.0 ml) and THF (8.0 ml), treated with pyridine (0.33 ml, 4.0 mmol), and cooled to 0° C. 4-Cyanobenzoyl chloride (612 mg, 3.7 mmol) was added and the reaction was stirred for 1.0 hour. The reaction was diluted with dichloromethane and methanol was added to dissolve all solids. The solution was washed with water once, brine once, dried with $MgSO_4$, and evaporated to an orange solid which was purified by silica gel flash column chromatography (50% ethyl acetate/50% hexanes) to afford 908 mg of N-(4-chloro-3-(pyridin-2-yl)phenyl)-4-cyanobenzamide as a yellow solid. N-(4-Chloro-3-(pyridin-2-yl)phenyl)-4-cyanobenzamide (500 mg, 1.5 mmol) was slurried in ethanol (75 ml) and heated until just dissolved. The solution was cooled in an ice bath, and saturated with HCl gas. The solution was heated briefly to 70° C. to dissolve precipitated solids, cooled in an ice bath, and resaturated with HCl gas. The solution was then stored at 0° C. for 18 hours. The solution was saturated again with HCl gas, heated to 70° C. until all solids dissolved, cooled to 0° C., resaturated with HCl gas, and stored at 0° C. for 18 hours. Finally, nitrogen gas was bubbled through the solution for 1.0 hour, and the solution was evaporated to dryness. The residue was dissolved in methanol, treated with MP-carbonate (2.57 g) and stirred 30 min. The solution was filtered to afford a neutral, methanolic solution of ethyl 4-(4-chloro-3-(pyridin-2-yl)phenylcarbamoyl)benzimidate, which was diluted with enough methanol to make a 0.075 M solution.

Ethyl 4-(4-chloro-3-(pyridin-2-yl)phenylcarbamoyl)benzimidate (2.0 ml of a 0.075 M methanol solution, 0.15 mmol) was treated with 3-(1H-imidazol-4-yl)propan-1-amine (27 μl, 0.23 mmol) via procedure W to afford 83 mg of 4-(N-(3-(1H-imidazol-4-yl)propyl)carbamimidoyl)-N-(4-chloro-3-(pyridin-2-yl)phenyl)benzamide. MS (Q1) 459 (M)$^+$.

Example 306

N-(4-Chloro-3-(pyridin-2-yl)phenyl)-4-(N-(2-(pyrrolidin-2-yl)ethyl)carbamimidoyl)benzamide

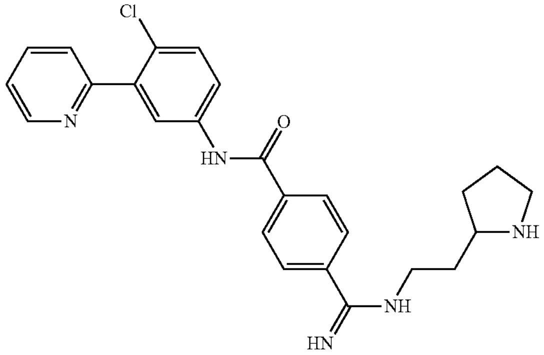 [SMILES: N=C(NCCC1CCCN1)c1ccc(C(=O)Nc2ccc(Cl)c(-c3ccccn3)c2)cc1]

Ethyl 4-(4-chloro-3-(pyridin-2-yl)phenylcarbamoyl)benzimidate (2.0 ml of a 0.075 M methanol solution, 0.15 mmol) was treated with 2-(pyrrolidin-2-yl)ethanamine (28 μl, 0.23 mmol) via procedure W to afford 90 mg of N-(4-chloro-3-(pyridin-2-yl)phenyl)-4-(N-(2-(pyrrolidin-2-yl)ethyl)carbamimidoyl)benzamide. MS (Q1) 448 (M)$^+$.

Example 307

N-(4-Chloro-3-(pyridin-2-yl)phenyl)-4-(N-((tetrahydrofuran-2-yl)methyl)carbamimidoyl)benzamide

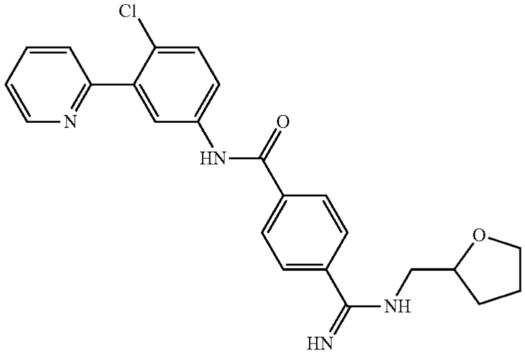 [SMILES: N=C(NCC1CCCO1)c1ccc(C(=O)Nc2ccc(Cl)c(-c3ccccn3)c2)cc1]

Ethyl 4-(4-chloro-3-(pyridin-2-yl)phenylcarbamoyl)benzimidate (2.0 ml of a 0.075 M methanol solution, 0.15 mmol) was treated with (tetrahydrofuran-2-yl)methanamine (23 μl, 0.23 mmol) via procedure W to afford 76 mg of N-(4-chloro-3-(pyridin-2-yl)phenyl)-4-(N-((tetrahydrofuran-2-yl)methyl)carbamimidoyl)benzamide. MS (Q1) 435 (M)$^+$.

Example 308

4-(N-(2-(1H-Imidazol-4-yl)ethyl)carbamimidoyl)-N-(4-chloro-3-(pyridin-2-yl)phenyl)benzamide

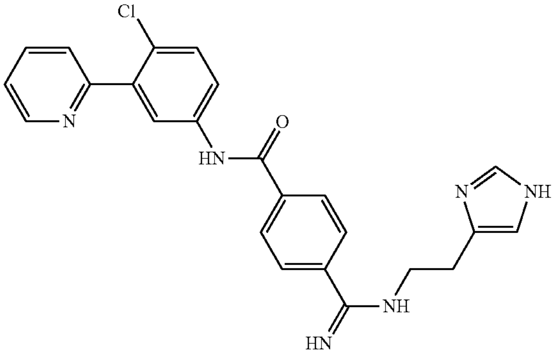 [SMILES: N=C(NCCc1c[nH]cn1)c1ccc(C(=O)Nc2ccc(Cl)c(-c3ccccn3)c2)cc1]

Ethyl 4-(4-chloro-3-(pyridin-2-yl)phenylcarbamoyl)benzimidate (2.0 ml of a 0.075 M methanol solution, 0.15 mmol) was treated with 2-(1H-imidazol-4-yl)ethanamine (25 mg, 0.23 mmol) via procedure W to afford 90 mg of 4-(N-(2-(1H-imidazol-4-yl)ethyl)carbamimidoyl)-N-(4-chloro-3-(pyridin-2-yl)phenyl)benzamide. MS (Q1) 445 (M)$^+$.

Example 309

N-(4-Chloro-3-(pyridin-2-yl)phenyl)-4-(N-(2,2,2-trifluoroethyl)carbamimidoyl)benzamide

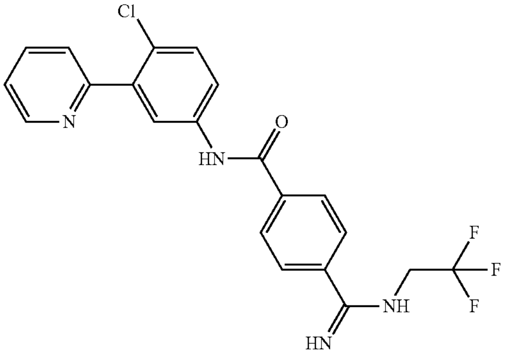 [SMILES: N=C(NCC(F)(F)F)c1ccc(C(=O)Nc2ccc(Cl)c(-c3ccccn3)c2)cc1]

Ethyl 4-(4-chloro-3-(pyridin-2-yl)phenylcarbamoyl)benzimidate (2.0 ml of a 0.075 M methanol solution, 0.15 mmol) was treated with 2,2,2-trifluoroethanamine (18 μl, 0.23 mmol) via procedure W to afford 56 mg of N-(4-chloro-3-

(pyridin-2-yl)phenyl)-4-(N-(2,2,2-trifluoroethyl)carbamimidoyl)benzamide. MS (Q1) 433 $(M)^+$.

Example 310

N-(4-Chloro-3-(pyridin-2-yl)phenyl)-4-((2,6-dimethylmorpholino)(imino)methyl)-benzamide

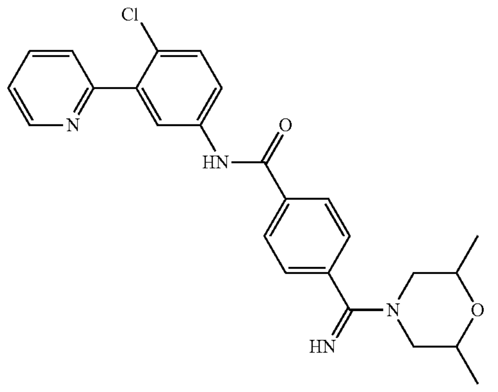 [SMILES: CC1CN(C(=N)c2ccc(C(=O)Nc3ccc(Cl)c(-c4ccccn4)c3)cc2)CC(C)O1]

Ethyl 4-(4-chloro-3-(pyridin-2-yl)phenylcarbamoyl)benzimidate (2.0 ml of a 0.075 M methanol solution, 0.15 mmol) was treated with 2,6-dimethylmorpholine (28 μl, 0.23 mmol) via procedure W to afford 74 mg of N-(4-chloro-3-(pyridin-2-yl)phenyl)-4-((2,6-dimethylmorpholino)(imino)methyl)-benzamide. MS (Q1) 449 $(M)^+$.

Example 311

N-(4-Chloro-3-(pyridin-2-yl)phenyl)-4-(N-(3-methoxypropyl)carbamimidoyl)-benzamide

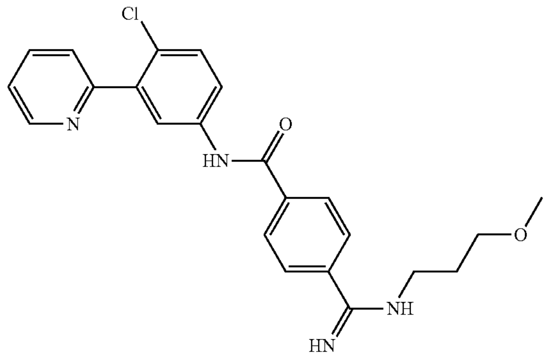 [SMILES: COCCCNC(=N)c1ccc(C(=O)Nc2ccc(Cl)c(-c3ccccn3)c2)cc1]

Ethyl 4-(4-chloro-3-(pyridin-2-yl)phenylcarbamoyl)benzimidate (2.0 ml of a 0.075 M methanol solution, 0.15 mmol) was treated with 3-methoxypropan-1-amine (23 μl, 0.23 mmol) via procedure W to afford 68 mg of N-(4-chloro-3-(pyridin-2-yl)phenyl)-4-(N-(3-methoxypropyl)carbamimidoyl)-benzamide. MS (Q1) 423 $(M)^+$.

Example 312

N-(4-Chloro-3-(pyridin-2-yl)phenyl)-4-(N-(2-methoxyethyl)carbamimidoyl)benzamide

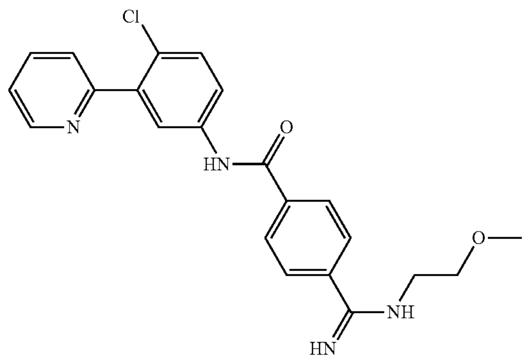 [SMILES: COCCNC(=N)c1ccc(C(=O)Nc2ccc(Cl)c(-c3ccccn3)c2)cc1]

Ethyl 4-(4-chloro-3-(pyridin-2-yl)phenylcarbamoyl)benzimidate (2.0 ml of a 0.075 M methanol solution, 0.15 mmol) was treated with 2-methoxyethanamine (19 μl, 0.23 mmol) via procedure W to afford 50 mg of N-(4-chloro-3-(pyridin-2-yl)phenyl)-4-(N-(2-methoxyethyl)carbamimidoyl)benzamide. MS (Q1) 409 $(M)^+$.

Example 313

N-(4-Chloro-3-(pyridin-2-yl)phenyl)-4-(N-cyclohexylcarbamimidoyl)benzamide

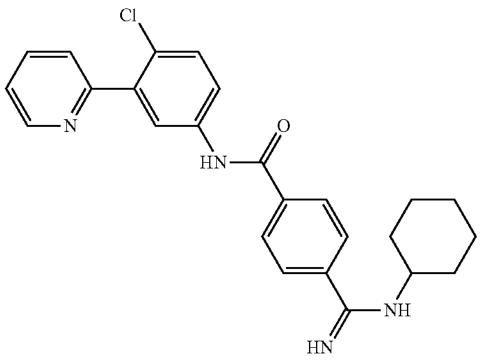 [SMILES: N=C(NC1CCCCC1)c1ccc(C(=O)Nc2ccc(Cl)c(-c3ccccn3)c2)cc1]

Ethyl 4-(4-chloro-3-(pyridin-2-yl)phenylcarbamoyl)benzimidate (2.0 ml of a 0.075 M methanol solution, 0.15 mmol) was treated with cyclohexanamine (26 μl, 0.23 mmol) via procedure W to afford 30 mg of N-(4-chloro-3-(pyridin-2-yl)phenyl)-4-(N-cyclohexylcarbamimidoyl)benzamide. MS (Q1) 433 (M)$^+$.

Example 314

N-(4-Chloro-3-(pyridin-2-yl)phenyl)-4-(imino(4-methylpiperazin-1-yl)methyl)benzamide

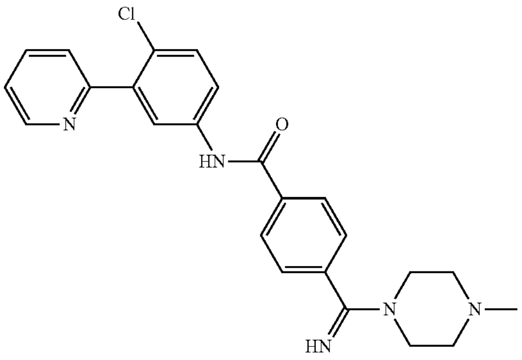 [SMILES: CN1CCN(C(=N)c2ccc(C(=O)Nc3ccc(Cl)c(-c4ccccn4)c3)cc2)CC1]

Ethyl 4-(4-chloro-3-(pyridin-2-yl)phenylcarbamoyl)benzimidate (2.0 ml of a 0.075 M methanol solution, 0.15 mmol) was treated with 1-methylpiperazine (23 mg, 0.23 mmol) via procedure W to afford 35 mg of N-(4-chloro-3-(pyridin-2-yl)phenyl)-4-(imino(4-methylpiperazin-1-yl)methyl)benzamide. MS (Q1) 434 (M)$^+$.

Example 315

N-(4-Chloro-3-(pyridin-2-yl)phenyl)-4-(N-propylcarbamimidoyl)benzamide

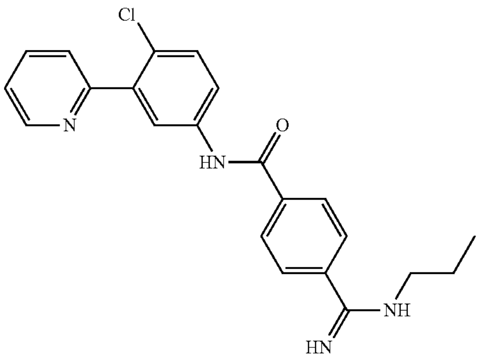 [SMILES: CCCNC(=N)c1ccc(C(=O)Nc2ccc(Cl)c(-c3ccccn3)c2)cc1]

Ethyl 4-(4-chloro-3-(pyridin-2-yl)phenylcarbamoyl)benzimidate (2.0 ml of a 0.075 M methanol solution, 0.15 mmol) was treated with propan-1-amine (18 μl, 0.23 mmol) via procedure W to afford 39 mg of N-(4-chloro-3-(pyridin-2-yl)phenyl)-4-(N-propylcarbamimidoyl)benzamide. MS (Q1) 393 (M)$^+$.

Example 316

N-(4-Chloro-3-(pyridin-2-yl)phenyl)-4-(imino(pyrrolidin-1-yl)methyl)benzamide

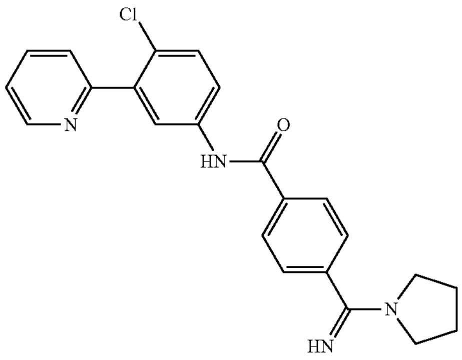 [SMILES: N=C(c1ccc(C(=O)Nc2ccc(Cl)c(-c3ccccn3)c2)cc1)N1CCCC1]

Ethyl 4-(4-chloro-3-(pyridin-2-yl)phenylcarbamoyl)benzimidate (2.0 ml of a 0.075 M methanol solution, 0.15 mmol) was treated with pyrrolidine (19 μl, 0.23 mmol) via procedure W to afford 25 mg of N-(4-chloro-3-(pyridin-2-yl)phenyl)-4-(imino(pyrrolidin-1-yl)methyl)benzamide. MS (Q1) 405 (M)$^+$.

Example 317

N-(4-Chloro-3-(pyridin-2-yl)phenyl)-4-(N-phenylcarbamimidoyl)benzamide

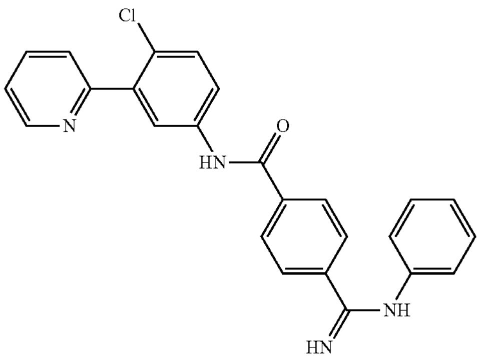 [SMILES: N=C(Nc1ccccc1)c1ccc(C(=O)Nc2ccc(Cl)c(-c3ccccn3)c2)cc1]

Ethyl 4-(4-chloro-3-(pyridin-2-yl)phenylcarbamoyl)benzimidate (2.0 ml of a 0.075 M methanol solution, 0.15 mmol) was treated with aniline (21 μl, 0.23 mmol) via procedure W to afford 7 mg of N-(4-chloro-3-(pyridin-2-yl)phenyl)-4-(N-phenylcarbamimidoyl)benzamide. MS (Q1) 427 $(M)^+$.

Example 318

N-(4-Chloro-3-(pyridin-2-yl)phenyl)-4-(imino(morpholino)methyl)benzamide

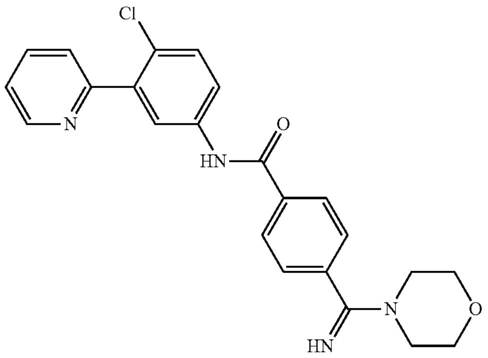 [SMILES: N=C(c1ccc(C(=O)Nc2ccc(Cl)c(-c3ccccn3)c2)cc1)N1CCOCC1]

N-(4-chloro-3-(pyridin-2-yl)phenyl)-4-cyanobenzamide (300 mg, 0.899 mmol) was slurried in 45 ml ethanol and treated with 10 ml of ethanol saturated with HCl. The reaction was stored at 0° C. for 3 days, then heated to 75° C. for 3.0 hours, and cooled to room temperature for 18 hours. The reaction was cooled in an ice bath, and saturated with HCl gas. After storing at 0° C. for an additional 3 days, $N_2$ gas was bubbled through the solution for 1.0 hour, and the solution was diluted with enough ethanol to make a 0.0155 M solution of ethyl 4-(4-chloro-3-(pyridin-2-yl)phenylcarbamoyl)benzimidate. Ethyl 4-(4-chloro-3-(pyridin-2-yl)phenylcarbamoyl)benzimidate (17.5 ml of a 0.0155 M ethanol solution, 0.27 mmol) was treated with morpholine (1.0 ml, 11.4 mmol) for 3 days. The ethanol was evaporated, and the residue purified by reverse phase HPLC to afford 30 mg of N-(4-chloro-3-(pyridin-2-yl)phenyl)-4-(imino(morpholino)methyl)benzamide. MS (Q1) 421 $(M)^+$.

Example 319

N-(4-chloro-3-(pyridin-2-yl)phenyl)-4-(imino(piperidin-1-yl)methyl)benzamide

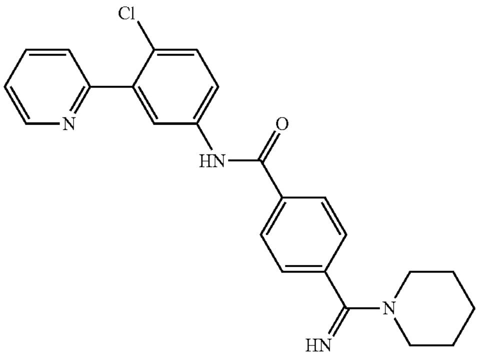 [SMILES: N=C(c1ccc(C(=O)Nc2ccc(Cl)c(-c3ccccn3)c2)cc1)N1CCCCC1]

Ethyl 4-(4-chloro-3-(pyridin-2-yl)phenylcarbamoyl)benzimidate (17.5 ml of a 0.0155 M solution, 0.27 mmol) was treated with piperidine (1.0 ml, 10.0 mmol) for 3 days. The ethanol was evaporated, and the residue purified by reverse phase HPLC to afford 26 mg of N-(4-chloro-3-(pyridin-2-yl)phenyl)-4-(imino(piperidin-1-yl)methyl)benzamide. MS (Q1) 419 $(M)^+$.

Example 320

Hedgehog Signalling Inhibition Assays

Mouse Reporter Cell lines—10T1/2-GliLuc [S12] cells (derived from cell line C3H10T1/2 ATCC #CCL-226); Mouse Embryonic Fibroblasts); Growth Medium: Dulbecco's modified Eagles' Medium (DMEM) supplemented with 10% Fetal Bovine Serum (FBS), 10 units/mL penicillin, 100 ug/mL streptomycin, 2 mM glutamine, and 10 mM HEPES.

Human Reporter Cell lines—HEPM-GliLuc [MZ24]—cells (derived from HEPM, Human Embryonic Palatal Mesenchyme ATCC #CRL-1486); Growth Medium: Minimum Essential Medium (MEM; with Earle's salts) supplemented with 10-20% Fetal Bovine Serium (FBS), 10 units/mL penicillin, 100 ug/mL streptomycin, 2 mM glutamine, and 10 mM HEPES pH 7.2.

Sonic hedgehog—recombinant human SHh N-terminal octylated conjugate.

Microtiter Plates (MTPs)—For the Luciferase assay cells are plated in 96-well MTPs (White, Flat-bottom, Clear-View).

Luciferase-Assay Medium—DMEM supplemented with 0.5% FBS, 10 units/mL penicillin, 100 ug/mL streptomycin, 2 mM glutamine, and 10 mM HEPES pH 7.2.

PBS/Ca/Mg Mix—Phosphate Buffered Saline (PBS) supplemented with 0.5 mM $CaCl_2$ and 1 mM $MgCl_2$.

Assay Procedure

S12 and MZ24 cells genetically modified to contain a luciferase reporter gene driven by the hedgehog-reseponsive Gli promoter were maintained on tissue culture dishes in Growth Medium at 37° C. and 5% $CO_2$. Cell cultures were passaged at sub-confluency at every 3-4 days. (1:20 to 1:40 for s12; 1:3 to 1:10 for MZ24). Cells were harvested and diluted in Growth Medium such that they could be plated in a microtitre plate at 10,000-20,000 cells (s12), or 20,000-30,000 cells (MZ24), per 100 ul, per well. Cells were further incubated for ~24-48 hours at 37° C. and 5% $CO_2$.

After ~24-48 hour incubation the Growth Medium in the microtitre plates was replaced by Luciferase-Assay Medium (100 ul per well), with and without Sonic hedgehog-octyl conjugate, at 0.1-0.3 ug/ml (S12) or 0.5-1.0 ug/ml (MZ24), and test compounds. Cells were then further incubated for and additional 24 hrs.

Microtitre plates were then subjected to the luciferase reporter gene assay kit (LucLite™), with modifications to the manufacturer's procedure wherein medium was removed and the substrate was reconstituted with 1:1 PBS/Ca/Mg: lysis buffer instead of straight lysis buffer. In brief, the PBS/Ca/Mg was mixed 1:1 with lysis buffer and 10 mL were added to each substrate vial (of the 1000-assay kit). Then the assay media from the microtitre plate was discarded, and 100 ul of this substrate mix was added to each well. Plates were incubated at room temperature for 20-30 minutes and then the Relative Light Units (RLUS) representing the relative expression level of the luciferase reporter gene were determined with a Top-count reader (Packard) or an Analyst reader (Molecular Devices). Compounds of the invention tested in the assays demonstrated reduced Gli expression in the reporter cell lines indicating hedgehog pathway signalling inhibition.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding U.S. Provisional Application Ser. No. 60/607,367, filed Sep. 2, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A method of treating cancer in a mammal, comprising administering a compound of formula I:

I

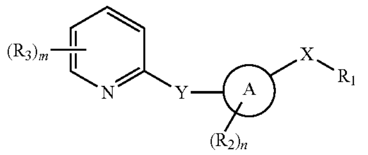

wherein

A is a carbocycle or heterocycle;

X is alkylene, $NR_4C(O)$, $NR_4C(S)$, $N(C(O)R_1)C(O)$, $NR_4SO$, $NR_4SO_2$, $NR_4C(O)NH$, $NR_4C(S)NH$, $C(O)NR_4$, $C(S)NR_4$, $NR_4PO$ or $NR_4PO(OH)$;

Y is absent, $CHR_4$, O, S, SO, $SO_2$ or $NR_4$;

$R_1$ is selected from the group consisting of alkyl, a carbocycle or a heterocycle each of which is optionally substituted with hydroxyl, halogen, amino, carboxyl, amidino, guanidino, carbonyl, nitro, cyano, acyl, alkyl, haloalkyl, sulfonyl, sulfinyl, alkoxy, alkylthio, carbamoyl, acylamino, sulfamoyl, sulfonamide, a carbocycle or a heterocycle; wherein said amino, amidino, alkyl, acyl, sulfonyl, sulfinyl, alkoxy, alkylthio, carbamoyl, acylamino, sulfamoyl, sulfonamide, carbocycle and heterocycle substituent is optionally substituted with, halogen, haloakyl, hydroxyl, carboxyl, carbonyl, or an amino, alkyl, alkoxy, acyl, sulfonyl, sulfinyl, phosphinate, carbocycle or heterocycle that is optionally substituted with hydroxyl, carboxyl, carbonyl, amino, halogen, haloalkyl, alkyl, alkoxy, alkylthio, sulfonyl, sulfinyl, acyl, a carbocycle or a heterocycle;

$R_2$ is halogen, hydroxyl, alkyl, acyl or alkoxy, wherein each alkyl, acyl and alkoxy is optionally substituted with hydroxyl, halogen, amino, nitro, alkyl, acyl, alkylsulfonyl or alkoxy;

$R_3$ is halogen, hydroxyl, carboxyl, alkyl, acyl, alkoxy, alkoxycarbonyl, carbamoyl, alkylsulfide, sulfinyl, sulfonyl, a carbocycle or a heterocycle wherein each alkyl, acyl, alkoxy, alkoxycarbonyl, carbamoyl, alkylsulfide, sulfinyl, sulfonyl, carbocycle and heterocycle is optionally substituted with hydroxyl, halogen, amino, nitro, alkyl, acyl, sulfonyl or alkoxy;

$R_4$ is H or alkyl;

m is 0-3;

n is 0-3;

or a salt or solvate thereof.

2. The method of claim 1, wherein A is a ring selected from the group consisting of $A^1$, $A^2$, $A^3$, $A^4$ $A^5$, $A^6$ and $A^7$:

$A^1$

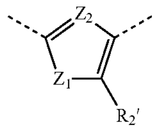

$A^2$

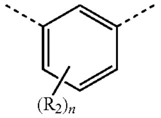

$A^3$

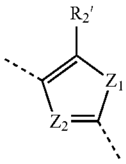

$A^4$

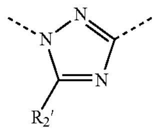

$A^5$

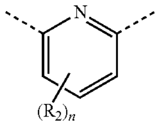

$A^6$

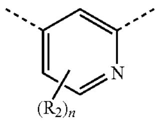

$A^7$

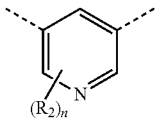

wherein $Z_1$ is O, S or $NR_5$ wherein $R_5$ is H or alkyl; $Z_2$ is CH, $CR_2$, or N; $R_2$ is halogen, hydroxyl, alkyl or alkoxy; $R_{2'}$ is H, halogen, hydroxyl, alkyl or alkoxy; and n is 0-3.

3. The method of claim 2, wherein A is ring $A^1$ wherein $Z_1$ is S and $Z_2$ is CH or N.

4. The method of claim 2, wherein A is the ring $A^2$.

5. The method of claim 2, wherein $R_2$ or $R_2$' is Cl.

6. The method of claim 1, wherein A is $A^{1a}$, $A^{1b}$, $A^{2a}$, $A^{3a}$, $A^{3b}$, $A^{4a}$, $A^{5a}$, $A^{6a}$, $A^{7a}$:

$A^{1a}$

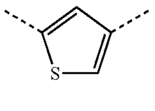

-continued

A[1b]

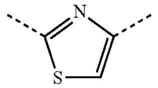

A[2a]

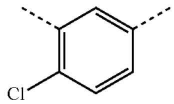

A[3a]

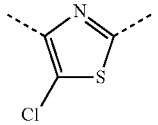

A[3b]

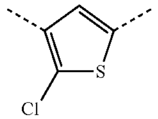

A[4a]

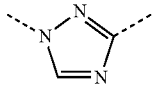

A[5a]

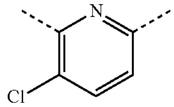

A[6a]

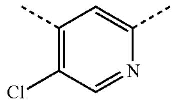

A[7a]

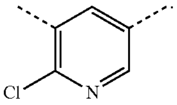

7. The method of claim 1, wherein X is $NR_4C(O)$.

8. The method of claim 1, wherein X is $NR_4SO_2$.

9. The method of claim 7, wherein $R_4$ is H or methyl.

10. The method of claim 9, wherein $R_4$ is H.

11. The method of claim 1, wherein $R_3$ is methyl or F.

12. The method of claim 1, wherein $R_3$ is methyl and m is 1 or 2.

13. The method of claim 1, wherein $R_3$ is F and m is 1 or 2.

14. The method of claim 1, wherein m is 0.

15. The method of claim 1, wherein $R_1$ is selected from the group consisting of formulae IIa-IIo:

IIa

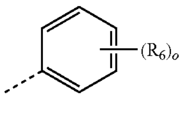

IIb

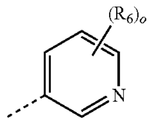

-continued

IIc

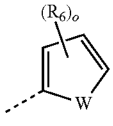

IId

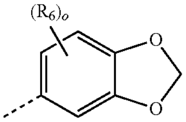

IIe

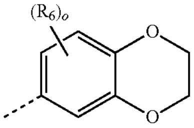

IIf

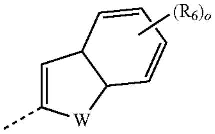

IIg

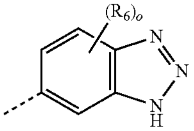

IIh

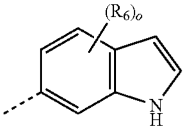

IIi

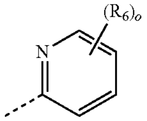

IIj

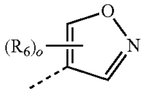

IIk

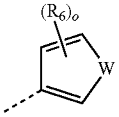

IIl

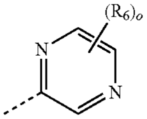

IIm

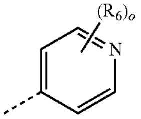

IIn

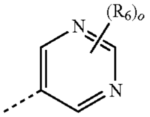

-continued

IIo

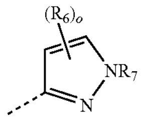

wherein

W is O, S or $NR_7$ wherein $R_7$ is H, alkyl, acyl, a carbocycle or a heterocycle wherein said alkyl, carbocycle and heterocycle are each optionally substituted with 1-3 amino, halogen, hydroxyl and haloalkyl;

$R_6$ in each instance is independently hydroxyl, halogen, amino, carbonyl, nitro, cyano, acyl, alkyl, sulfonyl, alkylsulfonyl, alkylsulfinyl, alkoxy, alkylcarbamoyl, alkanoylamine, alkylsulfamoyl, alkylsulfonamide, a carbocycle or a heterocycle; wherein said amino, alkyl, carbonyl, acyl, sulfonyl, alkylsulfonyl, alkylsulfinyl, alkoxy, alkylcarbamoyl, alkanoylamine, alkylsulfamoyl, alkylsulfonamide, carbocycle and heterocycle substituent is optionally substituted with amino, halogen, hydroxyl, carbonyl, or a carbocycle or heterocycle that is optionally substituted with hydroxyl, amino, halogen, haloalkyl, alkyl, alkoxy or acyl; and o is 0-3.

16. The method of claim 15, wherein $R_1$ is the group of formula IIa.

17. The method of claim 16, wherein $R_6$ is alkoxy and o is 1 or 2.

18. The method of claim 16, wherein $R_1$ is selected from the group of formulae $IIa^1$-$IIa^{28}$:

$IIa^1$

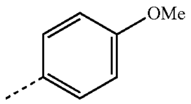

$IIa^2$

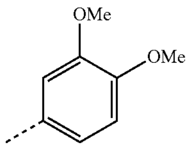

$IIa^3$

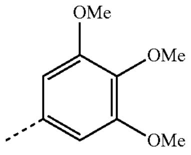

$IIa^4$

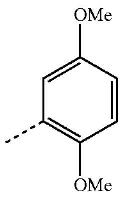

-continued $IIa^5$

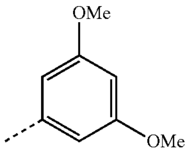

$IIa^6$

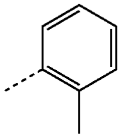

$IIa^7$

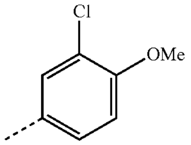

$IIa^8$

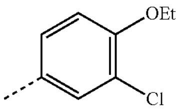

$IIa^9$

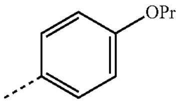

$IIa^{10}$

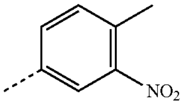

$IIa^{11}$

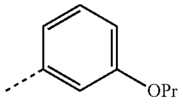

$IIa^{12}$

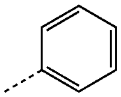

$IIa^{13}$

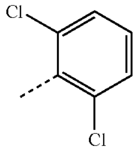

$IIa^{14}$

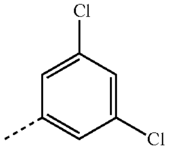

$IIa^{15}$

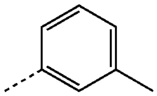

-continued $IIa^{16}$

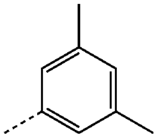

$IIa^{17}$

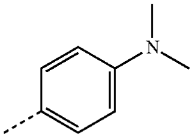

$IIa^{18}$

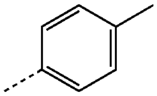

$IIa^{19}$

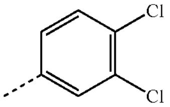

$IIa^{20}$

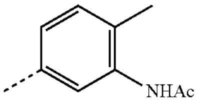

$IIa^{21}$

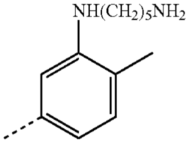

$IIa^{22}$

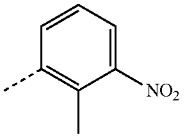

$IIa^{23}$

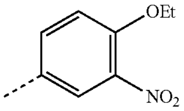

$IIa^{24}$

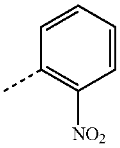

$IIa^{25}$

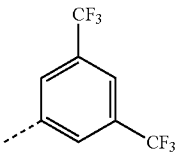

$IIa^{26}$

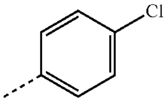

-continued $IIa^{27}$

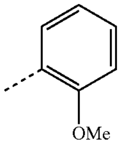

$IIa^{28}$

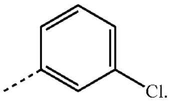

19. The method of claim 16, wherein A is

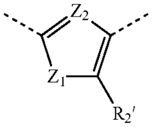

or

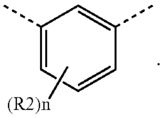

.

20. The method of claim 16, wherein A is

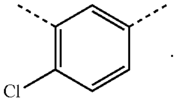

21. The method of claim 16, wherein $R_3$ is methyl or F.

22. The method of claim 3, wherein m is 0.

23. The method of claim 3, wherein X is $NR_4C(O)$.

24. The method of claim 15, wherein $R_1$ is the group of formula IIb.

25. The method of claim 24, wherein $R_6$ is alkyl or haloalkyl.

26. The method of claim 24, wherein $R_1$ is the group of the formula

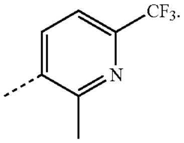

27. The method of claim 24, wherein A is

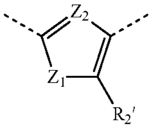

or

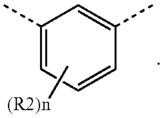

.

28. The method of claim 24, wherein A is

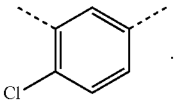

29. The method of claim 24, wherein $R_3$ is H, methyl or F.

30. The method of claim 24, wherein $R_3$ is H.

31. The method of claim 24, wherein X is $NR_4C(O)$.

32. The method of claim 1 comprising administering said compound in a composition further comprising a pharmaceutically acceptable carrier.

33. The method of claim 1, wherein said cancer is basal cell carcinoma, medullablastoma, pancreatic adenocarcinoma, small-cell lung carcinoma, breast carcinoma, rhabdomyosarcoma, oesophageal cancer, stomach cancer, or biliary tract cancer.

34. The method of claim 33 wherein said cancer is basal cell carcinoma.

35. The method of claim 1 wherein said administration is oral.

36. The method of claim 34 wherein said administration is oral.

37. A method of treating cancer in a mammal, comprising administering a compound of the formula

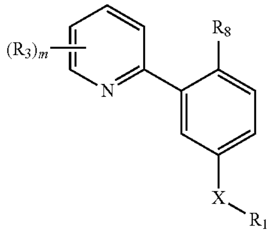

wherein $R_3$ is H or methyl, $R_8$ is halogen or alkyl substituted with halogen;

X is $NR_4C(O)$, m is 0-3, $R_4$ is H or alkyl, and $R^1$ is aryl or heteroaryl, each of which is optionally substituted with hydroxyl, halogen, amino, carboxyl, amidino, guanidino, carbonyl, nitro, cyano, acyl, alkyl, haloalkyl, sulfonyl, sulfinyl, alkoxy, alkylthio, carbamoyl, acylamino, sulfamoyl, sulfonamide, a carbocycle or a heterocycle; wherein said amino, amidino, alkyl, acyl, sulfonyl, sulfinyl, alkoxy, alkylthio, carbamoyl, acylamino, sulfamoyl, sulfonamide, carbocycle and heterocycle substituent is optionally substituted with, halogen, haloakyl, hydroxyl, carboxyl, carbonyl, or an amino, alkyl, alkoxy, acyl, sulfonyl, sulfinyl, phosphinate, carbocycle or heterocycle that is optionally substituted with hydroxyl, carboxyl, carbonyl, amino, halogen, haloalkyl, alkyl, alkoxy, alkylthio, sulfonyl, sulfinyl, acyl, a carbocycle or a heterocycle, or a salt or solvate thereof.

38. The method of claim 37 comprising administering said compound in a pharmaceutical composition further comprising a pharmaceutically acceptable carrier.

39. The method of claim 37 wherein $R_8$ is halogen and $R^1$ is substituted phenyl or substituted pyridyl.

40. The method of claim 39 wherein $R_4$ is H, m is 0 and $R_8$ is Cl.

41. The method of claim 39 wherein said substituted phenyl or pyridyl $R^1$ group comprises $—SO_2—$.

42. A method of treating cancer in a mammal, comprising administering a compound of the formula:

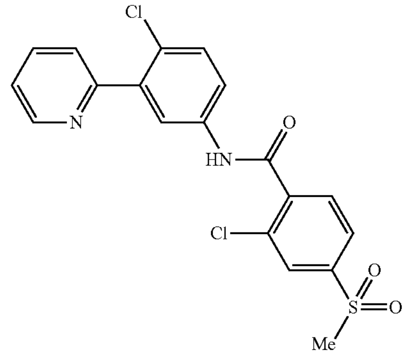 [SMILES: CS(=O)(=O)c1ccc(C(=O)Nc2ccc(Cl)c(-c3ccccn3)c2)c(Cl)c1]

or a salt or solvate thereof.

43. The method of claim 37 wherein said cancer is basal cell carcinoma.

44. The method of claim 42 wherein said cancer is basal cell carcinoma.

45. The method of claim 37 wherein said administration is oral.

46. The method of claim 42 wherein said administration is oral.

47. The method of claim 43 wherein said administration is oral.

48. The method of claim 44 wherein said administration is oral.

49. The method of claim 39 wherein said compound is

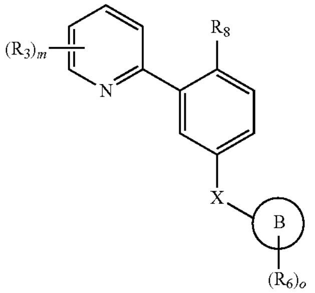

wherein ring B is phenyl or pyridyl, o is 1-3, and each $R_6$ independently is hydroxyl, halogen, amino, carboxyl, amidino, guanidino, carbonyl, nitro, cyano, acyl, alkyl, haloalkyl, sulfonyl, sulfinyl, alkoxy, akylthio, carbamoyl, acylamino, sulfamoyl, sulfonamide, a carbocycle or a heterocycle; wherein said amino, amidino, alkyl, acyl, sulfonyl, sulfinyl, alkoxy, alkylthio, carbamoyl, acylamino, sulfamoyl, sulfonamide, carbocycle and heterocycle substituent is optionally substituted with, halogen, haloakyl, hydroxyl, carboxyl, carbonyl, or an amino, alkyl, alkoxy, acyl, sulfonyl, sulfinyl, phosphinate, carbocycle or heterocycle that is optionally substituted with hydroxyl, carboxyl, carbonyl, amino, halogen, haloalkyl, alkyl, alkoxy, alkylthio, sulfonyl, sulfinyl, acyl, a carbocycle or a heterocycle.

50. The method of claim 49 wherein at least one $R_6$ is an optionally substituted sulfonyl.

51. The method of claim 49 wherein carbocycle is a mono-, bi-, or tricyclic ring having 3 to 14 carbon atoms which can be saturated or unsaturated aliphatic or aromatic and heterocycle is a mono-, bi-, or tricyclic ring which is saturated or unsaturated, or aromatic, having from 5 to about 14 ring atoms, where the ring atoms are carbon and from 1 to 4 heteroatoms which are nitrogen, sulfur or oxygen.

52. The method of claim 50 wherein m is 0.

53. The method of claim 50 wherein $R_8$ is Cl.

54. The method of claim 50 wherein o is 2.

55. The method of claim 50 wherein one $R_6$ is Cl.

56. The method of claim 50 wherein m is 0, o is 2, $R_8$ is Cl, one $R_6$ is Cl and one $R_6$ is an optionally substituted sulfonyl.

57. The method of claim 37 wherein m is 0 or 1.

58. The method of claim 37 wherein $R_6$ is independently in each instance optionally substituted alkyl, halogen, alkoxy, carbonyl, a heterocycle, alkylamino, arylamino, alkylcarbamoyl, alkylsulfamoyl or sulfonyl.

59. The method of claim 49 wherein $R_6$ is independently in each instance substituted alkyl, halogen, alkoxy, carbonyl, a heterocycle, alkylamino, arylamino, alkylcarbamoyl, alkylsulfamoyl or sulfonyl.

60. The method of claim 37 wherein $R_1$ is of formula IIa or IIb:

IIa

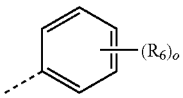

IIb

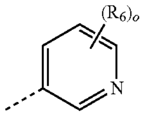

wherein $R_6$ is independently in each instance optionally substituted alkyl, halogen, alkoxy, carbonyl, a heterocycle, alkylamino, arylamino, alkylcarbamoyl, alkylsulfamoyl or sulfonyl; and o is 1-3.

61. The method of claim 37 wherein $R^1$ is of formula IIa.

62. The method of claim 60 wherein $R_8$ is halogen and $R^1$ is substituted phenyl or substituted pyridyl.

63. The method of claim 62 wherein $R_4$ is H, m is 0 and $R_8$ is Cl.

64. The method of claim 62 wherein said substituted phenyl or pyridyl $R^1$ group comprises —$SO_2$—.

65. The method of claim 60 wherein $R_1$ is substituted phenyl or substituted pyridyl, $R_3$ is H or methyl and X is —NHC(O)—.

66. A method of treating cancer in a mammal, comprising administering a compound of the formula:

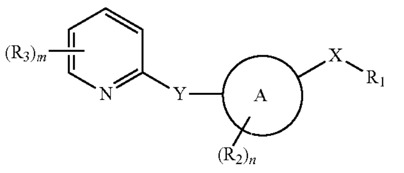

wherein

A is substituted benzene;

X is $NR_4C(O)$ or $NR_4C(S)$;

Y is absent;

$R_1$ is aryl or heteroaryl, each of which is optionally substituted;

$R_2$ is halogen, or alkyl substituted with halogen and an $R_2$ is in the o-position on said A benzene relative to pyridyl;

$R_3$ is halogen, hydroxyl, carboxyl, alkyl, acyl, alkoxy, alkoxycarbonyl, carbamoyl, alkylsulfide, sulfinyl, sulfonyl, a carbocycle or a heterocycle wherein each alkyl, acyl, alkoxy, alkoxycarbonyl, carbamoyl, alkylsulfide, sulfinyl, sulfonyl, carbocycle and heterocycle is optionally substituted with hydroxyl, halogen, amino, nitro, alkyl, acyl, sulfonyl or alkoxy;

$R_4$ is H or alkyl;

m is 0-3;

n is 1-3;

or a salt or solvate thereof.

67. The method of claim 66, wherein $R_4$ is H or methyl.

68. The method of claim 66, wherein $R_4$ is H.

69. The method of claim 66, wherein $R_1$ is substituted.

70. The method of claim 69, wherein $R_1$ is substituted phenyl or substituted pyridyl.

71. The method of claim 70, wherein $R_1$ is substituted phenyl.

72. The method of claim 70 wherein $R_1$ is substituted phenyl or substituted pyridyl, $R_3$ is H or methyl, ring A is o-chlorophenyl, and X is —NHC(O)—.

73. The method of claim 72 wherein $R_1$ substituted phenyl or pyridyl comprises —$SO_2$—.

74. The method of claim 70 wherein, ring A is o-chlorophenyl, X is —NHC(O)—, and $R_1$ substituted phenyl or substituted pyridyl comprises —$SO_2$—.

75. The method of claim 70 wherein A is

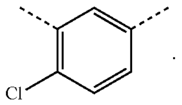

76. The method of claim 70 wherein $R_2$ is Cl.

77. The method of claim 70 wherein X is $NR_4C(O)$.

78. The method of claim 70 wherein $R_3$ is methyl or F.

79. The method of claim 70 wherein $R_3$ is methyl and m is 1 or 2.

80. The method of claim 70 wherein m is 0.

81. The method of claim 66 wherein $R_1$ is not naphthyl.

82. The method of claim 66 wherein $R_1$ is of formula IIa or IIb:

IIa

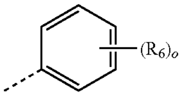

IIb

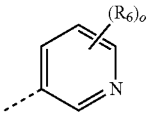

wherein $R_6$ is independently in each instance optionally substituted alkyl, halogen, alkoxy, carbonyl, a heterocycle, alkylamino, arylamino, alkylcarbamoyl, alkylsulfamoyl or sulfonyl; and o is 1-3.

83. The method of claim 82 wherein $R^1$ is of formula IIa.

84. The method of claim 66 wherein said compound or a salt thereof is administered.

85. The method of claim 72 wherein said compound or a salt thereof is administered.

86. The method of claim 70 wherein said compound or a salt thereof is administered.

87. The method of claim 49 wherein said compound or a salt thereof is administered.

88. The method of claim 75 wherein said compound or a salt thereof is administered.

89. The method of claim 60 wherein said compound or a salt thereof is administered.

90. The method of claim 42 wherein said compound or a salt thereof is administered.

91. The method of claim 42 comprising administering said compound in a composition further comprising a pharmaceutically acceptable carrier.

92. The method of claim 37 comprising administering said compound in a composition further comprising a pharmaceutically acceptable carrier.

93. A method of treating basal cell carcinoma in a human, comprising orally administering an effective amount of a compound of the formula:

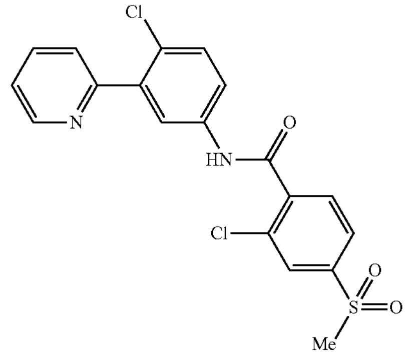 [SMILES: CS(=O)(=O)c1ccc(C(=O)Nc2ccc(Cl)c(-c3ccccn3)c2)c(Cl)c1]

or a salt or solvate thereof.

* * * * *